United States Patent
Ramshaw et al.

(10) Patent No.: US 10,053,501 B2
(45) Date of Patent: Aug. 21, 2018

(54) PURIFICATION OF TRIPLE HELICAL PROTEINS

(71) Applicant: Commonwealth Scientific and Industrial Research Organization, Campbell, Australian Capital Territory (AU)

(72) Inventors: John Alan Maurice Ramshaw, Pascoe Vale (AU); Jerome Anthony Werkmeister, Camberwell (AU); Yong Yi Peng, Bulleen (AU)

(73) Assignee: COMMONWEALTH SCIENTIFIC AND INDUSTRIAL RESEARCH ORGANISATION (AU)

( * ) Notice: Subject to any disclaimer, the term of this patent is extended or adjusted under 35 U.S.C. 154(b) by 0 days.

(21) Appl. No.: 14/778,845

(22) PCT Filed: Mar. 21, 2014

(86) PCT No.: PCT/AU2014/000303
§ 371 (c)(1),
(2) Date: Sep. 21, 2015

(87) PCT Pub. No.: WO2014/146175
PCT Pub. Date: Sep. 25, 2014

(65) Prior Publication Data
US 2016/0046692 A1 Feb. 18, 2016

(30) Foreign Application Priority Data

Mar. 21, 2013 (AU) .............................. 2013900990

(51) Int. Cl.
| | | |
|---|---|---|
| C07K 14/78 | (2006.01) | |
| C07K 1/30 | (2006.01) | |
| C07K 14/195 | (2006.01) | |
| C07K 1/14 | (2006.01) | |
| C07K 14/315 | (2006.01) | |

(52) U.S. Cl.
CPC .............. *C07K 14/78* (2013.01); *C07K 1/145* (2013.01); *C07K 1/30* (2013.01); *C07K 14/195* (2013.01); *C07K 14/315* (2013.01)

(58) Field of Classification Search
None
See application file for complete search history.

(56) References Cited

U.S. PATENT DOCUMENTS

| | | | |
|---|---|---|---|
| 4,837,148 A | 6/1989 | Cregg | |
| 4,855,231 A | 8/1989 | Stroman et al. | |
| 4,882,279 A | 11/1989 | Cregg | |
| 4,929,555 A | 5/1990 | Cregg et al. | |
| 5,122,465 A | 6/1992 | Cregg et al. | |
| 5,324,639 A | 6/1994 | Brierley et al. | |
| 5,593,859 A | 1/1997 | Prockop et al. | |
| 6,472,171 B1 | 10/2002 | Toman et al. | |
| 6,953,839 B2 | 10/2005 | Hook et al. | |
| 8,280,710 B2 | 10/2012 | Persikov et al. | |
| 2012/0116053 A1 | 5/2012 | Mirochnitchenko et al. | |
| 2012/0282817 A1 | 11/2012 | Finsterwalder | |

FOREIGN PATENT DOCUMENTS

| | | |
|---|---|---|
| EP | 0967226 A2 | 12/1999 |
| EP | 1809751 | 7/2007 |
| WO | 98/18918 A1 | 5/1998 |
| WO | 2010071938 A1 | 7/2010 |
| WO | 2010/091251 A2 | 8/2010 |
| WO | 2010091251 A2 | 8/2010 |
| WO | 2012117406 A2 | 9/2012 |
| WO | 2015/031950 A1 | 3/2015 |

OTHER PUBLICATIONS

Olsen et al., "Production of Human Type I Collagen in Yeast Reveals Unexpected New Insights into the Molecular Assembly of Collagen Trimers", The Journal of Biological Chemistry, 2001, vol. 276, No. 26, pp. 24038-24043.*
Ruggiero et al., "Triple helix assembly and processing of human collagen produced in transgenic tobacco plants", FEBS Letters, 2000, 469:132-136.*
Baez, et al., "Recombinant Microbial Systems for the Production of Human Collagen and Gelatin" Appl. Microbiol. Biotechnol., vol. 69, 2005, pp. 245-252.
Peng et al., "A Simple Cost Effective Methodology for Large Scale Purification of Recombinant Non-Animal Collagens" Appl. Microbiol. Biotechnol., vol. 98, 2014, pp. 1807-1815.
International Search Report corresponding to Int'l Pat. Appl. No. PCT/AU2014/000303, dated May 7, 2014, 4 pages.
Merle et al; Hydroxylated human homotrimeric collagen I in Agrobacterium tumefaciens-mediated transient expression and in transgenic tobacco plant; FEBS Letters, vol. 515, No. 1-3, Mar. 27, 2002, pp. 114-118.
Peng et al; A simple cost-effective methodology for large-scale purification of recombinant non-animal collagens; Applied Microbiology and Biotechnology, vol. 98, No. 4, Jan. 9, 2014, pp. 1807-1815.
Ruggiero et al; Making recombinant extracellular matrix proteins; Methods, Academic Press, U.S., vol. 45, No. 1, May 1, 2008, pp. 75-85.
Extended European Search Report for corresponding European Application Serial No. EP 14768321.3.
Ghosh, Neelanjana, et al. "Collagen-like proteins in pathogenic *E. coli* strains." PloS one 7.6 (2012): e37872.
Notbohm, Holger, et al. "Recombinant human type II collagens with low and high levels of hydroxylysine and its glycosylated forms show marked differences in fibrillogenesis in vitro." Journal of Biological Chemistry 274.13 (1999): 8988-8992.
Peng, Yong Y., et al. "A *Streptococcus pyogenes* derived collagen-like protein as a non-cytotoxic and non-immunogenic cross-linkable biomaterial." Biomaterials 31.10 (2010): 2755-2761.
Peng, Yong Y., et al. "Towards scalable production of a collagen-like protein from *Streptococcus pyogenes* for biomedical applications." Microbial cell factories 11.1 (2012): 146.

* cited by examiner

*Primary Examiner* — Suzanne Marie Noakes
(74) *Attorney, Agent, or Firm* — Tarolli, Sundheim, Covell & Tummino LLP

(57) ABSTRACT

The present invention relates to a method for purifying triple-helical or collagen-like proteins recombinantly produced from a bacterial, yeast or plant host cell.

25 Claims, 4 Drawing Sheets

SEQUENCE LISTING

<160> NUMBER OF SEQ ID NOS: 52

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      thrombin/trypsin cleavage site peptide

<400> SEQUENCE: 1

Leu Val Pro Arg Gly Ser Pro
1               5

<210> SEQ ID NO 2
<211> LENGTH: 978
<212> TYPE: DNA
<213> ORGANISM: Streptococcus pyogenes
<220> FEATURE:
<221> NAME/KEY: CDS
<222> LOCATION: (1)..(975)

<400> SEQUENCE: 2

```
atg cat cac cat cac cat cac gct gat gaa caa gaa gag aaa gct aaa      48
Met His His His His His His Ala Asp Glu Gln Glu Glu Lys Ala Lys
1               5                   10                  15 gtt aga act gaa tta att caa gag tta gct cag gga cta ggg ggt att      96
Val Arg Thr Glu Leu Ile Gln Glu Leu Ala Gln Gly Leu Gly Gly Ile
            20                  25                  30 gag aaa aaa aat ttt cca act cta ggt gat gaa gat tta gat cat act     144
Glu Lys Lys Asn Phe Pro Thr Leu Gly Asp Glu Asp Leu Asp His Thr
        35                  40                  45 tat atg aca aag cta tta aca tac cta cag gaa cga gaa caa gct gag     192
Tyr Met Thr Lys Leu Leu Thr Tyr Leu Gln Glu Arg Glu Gln Ala Glu
    50                  55                  60 aat agt tgg cga aaa aga cta cta aag ggt ata caa gat cat gcc ctt     240
Asn Ser Trp Arg Lys Arg Leu Leu Lys Gly Ile Gln Asp His Ala Leu
65                  70                  75                  80 gat ctg gtg cca cgc ggt agt ccc ggg ctg cca ggg ccc aga ggg gaa     288
Asp Leu Val Pro Arg Gly Ser Pro Gly Leu Pro Gly Pro Arg Gly Glu
                85                  90                  95 caa gga cca aca ggt cca acc gga cct gct ggt cca cga ggt cta caa     336
Gln Gly Pro Thr Gly Pro Thr Gly Pro Ala Gly Pro Arg Gly Leu Gln
            100                 105                 110 ggt cta caa ggt cta caa ggt gaa aga ggg gaa caa gga cca aca ggt     384
Gly Leu Gln Gly Leu Gln Gly Glu Arg Gly Glu Gln Gly Pro Thr Gly
        115                 120                 125 ccc gct ggt cca cga ggt cta caa ggt gaa aga ggg gaa caa gga cca     432
Pro Ala Gly Pro Arg Gly Leu Gln Gly Glu Arg Gly Glu Gln Gly Pro
    130                 135                 140 aca ggt ctc gct ggt aaa gcc ggt gaa gct gga gcc aaa ggc gaa acc     480
Thr Gly Leu Ala Gly Lys Ala Gly Glu Ala Gly Ala Lys Gly Glu Thr
145                 150                 155                 160 ggc ccc gct ggt cca cag ggt cca cgt ggt gaa caa ggc ccg caa ggt     528
Gly Pro Ala Gly Pro Gln Gly Pro Arg Gly Glu Gln Gly Pro Gln Gly
                165                 170                 175 ctt cca ggt aaa gat ggt gaa gct ggt gct caa ggc cca gca ggt cca     576
Leu Pro Gly Lys Asp Gly Glu Ala Gly Ala Gln Gly Pro Ala Gly Pro
            180                 185                 190 atg ggt cct gct ggt gag cga ggt gaa aaa gga gaa cct ggt acc caa     624
Met Gly Pro Ala Gly Glu Arg Gly Glu Lys Gly Glu Pro Gly Thr Gln
        195                 200                 205 ggc gct aaa ggt gat cgc ggt gaa acc ggt cca gta ggt cca cgt ggt     672
Gly Ala Lys Gly Asp Arg Gly Glu Thr Gly Pro Val Gly Pro Arg Gly
    210                 215                 220 gag cga ggc gaa gcc ggt ccc gct gga aaa gat ggt gaa cgt ggt cca     720
Glu Arg Gly Glu Ala Gly Pro Ala Gly Lys Asp Gly Glu Arg Gly Pro
225                 230                 235                 240 gta ggt cca gct ggt aag gac ggc caa aac ggc caa gat ggt ctt cca     768
Val Gly Pro Ala Gly Lys Asp Gly Gln Asn Gly Gln Asp Gly Leu Pro
```

```
                              245                 250                 255
ggt aaa gac ggt aag gac ggc caa aac ggt aaa gat ggt ctt cca ggt        816
Gly Lys Asp Gly Lys Asp Gly Gln Asn Gly Lys Asp Gly Leu Pro Gly
            260                 265                 270 aaa gac ggt aag gac ggc caa aac ggt aaa gat ggt ctt cca ggt aaa        864
Lys Asp Gly Lys Asp Gly Gln Asn Gly Lys Asp Gly Leu Pro Gly Lys
        275                 280                 285 gac ggt aag gac ggt caa gat ggt aaa gac ggc ctc cca ggt aaa gac        912
Asp Gly Lys Asp Gly Gln Asp Gly Lys Asp Gly Leu Pro Gly Lys Asp
    290                 295                 300 ggt aaa gat ggc ctc cca ggt aag gac ggt aag gac ggt caa cca ggt        960
Gly Lys Asp Gly Leu Pro Gly Lys Asp Gly Lys Asp Gly Gln Pro Gly
305                 310                 315                 320 aaa ccg ggt aaa tat taa                                                978
Lys Pro Gly Lys Tyr
                325

<210> SEQ ID NO 3
<211> LENGTH: 325
<212> TYPE: PRT
<213> ORGANISM: Streptococcus pyogenes

<400> SEQUENCE: 3

Met His His His His His Ala Asp Glu Gln Glu Lys Ala Lys
1               5                   10                  15

Val Arg Thr Glu Leu Ile Gln Glu Leu Ala Gln Gly Leu Gly Gly Ile
            20                  25                  30

Glu Lys Lys Asn Phe Pro Thr Leu Gly Asp Glu Asp Leu Asp His Thr
        35                  40                  45

Tyr Met Thr Lys Leu Leu Thr Tyr Leu Gln Glu Arg Glu Gln Ala Glu
    50                  55                  60

Asn Ser Trp Arg Lys Arg Leu Leu Lys Gly Ile Gln Asp His Ala Leu
65                  70                  75                  80

Asp Leu Val Pro Arg Gly Ser Pro Gly Leu Pro Gly Pro Arg Gly Glu
                85                  90                  95

Gln Gly Pro Thr Gly Pro Thr Gly Pro Ala Gly Pro Arg Gly Leu Gln
            100                 105                 110

Gly Leu Gln Gly Leu Gln Gly Glu Arg Gly Glu Gln Gly Pro Thr Gly
        115                 120                 125

Pro Ala Gly Pro Arg Gly Leu Gln Gly Glu Arg Gly Glu Gln Gly Pro
    130                 135                 140

Thr Gly Leu Ala Gly Lys Ala Gly Glu Ala Gly Ala Lys Gly Glu Thr
145                 150                 155                 160

Gly Pro Ala Gly Pro Gln Gly Pro Arg Gly Glu Gln Gly Pro Gln Gly
                165                 170                 175

Leu Pro Gly Lys Asp Gly Glu Ala Gly Ala Gln Gly Pro Ala Gly Pro
            180                 185                 190

Met Gly Pro Ala Gly Glu Arg Gly Glu Lys Gly Glu Pro Gly Thr Gln
        195                 200                 205

Gly Ala Lys Gly Asp Arg Gly Glu Thr Gly Pro Val Gly Pro Arg Gly
    210                 215                 220

Glu Arg Gly Glu Ala Gly Pro Ala Gly Lys Asp Gly Glu Arg Gly Pro
225                 230                 235                 240

Val Gly Pro Ala Gly Lys Asp Gly Gln Asn Gly Gln Asp Gly Leu Pro
                245                 250                 255

Gly Lys Asp Gly Lys Asp Gly Gln Asn Gly Lys Asp Gly Leu Pro Gly
```

```
                    260                 265                 270
Lys Asp Gly Lys Asp Gly Gln Asn Gly Lys Asp Gly Leu Pro Gly Lys
                275                 280                 285

Asp Gly Lys Asp Gly Gln Asp Gly Lys Asp Gly Leu Pro Gly Lys Asp
            290                 295                 300

Gly Lys Asp Gly Leu Pro Gly Lys Asp Gly Lys Asp Gly Gln Pro Gly
305                 310                 315                 320

Lys Pro Gly Lys Tyr
                325

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      insert sequence

<400> SEQUENCE: 4

Gly Ala Ala Gly Val Met
1               5

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgcggtagt cccggggcag cgggtgttat ggggcccaga gg                          42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgcgccatca gggccccgtc gcccacaata ccccgggtct cc                          42

<210> SEQ ID NO 7
<211> LENGTH: 1686
<212> TYPE: DNA
<213> ORGANISM: Streptococcus pyogenes
<220> FEATURE:
<221> NAME/KEY: CDS
<222> LOCATION: (1)..(1683)

<400> SEQUENCE: 7 atg cat cac cat cac cat cac gat gaa caa gaa gag aaa gct aaa gtt      48
Met His His His His His His Asp Glu Gln Glu Glu Lys Ala Lys Val
1               5                   10                  15 aga act gaa tta att caa gag tta gct cag gga cta ggg ggt ttt gag      96
Arg Thr Glu Leu Ile Gln Glu Leu Ala Gln Gly Leu Gly Gly Phe Glu
            20                  25                  30 aaa aaa aat ttt cca act cta ggt gat gaa gat tta gat cat act tat     144
Lys Lys Asn Phe Pro Thr Leu Gly Asp Glu Asp Leu Asp His Thr Tyr
        35                  40                  45 atg aca aag cta tta aca tac cta cag gaa cga gaa caa gct gag aat     192
Met Thr Lys Leu Leu Thr Tyr Leu Gln Glu Arg Glu Gln Ala Glu Asn
```

-continued

```
              50                  55                  60
agt tgg cga aaa aga cta cta aag ggt ata caa gat cat gcc ctt gat    240
Ser Trp Arg Lys Arg Leu Leu Lys Gly Ile Gln Asp His Ala Leu Asp
 65          70                  75                  80 ctg gtg cca cgc ggt agt ccc ggg ctg cca ggt ccc aga ggg gaa caa    288
Leu Val Pro Arg Gly Ser Pro Gly Leu Pro Gly Pro Arg Gly Glu Gln
                 85                  90                  95 gga cca aca ggt cca acc gga cct gct ggt cca cga ggt cta caa ggt    336
Gly Pro Thr Gly Pro Thr Gly Pro Ala Gly Pro Arg Gly Leu Gln Gly
            100                 105                 110 cta caa ggt cta caa ggt gaa aga ggg gaa caa gga cca aca ggt ccc    384
Leu Gln Gly Leu Gln Gly Glu Arg Gly Glu Gln Gly Pro Thr Gly Pro
        115                 120                 125 gct ggt cca cga ggt cta caa ggt gaa aga ggg gaa caa gga cca aca    432
Ala Gly Pro Arg Gly Leu Gln Gly Glu Arg Gly Glu Gln Gly Pro Thr
    130                 135                 140 ggt ctc gct ggt aaa gcc ggt gaa gct gga gcc aaa ggc gaa acc ggc    480
Gly Leu Ala Gly Lys Ala Gly Glu Ala Gly Ala Lys Gly Glu Thr Gly
145                 150                 155                 160 ccc gct ggt cca cag ggt cca cgt ggt gaa caa ggc ccg caa ggt ctt    528
Pro Ala Gly Pro Gln Gly Pro Arg Gly Glu Gln Gly Pro Gln Gly Leu
                165                 170                 175 cca ggt aaa gat ggt gaa gct ggt gct caa ggc cca gca ggt cca atg    576
Pro Gly Lys Asp Gly Glu Ala Gly Ala Gln Gly Pro Ala Gly Pro Met
            180                 185                 190 ggt cct gct ggt gag cga ggt gaa aaa gga gaa cct ggt acc caa ggc    624
Gly Pro Ala Gly Glu Arg Gly Glu Lys Gly Glu Pro Gly Thr Gln Gly
        195                 200                 205 gct aaa ggt gat cgc ggt gaa acc ggt cca gta ggt cca cgt ggt gag    672
Ala Lys Gly Asp Arg Gly Glu Thr Gly Pro Val Gly Pro Arg Gly Glu
    210                 215                 220 cga ggc gaa gcc ggt ccc gct gga aaa gat ggt gaa cgt ggt cca gta    720
Arg Gly Glu Ala Gly Pro Ala Gly Lys Asp Gly Glu Arg Gly Pro Val
225                 230                 235                 240 ggt cca gct ggt aag gac ggc caa aac ggc caa gat ggt ctt cca ggt    768
Gly Pro Ala Gly Lys Asp Gly Gln Asn Gly Gln Asp Gly Leu Pro Gly
                245                 250                 255 aaa gac ggt aag gac ggc caa aac ggt aaa gat ggt ctt cca ggt aaa    816
Lys Asp Gly Lys Asp Gly Gln Asn Gly Lys Asp Gly Leu Pro Gly Lys
            260                 265                 270 gac ggt aag gac ggc caa aac ggt aaa gat ggt ctt cca ggt aaa gac    864
Asp Gly Lys Asp Gly Gln Asn Gly Lys Asp Gly Leu Pro Gly Lys Asp
        275                 280                 285 ggt aag gac ggt caa gat ggt aaa gac ggc ctc cca ggt aaa gac ggt    912
Gly Lys Asp Gly Gln Asp Gly Lys Asp Gly Leu Pro Gly Lys Asp Gly
    290                 295                 300 aaa gat ggc ctc cca ggt aag gac ggt aag gac ggt caa cca ggt aaa    960
Lys Asp Gly Leu Pro Gly Lys Asp Gly Lys Asp Gly Gln Pro Gly Lys
305                 310                 315                 320 ccc ggg gca gcg ggt gtt atg ggg cca aga ggg gaa caa gga cca aca   1008
Pro Gly Ala Ala Gly Val Met Gly Pro Arg Gly Glu Gln Gly Pro Thr
                325                 330                 335 ggt cca acc gga cct gct ggt cca cga ggt cta caa ggt cta caa ggt   1056
Gly Pro Thr Gly Pro Ala Gly Pro Arg Gly Leu Gln Gly Leu Gln Gly
            340                 345                 350 cta caa ggt gaa aga ggg gaa caa gga cca aca ggt ccc gct ggt cca   1104
Leu Gln Gly Glu Arg Gly Glu Gln Gly Pro Thr Gly Pro Ala Gly Pro
        355                 360                 365 cga ggt cta caa ggt gaa aga ggg gaa caa gga cca aca ggt ctc gct   1152
```

```
Arg Gly Leu Gln Gly Glu Arg Gly Glu Gln Gly Pro Thr Gly Leu Ala
    370                 375                 380 ggt aaa gcc ggt gaa gct gga gcc aaa ggc gaa acc ggc ccc gct ggt         1200
Gly Lys Ala Gly Glu Ala Gly Ala Lys Gly Glu Thr Gly Pro Ala Gly
385                 390                 395                 400 cca cag ggt cca cgt ggt gaa caa ggc ccg caa ggt ctt cca ggt aaa         1248
Pro Gln Gly Pro Arg Gly Glu Gln Gly Pro Gln Gly Leu Pro Gly Lys
                405                 410                 415 gat ggt gaa gct ggt gct caa ggc cca gca ggt cca atg ggt cct gct         1296
Asp Gly Glu Ala Gly Ala Gln Gly Pro Ala Gly Pro Met Gly Pro Ala
            420                 425                 430 ggt gag cga ggt gaa aaa gga gaa cct ggt acc caa ggc gct aaa ggt         1344
Gly Glu Arg Gly Glu Lys Gly Glu Pro Gly Thr Gln Gly Ala Lys Gly
        435                 440                 445 gat cgc ggt gaa acc ggt cca gta ggt cca cgt ggt gag cga ggc gaa         1392
Asp Arg Gly Glu Thr Gly Pro Val Gly Pro Arg Gly Glu Arg Gly Glu
    450                 455                 460 gcc ggt ccc gct gga aaa gat ggt gaa cgt ggt cca gta ggt cca gct         1440
Ala Gly Pro Ala Gly Lys Asp Gly Glu Arg Gly Pro Val Gly Pro Ala
465                 470                 475                 480 ggt aag gac ggc caa aac ggc caa gat ggt ctt cca ggt aaa gac ggt         1488
Gly Lys Asp Gly Gln Asn Gly Gln Asp Gly Leu Pro Gly Lys Asp Gly
                485                 490                 495 aag gac ggc caa aac ggt aaa gat ggt ctt cca ggt aaa gac ggt aag         1536
Lys Asp Gly Gln Asn Gly Lys Asp Gly Leu Pro Gly Lys Asp Gly Lys
            500                 505                 510 gac ggc caa aac ggt aaa gat ggt ctt cca ggt aaa gac ggt aag gac         1584
Asp Gly Gln Asn Gly Lys Asp Gly Leu Pro Gly Lys Asp Gly Lys Asp
        515                 520                 525 ggt caa gat ggt aaa gac ggc ctc cca ggt aaa gac ggt aaa gat ggc         1632
Gly Gln Asp Gly Lys Asp Gly Leu Pro Gly Lys Asp Gly Lys Asp Gly
    530                 535                 540 ctc cca ggt aag gac ggt aag gac ggt caa cca ggt aaa ccg ggt aaa         1680
Leu Pro Gly Lys Asp Gly Lys Asp Gly Gln Pro Gly Lys Pro Gly Lys
545                 550                 555                 560 tat taa                                                                 1686
Tyr <210> SEQ ID NO 8
<211> LENGTH: 561
<212> TYPE: PRT
<213> ORGANISM: Streptococcus pyogenes

<400> SEQUENCE: 8

Met His His His His His Asp Glu Gln Glu Glu Lys Ala Lys Val
1               5                   10                  15

Arg Thr Glu Leu Ile Gln Glu Leu Ala Gln Gly Leu Gly Gly Phe Glu
                20                  25                  30

Lys Lys Asn Phe Pro Thr Leu Gly Asp Glu Asp Leu Asp His Thr Tyr
            35                  40                  45

Met Thr Lys Leu Leu Thr Tyr Leu Gln Glu Arg Glu Gln Ala Glu Asn
        50                  55                  60

Ser Trp Arg Lys Arg Leu Leu Lys Gly Ile Gln Asp His Ala Leu Asp
65                  70                  75                  80

Leu Val Pro Arg Gly Ser Pro Gly Leu Pro Gly Pro Arg Gly Glu Gln
                85                  90                  95

Gly Pro Thr Gly Pro Thr Gly Pro Ala Gly Pro Arg Gly Leu Gln Gly
            100                 105                 110
```

```
Leu Gln Gly Leu Gln Gly Glu Arg Gly Glu Gln Pro Thr Gly Pro
            115                 120                 125
Ala Gly Pro Arg Gly Leu Gln Gly Glu Arg Gly Glu Gln Gly Pro Thr
            130                 135                 140
Gly Leu Ala Gly Lys Ala Gly Glu Ala Gly Ala Lys Gly Glu Thr Gly
145                 150                 155                 160
Pro Ala Gly Pro Gln Gly Pro Arg Gly Glu Gln Gly Pro Gln Gly Leu
                165                 170                 175
Pro Gly Lys Asp Gly Glu Ala Gly Ala Gln Gly Pro Ala Gly Pro Met
            180                 185                 190
Gly Pro Ala Gly Glu Arg Gly Glu Lys Gly Glu Pro Gly Thr Gln Gly
            195                 200                 205
Ala Lys Gly Asp Arg Gly Glu Thr Gly Pro Val Gly Pro Arg Gly Glu
            210                 215                 220
Arg Gly Glu Ala Gly Pro Ala Gly Lys Asp Gly Glu Arg Gly Pro Val
225                 230                 235                 240
Gly Pro Ala Gly Lys Asp Gly Gln Asn Gly Gln Asp Gly Leu Pro Gly
                245                 250                 255
Lys Asp Gly Lys Asp Gly Gln Asn Gly Lys Asp Gly Leu Pro Gly Lys
            260                 265                 270
Asp Gly Lys Asp Gly Gln Asn Gly Lys Asp Gly Leu Pro Gly Lys Asp
            275                 280                 285
Gly Lys Asp Gly Gln Asp Gly Lys Asp Gly Leu Pro Gly Lys Asp Gly
            290                 295                 300
Lys Asp Gly Leu Pro Gly Lys Asp Gly Lys Asp Gly Gln Pro Gly Lys
305                 310                 315                 320
Pro Gly Ala Ala Gly Val Met Gly Pro Arg Gly Glu Gln Gly Pro Thr
                325                 330                 335
Gly Pro Thr Gly Pro Ala Gly Pro Arg Gly Leu Gln Gly Leu Gln Gly
            340                 345                 350
Leu Gln Gly Glu Arg Gly Glu Gln Gly Pro Thr Gly Pro Ala Gly Pro
            355                 360                 365
Arg Gly Leu Gln Gly Glu Arg Gly Glu Gln Gly Pro Thr Gly Leu Ala
370                 375                 380
Gly Lys Ala Gly Glu Ala Gly Ala Lys Gly Glu Thr Gly Pro Ala Gly
385                 390                 395                 400
Pro Gln Gly Pro Arg Gly Glu Gln Gly Pro Gln Gly Leu Pro Gly Lys
                405                 410                 415
Asp Gly Glu Ala Gly Ala Gln Gly Pro Ala Gly Pro Met Gly Pro Ala
            420                 425                 430
Gly Glu Arg Gly Glu Lys Gly Glu Pro Gly Thr Gln Gly Ala Lys Gly
            435                 440                 445
Asp Arg Gly Glu Thr Gly Pro Val Gly Pro Arg Gly Glu Arg Gly Glu
            450                 455                 460
Ala Gly Pro Ala Gly Lys Asp Gly Glu Arg Gly Pro Val Gly Pro Ala
465                 470                 475                 480
Gly Lys Asp Gly Gln Asn Gly Gln Asp Gly Leu Pro Gly Lys Asp Gly
                485                 490                 495
Lys Asp Gly Gln Asn Gly Lys Asp Gly Leu Pro Gly Lys Asp Gly Lys
            500                 505                 510
Asp Gly Gln Asn Gly Lys Asp Gly Leu Pro Gly Lys Asp Gly Lys Asp
            515                 520                 525
Gly Gln Asp Gly Lys Asp Gly Leu Pro Gly Lys Asp Gly Lys Asp Gly
```

```
                530                 535                 540
Leu Pro Gly Lys Asp Gly Lys Asp Gly Gln Pro Gly Lys Pro Gly Lys
545                 550                 555                 560

Tyr

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      heparin binding sequence

<400> SEQUENCE: 9

Gly Arg Pro Gly Lys Arg Gly Lys Gln Gly Gln Lys
1               5                   10

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaagctggt gctcaaggca ggccgggtcc aatgggtcct gctg              44

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acttcgacca cgagttccgt ccggccaggt tacccaggac gac               43

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caaggcaggc cgggtaagcg gggtcctgct ggtgagcg                     38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttccgtccg gcccattcgc cccaggacga ccactcgc                     38

<210> SEQ ID NO 14
<211> LENGTH: 50
<212> TYPE: DNA
<213> ORGANISM: Artificial Sequence
<220> FEATURE:
```

<223> OTHER INFORMATION: Description of Artificial Sequence: Synthetic
primer

<400> SEQUENCE: 14
ccgggtaagc ggggtaaaca gggccagaag ggtgaaaaag gagaacctgg         50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
ggcccattcg ccccatttgt cccggtcttc ccacttttc ctcttggacc          50

<210> SEQ ID NO 16
<211> LENGTH: 981
<212> TYPE: DNA
<213> ORGANISM: Streptococcus pyogenes
<220> FEATURE:
<221> NAME/KEY: CDS
<222> LOCATION: (1)..(975)

<400> SEQUENCE: 16

```
atg cat cac cat cac cat cac gct gat gaa caa gaa gag aaa gct aaa      48
Met His His His His His His Ala Asp Glu Gln Glu Glu Lys Ala Lys
1               5                   10                  15 gtt aga act gaa tta att caa gag tta gct cag gga cta ggg ggt att      96
Val Arg Thr Glu Leu Ile Gln Glu Leu Ala Gln Gly Leu Gly Gly Ile
            20                  25                  30 gag aaa aaa aat ttt cca act cta ggt gat gaa gat tta gat cat act     144
Glu Lys Lys Asn Phe Pro Thr Leu Gly Asp Glu Asp Leu Asp His Thr
        35                  40                  45 tat atg aca aag cta tta aca tac cta cag gaa cga gaa caa gct gag     192
Tyr Met Thr Lys Leu Leu Thr Tyr Leu Gln Glu Arg Glu Gln Ala Glu
    50                  55                  60 aat agt tgg cga aaa aga cta cta aag ggt ata caa gat cat gcc ctt     240
Asn Ser Trp Arg Lys Arg Leu Leu Lys Gly Ile Gln Asp His Ala Leu
65                  70                  75                  80 gat ctg gtg cca cgc ggt agt ccc ggg ctg cca ggg ccc aga ggg gaa     288
Asp Leu Val Pro Arg Gly Ser Pro Gly Leu Pro Gly Pro Arg Gly Glu
                85                  90                  95 caa gga cca aca ggt cca acc gga cct gct ggt cca cga ggt cta caa     336
Gln Gly Pro Thr Gly Pro Thr Gly Pro Ala Gly Pro Arg Gly Leu Gln
            100                 105                 110 ggt cta caa ggt cta caa ggt gaa aga ggg gaa caa gga cca aca ggt     384
Gly Leu Gln Gly Leu Gln Gly Glu Arg Gly Glu Gln Gly Pro Thr Gly
        115                 120                 125 ccc gct ggt cca cga ggt cta caa ggt gaa aga ggg gaa caa gga cca     432
Pro Ala Gly Pro Arg Gly Leu Gln Gly Glu Arg Gly Glu Gln Gly Pro
    130                 135                 140 aca ggt ctc gct ggt aaa gcc ggt gaa gct gga gcc aaa ggc gaa acc     480
Thr Gly Leu Ala Gly Lys Ala Gly Glu Ala Gly Ala Lys Gly Glu Thr
145                 150                 155                 160 ggc ccc gct ggt cca cag ggt cca cgt ggt gaa caa ggc ccg caa ggt     528
Gly Pro Ala Gly Pro Gln Gly Pro Arg Gly Glu Gln Gly Pro Gln Gly
                165                 170                 175 ctt cca ggt aaa gat ggt gaa gct ggt gct caa ggc agg ccg ggt aag     576
Leu Pro Gly Lys Asp Gly Glu Ala Gly Ala Gln Gly Arg Pro Gly Lys
            180                 185                 190
```

-continued

```
cgg ggt aaa cag ggc cag aag ggt gaa aaa gga gaa cct ggt acc caa        624
Arg Gly Lys Gln Gly Gln Lys Gly Glu Lys Gly Glu Pro Gly Thr Gln
        195                 200                 205 ggc gct aaa ggt gat cgc ggt gaa acc ggt cca gta ggt cca cgt ggt        672
Gly Ala Lys Gly Asp Arg Gly Glu Thr Gly Pro Val Gly Pro Arg Gly
    210                 215                 220 gag cga ggc gaa gcc ggt ccc gct gga aaa gat ggt gaa cgt ggt cca        720
Glu Arg Gly Glu Ala Gly Pro Ala Gly Lys Asp Gly Glu Arg Gly Pro
225                 230                 235                 240 gta ggt cca gct ggt aag gac ggc caa aac ggc caa gat ggt ctt cca        768
Val Gly Pro Ala Gly Lys Asp Gly Gln Asn Gly Gln Asp Gly Leu Pro
                245                 250                 255 ggt aaa gac ggt aag gac ggc caa aac ggt aaa gat ggt ctt cca ggt        816
Gly Lys Asp Gly Lys Asp Gly Gln Asn Gly Lys Asp Gly Leu Pro Gly
            260                 265                 270 aaa gac ggt aag gac ggc caa aac ggt aaa gat ggt ctt cca ggt aaa        864
Lys Asp Gly Lys Asp Gly Gln Asn Gly Lys Asp Gly Leu Pro Gly Lys
        275                 280                 285 gac ggt aag gac ggt caa gat ggt aaa gac ggc ctc cca ggt aaa gac        912
Asp Gly Lys Asp Gly Gln Asp Gly Lys Asp Gly Leu Pro Gly Lys Asp
    290                 295                 300 ggt aaa gat ggc ctc cca ggt aag gac ggt aag gac ggt caa cca ggt        960
Gly Lys Asp Gly Leu Pro Gly Lys Asp Gly Lys Asp Gly Gln Pro Gly
305                 310                 315                 320 aaa ccg ggt aaa tat taagga                                             981
Lys Pro Gly Lys Tyr
                325

<210> SEQ ID NO 17
<211> LENGTH: 325
<212> TYPE: PRT
<213> ORGANISM: Streptococcus pyogenes

<400> SEQUENCE: 17

Met His His His His His Ala Asp Glu Gln Glu Glu Lys Ala Lys
1               5                   10                  15

Val Arg Thr Glu Leu Ile Gln Glu Leu Ala Gln Gly Leu Gly Gly Ile
            20                  25                  30

Glu Lys Lys Asn Phe Pro Thr Leu Gly Asp Glu Asp Leu Asp His Thr
        35                  40                  45

Tyr Met Thr Lys Leu Leu Thr Tyr Leu Gln Glu Arg Glu Gln Ala Glu
    50                  55                  60

Asn Ser Trp Arg Lys Arg Leu Leu Lys Gly Ile Gln Asp His Ala Leu
65                  70                  75                  80

Asp Leu Val Pro Arg Gly Ser Pro Gly Leu Pro Gly Pro Arg Gly Glu
                85                  90                  95

Gln Gly Pro Thr Gly Pro Thr Gly Pro Ala Gly Pro Arg Gly Leu Gln
            100                 105                 110

Gly Leu Gln Gly Leu Gln Gly Glu Arg Gly Gln Gly Pro Thr Gly
        115                 120                 125

Pro Ala Gly Pro Arg Gly Leu Gln Gly Glu Arg Gly Glu Gln Gly Pro
    130                 135                 140

Thr Gly Leu Ala Gly Lys Ala Gly Glu Ala Gly Ala Lys Gly Glu Thr
145                 150                 155                 160

Gly Pro Ala Gly Pro Gln Gly Pro Arg Gly Glu Gln Gly Pro Gln Gly
                165                 170                 175

Leu Pro Gly Lys Asp Gly Glu Ala Gly Ala Gln Gly Arg Pro Gly Lys
            180                 185                 190
```

Arg Gly Lys Gln Gly Gln Lys Gly Glu Lys Gly Glu Pro Gly Thr Gln
        195                 200                 205

Gly Ala Lys Gly Asp Arg Gly Glu Thr Gly Pro Val Gly Pro Arg Gly
    210                 215                 220

Glu Arg Gly Glu Ala Gly Pro Ala Gly Lys Asp Gly Glu Arg Gly Pro
225                 230                 235                 240

Val Gly Pro Ala Gly Lys Asp Gly Gln Asn Gly Gln Asp Gly Leu Pro
            245                 250                 255

Gly Lys Asp Gly Lys Asp Gly Gln Asn Gly Lys Asp Gly Leu Pro Gly
        260                 265                 270

Lys Asp Gly Lys Asp Gly Gln Asn Gly Lys Asp Gly Leu Pro Gly Lys
        275                 280                 285

Asp Gly Lys Asp Gly Gln Asp Gly Lys Asp Gly Leu Pro Gly Lys Asp
        290                 295                 300

Gly Lys Asp Gly Leu Pro Gly Lys Asp Gly Lys Asp Gly Gln Pro Gly
305                 310                 315                 320

Lys Pro Gly Lys Tyr
                325

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      integrin binding sequence

<400> SEQUENCE: 18

Gly Glu Arg Gly Phe Pro Gly Glu Arg Gly Val Glu
1               5                   10

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaaaagatg gtgaacgtgg tttcccgggt ccagctggta aggacg        46

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccttttctac cacttgcacc aaagggccca ggtcgaccat tcctgc        46

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
gaacgtggtt tcccgggtga gagggggcgtc gagggccaaa acggccaaga t            51
```

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
cttgcaccaa agggcccact ctccccgcag ctcccggttt tgccggttct a             51
```

<210> SEQ ID NO 23
<211> LENGTH: 978
<212> TYPE: DNA
<213> ORGANISM: Streptococcus pyogenes
<220> FEATURE:
<221> NAME/KEY: CDS
<222> LOCATION: (1)..(975)

<400> SEQUENCE: 23

```
atg cat cac cat cac cat cac gct gat gaa caa gaa gag aaa gct aaa      48
Met His His His His His His Ala Asp Glu Gln Glu Glu Lys Ala Lys
1               5                   10                  15 gtt aga act gaa tta att caa gag tta gct cag gga cta ggg ggt att      96
Val Arg Thr Glu Leu Ile Gln Glu Leu Ala Gln Gly Leu Gly Gly Ile
                20                  25                  30 gag aaa aaa aat ttt cca act cta ggt gat gaa gat tta gat cat act     144
Glu Lys Lys Asn Phe Pro Thr Leu Gly Asp Glu Asp Leu Asp His Thr
            35                  40                  45 tat atg aca aag cta tta aca tac cta cag gaa cga gaa caa gct gag     192
Tyr Met Thr Lys Leu Leu Thr Tyr Leu Gln Glu Arg Glu Gln Ala Glu
        50                  55                  60 aat agt tgg cga aaa aga cta cta aag ggt ata caa gat cat gcc ctt     240
Asn Ser Trp Arg Lys Arg Leu Leu Lys Gly Ile Gln Asp His Ala Leu
65                  70                  75                  80 gat ctg gtg cca cgc ggt agt ccc ggg ctg cca ggg ccc aga ggg gaa     288
Asp Leu Val Pro Arg Gly Ser Pro Gly Leu Pro Gly Pro Arg Gly Glu
                85                  90                  95 caa gga cca aca ggt cca acc gga cct gct ggt cca cga ggt cta caa     336
Gln Gly Pro Thr Gly Pro Thr Gly Pro Ala Gly Pro Arg Gly Leu Gln
                100                 105                 110 ggt cta caa ggt cta caa ggt gaa aga ggg gaa caa gga cca aca ggt     384
Gly Leu Gln Gly Leu Gln Gly Glu Arg Gly Glu Gln Gly Pro Thr Gly
            115                 120                 125 ccc gct ggt cca cga ggt cta caa ggt gaa aga ggg gaa caa gga cca     432
Pro Ala Gly Pro Arg Gly Leu Gln Gly Glu Arg Gly Glu Gln Gly Pro
        130                 135                 140 aca ggt ctc gct ggt aaa gcc ggt gaa gct gga gcc aaa ggc gaa acc     480
Thr Gly Leu Ala Gly Lys Ala Gly Glu Ala Gly Ala Lys Gly Glu Thr
145                 150                 155                 160 ggc ccc gct ggt cca cag ggt cca cgt ggt gaa caa ggc ccg caa ggt     528
Gly Pro Ala Gly Pro Gln Gly Pro Arg Gly Glu Gln Gly Pro Gln Gly
                165                 170                 175 ctt cca ggt aaa gat ggt gaa gct ggt gct caa ggc cca gca ggt cca     576
Leu Pro Gly Lys Asp Gly Glu Ala Gly Ala Gln Gly Pro Ala Gly Pro
                180                 185                 190 atg ggt cct gct ggt gag cga ggt gaa aaa gga gaa cct ggt acc caa     624
Met Gly Pro Ala Gly Glu Arg Gly Glu Lys Gly Glu Pro Gly Thr Gln
            195                 200                 205 ggc gct aaa ggt gat cgc ggt gaa acc ggt cca gta ggt cca cgt ggt     672
Gly Ala Lys Gly Asp Arg Gly Glu Thr Gly Pro Val Gly Pro Arg Gly
```

```
Gly Ala Lys Gly Asp Arg Gly Glu Thr Gly Pro Val Gly Pro Arg Gly
            210                 215                 220 gag cga ggc gaa gcc ggt ccc gct gga aaa gat ggt gaa cgt ggt ttc       720
Glu Arg Gly Glu Ala Gly Pro Ala Gly Lys Asp Gly Glu Arg Gly Phe
225                 230                 235                 240 ccg ggt gag agg ggc gtc gag ggc caa aac ggc caa gat ggt ctt cca       768
Pro Gly Glu Arg Gly Val Glu Gly Gln Asn Gly Gln Asp Gly Leu Pro
                245                 250                 255 ggt aaa gac ggt aag gac ggc caa aac ggt aaa gat ggt ctt cca ggt       816
Gly Lys Asp Gly Lys Asp Gly Gln Asn Gly Lys Asp Gly Leu Pro Gly
            260                 265                 270 aaa gac ggt aag gac ggc caa aac ggt aaa gat ggt ctt cca ggt aaa       864
Lys Asp Gly Lys Asp Gly Gln Asn Gly Lys Asp Gly Leu Pro Gly Lys
        275                 280                 285 gac ggt aag gac ggt caa gat ggt aaa gac ggc ctc cca ggt aaa gac       912
Asp Gly Lys Asp Gly Gln Asp Gly Lys Asp Gly Leu Pro Gly Lys Asp
    290                 295                 300 ggt aaa gat ggc ctc cca ggt aag gac ggt aag gac ggt caa cca ggt       960
Gly Lys Asp Gly Leu Pro Gly Lys Asp Gly Lys Asp Gly Gln Pro Gly
305                 310                 315                 320 aaa ccg ggt aaa tat taa                                               978
Lys Pro Gly Lys Tyr
                325

<210> SEQ ID NO 24
<211> LENGTH: 325
<212> TYPE: PRT
<213> ORGANISM: Streptococcus pyogenes

<400> SEQUENCE: 24

Met His His His His His Ala Asp Glu Gln Glu Glu Lys Ala Lys
1               5                   10                  15

Val Arg Thr Glu Leu Ile Gln Glu Leu Ala Gln Gly Leu Gly Gly Ile
            20                  25                  30

Glu Lys Lys Asn Phe Pro Thr Leu Gly Asp Glu Asp Leu Asp His Thr
        35                  40                  45

Tyr Met Thr Lys Leu Leu Thr Tyr Leu Gln Glu Arg Glu Gln Ala Glu
50                  55                  60

Asn Ser Trp Arg Lys Arg Leu Leu Lys Gly Ile Gln Asp His Ala Leu
65                  70                  75                  80

Asp Leu Val Pro Arg Gly Ser Pro Gly Leu Pro Gly Pro Arg Gly Glu
                85                  90                  95

Gln Gly Pro Thr Gly Pro Thr Gly Pro Ala Gly Pro Arg Gly Leu Gln
            100                 105                 110

Gly Leu Gln Gly Leu Gln Gly Glu Arg Gly Glu Gln Gly Pro Thr Gly
        115                 120                 125

Pro Ala Gly Pro Arg Gly Leu Gln Gly Glu Arg Gly Glu Gln Gly Pro
    130                 135                 140

Thr Gly Leu Ala Gly Lys Ala Gly Glu Ala Gly Ala Lys Gly Glu Thr
145                 150                 155                 160

Gly Pro Ala Gly Pro Gln Gly Pro Arg Gly Glu Gln Gly Pro Gln Gly
                165                 170                 175

Leu Pro Gly Lys Asp Gly Glu Ala Gly Ala Gln Gly Pro Ala Gly Pro
            180                 185                 190

Met Gly Pro Ala Gly Glu Arg Gly Glu Lys Gly Glu Pro Gly Thr Gln
        195                 200                 205

Gly Ala Lys Gly Asp Arg Gly Glu Thr Gly Pro Val Gly Pro Arg Gly
```

```
                      210                 215                 220
Glu Arg Gly Glu Ala Gly Pro Ala Gly Lys Asp Gly Glu Arg Gly Phe
225                 230                 235                 240

Pro Gly Glu Arg Gly Val Glu Gly Gln Asn Gly Gln Asp Gly Leu Pro
                245                 250                 255

Gly Lys Asp Gly Lys Asp Gly Gln Asn Gly Lys Asp Gly Leu Pro Gly
            260                 265                 270

Lys Asp Gly Lys Asp Gly Gln Asn Gly Lys Asp Gly Leu Pro Gly Lys
        275                 280                 285

Asp Gly Lys Asp Gly Gln Asp Gly Lys Asp Gly Leu Pro Gly Lys Asp
    290                 295                 300

Gly Lys Asp Gly Leu Pro Gly Lys Asp Gly Lys Asp Gly Gln Pro Gly
305                 310                 315                 320

Lys Pro Gly Lys Tyr
                325

<210> SEQ ID NO 25
<211> LENGTH: 978
<212> TYPE: DNA
<213> ORGANISM: Streptococcus pyogenes
<220> FEATURE:
<221> NAME/KEY: CDS
<222> LOCATION: (1)..(975)

<400> SEQUENCE: 25 atg cat cac cat cac cat cac gct gat gaa caa gaa gag aaa gct aaa      48
Met His His His His His His Ala Asp Glu Gln Glu Glu Lys Ala Lys
1               5                   10                  15 gtt aga act gaa tta att caa gag tta gct cag gga cta ggg ggt att      96
Val Arg Thr Glu Leu Ile Gln Glu Leu Ala Gln Gly Leu Gly Gly Ile
            20                  25                  30 gag aaa aaa aat ttt cca act cta ggt gat gaa gat tta gat cat act     144
Glu Lys Lys Asn Phe Pro Thr Leu Gly Asp Glu Asp Leu Asp His Thr
        35                  40                  45 tat atg aca aag cta tta aca tac cta cag gaa cga gaa caa gct gag     192
Tyr Met Thr Lys Leu Leu Thr Tyr Leu Gln Glu Arg Glu Gln Ala Glu
    50                  55                  60 aat agt tgg cga aaa aga cta cta aag ggt ata caa gat cat gcc ctt     240
Asn Ser Trp Arg Lys Arg Leu Leu Lys Gly Ile Gln Asp His Ala Leu
65                  70                  75                  80 gat ctg gtg cca cgc ggt agt ccc ggg ctg cca ggg ccc aga ggg gaa     288
Asp Leu Val Pro Arg Gly Ser Pro Gly Leu Pro Gly Pro Arg Gly Glu
                85                  90                  95 caa gga cca aca ggt cca acc gga cct gct ggt cca cga ggt cta caa     336
Gln Gly Pro Thr Gly Pro Thr Gly Pro Ala Gly Pro Arg Gly Leu Gln
            100                 105                 110 ggt cta caa ggt cta caa ggt gaa aga ggg gaa caa gga cca aca ggt     384
Gly Leu Gln Gly Leu Gln Gly Glu Arg Gly Glu Gln Gly Pro Thr Gly
        115                 120                 125 ccc gct ggt cca cga ggt cta caa ggt gaa aga ggg gaa caa gga cca     432
Pro Ala Gly Pro Arg Gly Leu Gln Gly Glu Arg Gly Glu Gln Gly Pro
    130                 135                 140 aca ggt ctc gct ggt aaa gcc ggt gaa gct gga gcc aaa ggc gaa acc     480
Thr Gly Leu Ala Gly Lys Ala Gly Glu Ala Gly Ala Lys Gly Glu Thr
145                 150                 155                 160 ggc ccc gct ggt cca cag ggt cca cgt ggt gaa caa ggc ccg caa ggt     528
Gly Pro Ala Gly Pro Gln Gly Pro Arg Gly Glu Gln Gly Pro Gln Gly
                165                 170                 175 ctt cca ggt aaa gat ggt gaa gct ggt gct caa ggc agg ccg ggt aag     576
Leu Pro Gly Lys Asp Gly Glu Ala Gly Ala Gln Gly Arg Pro Gly Lys
```

```
Leu Pro Gly Lys Asp Gly Glu Ala Gly Ala Gln Gly Arg Pro Gly Lys
                180                 185                 190 cgg ggt aaa cag ggc cag aag ggt gaa aaa gga gaa cct ggt acc caa       624
Arg Gly Lys Gln Gly Gln Lys Gly Glu Lys Gly Glu Pro Gly Thr Gln
            195                 200                 205 ggc gct aaa ggt gat cgc ggt gaa acc ggt cca gta ggt cca cgt ggt       672
Gly Ala Lys Gly Asp Arg Gly Glu Thr Gly Pro Val Gly Pro Arg Gly
210                 215                 220 gag cga ggc gaa gcc ggt ccc gct gga aaa gat ggt gaa cgt ggt ttc       720
Glu Arg Gly Glu Ala Gly Pro Ala Gly Lys Asp Gly Glu Arg Gly Phe
225                 230                 235                 240 ccg ggt gag agg ggc gtc gag ggc caa aac ggc caa gat ggt ctt cca       768
Pro Gly Glu Arg Gly Val Glu Gly Gln Asn Gly Gln Asp Gly Leu Pro
                245                 250                 255 ggt aaa gac ggt aag gac ggc caa aac ggt aaa gat ggt ctt cca ggt       816
Gly Lys Asp Gly Lys Asp Gly Gln Asn Gly Lys Asp Gly Leu Pro Gly
                260                 265                 270 aaa gac ggt aag gac ggc caa aac ggt aaa gat ggt ctt cca ggt aaa       864
Lys Asp Gly Lys Asp Gly Gln Asn Gly Lys Asp Gly Leu Pro Gly Lys
            275                 280                 285 gac ggt aag gac ggt caa gat ggt aaa gac ggc ctc cca ggt aaa gac       912
Asp Gly Lys Asp Gly Gln Asp Gly Lys Asp Gly Leu Pro Gly Lys Asp
290                 295                 300 ggt aaa gat ggc ctc cca ggt aag gac ggt aag gac ggt caa cca ggt       960
Gly Lys Asp Gly Leu Pro Gly Lys Asp Gly Lys Asp Gly Gln Pro Gly
305                 310                 315                 320 aaa ccg ggt aaa tat taa                                               978
Lys Pro Gly Lys Tyr
                325

<210> SEQ ID NO 26
<211> LENGTH: 325
<212> TYPE: PRT
<213> ORGANISM: Streptococcus pyogenes

<400> SEQUENCE: 26

Met His His His His His Ala Asp Glu Gln Glu Glu Lys Ala Lys
1               5                   10                  15

Val Arg Thr Glu Leu Ile Gln Glu Leu Ala Gln Gly Leu Gly Gly Ile
                20                  25                  30

Glu Lys Lys Asn Phe Pro Thr Leu Gly Asp Glu Asp Leu Asp His Thr
            35                  40                  45

Tyr Met Thr Lys Leu Leu Thr Tyr Leu Gln Glu Arg Glu Gln Ala Glu
50                  55                  60

Asn Ser Trp Arg Lys Arg Leu Leu Lys Gly Ile Gln Asp His Ala Leu
65                  70                  75                  80

Asp Leu Val Pro Arg Gly Ser Pro Gly Leu Pro Gly Pro Arg Gly Glu
                85                  90                  95

Gln Gly Pro Thr Gly Pro Thr Gly Pro Ala Gly Pro Arg Gly Leu Gln
                100                 105                 110

Gly Leu Gln Gly Leu Gln Gly Glu Arg Gly Glu Gln Gly Pro Thr Gly
            115                 120                 125

Pro Ala Gly Pro Arg Gly Leu Gln Gly Glu Arg Gly Glu Gln Gly Pro
130                 135                 140

Thr Gly Leu Ala Gly Lys Ala Gly Glu Ala Gly Ala Lys Gly Glu Thr
145                 150                 155                 160

Gly Pro Ala Gly Pro Gln Gly Pro Arg Gly Glu Gln Gly Pro Gln Gly
                165                 170                 175
```

```
Leu Pro Gly Lys Asp Gly Glu Ala Gly Ala Gln Gly Arg Pro Gly Lys
                180                 185                 190

Arg Gly Lys Gln Gly Gln Lys Gly Glu Lys Gly Glu Pro Gly Thr Gln
            195                 200                 205

Gly Ala Lys Gly Asp Arg Gly Glu Thr Gly Pro Val Gly Pro Arg Gly
        210                 215                 220

Glu Arg Gly Glu Ala Gly Pro Ala Gly Lys Asp Gly Glu Arg Gly Phe
225                 230                 235                 240

Pro Gly Glu Arg Gly Val Glu Gly Gln Asn Gly Gln Asp Gly Leu Pro
                245                 250                 255

Gly Lys Asp Gly Lys Asp Gly Gln Asn Gly Lys Asp Gly Leu Pro Gly
            260                 265                 270

Lys Asp Gly Lys Asp Gly Gln Asn Gly Lys Asp Gly Leu Pro Gly Lys
        275                 280                 285

Asp Gly Lys Asp Gly Gln Asp Gly Lys Asp Gly Leu Pro Gly Lys Asp
    290                 295                 300

Gly Lys Asp Gly Leu Pro Gly Lys Asp Gly Lys Asp Gly Gln Pro Gly
305                 310                 315                 320

Lys Pro Gly Lys Tyr
            325

<210> SEQ ID NO 27
<211> LENGTH: 1017
<212> TYPE: DNA
<213> ORGANISM: Solibacter usitatus
<220> FEATURE:
<223> OTHER INFORMATION: Candidatus solibacter usitatus
<220> FEATURE:
<221> NAME/KEY: CDS
<222> LOCATION: (1)..(1014)

<400> SEQUENCE: 27 atg ggc ccg gcg ggc ccg gcg ggc ccg cag ggc ccg gcg ggc ccg gcg      48
Met Gly Pro Ala Gly Pro Ala Gly Pro Gln Gly Pro Ala Gly Pro Ala
1               5                   10                  15 ggc gcg cag ggc ccg gcg ggc ccg gcg ggc ccg cag ggc ccg gcg ggc      96
Gly Ala Gln Gly Pro Ala Gly Pro Ala Gly Pro Gln Gly Pro Ala Gly
            20                  25                  30 ccg cag ggc agc gcg ggc gcg cag ggc ccg aaa ggc gat acc ggc gcg     144
Pro Gln Gly Ser Ala Gly Ala Gln Gly Pro Lys Gly Asp Thr Gly Ala
        35                  40                  45 gcg ggc ccg gcg ggc gaa gcg ggc ccg aaa ggc gaa acc ggc gcg gcg     192
Ala Gly Pro Ala Gly Glu Ala Gly Pro Lys Gly Glu Thr Gly Ala Ala
    50                  55                  60 ggc ccg aaa ggc gat acc ggc gcg gcg ggc ccg gcg ggc ccg aaa ggc     240
Gly Pro Lys Gly Asp Thr Gly Ala Ala Gly Pro Ala Gly Pro Lys Gly
65                  70                  75                  80 gat acc ggc gcg gcg ggc ccg gcg ggc ccg aaa ggc gat acc ggc gcg     288
Asp Thr Gly Ala Ala Gly Pro Ala Gly Pro Lys Gly Asp Thr Gly Ala
                85                  90                  95 gcg ggc gcg acc ggc ccg aaa ggc gaa aaa ggc gaa acc ggc gcg gcg     336
Ala Gly Ala Thr Gly Pro Lys Gly Glu Lys Gly Glu Thr Gly Ala Ala
            100                 105                 110 ggc ccg aaa ggc gat aaa ggc gaa acc ggc gcg gcg ggc ccg aaa ggc     384
Gly Pro Lys Gly Asp Lys Gly Glu Thr Gly Ala Ala Gly Pro Lys Gly
        115                 120                 125 gat aaa ggc gaa acc ggc gcg gcg ggc ccg aaa ggc gaa aaa ggc gaa     432
Asp Lys Gly Glu Thr Gly Ala Ala Gly Pro Lys Gly Glu Lys Gly Glu
    130                 135                 140
```

```
acc ggc gcg gtg ggc ccg aaa ggc gat aaa ggc gaa acc ggc gcg gcg      480
Thr Gly Ala Val Gly Pro Lys Gly Asp Lys Gly Glu Thr Gly Ala Ala
145                 150                 155                 160 ggc ccg aaa ggc gat cgc ggc gaa acc ggc gcg gtg ggc ccg aaa ggc      528
Gly Pro Lys Gly Asp Arg Gly Glu Thr Gly Ala Val Gly Pro Lys Gly
                165                 170                 175 gat aaa ggc gaa acc ggc gcg gtg ggc ccg aaa ggc gat aaa ggc gaa      576
Asp Lys Gly Glu Thr Gly Ala Val Gly Pro Lys Gly Asp Lys Gly Glu
            180                 185                 190 acc ggc gcg att ggc ccg aaa ggc gat aaa ggc gat aaa ggc gat aaa      624
Thr Gly Ala Ile Gly Pro Lys Gly Asp Lys Gly Asp Lys Gly Asp Lys
        195                 200                 205 ggc gat gcg ggc gtg gcg ggc ccg cag ggc att cag ggc gtg aaa ggc      672
Gly Asp Ala Gly Val Ala Gly Pro Gln Gly Ile Gln Gly Val Lys Gly
    210                 215                 220 gat acc ggc ctg cag ggc ccg aaa ggc gat gcg ggc ccg cag ggc gcg      720
Asp Thr Gly Leu Gln Gly Pro Lys Gly Asp Ala Gly Pro Gln Gly Ala
225                 230                 235                 240 ccg ggc acc ccg ggc ggc ccg agc att gaa cag gtg atg ccg tgg ctg      768
Pro Gly Thr Pro Gly Gly Pro Ser Ile Glu Gln Val Met Pro Trp Leu
                245                 250                 255 cat ctg att ttt gat gcg tat gaa gat tat aaa gcg cag cgc gcg cgc      816
His Leu Ile Phe Asp Ala Tyr Glu Asp Tyr Lys Ala Gln Arg Ala Arg
            260                 265                 270 gaa gcg cgc gaa ctg gaa gaa cgc ctg gcg gcg gaa gcg ctg gaa cag      864
Glu Ala Arg Glu Leu Glu Glu Arg Leu Ala Ala Glu Ala Leu Glu Gln
        275                 280                 285 gcg gcg cgc gaa gcg gcg gaa cgc gaa gtg gcg gcg gcg att gaa gcg      912
Ala Ala Arg Glu Ala Ala Glu Arg Glu Val Ala Ala Ala Ile Glu Ala
    290                 295                 300 gcg aac gcg gaa gcg gaa att atg ctg gat gat gaa acc cat gcg gaa      960
Ala Asn Ala Glu Ala Glu Ile Met Leu Asp Asp Glu Thr His Ala Glu
305                 310                 315                 320 ggc ggc aaa aaa aaa aaa aaa cgc aaa cat aaa gat cac cac cat cac     1008
Gly Gly Lys Lys Lys Lys Lys Arg Lys His Lys Asp His His His His
                325                 330                 335 cat cat taa                                                         1017
His His
```

<210> SEQ ID NO 28
<211> LENGTH: 338
<212> TYPE: PRT
<213> ORGANISM: Solibacter usitatus
<220> FEATURE:
<223> OTHER INFORMATION: Candidatus solibacter usitatus

<400> SEQUENCE: 28

```
Met Gly Pro Ala Gly Pro Ala Gly Pro Gln Gly Pro Ala Gly Pro Ala
1               5                   10                  15

Gly Ala Gln Gly Pro Ala Gly Pro Ala Gly Pro Gln Gly Pro Ala Gly
                20                  25                  30

Pro Gln Gly Ser Ala Gly Ala Gln Gly Pro Lys Gly Asp Thr Gly Ala
            35                  40                  45

Ala Gly Pro Ala Gly Glu Ala Gly Pro Lys Gly Glu Thr Gly Ala Ala
        50                  55                  60

Gly Pro Lys Gly Asp Thr Gly Ala Ala Gly Pro Ala Gly Pro Lys Gly
65                  70                  75                  80

Asp Thr Gly Ala Ala Gly Pro Ala Gly Pro Lys Gly Asp Thr Gly Ala
                85                  90                  95
```

```
Ala Gly Ala Thr Gly Pro Lys Gly Glu Lys Gly Glu Thr Gly Ala Ala
            100                 105                 110

Gly Pro Lys Gly Asp Lys Gly Glu Thr Gly Ala Ala Gly Pro Lys Gly
        115                 120                 125

Asp Lys Gly Glu Thr Gly Ala Ala Gly Pro Lys Gly Glu Lys Gly Glu
    130                 135                 140

Thr Gly Ala Val Gly Pro Lys Gly Asp Lys Gly Glu Thr Gly Ala Ala
145                 150                 155                 160

Gly Pro Lys Gly Asp Arg Gly Glu Thr Gly Ala Val Gly Pro Lys Gly
                165                 170                 175

Asp Lys Gly Glu Thr Gly Ala Val Gly Pro Lys Gly Asp Lys Gly Glu
            180                 185                 190

Thr Gly Ala Ile Gly Pro Lys Gly Asp Lys Gly Asp Lys Gly Asp Lys
        195                 200                 205

Gly Asp Ala Gly Val Ala Gly Pro Gln Gly Ile Gln Gly Val Lys Gly
    210                 215                 220

Asp Thr Gly Leu Gln Gly Pro Lys Gly Asp Ala Gly Pro Gln Gly Ala
225                 230                 235                 240

Pro Gly Thr Pro Gly Pro Ser Ile Glu Gln Val Met Pro Trp Leu
                245                 250                 255

His Leu Ile Phe Asp Ala Tyr Glu Asp Tyr Lys Ala Gln Arg Ala Arg
            260                 265                 270

Glu Ala Arg Glu Leu Glu Glu Arg Leu Ala Ala Glu Ala Leu Glu Gln
        275                 280                 285

Ala Ala Arg Glu Ala Ala Glu Arg Glu Val Ala Ala Ile Glu Ala
    290                 295                 300

Ala Asn Ala Glu Ala Glu Ile Met Leu Asp Asp Glu Thr His Ala Glu
305                 310                 315                 320

Gly Gly Lys Lys Lys Lys Arg Lys His Lys Asp His His His
                325                 330                 335

His His

<210> SEQ ID NO 29
<211> LENGTH: 860
<212> TYPE: DNA
<213> ORGANISM: Nematus oligospilus
<220> FEATURE:
<221> NAME/KEY: CDS
<222> LOCATION: (9)..(842)

<400> SEQUENCE: 29 ggtaccat atg cgt cag gtt agc tat ttt atc ctg gca gca gtt gca ctg     50
         Met Arg Gln Val Ser Tyr Phe Ile Leu Ala Ala Val Ala Leu
           1               5                  10 ttt gca att ttt gca gaa gca gtt ccg gtt gca acc ccg agc aaa ggt     98
Phe Ala Ile Phe Ala Glu Ala Val Pro Val Ala Thr Pro Ser Lys Gly
15                  20                  25                  30 agc aaa agc ggt cat ggt ggt gaa agc ggt aat tat ggt cat ggt ggc    146
Ser Lys Ser Gly His Gly Gly Glu Ser Gly Asn Tyr Gly His Gly Gly
                35                  40                  45 cgt ggt ggt gat ggt tct gat ggt ggt gcc ggt ggt gtt ggt ggt ggt    194
Arg Gly Gly Asp Gly Ser Asp Gly Gly Ala Gly Gly Val Gly Gly Gly
            50                  55                  60 cgt agc ggt ggt agc ggt tgg gca ggt ccg caa ggt ccg cgt ggt gca    242
Arg Ser Gly Gly Ser Gly Trp Ala Gly Pro Gln Gly Pro Arg Gly Ala
65                  70                  75
```

```
gat ggt aaa att ggt ccg gct ggt ccg cag ggt cct tct ggt ccg gca      290
Asp Gly Lys Ile Gly Pro Ala Gly Pro Gln Gly Pro Ser Gly Pro Ala
         80                  85                  90 ggt cca aca ggt ccg gtg ggt cct cgt ggt gat gca ggt cgt ccg ggt      338
Gly Pro Thr Gly Pro Val Gly Pro Arg Gly Asp Ala Gly Arg Pro Gly
 95                 100                 105                 110 gca acc ggt gct aca ggt ccg gat ggt ccg aaa ggt gaa ttt ggt cct      386
Ala Thr Gly Ala Thr Gly Pro Asp Gly Pro Lys Gly Glu Phe Gly Pro
                115                 120                 125 cag ggt ccg agc ggt cca cgt ggt gca cca ggt cca cag ggt cct gca      434
Gln Gly Pro Ser Gly Pro Arg Gly Ala Pro Gly Pro Gln Gly Pro Ala
            130                 135                 140 ggt cct acc ggt cgt gat ggt cct aaa ggc gca gca ggt ccg gca ggc      482
Gly Pro Thr Gly Arg Asp Gly Pro Lys Gly Ala Ala Gly Pro Ala Gly
        145                 150                 155 gca gct ggt cct gct ggt tct ccg ggt gca cag ggt gaa acc ggt gat      530
Ala Ala Gly Pro Ala Gly Ser Pro Gly Ala Gln Gly Glu Thr Gly Asp
    160                 165                 170 cgt ggt gat cgc ggt ctg aaa ggt gat gtt ggt gcg cag ggt ggt aaa      578
Arg Gly Asp Arg Gly Leu Lys Gly Asp Val Gly Ala Gln Gly Gly Lys
175                 180                 185                 190 ggt att ccg ggt ccg gca gga cct cgt ggt cag acc ggt ccg aat ggt      626
Gly Ile Pro Gly Pro Ala Gly Pro Arg Gly Gln Thr Gly Pro Asn Gly
                195                 200                 205 ctg cct ggt gca aaa ggc gaa acc ggt ccg aaa ggc gct caa ggt ccg      674
Leu Pro Gly Ala Lys Gly Glu Thr Gly Pro Lys Gly Ala Gln Gly Pro
            210                 215                 220 gct ggc cct gcc ggt cct aaa ggt gaa gat ggt gcc acc ggt gaa aca      722
Ala Gly Pro Ala Gly Pro Lys Gly Glu Asp Gly Ala Thr Gly Glu Thr
        225                 230                 235 ggt cct cgt ggc cct gca ggt cca gcc ggt gca gca ggt aaa gat att      770
Gly Pro Arg Gly Pro Ala Gly Pro Ala Gly Ala Ala Gly Lys Asp Ile
    240                 245                 250 atc att tgg aaa ggt cag aaa ggt tgg cgt agc ccg agc gaa cgt aaa      818
Ile Ile Trp Lys Gly Gln Lys Gly Trp Arg Ser Pro Ser Glu Arg Lys
255                 260                 265                 270 agc tat cat cat cat cac cat cat taataagaat tcgagctc                  860
Ser Tyr His His His His His His
                275
```

<210> SEQ ID NO 30
<211> LENGTH: 278
<212> TYPE: PRT
<213> ORGANISM: Nematus oligospilus

<400> SEQUENCE: 30

```
Met Arg Gln Val Ser Tyr Phe Ile Leu Ala Ala Val Ala Leu Phe Ala
  1               5                  10                  15

Ile Phe Ala Glu Ala Val Pro Val Ala Thr Pro Ser Lys Gly Ser Lys
             20                  25                  30

Ser Gly His Gly Gly Glu Ser Gly Asn Tyr Gly His Gly Gly Arg Gly
         35                  40                  45

Gly Asp Gly Ser Asp Gly Gly Ala Gly Gly Val Gly Gly Gly Arg Ser
     50                  55                  60

Gly Gly Ser Gly Trp Ala Gly Pro Gln Gly Pro Arg Gly Ala Asp Gly
 65                  70                  75                  80

Lys Ile Gly Pro Ala Gly Pro Gln Gly Pro Ser Gly Pro Ala Gly Pro
                 85                  90                  95

Thr Gly Pro Val Gly Pro Arg Gly Asp Ala Gly Arg Pro Gly Ala Thr
```

100                 105                 110
Gly Ala Thr Gly Pro Asp Gly Pro Lys Gly Glu Phe Gly Pro Gln Gly
        115                 120                 125

Pro Ser Gly Pro Arg Gly Ala Pro Gly Pro Gln Gly Pro Ala Gly Pro
    130                 135                 140

Thr Gly Arg Asp Gly Pro Lys Gly Ala Ala Gly Pro Ala Gly Ala Ala
145                 150                 155                 160

Gly Pro Ala Gly Ser Pro Gly Ala Gln Gly Glu Thr Gly Asp Arg Gly
                165                 170                 175

Asp Arg Gly Leu Lys Gly Asp Val Gly Ala Gln Gly Gly Lys Gly Ile
            180                 185                 190

Pro Gly Pro Ala Gly Pro Arg Gly Gln Thr Gly Pro Asn Gly Leu Pro
        195                 200                 205

Gly Ala Lys Gly Glu Thr Gly Pro Lys Gly Ala Gln Gly Pro Ala Gly
    210                 215                 220

Pro Ala Gly Pro Lys Gly Glu Asp Gly Ala Thr Gly Glu Thr Gly Pro
225                 230                 235                 240

Arg Gly Pro Ala Gly Pro Ala Gly Ala Ala Gly Lys Asp Ile Ile Ile
                245                 250                 255

Trp Lys Gly Gln Lys Gly Trp Arg Ser Pro Ser Glu Arg Lys Ser Tyr
                260                 265                 270

His His His His His His
        275

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccggaattcg gtgccatggg tgctccaggt gctccaggt                                39

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcccccgggg agcacctggt ggacctggtg gac                                      33

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcccccgggg gatgccggtg gtaaggttga cgctggt                                  37

<210> SEQ ID NO 34
<211> LENGTH: 31
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 34
cgcggatcca cctggtggac ctggtggacc a                                    31

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccgggatccg gtggtaaggg tgacgctggt gctcca                               36

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctccccgcgg ttaaggtggc cctggtggac ctgga                                35

<210> SEQ ID NO 37
<211> LENGTH: 501
<212> TYPE: DNA
<213> ORGANISM: Artificial Sequence
<220> FEATURE:
<223> OTHER INFORMATION: Description of Artificial Sequence: Synthetic
      repeats of a fragment of human type III collagen

<400> SEQUENCE: 37
gactacaagg atgacgatga caaggaattc ggtgccatgg gtgctccagg tgctccaggt     60
ggtaagggtg acgctggtgc tccaggtgaa agaggtccac caggtttggc tggtgctcca    120
ggtttgagag gtggtgctgg tccaccaggt ccagaaggtg gtaagggtgc tgctggtcca    180
ccaggtccac caggtgctcc cggtggtaag ggtgacgctg gtgctccagg tgaaagaggt    240
ccaccaggtt tggctggtgc tccaggtttg agaggtggtg ctggtccacc aggtccagaa    300
ggtggtaagg gtgctgctgg tccaccaggt ccaccaggtg gatccggtgg taagggtgac    360
gctggtgctc caggtgaaag aggtccacca ggtttggctg gtgctccagg tttgagaggt    420
ggtgctggtc caccaggtcc agaaggtggt aagggtgctg ctggtccacc aggtccacca    480
gggccacctt aaccgcggta a                                              501

<210> SEQ ID NO 38
<211> LENGTH: 163
<212> TYPE: PRT
<213> ORGANISM: Artificial Sequence
<220> FEATURE:
<223> OTHER INFORMATION: Description of Artificial Sequence: Synthetic
      repeats of a fragment of human type III collagen

<400> SEQUENCE: 38

Asp Tyr Lys Asp Asp Asp Asp Lys Glu Ser Gly Ala Met Gly Ala Pro
1               5                   10                  15

Gly Ala Pro Gly Gly Lys Gly Asp Ala Gly Ala Pro Gly Glu Arg Gly
            20                  25                  30
```

```
Pro Pro Gly Leu Ala Gly Ala Pro Gly Leu Arg Gly Gly Ala Gly Pro
            35                  40                  45

Pro Gly Pro Glu Gly Gly Lys Gly Ala Ala Gly Pro Pro Gly Pro Pro
        50                  55                  60

Gly Ala Pro Gly Gly Lys Gly Asp Ala Gly Ala Pro Gly Glu Arg Gly
 65                  70                  75                  80

Pro Pro Gly Leu Ala Gly Ala Pro Gly Leu Arg Gly Gly Ala Gly Pro
                85                  90                  95

Pro Gly Pro Glu Gly Gly Lys Gly Ala Ala Gly Pro Pro Gly Pro Pro
            100                 105                 110

Gly Gly Ser Gly Gly Lys Gly Asp Ala Gly Ala Pro Gly Glu Arg Gly
            115                 120                 125

Pro Pro Gly Leu Ala Gly Ala Pro Gly Leu Arg Gly Gly Ala Gly Pro
        130                 135                 140

Pro Gly Pro Glu Gly Gly Lys Gly Ala Ala Gly Pro Pro Gly Pro Pro
145                 150                 155                 160

Gly Pro Pro

<210> SEQ ID NO 39
<211> LENGTH: 484
<212> TYPE: DNA
<213> ORGANISM: Artificial Sequence
<220> FEATURE:
<223> OTHER INFORMATION: Description of Artificial Sequence: Synthetic
      alpha 1 chain CB3 fragment
<220> FEATURE:
<221> NAME/KEY: CDS
<222> LOCATION: (1)..(471)

<400> SEQUENCE: 39 cat atg ggt ttt ccg ggt ccg aaa ggt gca gcc ggt gaa ccg ggt aaa      48
His Met Gly Phe Pro Gly Pro Lys Gly Ala Ala Gly Glu Pro Gly Lys
  1               5                  10                  15 gcc ggt gaa cgt ggt gtt ccg ggt ccg cct ggt gca gtt ggt ccg gca      96
Ala Gly Glu Arg Gly Val Pro Gly Pro Pro Gly Ala Val Gly Pro Ala
                 20                  25                  30 ggc aaa gat ggt gaa gcc ggt gca cag ggt cct cca ggt ccg gct ggt     144
Gly Lys Asp Gly Glu Ala Gly Ala Gln Gly Pro Pro Gly Pro Ala Gly
             35                  40                  45 cct gca ggc gaa cgt ggt gaa cag ggt ccg gct ggc tct ccg ggt ttt     192
Pro Ala Gly Glu Arg Gly Glu Gln Gly Pro Ala Gly Ser Pro Gly Phe
         50                  55                  60 cag ggt ctg cct ggt cct gct ggt ccg cca ggt gaa gca ggc aaa ccg     240
Gln Gly Leu Pro Gly Pro Ala Gly Pro Pro Gly Glu Ala Gly Lys Pro
 65                  70                  75                  80 ggt gaa caa ggc gtt ccg ggt gat ctg ggt gca ccg ggt ccg tca ggt     288
Gly Glu Gln Gly Val Pro Gly Asp Leu Gly Ala Pro Gly Pro Ser Gly
                 85                  90                  95 gca cgt ggt gaa cgt ggc ttt cct ggt gaa cgc ggt gtg cag ggt cca     336
Ala Arg Gly Glu Arg Gly Phe Pro Gly Glu Arg Gly Val Gln Gly Pro
            100                 105                 110 cca gga cca gca ggc cct cgt ggt gca aat ggt gct ccg ggt aat gat     384
Pro Gly Pro Ala Gly Pro Arg Gly Ala Asn Gly Ala Pro Gly Asn Asp
        115                 120                 125 ggt gca aaa ggt gat gca ggc gca ccg ggt gca cct ggt agc cag ggt     432
Gly Ala Lys Gly Asp Ala Gly Ala Pro Gly Ala Pro Gly Ser Gln Gly
    130                 135                 140 gca cca ggt ctg cag ggt atg cac cac cat cac cat cat tgaattcaag     481
Ala Pro Gly Leu Gln Gly Met His His His His His His
145                 150                 155
```

```
                145                 150                 155
ctt                                                                      484

<210> SEQ ID NO 40
<211> LENGTH: 157
<212> TYPE: PRT
<213> ORGANISM: Artificial Sequence
<220> FEATURE:
<223> OTHER INFORMATION: Description of Artificial Sequence: Synthetic
      alpha 1 chain CB3 fragment

<400> SEQUENCE: 40

His Met Gly Phe Pro Gly Pro Lys Gly Ala Ala Gly Glu Pro Gly Lys
1               5                   10                  15

Ala Gly Glu Arg Gly Val Pro Gly Pro Pro Gly Ala Val Gly Pro Ala
            20                  25                  30

Gly Lys Asp Gly Glu Ala Gly Ala Gln Gly Pro Pro Gly Pro Ala Gly
        35                  40                  45

Pro Ala Gly Glu Arg Gly Glu Gln Gly Pro Ala Gly Ser Pro Gly Phe
    50                  55                  60

Gln Gly Leu Pro Gly Pro Ala Gly Pro Pro Gly Glu Ala Gly Lys Pro
65                  70                  75                  80

Gly Glu Gln Gly Val Pro Gly Asp Leu Gly Ala Pro Gly Pro Ser Gly
                85                  90                  95

Ala Arg Gly Glu Arg Gly Phe Pro Gly Glu Arg Gly Val Gln Gly Pro
            100                 105                 110

Pro Gly Pro Ala Gly Pro Arg Gly Ala Asn Gly Ala Pro Gly Asn Asp
        115                 120                 125

Gly Ala Lys Gly Asp Ala Gly Ala Pro Gly Ala Pro Gly Ser Gln Gly
    130                 135                 140

Ala Pro Gly Leu Gln Gly Met His His His His His
145                 150                 155

<210> SEQ ID NO 41
<211> LENGTH: 4018
<212> TYPE: DNA
<213> ORGANISM: Artificial Sequence
<220> FEATURE:
<223> OTHER INFORMATION: Description of Artificial Sequence: Synthetic
      segments of human collagen type I and type III

<400> SEQUENCE: 41
gcggccgacc atgttcagct tgtggaccct ccggctcctg ctcctcttag cggccaccgc       60
cctcctgacg cacggccagc tgtcttatgg ctatgatgag aaatcaaccg gtggaatttc      120
cgtgcctggc cccatgggtc cctctggtcc tcgtggtctc cctggccccc tggtgcacc       180 tggtccccaa ggcttccaag gtccccctgg tgagcctggc gagcctggag cttcaggtcc      240
catgggtccc cgaggtcccc caggtccccc tggaaagaat ggagatgatg gggaagctgg      300
aaaacctggt cgtcctggtg agcgtgggcc tcctgggcct caggggctc gaggattgcc       360 cggaacagct ggcctcccctg gaatgaaggg acacagaggt ttcagtggtt tggatggtgc     420
caagggagat gctggtcctg ctggtcctaa gggtgagcct gcagccctg tgaaaatgg        480 agctcctggt cagatgggcc ctaggggcct gctggtgag agaggtcgcc ctggagcccc       540
tggccctgct ggtgctcgtg gaaatgatgg tgctactggt gctgccgggc cccctggtcc      600
caccggcccc gctggtcctc ctggcttccc tggtgctgtt ggtgctaagg gtgaagctgg      660
tccccaaggg ccccgaggct ctgaaggtcc ccagggtgtg cgtggtgagc ctggccccc      720
```

-continued

```
tggccctgct ggtgctgctg gccctgctgg aaaccctggt gctgatggac agcctggtgc    780
taaaggtgcc aatggtgctc ctggtattgc tggtgctcct ggcttccctg gtgcccgagg    840
cccctctgga ccccagggcc ccggcggccc tcctggtccc aagggtaaca gcggtgaacc    900
tggtgctcct ggcagcaaag gagacactgg tgctaaggga gagcctggcc ctgttggtgt    960
tcaaggaccc cctggccctg ctggagagga aggaaagcga ggagctcgag gtgaacccgg   1020
acccactggc ctgcccggac cccctggcga gcgtggtgga cctggtagcc gtggtttccc   1080
tggcgcagat ggtgttgctg gtcccaaggg tcccgctggt gaacgtggtt ctcctggccc   1140
tgctggcccc aaaggatctc ctggtgaagc tggtcgtccc ggtgaagctg gtctgcctgg   1200
tgccaagggt ctgactggaa gccctggcag cctggtcct gatggcaaaa ctggcccccc   1260
tggtcccgcc ggtcaagatg gtcgcccgg accccaggc ccacctggtg cccgtggtca    1320
ggctggtgtg atgggattcc ctggacctaa aggtgctgct ggagagcccg gcaaggctgg   1380
agagcgaggt gttcccggac cccctggcgc tgtcggtcct gctggcaaag atggagaggc   1440
tggagctcag ggacccccctg gccctgctgg tcccgctggc gagagaggtg aacaaggccc   1500
tgctggctcc cccggattcc agggtctccc tggtcctgct ggtcctccag gtgaagcagg   1560
caaacctggt gaacagggtg ttcctggaga ccttggcgcc cctggcccct ctggagcaag   1620
aggcgagaga ggtttccctg gcgagcgtgg tgtgcaaggt ccccctggtc ctgctggtcc   1680
ccgaggggcc aacggtgctc ccggcaacga tggtgctaag ggtgatgctg gtgccctgg   1740 agctcccggt agccagggcg ccctggcct tcagggaatg cctggtgaac gtggtgcagc   1800
tggtcttcca gggcctaagg gtgacagagg tgatgctggt cccaaggtg ctgatggctc   1860 tcctggcaaa gatggcgtcc gtggtctgac tggccccatt ggtcctcctg gccctgctgg   1920
tgcccctggt gacaagggtg aaagtggtcc cagcggccct gctggtccca ctggagctcg   1980
tggtgccccc ggagaccgtg gtgagcctgg tccccccggc cctgctggct tgctggccc   2040 ccctggtgct gacggccaac tggtgctaa aggcgaacct ggtgatgctg gtgctaaagg   2100
cgatgctggt ccccctggcc ctgccggacc cgctggaccc cctggcccca ttggtaatgt   2160
tggtgctcct ggagccaaag gtgctcgcgg cagcgctggt cccccctggtg ctactggtt   2220 ccctggtgct gctggccgag tcggtcctcc tggccctct ggaaatgctg accccctgg    2280 ccctcctggt cctgctggca agaaggcgg caaaggtccc cgtggtgaga ctggccctgc   2340
tggacgtcct ggtgaagttg gtccccctgg tccccctggc cctgctggcg agaaaggatc   2400
ccctggtgct gatggtcctg ctggtgctcc tggtactccc gggcctcaag gtattgctgg   2460
acagcgtggt gtggtcggcc tgcctggtca gagaggagag agaggcttcc ctggtcttcc   2520
tggcccctct ggtgaacctg gcaaacaagg tccctctgga gcaagtggtg aacgtggtcc   2580
ccctggtccc atgggccccc tggattggc tggacccct ggtgaatctg gacgtgaggg   2640
ggctcctggt gccgaaggtt cccctggacg agacggttct cctggcgcca agggtgaccg   2700
tggtgagacc ggccccgctg accccctggg tgctcctggt gctcctggtg cccctggtcc   2760
tgtcggtcca gctggaaaga gtggtgacag aggagaaagt ggccctgctg gccctgctgg   2820
tgctcccggt cctgctggtt cccgaggtgc tctggtcctc aaggcccacg tggtgacaaa   2880
ggtgaaacag gtgaacgtgg agctgctggc atcaaaggac atcgaggatt ccctggtaat   2940
ccaggtgccc caggttctcc aggccctgct ggtcagcagg gtgcaatcgg cagtccagga   3000
cctgcaggcc ccagaggacc tgttggaccc agtggacctc ctggcaaaga tggaaccagt   3060
```

```
ggacatccag gtcccattgg accaccaggg cctcgaggta acagaggtga aagaggatct    3120
gagggctccc caggccaccc agggcaacca ggccctcctg gcttgctgta cctcctggtg    3180
cccctggtcc ttgctgtgcc ggcttcgact tcagcttcct gccccagcca cctcaagaga    3240
aggctcacga tggtggccgc tactaccggg ctgatgatgc caatgtggtt cgtgaccgtg    3300
acctcgaggt ggacaccacc ctcaagagcc tgagccagca gatcgagaac atccggagcc    3360
cagagggcag ccgcaagaac cccgcccgca cctgccgtga cctcaagatg tgccactctg    3420
actggaagag tggagagtac tggattgacc ccaaccaagg ctgcaacctg gatgccatca    3480
aagtcttctg caacatggag actggtgaga cctgcgtgta ccccactcag cccagtgtgg    3540
cccagaagaa ctggtacatc agcaagaacc ccaaggacaa gaggcatgtc tggttcggcg    3600
agagcatgac cgatggattc cagttcgagt atggcggcca gggctccgac cctgccgatg    3660
tggccatcca gctgaccttc ctgcgcctga tgccaccgag gcctcccaga acatcaccta    3720
ccactgcaag aacagcgtgg cctacatgga ccagcagact ggcaacctca agaaggccct    3780
gctcctccag ggctccaacg agatcgagat ccgcccgag gcaacagcc gcttcaccta    3840 cagcgtcact gtcgatggct gcacgagtca caccggagcc tggggcaaga cagtgattga    3900
atacaaaacc accaagacct cccgcctgcc catcatcgat gtggccccct tggacgttgg    3960
tgccccagac caggaattcg gcttcgacgt tggccctgtc tgcttcctgt aagtcgac     4018
```

<210> SEQ ID NO 42
<211> LENGTH: 1500
<212> TYPE: DNA
<213> ORGANISM: Artificial Sequence
<220> FEATURE:
<223> OTHER INFORMATION: Description of Artificial Sequence: Synthetic
    chimera of Methylobacterium sp. and S. usitatus
<220> FEATURE:
<221> NAME/KEY: CDS
<222> LOCATION: (1)..(1491)

<400> SEQUENCE: 42

```
cat atg ggt gaa gca gca ccg gca ccg gca gca ccg aaa cct gaa gca      48
His Met Gly Glu Ala Ala Pro Ala Pro Ala Ala Pro Lys Pro Glu Ala
1               5                  10                  15 ccg cgt ggt gca gca cgt aaa ccg gca agc agc gca att cag att tgg     96
Pro Arg Gly Ala Ala Arg Lys Pro Ala Ser Ser Ala Ile Gln Ile Trp
            20                  25                  30 gat gca cgt att gaa ggt ggt gat ctg cgt att agc ggt aat gtt ggt    144
Asp Ala Arg Ile Glu Gly Gly Asp Leu Arg Ile Ser Gly Asn Val Gly
        35                  40                  45 aaa gcc ggt gtt acc gtt agc ctg gat gat gaa gtt gca gtt cag agc    192
Lys Ala Gly Val Thr Val Ser Leu Asp Asp Glu Val Ala Val Gln Ser
    50                  55                  60 gat cgt cgt ggt cgt ttt gca att aaa gtt ccg tat gtt ccg cag acc    240
Asp Arg Arg Gly Arg Phe Ala Ile Lys Val Pro Tyr Val Pro Gln Thr
65                  70                  75                  80 tgt gtt gca acc ctg acc gca ggc gaa gaa agc cgt gaa gtt gcc gtt    288
Cys Val Ala Thr Leu Thr Ala Gly Glu Glu Ser Arg Glu Val Ala Val
                85                  90                  95 gca aat tgt gca ccg cag cgt gca ggt cag cct ggt ccg gca ggt caa    336
Ala Asn Cys Ala Pro Gln Arg Ala Gly Gln Pro Gly Pro Ala Gly Gln
            100                 105                 110 ccg ggt cct aca ggt ccg cag ggt gtt gcc ggt ctg cca ggt ccg aaa    384
Pro Gly Pro Thr Gly Pro Gln Gly Val Ala Gly Leu Pro Gly Pro Lys
        115                 120                 125 ggt gat ccg ggt ccg caa ggt cct gcg ggt cct aaa ggc gaa ccg gga    432
```

```
       Gly Asp Pro Gly Pro Gln Gly Pro Ala Gly Pro Lys Gly Glu Pro Gly
           130                 135                 140 cca aaa ggt gaa cct ggt ccg aaa ggc gag cct ggc cct aaa ggt gag             480
Pro Lys Gly Glu Pro Gly Pro Lys Gly Glu Pro Gly Pro Lys Gly Glu
145                 150                 155                 160 cca ggg cca aaa ggc gaa cca ggt cct aaa ggt gaa cca ggc cct aaa             528
Pro Gly Pro Lys Gly Glu Pro Gly Pro Lys Gly Glu Pro Gly Pro Lys
                165                 170                 175 ggt gag cct gga ccg aaa ggt gaa ccg gga cct cgt ggt gaa gcc ggt             576
Gly Glu Pro Gly Pro Lys Gly Glu Pro Gly Pro Arg Gly Glu Ala Gly
            180                 185                 190 cct cag ggt gca ctg gga ccg aaa ggc gaa gca ggt agc cgt ggt gaa             624
Pro Gln Gly Ala Leu Gly Pro Lys Gly Glu Ala Gly Ser Arg Gly Glu
        195                 200                 205 cca ggt ccg cgt ggc gaa cca ggc cca aaa ggc gag gca ggt ctg gca             672
Pro Gly Pro Arg Gly Glu Pro Gly Pro Lys Gly Glu Ala Gly Leu Ala
    210                 215                 220 ggc gca cct gga cct aaa ggc gaa gcc ggt ccg cgt ggt ccg cag ggc             720
Gly Ala Pro Gly Pro Lys Gly Glu Ala Gly Pro Arg Gly Pro Gln Gly
225                 230                 235                 240 gaa cgt ggt cct cct ggt gct ccg ggt gca gca ggt ccg gct ggt cct             768
Glu Arg Gly Pro Pro Gly Ala Pro Gly Ala Ala Gly Pro Ala Gly Pro
                245                 250                 255 gca ggt ccg cag ggt cca gcc ggt cca gct ggt gca caa ggt cca gca             816
Ala Gly Pro Gln Gly Pro Ala Gly Pro Ala Gly Ala Gln Gly Pro Ala
            260                 265                 270 ggc cct gcc ggt cct caa ggt cct gct ggc cca cag ggt agt gcc ggt             864
Gly Pro Ala Gly Pro Gln Gly Pro Ala Gly Pro Gln Gly Ser Ala Gly
        275                 280                 285 gcc cag ggt ccg aaa ggt gat acc ggt gca gca ggt cct gcg ggt gaa             912
Ala Gln Gly Pro Lys Gly Asp Thr Gly Ala Ala Gly Pro Ala Gly Glu
    290                 295                 300 gcg ggt cct aaa ggc gaa aca ggc gca gcg gga cca aaa ggt gac act             960
Ala Gly Pro Lys Gly Glu Thr Gly Ala Ala Gly Pro Lys Gly Asp Thr
305                 310                 315                 320 ggc gct gcg ggt ccg gca gga ccg aaa ggc gac aca ggt gct gca ggc            1008
Gly Ala Ala Gly Pro Ala Gly Pro Lys Gly Asp Thr Gly Ala Ala Gly
                325                 330                 335 cca gca ggt cca aaa ggc gat acg ggt gcc gct ggt gca aca ggc cct            1056
Pro Ala Gly Pro Lys Gly Asp Thr Gly Ala Ala Gly Ala Thr Gly Pro
            340                 345                 350 aaa ggt gag aaa ggt gaa aca ggt gcg gct ggt ccg aaa ggc gat aaa            1104
Lys Gly Glu Lys Gly Glu Thr Gly Ala Ala Gly Pro Lys Gly Asp Lys
        355                 360                 365 ggc gaa acc ggt gct gcc ggt cct aaa ggt gac aaa ggc gag act ggc            1152
Gly Glu Thr Gly Ala Ala Gly Pro Lys Gly Asp Lys Gly Glu Thr Gly
    370                 375                 380 gca gct ggc cct aaa ggt gaa aaa ggg gag aca ggg gca gta gga cct            1200
Ala Ala Gly Pro Lys Gly Glu Lys Gly Glu Thr Gly Ala Val Gly Pro
385                 390                 395                 400 aaa ggc gat aaa ggt gag act ggt gcc gca ggg cct aaa ggc gac cgt            1248
Lys Gly Asp Lys Gly Glu Thr Gly Ala Ala Gly Pro Lys Gly Asp Arg
                405                 410                 415 ggt gaa acc ggt gcc gtg gga ccg aaa ggt gat aaa ggg gaa act ggc            1296
Gly Glu Thr Gly Ala Val Gly Pro Lys Gly Asp Lys Gly Glu Thr Gly
            420                 425                 430 gct gtt ggg cca aaa ggc gac aaa ggt gaa acg ggt gca att ggc cca            1344
Ala Val Gly Pro Lys Gly Asp Lys Gly Glu Thr Gly Ala Ile Gly Pro
        435                 440                 445
```

```
aaa ggt gat aaa ggc gac aaa ggc gat aaa ggg gat gca ggc gtt gcc      1392
Lys Gly Asp Lys Gly Asp Lys Gly Asp Lys Gly Asp Ala Gly Val Ala
450                 455                 460 ggt ccg cag ggc att cag ggt gtt aaa ggt gat aca ggt ctg caa ggt      1440
Gly Pro Gln Gly Ile Gln Gly Val Lys Gly Asp Thr Gly Leu Gln Gly
465                 470                 475                 480 cca aaa ggt gat gca ggt cct cag ggt gca ccg ggt aca ccg ggt ggt      1488
Pro Lys Gly Asp Ala Gly Pro Gln Gly Ala Pro Gly Thr Pro Gly Gly
                485                 490                 495 ggt taagtcgac                                                        1500
Gly

<210> SEQ ID NO 43
<211> LENGTH: 497
<212> TYPE: PRT
<213> ORGANISM: Artificial Sequence
<220> FEATURE:
<223> OTHER INFORMATION: Description of Artificial Sequence: Synthetic
      chimera of Methylobacterium sp. and S. usitatus

<400> SEQUENCE: 43

His Met Gly Glu Ala Ala Pro Ala Pro Ala Ala Pro Lys Pro Glu Ala
1               5                   10                  15

Pro Arg Gly Ala Ala Arg Lys Pro Ala Ser Ser Ala Ile Gln Ile Trp
            20                  25                  30

Asp Ala Arg Ile Glu Gly Gly Asp Leu Arg Ile Ser Gly Asn Val Gly
        35                  40                  45

Lys Ala Gly Val Thr Val Ser Leu Asp Asp Glu Val Ala Val Gln Ser
    50                  55                  60

Asp Arg Arg Gly Arg Phe Ala Ile Lys Val Pro Tyr Val Pro Gln Thr
65                  70                  75                  80

Cys Val Ala Thr Leu Thr Ala Gly Glu Glu Ser Arg Glu Val Ala Val
                85                  90                  95

Ala Asn Cys Ala Pro Gln Arg Ala Gly Gln Pro Gly Pro Ala Gly Gln
            100                 105                 110

Pro Gly Pro Thr Gly Pro Gln Gly Val Ala Gly Leu Pro Gly Pro Lys
        115                 120                 125

Gly Asp Pro Gly Pro Gln Gly Pro Ala Gly Pro Lys Gly Glu Pro Gly
    130                 135                 140

Pro Lys Gly Glu Pro Gly Pro Lys Gly Glu Pro Gly Pro Lys Gly Glu
145                 150                 155                 160

Pro Gly Pro Lys Gly Glu Pro Gly Pro Lys Gly Glu Pro Gly Pro Lys
                165                 170                 175

Gly Glu Pro Gly Pro Lys Gly Glu Pro Gly Pro Arg Gly Glu Ala Gly
            180                 185                 190

Pro Gln Gly Ala Leu Gly Pro Lys Gly Glu Ala Gly Ser Arg Gly Glu
        195                 200                 205

Pro Gly Pro Arg Gly Glu Pro Gly Pro Lys Gly Glu Ala Gly Leu Ala
    210                 215                 220

Gly Ala Pro Gly Pro Lys Gly Glu Ala Gly Pro Arg Gly Pro Gln Gly
225                 230                 235                 240

Glu Arg Gly Pro Pro Gly Ala Pro Gly Ala Ala Gly Pro Ala Gly Pro
                245                 250                 255

Ala Gly Pro Gln Gly Pro Ala Gly Pro Ala Gly Ala Gln Gly Pro Ala
            260                 265                 270

Gly Pro Ala Gly Pro Gln Gly Pro Ala Gly Pro Gln Gly Ser Ala Gly
        275                 280                 285
```

Ala Gln Gly Pro Lys Gly Asp Thr Gly Ala Ala Gly Pro Ala Gly Glu
    290                 295                 300

Ala Gly Pro Lys Gly Glu Thr Gly Ala Ala Gly Pro Lys Gly Asp Thr
305                 310                 315                 320

Gly Ala Ala Gly Pro Ala Gly Pro Lys Gly Asp Thr Gly Ala Ala Gly
            325                 330                 335

Pro Ala Gly Pro Lys Gly Asp Thr Gly Ala Gly Ala Thr Gly Pro
            340                 345                 350

Lys Gly Glu Lys Gly Glu Thr Gly Ala Ala Gly Pro Lys Gly Asp Lys
    355                 360                 365

Gly Glu Thr Gly Ala Ala Gly Pro Lys Gly Asp Lys Gly Glu Thr Gly
    370                 375                 380

Ala Ala Gly Pro Lys Gly Glu Lys Gly Glu Thr Gly Ala Val Gly Pro
385                 390                 395                 400

Lys Gly Asp Lys Gly Glu Thr Gly Ala Ala Gly Pro Lys Gly Asp Arg
                405                 410                 415

Gly Glu Thr Gly Ala Val Gly Pro Lys Gly Asp Lys Gly Glu Thr Gly
                420                 425                 430

Ala Val Gly Pro Lys Gly Asp Lys Gly Glu Thr Gly Ala Ile Gly Pro
            435                 440                 445

Lys Gly Asp Lys Gly Asp Lys Gly Asp Lys Gly Asp Ala Gly Val Ala
    450                 455                 460

Gly Pro Gln Gly Ile Gln Gly Val Lys Gly Asp Thr Gly Leu Gln Gly
465                 470                 475                 480

Pro Lys Gly Asp Ala Gly Pro Gln Gly Ala Pro Gly Thr Pro Gly Gly
                485                 490                 495

Gly

<210> SEQ ID NO 44
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid
<220> FEATURE:

```
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
<222> LOCATION: (38)..(39)
<223> OTHER INFORMATION: Any amino acid
<220> FEATURE:
<221> NAME/KEY: MOD_RES
<222> LOCATION: (41)..(42)
<223> OTHER INFORMATION: Any amino acid
<220> FEATURE:
<221> NAME/KEY: MOD_RES
<222> LOCATION: (44)..(45)
<223> OTHER INFORMATION: Any amino acid
<220> FEATURE:
<221> NAME/KEY: MOD_RES
<222> LOCATION: (47)..(48)
<223> OTHER INFORMATION: Any amino acid
<220> FEATURE:
<221> NAME/KEY: MOD_RES
<222> LOCATION: (50)..(51)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (62)..(63)
<223> OTHER INFORMATION: Any amino acid
<220> FEATURE:
<221> NAME/KEY: MOD_RES
<222> LOCATION: (65)..(66)
<223> OTHER INFORMATION: Any amino acid
<220> FEATURE:
<221> NAME/KEY: MOD_RES
<222> LOCATION: (68)..(69)
<223> OTHER INFORMATION: Any amino acid
<220> FEATURE:
<221> NAME/KEY: MOD_RES
<222> LOCATION: (71)..(72)
<223> OTHER INFORMATION: Any amino acid
<220> FEATURE:
<221> NAME/KEY: MOD_RES
<222> LOCATION: (74)..(75)
<223> OTHER INFORMATION: Any amino acid
<220> FEATURE:
<221> NAME/KEY: MOD_RES
<222> LOCATION: (77)..(78)
<223> OTHER INFORMATION: Any amino acid
<220> FEATURE:
<221> NAME/KEY: MOD_RES
<222> LOCATION: (80)..(81)
<223> OTHER INFORMATION: Any amino acid
```

-continued

```
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (89)..(90)
<223> OTHER INFORMATION: Any amino acid
<220> FEATURE:
<221> NAME/KEY: MOD_RES
<222> LOCATION: (92)..(93)
<223> OTHER INFORMATION: Any amino acid
<220> FEATURE:
<221> NAME/KEY: MOD_RES
<222> LOCATION: (95)..(96)
<223> OTHER INFORMATION: Any amino acid
<220> FEATURE:
<221> NAME/KEY: MOD_RES
<222> LOCATION: (98)..(99)
<223> OTHER INFORMATION: Any amino acid
<220> FEATURE:
<221> NAME/KEY: MOD_RES
<222> LOCATION: (101)..(102)
<223> OTHER INFORMATION: Any amino acid
<220> FEATURE:
<221> NAME/KEY: MOD_RES
<222> LOCATION: (104)..(105)
<223> OTHER INFORMATION: Any amino acid
<220> FEATURE:
<221> NAME/KEY: MOD_RES
<222> LOCATION: (107)..(108)
<223> OTHER INFORMATION: Any amino acid
<220> FEATURE:
<221> NAME/KEY: MOD_RES
<222> LOCATION: (110)..(111)
<223> OTHER INFORMATION: Any amino acid
<220> FEATURE:
<221> NAME/KEY: MOD_RES
<222> LOCATION: (113)..(114)
<223> OTHER INFORMATION: Any amino acid
<220> FEATURE:
<221> NAME/KEY: MOD_RES
<222> LOCATION: (116)..(117)
<223> OTHER INFORMATION: Any amino acid
<220> FEATURE:
<221> NAME/KEY: MOD_RES
<222> LOCATION: (119)..(120)
<223> OTHER INFORMATION: Any amino acid
<220> FEATURE:
<221> NAME/KEY: MOD_RES
<222> LOCATION: (122)..(123)
<223> OTHER INFORMATION: Any amino acid
<220> FEATURE:
<221> NAME/KEY: MOD_RES
<222> LOCATION: (125)..(126)
<223> OTHER INFORMATION: Any amino acid
<220> FEATURE:
<221> NAME/KEY: MOD_RES
<222> LOCATION: (128)..(129)
<223> OTHER INFORMATION: Any amino acid
<220> FEATURE:
<221> NAME/KEY: MOD_RES
<222> LOCATION: (131)..(132)
<223> OTHER INFORMATION: Any amino acid
<220> FEATURE:
<221> NAME/KEY: MOD_RES
<222> LOCATION: (134)..(135)
<223> OTHER INFORMATION: Any amino acid
<220> FEATURE:
<221> NAME/KEY: MOD_RES
<222> LOCATION: (137)..(138)
<223> OTHER INFORMATION: Any amino acid
<220> FEATURE:
<221> NAME/KEY: MOD_RES
<222> LOCATION: (140)..(141)
```

```
<223> OTHER INFORMATION: Any amino acid
<220> FEATURE:
<221> NAME/KEY: MOD_RES
<222> LOCATION: (143)..(144)
<223> OTHER INFORMATION: Any amino acid
<220> FEATURE:
<221> NAME/KEY: MOD_RES
<222> LOCATION: (146)..(147)
<223> OTHER INFORMATION: Any amino acid
<220> FEATURE:
<221> NAME/KEY: MOD_RES
<222> LOCATION: (149)..(150)
<223> OTHER INFORMATION: Any amino acid
<220> FEATURE:
<221> NAME/KEY: MOD_RES
<222> LOCATION: (152)..(153)
<223> OTHER INFORMATION: Any amino acid
<220> FEATURE:
<221> NAME/KEY: MOD_RES
<222> LOCATION: (155)..(156)
<223> OTHER INFORMATION: Any amino acid
<220> FEATURE:
<221> NAME/KEY: MOD_RES
<222> LOCATION: (158)..(159)
<223> OTHER INFORMATION: Any amino acid
<220> FEATURE:
<221> NAME/KEY: MOD_RES
<222> LOCATION: (161)..(162)
<223> OTHER INFORMATION: Any amino acid
<220> FEATURE:
<221> NAME/KEY: MOD_RES
<222> LOCATION: (164)..(165)
<223> OTHER INFORMATION: Any amino acid
<220> FEATURE:
<221> NAME/KEY: MOD_RES
<222> LOCATION: (167)..(168)
<223> OTHER INFORMATION: Any amino acid
<220> FEATURE:
<221> NAME/KEY: MOD_RES
<222> LOCATION: (170)..(171)
<223> OTHER INFORMATION: Any amino acid
<220> FEATURE:
<221> NAME/KEY: MOD_RES
<222> LOCATION: (173)..(174)
<223> OTHER INFORMATION: Any amino acid
<220> FEATURE:
<221> NAME/KEY: MOD_RES
<222> LOCATION: (176)..(177)
<223> OTHER INFORMATION: Any amino acid
<220> FEATURE:
<221> NAME/KEY: MOD_RES
<222> LOCATION: (179)..(180)
<223> OTHER INFORMATION: Any amino acid
<220> FEATURE:
<221> NAME/KEY: MOD_RES
<222> LOCATION: (182)..(183)
<223> OTHER INFORMATION: Any amino acid
<220> FEATURE:
<221> NAME/KEY: MOD_RES
<222> LOCATION: (185)..(186)
<223> OTHER INFORMATION: Any amino acid
<220> FEATURE:
<221> NAME/KEY: MOD_RES
<222> LOCATION: (188)..(189)
<223> OTHER INFORMATION: Any amino acid
<220> FEATURE:
<221> NAME/KEY: MOD_RES
<222> LOCATION: (191)..(192)
<223> OTHER INFORMATION: Any amino acid
<220> FEATURE:
<221> NAME/KEY: MOD_RES
<222> LOCATION: (194)..(195)
<223> OTHER INFORMATION: Any amino acid
<220> FEATURE:
<221> NAME/KEY: MOD_RES
<222> LOCATION: (197)..(198)
<223> OTHER INFORMATION: Any amino acid
<220> FEATURE:
<221> NAME/KEY: MOD_RES
```

```
<222> LOCATION: (200)..(201)
<223> OTHER INFORMATION: Any amino acid
<220> FEATURE:
<221> NAME/KEY: MOD_RES
<222> LOCATION: (203)..(204)
<223> OTHER INFORMATION: Any amino acid
<220> FEATURE:
<221> NAME/KEY: MOD_RES
<222> LOCATION: (206)..(207)
<223> OTHER INFORMATION: Any amino acid
<220> FEATURE:
<221> NAME/KEY: MOD_RES
<222> LOCATION: (209)..(210)
<223> OTHER INFORMATION: Any amino acid
<220> FEATURE:
<221> NAME/KEY: MOD_RES
<222> LOCATION: (212)..(213)
<223> OTHER INFORMATION: Any amino acid
<220> FEATURE:
<221> NAME/KEY: MOD_RES
<222> LOCATION: (215)..(216)
<223> OTHER INFORMATION: Any amino acid
<220> FEATURE:
<221> NAME/KEY: MOD_RES
<222> LOCATION: (218)..(219)
<223> OTHER INFORMATION: Any amino acid
<220> FEATURE:
<221> NAME/KEY: MOD_RES
<222> LOCATION: (221)..(222)
<223> OTHER INFORMATION: Any amino acid
<220> FEATURE:
<221> NAME/KEY: MOD_RES
<222> LOCATION: (224)..(225)
<223> OTHER INFORMATION: Any amino acid
<220> FEATURE:
<221> NAME/KEY: MOD_RES
<222> LOCATION: (227)..(228)
<223> OTHER INFORMATION: Any amino acid
<220> FEATURE:
<221> NAME/KEY: MOD_RES
<222> LOCATION: (230)..(231)
<223> OTHER INFORMATION: Any amino acid
<220> FEATURE:
<221> NAME/KEY: MOD_RES
<222> LOCATION: (233)..(234)
<223> OTHER INFORMATION: Any amino acid
<220> FEATURE:
<221> NAME/KEY: MOD_RES
<222> LOCATION: (236)..(237)
<223> OTHER INFORMATION: Any amino acid
<220> FEATURE:
<221> NAME/KEY: MOD_RES
<222> LOCATION: (239)..(240)
<223> OTHER INFORMATION: Any amino acid
<220> FEATURE:
<221> NAME/KEY: MOD_RES
<222> LOCATION: (242)..(243)
<223> OTHER INFORMATION: Any amino acid
<220> FEATURE:
<221> NAME/KEY: MOD_RES
<222> LOCATION: (245)..(246)
<223> OTHER INFORMATION: Any amino acid
<220> FEATURE:
<221> NAME/KEY: MOD_RES
<222> LOCATION: (248)..(249)
<223> OTHER INFORMATION: Any amino acid
<220> FEATURE:
<221> NAME/KEY: MOD_RES
<222> LOCATION: (251)..(252)
<223> OTHER INFORMATION: Any amino acid
<220> FEATURE:
<221> NAME/KEY: MOD_RES
<222> LOCATION: (254)..(255)
<223> OTHER INFORMATION: Any amino acid
<220> FEATURE:
<221> NAME/KEY: MOD_RES
<222> LOCATION: (257)..(258)
<223> OTHER INFORMATION: Any amino acid
<220> FEATURE:
```

```
<221> NAME/KEY: MOD_RES
<222> LOCATION: (260)..(261)
<223> OTHER INFORMATION: Any amino acid
<220> FEATURE:
<221> NAME/KEY: MOD_RES
<222> LOCATION: (263)..(264)
<223> OTHER INFORMATION: Any amino acid
<220> FEATURE:
<221> NAME/KEY: MOD_RES
<222> LOCATION: (266)..(267)
<223> OTHER INFORMATION: Any amino acid
<220> FEATURE:
<221> NAME/KEY: MOD_RES
<222> LOCATION: (269)..(270)
<223> OTHER INFORMATION: Any amino acid
<220> FEATURE:
<221> NAME/KEY: MOD_RES
<222> LOCATION: (272)..(273)
<223> OTHER INFORMATION: Any amino acid
<220> FEATURE:
<221> NAME/KEY: MOD_RES
<222> LOCATION: (275)..(276)
<223> OTHER INFORMATION: Any amino acid
<220> FEATURE:
<221> NAME/KEY: MOD_RES
<222> LOCATION: (278)..(279)
<223> OTHER INFORMATION: Any amino acid
<220> FEATURE:
<221> NAME/KEY: MOD_RES
<222> LOCATION: (281)..(282)
<223> OTHER INFORMATION: Any amino acid
<220> FEATURE:
<221> NAME/KEY: MOD_RES
<222> LOCATION: (284)..(285)
<223> OTHER INFORMATION: Any amino acid
<220> FEATURE:
<221> NAME/KEY: MOD_RES
<222> LOCATION: (287)..(288)
<223> OTHER INFORMATION: Any amino acid
<220> FEATURE:
<221> NAME/KEY: MOD_RES
<222> LOCATION: (290)..(291)
<223> OTHER INFORMATION: Any amino acid
<220> FEATURE:
<221> NAME/KEY: MOD_RES
<222> LOCATION: (293)..(294)
<223> OTHER INFORMATION: Any amino acid
<220> FEATURE:
<221> NAME/KEY: MOD_RES
<222> LOCATION: (296)..(297)
<223> OTHER INFORMATION: Any amino acid
<220> FEATURE:
<221> NAME/KEY: MOD_RES
<222> LOCATION: (299)..(300)
<223> OTHER INFORMATION: Any amino acid
<220> FEATURE:
<221> NAME/KEY: MOD_RES
<222> LOCATION: (302)..(303)
<223> OTHER INFORMATION: Any amino acid
<220> FEATURE:
<221> NAME/KEY: MOD_RES
<222> LOCATION: (305)..(306)
<223> OTHER INFORMATION: Any amino acid
<220> FEATURE:
<221> NAME/KEY: MOD_RES
<222> LOCATION: (308)..(309)
<223> OTHER INFORMATION: Any amino acid
<220> FEATURE:
<221> NAME/KEY: MOD_RES
<222> LOCATION: (311)..(312)
<223> OTHER INFORMATION: Any amino acid
<220> FEATURE:
<221> NAME/KEY: MOD_RES
<222> LOCATION: (314)..(315)
<223> OTHER INFORMATION: Any amino acid
<220> FEATURE:
<221> NAME/KEY: MOD_RES
<222> LOCATION: (317)..(318)
<223> OTHER INFORMATION: Any amino acid
```

```
<220> FEATURE:
<221> NAME/KEY: MOD_RES
<222> LOCATION: (320)..(321)
<223> OTHER INFORMATION: Any amino acid
<220> FEATURE:
<221> NAME/KEY: MOD_RES
<222> LOCATION: (323)..(324)
<223> OTHER INFORMATION: Any amino acid
<220> FEATURE:
<221> NAME/KEY: MOD_RES
<222> LOCATION: (326)..(327)
<223> OTHER INFORMATION: Any amino acid
<220> FEATURE:
<221> NAME/KEY: MOD_RES
<222> LOCATION: (329)..(330)
<223> OTHER INFORMATION: Any amino acid
<220> FEATURE:
<221> NAME/KEY: MOD_RES
<222> LOCATION: (332)..(333)
<223> OTHER INFORMATION: Any amino acid
<220> FEATURE:
<221> NAME/KEY: MOD_RES
<222> LOCATION: (335)..(336)
<223> OTHER INFORMATION: Any amino acid
<220> FEATURE:
<221> NAME/KEY: MOD_RES
<222> LOCATION: (338)..(339)
<223> OTHER INFORMATION: Any amino acid
<220> FEATURE:
<221> NAME/KEY: MOD_RES
<222> LOCATION: (341)..(342)
<223> OTHER INFORMATION: Any amino acid
<220> FEATURE:
<221> NAME/KEY: MOD_RES
<222> LOCATION: (344)..(345)
<223> OTHER INFORMATION: Any amino acid
<220> FEATURE:
<221> NAME/KEY: MOD_RES
<222> LOCATION: (347)..(348)
<223> OTHER INFORMATION: Any amino acid
<220> FEATURE:
<221> NAME/KEY: MOD_RES
<222> LOCATION: (350)..(351)
<223> OTHER INFORMATION: Any amino acid
<220> FEATURE:
<221> NAME/KEY: MOD_RES
<222> LOCATION: (353)..(354)
<223> OTHER INFORMATION: Any amino acid
<220> FEATURE:
<221> NAME/KEY: MOD_RES
<222> LOCATION: (356)..(357)
<223> OTHER INFORMATION: Any amino acid
<220> FEATURE:
<221> NAME/KEY: MOD_RES
<222> LOCATION: (359)..(360)
<223> OTHER INFORMATION: Any amino acid
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (365)..(366)
<223> OTHER INFORMATION: Any amino acid
<220> FEATURE:
<221> NAME/KEY: MOD_RES
<222> LOCATION: (368)..(369)
<223> OTHER INFORMATION: Any amino acid
<220> FEATURE:
<221> NAME/KEY: MOD_RES
<222> LOCATION: (371)..(372)
<223> OTHER INFORMATION: Any amino acid
<220> FEATURE:
<221> NAME/KEY: MOD_RES
<222> LOCATION: (374)..(375)
<223> OTHER INFORMATION: Any amino acid
<220> FEATURE:
<221> NAME/KEY: MOD_RES
<222> LOCATION: (377)..(378)
```

```
<223> OTHER INFORMATION: Any amino acid
<220> FEATURE:
<221> NAME/KEY: MOD_RES
<222> LOCATION: (380)..(381)
<223> OTHER INFORMATION: Any amino acid
<220> FEATURE:
<221> NAME/KEY: MOD_RES
<222> LOCATION: (383)..(384)
<223> OTHER INFORMATION: Any amino acid
<220> FEATURE:
<221> NAME/KEY: MOD_RES
<222> LOCATION: (386)..(387)
<223> OTHER INFORMATION: Any amino acid
<220> FEATURE:
<221> NAME/KEY: MOD_RES
<222> LOCATION: (389)..(390)
<223> OTHER INFORMATION: Any amino acid
<220> FEATURE:
<221> NAME/KEY: MOD_RES
<222> LOCATION: (392)..(393)
<223> OTHER INFORMATION: Any amino acid
<220> FEATURE:
<221> NAME/KEY: MOD_RES
<222> LOCATION: (395)..(396)
<223> OTHER INFORMATION: Any amino acid
<220> FEATURE:
<221> NAME/KEY: MOD_RES
<222> LOCATION: (398)..(399)
<223> OTHER INFORMATION: Any amino acid
<220> FEATURE:
<221> NAME/KEY: MOD_RES
<222> LOCATION: (401)..(402)
<223> OTHER INFORMATION: Any amino acid
<220> FEATURE:
<221> NAME/KEY: MOD_RES
<222> LOCATION: (404)..(405)
<223> OTHER INFORMATION: Any amino acid
<220> FEATURE:
<221> NAME/KEY: MOD_RES
<222> LOCATION: (407)..(408)
<223> OTHER INFORMATION: Any amino acid
<220> FEATURE:
<221> NAME/KEY: MOD_RES
<222> LOCATION: (410)..(411)
<223> OTHER INFORMATION: Any amino acid
<220> FEATURE:
<221> NAME/KEY: MOD_RES
<222> LOCATION: (413)..(414)
<223> OTHER INFORMATION: Any amino acid
<220> FEATURE:
<221> NAME/KEY: MOD_RES
<222> LOCATION: (416)..(417)
<223> OTHER INFORMATION: Any amino acid
<220> FEATURE:
<221> NAME/KEY: MOD_RES
<222> LOCATION: (419)..(420)
<223> OTHER INFORMATION: Any amino acid
<220> FEATURE:
<221> NAME/KEY: MOD_RES
<222> LOCATION: (422)..(423)
<223> OTHER INFORMATION: Any amino acid
<220> FEATURE:
<221> NAME/KEY: MOD_RES
<222> LOCATION: (425)..(426)
<223> OTHER INFORMATION: Any amino acid
<220> FEATURE:
<221> NAME/KEY: MOD_RES
<222> LOCATION: (428)..(429)
<223> OTHER INFORMATION: Any amino acid
<220> FEATURE:
<221> NAME/KEY: MOD_RES
<222> LOCATION: (431)..(432)
<223> OTHER INFORMATION: Any amino acid
<220> FEATURE:
<221> NAME/KEY: MOD_RES
<222> LOCATION: (434)..(435)
<223> OTHER INFORMATION: Any amino acid
<220> FEATURE:
<221> NAME/KEY: MOD_RES
```

```
<222> LOCATION: (437)..(438)
<223> OTHER INFORMATION: Any amino acid
<220> FEATURE:
<221> NAME/KEY: MOD_RES
<222> LOCATION: (440)..(441)
<223> OTHER INFORMATION: Any amino acid
<220> FEATURE:
<221> NAME/KEY: MOD_RES
<222> LOCATION: (443)..(444)
<223> OTHER INFORMATION: Any amino acid
<220> FEATURE:
<221> NAME/KEY: MOD_RES
<222> LOCATION: (446)..(447)
<223> OTHER INFORMATION: Any amino acid
<220> FEATURE:
<221> NAME/KEY: MOD_RES
<222> LOCATION: (449)..(450)
<223> OTHER INFORMATION: Any amino acid
<220> FEATURE:
<221> NAME/KEY: MOD_RES
<222> LOCATION: (452)..(453)
<223> OTHER INFORMATION: Any amino acid
<220> FEATURE:
<221> NAME/KEY: MOD_RES
<222> LOCATION: (455)..(456)
<223> OTHER INFORMATION: Any amino acid
<220> FEATURE:
<221> NAME/KEY: MOD_RES
<222> LOCATION: (458)..(459)
<223> OTHER INFORMATION: Any amino acid
<220> FEATURE:
<221> NAME/KEY: MOD_RES
<222> LOCATION: (461)..(462)
<223> OTHER INFORMATION: Any amino acid
<220> FEATURE:
<221> NAME/KEY: MOD_RES
<222> LOCATION: (464)..(465)
<223> OTHER INFORMATION: Any amino acid
<220> FEATURE:
<221> NAME/KEY: MOD_RES
<222> LOCATION: (467)..(468)
<223> OTHER INFORMATION: Any amino acid
<220> FEATURE:
<221> NAME/KEY: MOD_RES
<222> LOCATION: (470)..(471)
<223> OTHER INFORMATION: Any amino acid
<220> FEATURE:
<221> NAME/KEY: MOD_RES
<222> LOCATION: (473)..(474)
<223> OTHER INFORMATION: Any amino acid
<220> FEATURE:
<221> NAME/KEY: MOD_RES
<222> LOCATION: (476)..(477)
<223> OTHER INFORMATION: Any amino acid
<220> FEATURE:
<221> NAME/KEY: MOD_RES
<222> LOCATION: (479)..(480)
<223> OTHER INFORMATION: Any amino acid
<220> FEATURE:
<221> NAME/KEY: MOD_RES
<222> LOCATION: (482)..(483)
<223> OTHER INFORMATION: Any amino acid
<220> FEATURE:
<221> NAME/KEY: MOD_RES
<222> LOCATION: (485)..(486)
<223> OTHER INFORMATION: Any amino acid
<220> FEATURE:
<221> NAME/KEY: MOD_RES
<222> LOCATION: (488)..(489)
<223> OTHER INFORMATION: Any amino acid
<220> FEATURE:
<221> NAME/KEY: MOD_RES
<222> LOCATION: (491)..(492)
<223> OTHER INFORMATION: Any amino acid
<220> FEATURE:
<221> NAME/KEY: MOD_RES
<222> LOCATION: (494)..(495)
<223> OTHER INFORMATION: Any amino acid
<220> FEATURE:
```

```
<221> NAME/KEY: MOD_RES
<222> LOCATION: (497)..(498)
<223> OTHER INFORMATION: Any amino acid
<220> FEATURE:
<221> NAME/KEY: MOD_RES
<222> LOCATION: (500)..(501)
<223> OTHER INFORMATION: Any amino acid
<220> FEATURE:
<221> NAME/KEY: MOD_RES
<222> LOCATION: (503)..(504)
<223> OTHER INFORMATION: Any amino acid
<220> FEATURE:
<221> NAME/KEY: MOD_RES
<222> LOCATION: (506)..(507)
<223> OTHER INFORMATION: Any amino acid
<220> FEATURE:
<221> NAME/KEY: MOD_RES
<222> LOCATION: (509)..(510)
<223> OTHER INFORMATION: Any amino acid
<220> FEATURE:
<221> NAME/KEY: MOD_RES
<222> LOCATION: (512)..(513)
<223> OTHER INFORMATION: Any amino acid
<220> FEATURE:
<221> NAME/KEY: MOD_RES
<222> LOCATION: (515)..(516)
<223> OTHER INFORMATION: Any amino acid
<220> FEATURE:
<221> NAME/KEY: MOD_RES
<222> LOCATION: (518)..(519)
<223> OTHER INFORMATION: Any amino acid
<220> FEATURE:
<221> NAME/KEY: MOD_RES
<222> LOCATION: (521)..(522)
<223> OTHER INFORMATION: Any amino acid
<220> FEATURE:
<221> NAME/KEY: MOD_RES
<222> LOCATION: (524)..(525)
<223> OTHER INFORMATION: Any amino acid
<220> FEATURE:
<221> NAME/KEY: MOD_RES
<222> LOCATION: (527)..(528)
<223> OTHER INFORMATION: Any amino acid
<220> FEATURE:
<221> NAME/KEY: MOD_RES
<222> LOCATION: (530)..(531)
<223> OTHER INFORMATION: Any amino acid
<220> FEATURE:
<221> NAME/KEY: MOD_RES
<222> LOCATION: (533)..(534)
<223> OTHER INFORMATION: Any amino acid
<220> FEATURE:
<221> NAME/KEY: MOD_RES
<222> LOCATION: (536)..(537)
<223> OTHER INFORMATION: Any amino acid
<220> FEATURE:
<221> NAME/KEY: MOD_RES
<222> LOCATION: (539)..(540)
<223> OTHER INFORMATION: Any amino acid
<220> FEATURE:
<221> NAME/KEY: MOD_RES
<222> LOCATION: (542)..(543)
<223> OTHER INFORMATION: Any amino acid
<220> FEATURE:
<221> NAME/KEY: MOD_RES
<222> LOCATION: (545)..(546)
<223> OTHER INFORMATION: Any amino acid
<220> FEATURE:
<221> NAME/KEY: MOD_RES
<222> LOCATION: (548)..(549)
<223> OTHER INFORMATION: Any amino acid
<220> FEATURE:
<221> NAME/KEY: MOD_RES
<222> LOCATION: (551)..(552)
<223> OTHER INFORMATION: Any amino acid
<220> FEATURE:
<221> NAME/KEY: MOD_RES
<222> LOCATION: (554)..(555)
<223> OTHER INFORMATION: Any amino acid
```

-continued

```
<220> FEATURE:
<221> NAME/KEY: MOD_RES
<222> LOCATION: (557)..(558)
<223> OTHER INFORMATION: Any amino acid
<220> FEATURE:
<221> NAME/KEY: MOD_RES
<222> LOCATION: (560)..(561)
<223> OTHER INFORMATION: Any amino acid
<220> FEATURE:
<221> NAME/KEY: MOD_RES
<222> LOCATION: (563)..(564)
<223> OTHER INFORMATION: Any amino acid
<220> FEATURE:
<221> NAME/KEY: MOD_RES
<222> LOCATION: (566)..(567)
<223> OTHER INFORMATION: Any amino acid
<220> FEATURE:
<221> NAME/KEY: MOD_RES
<222> LOCATION: (569)..(570)
<223> OTHER INFORMATION: Any amino acid
<220> FEATURE:
<221> NAME/KEY: MOD_RES
<222> LOCATION: (572)..(573)
<223> OTHER INFORMATION: Any amino acid
<220> FEATURE:
<221> NAME/KEY: MOD_RES
<222> LOCATION: (575)..(576)
<223> OTHER INFORMATION: Any amino acid
<220> FEATURE:
<221> NAME/KEY: MOD_RES
<222> LOCATION: (578)..(579)
<223> OTHER INFORMATION: Any amino acid
<220> FEATURE:
<221> NAME/KEY: MOD_RES
<222> LOCATION: (581)..(582)
<223> OTHER INFORMATION: Any amino acid
<220> FEATURE:
<221> NAME/KEY: MOD_RES
<222> LOCATION: (584)..(585)
<223> OTHER INFORMATION: Any amino acid
<220> FEATURE:
<221> NAME/KEY: MOD_RES
<222> LOCATION: (587)..(588)
<223> OTHER INFORMATION: Any amino acid
<220> FEATURE:
<221> NAME/KEY: MOD_RES
<222> LOCATION: (590)..(591)
<223> OTHER INFORMATION: Any amino acid
<220> FEATURE:
<221> NAME/KEY: MOD_RES
<222> LOCATION: (593)..(594)
<223> OTHER INFORMATION: Any amino acid
<220> FEATURE:
<221> NAME/KEY: MOD_RES
<222> LOCATION: (596)..(597)
<223> OTHER INFORMATION: Any amino acid
<220> FEATURE:
<221> NAME/KEY: MOD_RES
<222> LOCATION: (599)..(600)
<223> OTHER INFORMATION: Any amino acid
<220> FEATURE:
<221> NAME/KEY: MOD_RES
<222> LOCATION: (602)..(603)
<223> OTHER INFORMATION: Any amino acid
<220> FEATURE:
<221> NAME/KEY: MOD_RES
<222> LOCATION: (605)..(606)
<223> OTHER INFORMATION: Any amino acid
<220> FEATURE:
<221> NAME/KEY: MOD_RES
<222> LOCATION: (608)..(609)
<223> OTHER INFORMATION: Any amino acid
<220> FEATURE:
<221> NAME/KEY: MOD_RES
<222> LOCATION: (611)..(612)
<223> OTHER INFORMATION: Any amino acid
<220> FEATURE:
<221> NAME/KEY: MOD_RES
<222> LOCATION: (614)..(615)
```

```
<223> OTHER INFORMATION: Any amino acid
<220> FEATURE:
<221> NAME/KEY: MOD_RES
<222> LOCATION: (617)..(618)
<223> OTHER INFORMATION: Any amino acid
<220> FEATURE:
<221> NAME/KEY: MOD_RES
<222> LOCATION: (620)..(621)
<223> OTHER INFORMATION: Any amino acid
<220> FEATURE:
<221> NAME/KEY: MOD_RES
<222> LOCATION: (623)..(624)
<223> OTHER INFORMATION: Any amino acid
<220> FEATURE:
<221> NAME/KEY: MOD_RES
<222> LOCATION: (626)..(627)
<223> OTHER INFORMATION: Any amino acid
<220> FEATURE:
<221> NAME/KEY: MOD_RES
<222> LOCATION: (629)..(630)
<223> OTHER INFORMATION: Any amino acid
<220> FEATURE:
<221> NAME/KEY: MOD_RES
<222> LOCATION: (632)..(633)
<223> OTHER INFORMATION: Any amino acid
<220> FEATURE:
<221> NAME/KEY: MOD_RES
<222> LOCATION: (635)..(636)
<223> OTHER INFORMATION: Any amino acid
<220> FEATURE:
<221> NAME/KEY: MOD_RES
<222> LOCATION: (638)..(639)
<223> OTHER INFORMATION: Any amino acid
<220> FEATURE:
<221> NAME/KEY: MOD_RES
<222> LOCATION: (641)..(642)
<223> OTHER INFORMATION: Any amino acid
<220> FEATURE:
<221> NAME/KEY: MOD_RES
<222> LOCATION: (644)..(645)
<223> OTHER INFORMATION: Any amino acid
<220> FEATURE:
<221> NAME/KEY: MOD_RES
<222> LOCATION: (647)..(648)
<223> OTHER INFORMATION: Any amino acid
<220> FEATURE:
<221> NAME/KEY: MOD_RES
<222> LOCATION: (650)..(651)
<223> OTHER INFORMATION: Any amino acid
<220> FEATURE:
<221> NAME/KEY: MOD_RES
<222> LOCATION: (653)..(654)
<223> OTHER INFORMATION: Any amino acid
<220> FEATURE:
<221> NAME/KEY: MOD_RES
<222> LOCATION: (656)..(657)
<223> OTHER INFORMATION: Any amino acid
<220> FEATURE:
<221> NAME/KEY: MOD_RES
<222> LOCATION: (659)..(660)
<223> OTHER INFORMATION: Any amino acid
<220> FEATURE:
<221> NAME/KEY: MOD_RES
<222> LOCATION: (662)..(663)
<223> OTHER INFORMATION: Any amino acid
<220> FEATURE:
<221> NAME/KEY: MOD_RES
<222> LOCATION: (665)..(666)
<223> OTHER INFORMATION: Any amino acid
<220> FEATURE:
<221> NAME/KEY: MOD_RES
<222> LOCATION: (668)..(669)
<223> OTHER INFORMATION: Any amino acid
<220> FEATURE:
<221> NAME/KEY: MOD_RES
<222> LOCATION: (671)..(672)
<223> OTHER INFORMATION: Any amino acid
<220> FEATURE:
<221> NAME/KEY: MOD_RES
```

```
<222> LOCATION: (674)..(675)
<223> OTHER INFORMATION: Any amino acid
<220> FEATURE:
<221> NAME/KEY: MOD_RES
<222> LOCATION: (677)..(678)
<223> OTHER INFORMATION: Any amino acid
<220> FEATURE:
<221> NAME/KEY: MOD_RES
<222> LOCATION: (680)..(681)
<223> OTHER INFORMATION: Any amino acid
<220> FEATURE:
<221> NAME/KEY: MOD_RES
<222> LOCATION: (683)..(684)
<223> OTHER INFORMATION: Any amino acid
<220> FEATURE:
<221> NAME/KEY: MOD_RES
<222> LOCATION: (686)..(687)
<223> OTHER INFORMATION: Any amino acid
<220> FEATURE:
<221> NAME/KEY: MOD_RES
<222> LOCATION: (689)..(690)
<223> OTHER INFORMATION: Any amino acid
<220> FEATURE:
<221> NAME/KEY: MOD_RES
<222> LOCATION: (692)..(693)
<223> OTHER INFORMATION: Any amino acid
<220> FEATURE:
<221> NAME/KEY: MOD_RES
<222> LOCATION: (695)..(696)
<223> OTHER INFORMATION: Any amino acid
<220> FEATURE:
<221> NAME/KEY: MOD_RES
<222> LOCATION: (698)..(699)
<223> OTHER INFORMATION: Any amino acid
<220> FEATURE:
<221> NAME/KEY: MOD_RES
<222> LOCATION: (701)..(702)
<223> OTHER INFORMATION: Any amino acid
<220> FEATURE:
<221> NAME/KEY: MOD_RES
<222> LOCATION: (704)..(705)
<223> OTHER INFORMATION: Any amino acid
<220> FEATURE:
<221> NAME/KEY: MOD_RES
<222> LOCATION: (707)..(708)
<223> OTHER INFORMATION: Any amino acid
<220> FEATURE:
<221> NAME/KEY: MOD_RES
<222> LOCATION: (710)..(711)
<223> OTHER INFORMATION: Any amino acid
<220> FEATURE:
<221> NAME/KEY: MOD_RES
<222> LOCATION: (713)..(714)
<223> OTHER INFORMATION: Any amino acid
<220> FEATURE:
<221> NAME/KEY: MOD_RES
<222> LOCATION: (716)..(717)
<223> OTHER INFORMATION: Any amino acid
<220> FEATURE:
<221> NAME/KEY: MOD_RES
<222> LOCATION: (719)..(720)
<223> OTHER INFORMATION: Any amino acid
<220> FEATURE:
<221> NAME/KEY: MOD_RES
<222> LOCATION: (722)..(723)
<223> OTHER INFORMATION: Any amino acid
<220> FEATURE:
<221> NAME/KEY: MOD_RES
<222> LOCATION: (725)..(726)
<223> OTHER INFORMATION: Any amino acid
<220> FEATURE:
<221> NAME/KEY: MOD_RES
<222> LOCATION: (728)..(729)
<223> OTHER INFORMATION: Any amino acid
<220> FEATURE:
<221> NAME/KEY: MOD_RES
<222> LOCATION: (731)..(732)
<223> OTHER INFORMATION: Any amino acid
<220> FEATURE:
```

```
<221> NAME/KEY: MOD_RES
<222> LOCATION: (734)..(735)
<223> OTHER INFORMATION: Any amino acid
<220> FEATURE:
<221> NAME/KEY: MOD_RES
<222> LOCATION: (737)..(738)
<223> OTHER INFORMATION: Any amino acid
<220> FEATURE:
<221> NAME/KEY: MOD_RES
<222> LOCATION: (740)..(741)
<223> OTHER INFORMATION: Any amino acid
<220> FEATURE:
<221> NAME/KEY: MOD_RES
<222> LOCATION: (743)..(744)
<223> OTHER INFORMATION: Any amino acid
<220> FEATURE:
<221> NAME/KEY: MOD_RES
<222> LOCATION: (746)..(747)
<223> OTHER INFORMATION: Any amino acid
<220> FEATURE:
<221> NAME/KEY: MOD_RES
<222> LOCATION: (749)..(750)
<223> OTHER INFORMATION: Any amino acid
<220> FEATURE:
<221> NAME/KEY: MOD_RES
<222> LOCATION: (752)..(753)
<223> OTHER INFORMATION: Any amino acid
<220> FEATURE:
<221> NAME/KEY: MOD_RES
<222> LOCATION: (755)..(756)
<223> OTHER INFORMATION: Any amino acid
<220> FEATURE:
<221> NAME/KEY: MOD_RES
<222> LOCATION: (758)..(759)
<223> OTHER INFORMATION: Any amino acid
<220> FEATURE:
<221> NAME/KEY: MOD_RES
<222> LOCATION: (761)..(762)
<223> OTHER INFORMATION: Any amino acid
<220> FEATURE:
<221> NAME/KEY: MOD_RES
<222> LOCATION: (764)..(765)
<223> OTHER INFORMATION: Any amino acid
<220> FEATURE:
<221> NAME/KEY: MOD_RES
<222> LOCATION: (767)..(768)
<223> OTHER INFORMATION: Any amino acid
<220> FEATURE:
<221> NAME/KEY: MOD_RES
<222> LOCATION: (770)..(771)
<223> OTHER INFORMATION: Any amino acid
<220> FEATURE:
<221> NAME/KEY: MOD_RES
<222> LOCATION: (773)..(774)
<223> OTHER INFORMATION: Any amino acid
<220> FEATURE:
<221> NAME/KEY: MOD_RES
<222> LOCATION: (776)..(777)
<223> OTHER INFORMATION: Any amino acid
<220> FEATURE:
<221> NAME/KEY: MOD_RES
<222> LOCATION: (779)..(780)
<223> OTHER INFORMATION: Any amino acid
<220> FEATURE:
<221> NAME/KEY: MOD_RES
<222> LOCATION: (782)..(783)
<223> OTHER INFORMATION: Any amino acid
<220> FEATURE:
<221> NAME/KEY: MOD_RES
<222> LOCATION: (785)..(786)
<223> OTHER INFORMATION: Any amino acid
<220> FEATURE:
<221> NAME/KEY: MOD_RES
<222> LOCATION: (788)..(789)
<223> OTHER INFORMATION: Any amino acid
<220> FEATURE:
<221> NAME/KEY: MOD_RES
<222> LOCATION: (791)..(792)
<223> OTHER INFORMATION: Any amino acid
```

```
<220> FEATURE:
<221> NAME/KEY: MOD_RES
<222> LOCATION: (794)..(795)
<223> OTHER INFORMATION: Any amino acid
<220> FEATURE:
<221> NAME/KEY: MOD_RES
<222> LOCATION: (797)..(798)
<223> OTHER INFORMATION: Any amino acid
<220> FEATURE:
<221> NAME/KEY: MOD_RES
<222> LOCATION: (800)..(801)
<223> OTHER INFORMATION: Any amino acid
<220> FEATURE:
<221> NAME/KEY: MOD_RES
<222> LOCATION: (803)..(804)
<223> OTHER INFORMATION: Any amino acid
<220> FEATURE:
<221> NAME/KEY: MOD_RES
<222> LOCATION: (806)..(807)
<223> OTHER INFORMATION: Any amino acid
<220> FEATURE:
<221> NAME/KEY: MOD_RES
<222> LOCATION: (809)..(810)
<223> OTHER INFORMATION: Any amino acid
<220> FEATURE:
<221> NAME/KEY: MOD_RES
<222> LOCATION: (812)..(813)
<223> OTHER INFORMATION: Any amino acid
<220> FEATURE:
<221> NAME/KEY: MOD_RES
<222> LOCATION: (815)..(816)
<223> OTHER INFORMATION: Any amino acid
<220> FEATURE:
<221> NAME/KEY: MOD_RES
<222> LOCATION: (818)..(819)
<223> OTHER INFORMATION: Any amino acid
<220> FEATURE:
<221> NAME/KEY: MOD_RES
<222> LOCATION: (821)..(822)
<223> OTHER INFORMATION: Any amino acid
<220> FEATURE:
<221> NAME/KEY: MOD_RES
<222> LOCATION: (824)..(825)
<223> OTHER INFORMATION: Any amino acid
<220> FEATURE:
<221> NAME/KEY: MOD_RES
<222> LOCATION: (827)..(828)
<223> OTHER INFORMATION: Any amino acid
<220> FEATURE:
<221> NAME/KEY: MOD_RES
<222> LOCATION: (830)..(831)
<223> OTHER INFORMATION: Any amino acid
<220> FEATURE:
<221> NAME/KEY: MOD_RES
<222> LOCATION: (833)..(834)
<223> OTHER INFORMATION: Any amino acid
<220> FEATURE:
<221> NAME/KEY: MOD_RES
<222> LOCATION: (836)..(837)
<223> OTHER INFORMATION: Any amino acid
<220> FEATURE:
<221> NAME/KEY: MOD_RES
<222> LOCATION: (839)..(840)
<223> OTHER INFORMATION: Any amino acid
<220> FEATURE:
<221> NAME/KEY: MOD_RES
<222> LOCATION: (842)..(843)
<223> OTHER INFORMATION: Any amino acid
<220> FEATURE:
<221> NAME/KEY: MOD_RES
<222> LOCATION: (845)..(846)
<223> OTHER INFORMATION: Any amino acid
<220> FEATURE:
<221> NAME/KEY: MOD_RES
<222> LOCATION: (848)..(849)
<223> OTHER INFORMATION: Any amino acid
<220> FEATURE:
<221> NAME/KEY: MOD_RES
<222> LOCATION: (851)..(852)
```

```
<223> OTHER INFORMATION: Any amino acid
<220> FEATURE:
<221> NAME/KEY: MOD_RES
<222> LOCATION: (854)..(855)
<223> OTHER INFORMATION: Any amino acid
<220> FEATURE:
<221> NAME/KEY: MOD_RES
<222> LOCATION: (857)..(858)
<223> OTHER INFORMATION: Any amino acid
<220> FEATURE:
<221> NAME/KEY: MOD_RES
<222> LOCATION: (860)..(861)
<223> OTHER INFORMATION: Any amino acid
<220> FEATURE:
<221> NAME/KEY: MOD_RES
<222> LOCATION: (863)..(864)
<223> OTHER INFORMATION: Any amino acid
<220> FEATURE:
<221> NAME/KEY: MOD_RES
<222> LOCATION: (866)..(867)
<223> OTHER INFORMATION: Any amino acid
<220> FEATURE:
<221> NAME/KEY: MOD_RES
<222> LOCATION: (869)..(870)
<223> OTHER INFORMATION: Any amino acid
<220> FEATURE:
<221> NAME/KEY: MOD_RES
<222> LOCATION: (872)..(873)
<223> OTHER INFORMATION: Any amino acid
<220> FEATURE:
<221> NAME/KEY: MOD_RES
<222> LOCATION: (875)..(876)
<223> OTHER INFORMATION: Any amino acid
<220> FEATURE:
<221> NAME/KEY: MOD_RES
<222> LOCATION: (878)..(879)
<223> OTHER INFORMATION: Any amino acid
<220> FEATURE:
<221> NAME/KEY: MOD_RES
<222> LOCATION: (881)..(882)
<223> OTHER INFORMATION: Any amino acid
<220> FEATURE:
<221> NAME/KEY: MOD_RES
<222> LOCATION: (884)..(885)
<223> OTHER INFORMATION: Any amino acid
<220> FEATURE:
<221> NAME/KEY: MOD_RES
<222> LOCATION: (887)..(888)
<223> OTHER INFORMATION: Any amino acid
<220> FEATURE:
<221> NAME/KEY: MOD_RES
<222> LOCATION: (890)..(891)
<223> OTHER INFORMATION: Any amino acid
<220> FEATURE:
<221> NAME/KEY: MOD_RES
<222> LOCATION: (893)..(894)
<223> OTHER INFORMATION: Any amino acid
<220> FEATURE:
<221> NAME/KEY: MOD_RES
<222> LOCATION: (896)..(897)
<223> OTHER INFORMATION: Any amino acid
<220> FEATURE:
<221> NAME/KEY: MOD_RES
<222> LOCATION: (899)..(900)
<223> OTHER INFORMATION: Any amino acid
<220> FEATURE:
<221> NAME/KEY: MOD_RES
<222> LOCATION: (902)..(903)
<223> OTHER INFORMATION: Any amino acid
<220> FEATURE:
<221> NAME/KEY: MOD_RES
<222> LOCATION: (905)..(906)
<223> OTHER INFORMATION: Any amino acid
<220> FEATURE:
<221> NAME/KEY: MOD_RES
<222> LOCATION: (908)..(909)
<223> OTHER INFORMATION: Any amino acid
<220> FEATURE:
<221> NAME/KEY: MOD_RES
```

```
<222> LOCATION: (911)..(912)
<223> OTHER INFORMATION: Any amino acid
<220> FEATURE:
<221> NAME/KEY: MOD_RES
<222> LOCATION: (914)..(915)
<223> OTHER INFORMATION: Any amino acid
<220> FEATURE:
<221> NAME/KEY: MOD_RES
<222> LOCATION: (917)..(918)
<223> OTHER INFORMATION: Any amino acid
<220> FEATURE:
<221> NAME/KEY: MOD_RES
<222> LOCATION: (920)..(921)
<223> OTHER INFORMATION: Any amino acid
<220> FEATURE:
<221> NAME/KEY: MOD_RES
<222> LOCATION: (923)..(924)
<223> OTHER INFORMATION: Any amino acid
<220> FEATURE:
<221> NAME/KEY: MOD_RES
<222> LOCATION: (926)..(927)
<223> OTHER INFORMATION: Any amino acid
<220> FEATURE:
<221> NAME/KEY: MOD_RES
<222> LOCATION: (929)..(930)
<223> OTHER INFORMATION: Any amino acid
<220> FEATURE:
<221> NAME/KEY: MOD_RES
<222> LOCATION: (932)..(933)
<223> OTHER INFORMATION: Any amino acid
<220> FEATURE:
<221> NAME/KEY: MOD_RES
<222> LOCATION: (935)..(936)
<223> OTHER INFORMATION: Any amino acid
<220> FEATURE:
<221> NAME/KEY: MOD_RES
<222> LOCATION: (938)..(939)
<223> OTHER INFORMATION: Any amino acid
<220> FEATURE:
<221> NAME/KEY: MOD_RES
<222> LOCATION: (941)..(942)
<223> OTHER INFORMATION: Any amino acid
<220> FEATURE:
<221> NAME/KEY: MOD_RES
<222> LOCATION: (944)..(945)
<223> OTHER INFORMATION: Any amino acid
<220> FEATURE:
<221> NAME/KEY: MOD_RES
<222> LOCATION: (947)..(948)
<223> OTHER INFORMATION: Any amino acid
<220> FEATURE:
<221> NAME/KEY: MOD_RES
<222> LOCATION: (950)..(951)
<223> OTHER INFORMATION: Any amino acid
<220> FEATURE:
<221> NAME/KEY: MOD_RES
<222> LOCATION: (953)..(954)
<223> OTHER INFORMATION: Any amino acid
<220> FEATURE:
<221> NAME/KEY: MOD_RES
<222> LOCATION: (956)..(957)
<223> OTHER INFORMATION: Any amino acid
<220> FEATURE:
<221> NAME/KEY: MOD_RES
<222> LOCATION: (959)..(960)
<223> OTHER INFORMATION: Any amino acid
<220> FEATURE:
<221> NAME/KEY: MOD_RES
<222> LOCATION: (962)..(963)
<223> OTHER INFORMATION: Any amino acid
<220> FEATURE:
<221> NAME/KEY: MOD_RES
<222> LOCATION: (965)..(966)
<223> OTHER INFORMATION: Any amino acid
<220> FEATURE:
<221> NAME/KEY: MOD_RES
<222> LOCATION: (968)..(969)
<223> OTHER INFORMATION: Any amino acid
<220> FEATURE:
```

-continued

```
<221> NAME/KEY: MOD_RES
<222> LOCATION: (971)..(972)
<223> OTHER INFORMATION: Any amino acid
<220> FEATURE:
<221> NAME/KEY: MOD_RES
<222> LOCATION: (974)..(975)
<223> OTHER INFORMATION: Any amino acid
<220> FEATURE:
<221> NAME/KEY: MOD_RES
<222> LOCATION: (977)..(978)
<223> OTHER INFORMATION: Any amino acid
<220> FEATURE:
<221> NAME/KEY: MOD_RES
<222> LOCATION: (980)..(981)
<223> OTHER INFORMATION: Any amino acid
<220> FEATURE:
<221> NAME/KEY: MOD_RES
<222> LOCATION: (983)..(984)
<223> OTHER INFORMATION: Any amino acid
<220> FEATURE:
<221> NAME/KEY: MOD_RES
<222> LOCATION: (986)..(987)
<223> OTHER INFORMATION: Any amino acid
<220> FEATURE:
<221> NAME/KEY: MOD_RES
<222> LOCATION: (989)..(990)
<223> OTHER INFORMATION: Any amino acid
<220> FEATURE:
<221> NAME/KEY: MOD_RES
<222> LOCATION: (992)..(993)
<223> OTHER INFORMATION: Any amino acid
<220> FEATURE:
<221> NAME/KEY: MOD_RES
<222> LOCATION: (995)..(996)
<223> OTHER INFORMATION: Any amino acid
<220> FEATURE:
<221> NAME/KEY: MOD_RES
<222> LOCATION: (998)..(999)
<223> OTHER INFORMATION: Any amino acid
<220> FEATURE:
<221> NAME/KEY: MOD_RES
<222> LOCATION: (1001)..(1002)
<223> OTHER INFORMATION: Any amino acid
<220> FEATURE:
<221> NAME/KEY: MOD_RES
<222> LOCATION: (1004)..(1005)
<223> OTHER INFORMATION: Any amino acid
<220> FEATURE:
<221> NAME/KEY: MOD_RES
<222> LOCATION: (1007)..(1008)
<223> OTHER INFORMATION: Any amino acid
<220> FEATURE:
<221> NAME/KEY: MOD_RES
<222> LOCATION: (1010)..(1011)
<223> OTHER INFORMATION: Any amino acid
<220> FEATURE:
<221> NAME/KEY: MOD_RES
<222> LOCATION: (1013)..(1014)
<223> OTHER INFORMATION: Any amino acid
<220> FEATURE:
<221> NAME/KEY: MOD_RES
<222> LOCATION: (1016)..(1017)
<223> OTHER INFORMATION: Any amino acid
<220> FEATURE:
<221> NAME/KEY: MOD_RES
<222> LOCATION: (1019)..(1020)
<223> OTHER INFORMATION: Any amino acid
<220> FEATURE:
<221> NAME/KEY: MOD_RES
<222> LOCATION: (1022)..(1023)
<223> OTHER INFORMATION: Any amino acid
<220> FEATURE:
<221> NAME/KEY: MOD_RES
<222> LOCATION: (1025)..(1026)
<223> OTHER INFORMATION: Any amino acid
<220> FEATURE:
<221> NAME/KEY: MOD_RES
<222> LOCATION: (1028)..(1029)
<223> OTHER INFORMATION: Any amino acid
```

-continued

```
<220> FEATURE:
<221> NAME/KEY: MOD_RES
<222> LOCATION: (1031)..(1032)
<223> OTHER INFORMATION: Any amino acid
<220> FEATURE:
<221> NAME/KEY: MOD_RES
<222> LOCATION: (1034)..(1035)
<223> OTHER INFORMATION: Any amino acid
<220> FEATURE:
<221> NAME/KEY: MOD_RES
<222> LOCATION: (1037)..(1038)
<223> OTHER INFORMATION: Any amino acid
<220> FEATURE:
<221> NAME/KEY: MOD_RES
<222> LOCATION: (1040)..(1041)
<223> OTHER INFORMATION: Any amino acid
<220> FEATURE:
<221> NAME/KEY: MOD_RES
<222> LOCATION: (1043)..(1044)
<223> OTHER INFORMATION: Any amino acid
<220> FEATURE:
<221> NAME/KEY: MOD_RES
<222> LOCATION: (1046)..(1047)
<223> OTHER INFORMATION: Any amino acid
<220> FEATURE:
<221> NAME/KEY: MOD_RES
<222> LOCATION: (1049)..(1050)
<223> OTHER INFORMATION: Any amino acid
<220> FEATURE:
<221> NAME/KEY: MOD_RES
<222> LOCATION: (1052)..(1053)
<223> OTHER INFORMATION: Any amino acid
<220> FEATURE:
<221> NAME/KEY: MOD_RES
<222> LOCATION: (1055)..(1056)
<223> OTHER INFORMATION: Any amino acid
<220> FEATURE:
<221> NAME/KEY: MOD_RES
<222> LOCATION: (1058)..(1059)
<223> OTHER INFORMATION: Any amino acid
<220> FEATURE:
<221> NAME/KEY: MOD_RES
<222> LOCATION: (1061)..(1062)
<223> OTHER INFORMATION: Any amino acid
<220> FEATURE:
<221> NAME/KEY: MOD_RES
<222> LOCATION: (1064)..(1065)
<223> OTHER INFORMATION: Any amino acid
<220> FEATURE:
<221> NAME/KEY: MOD_RES
<222> LOCATION: (1067)..(1068)
<223> OTHER INFORMATION: Any amino acid
<220> FEATURE:
<221> NAME/KEY: MOD_RES
<222> LOCATION: (1070)..(1071)
<223> OTHER INFORMATION: Any amino acid
<220> FEATURE:
<221> NAME/KEY: MOD_RES
<222> LOCATION: (1073)..(1074)
<223> OTHER INFORMATION: Any amino acid
<220> FEATURE:
<221> NAME/KEY: MOD_RES
<222> LOCATION: (1076)..(1077)
<223> OTHER INFORMATION: Any amino acid
<220> FEATURE:
<221> NAME/KEY: MOD_RES
<222> LOCATION: (1079)..(1080)
<223> OTHER INFORMATION: Any amino acid
<220> FEATURE:
<221> NAME/KEY: MOD_RES
<222> LOCATION: (1082)..(1083)
<223> OTHER INFORMATION: Any amino acid
<220> FEATURE:
<221> NAME/KEY: MOD_RES
<222> LOCATION: (1085)..(1086)
<223> OTHER INFORMATION: Any amino acid
<220> FEATURE:
<221> NAME/KEY: MOD_RES
<222> LOCATION: (1088)..(1089)
```

```
<223> OTHER INFORMATION: Any amino acid
<220> FEATURE:
<221> NAME/KEY: MOD_RES
<222> LOCATION: (1091)..(1092)
<223> OTHER INFORMATION: Any amino acid
<220> FEATURE:
<221> NAME/KEY: MOD_RES
<222> LOCATION: (1094)..(1095)
<223> OTHER INFORMATION: Any amino acid
<220> FEATURE:
<221> NAME/KEY: MOD_RES
<222> LOCATION: (1097)..(1098)
<223> OTHER INFORMATION: Any amino acid
<220> FEATURE:
<221> NAME/KEY: MOD_RES
<222> LOCATION: (1100)..(1101)
<223> OTHER INFORMATION: Any amino acid
<220> FEATURE:
<221> NAME/KEY: MOD_RES
<222> LOCATION: (1103)..(1104)
<223> OTHER INFORMATION: Any amino acid
<220> FEATURE:
<221> NAME/KEY: MOD_RES
<222> LOCATION: (1106)..(1107)
<223> OTHER INFORMATION: Any amino acid
<220> FEATURE:
<221> NAME/KEY: MOD_RES
<222> LOCATION: (1109)..(1110)
<223> OTHER INFORMATION: Any amino acid
<220> FEATURE:
<221> NAME/KEY: MOD_RES
<222> LOCATION: (1112)..(1113)
<223> OTHER INFORMATION: Any amino acid
<220> FEATURE:
<221> NAME/KEY: MOD_RES
<222> LOCATION: (1115)..(1116)
<223> OTHER INFORMATION: Any amino acid
<220> FEATURE:
<221> NAME/KEY: MOD_RES
<222> LOCATION: (1118)..(1119)
<223> OTHER INFORMATION: Any amino acid
<220> FEATURE:
<221> NAME/KEY: MOD_RES
<222> LOCATION: (1121)..(1122)
<223> OTHER INFORMATION: Any amino acid
<220> FEATURE:
<221> NAME/KEY: MOD_RES
<222> LOCATION: (1124)..(1125)
<223> OTHER INFORMATION: Any amino acid
<220> FEATURE:
<221> NAME/KEY: MOD_RES
<222> LOCATION: (1127)..(1128)
<223> OTHER INFORMATION: Any amino acid
<220> FEATURE:
<221> NAME/KEY: MOD_RES
<222> LOCATION: (1130)..(1131)
<223> OTHER INFORMATION: Any amino acid
<220> FEATURE:
<221> NAME/KEY: MOD_RES
<222> LOCATION: (1133)..(1134)
<223> OTHER INFORMATION: Any amino acid
<220> FEATURE:
<221> NAME/KEY: MOD_RES
<222> LOCATION: (1136)..(1137)
<223> OTHER INFORMATION: Any amino acid
<220> FEATURE:
<221> NAME/KEY: MOD_RES
<222> LOCATION: (1139)..(1140)
<223> OTHER INFORMATION: Any amino acid
<220> FEATURE:
<221> NAME/KEY: MOD_RES
<222> LOCATION: (1142)..(1143)
<223> OTHER INFORMATION: Any amino acid
<220> FEATURE:
<221> NAME/KEY: MOD_RES
<222> LOCATION: (1145)..(1146)
<223> OTHER INFORMATION: Any amino acid
<220> FEATURE:
<221> NAME/KEY: MOD_RES
```

-continued

```
<222> LOCATION: (1148)..(1149)
<223> OTHER INFORMATION: Any amino acid
<220> FEATURE:
<221> NAME/KEY: MOD_RES
<222> LOCATION: (1151)..(1152)
<223> OTHER INFORMATION: Any amino acid
<220> FEATURE:
<221> NAME/KEY: MOD_RES
<222> LOCATION: (1154)..(1155)
<223> OTHER INFORMATION: Any amino acid
<220> FEATURE:
<221> NAME/KEY: MOD_RES
<222> LOCATION: (1157)..(1158)
<223> OTHER INFORMATION: Any amino acid
<220> FEATURE:
<221> NAME/KEY: MOD_RES
<222> LOCATION: (1160)..(1161)
<223> OTHER INFORMATION: Any amino acid
<220> FEATURE:
<221> NAME/KEY: MOD_RES
<222> LOCATION: (1163)..(1164)
<223> OTHER INFORMATION: Any amino acid
<220> FEATURE:
<221> NAME/KEY: MOD_RES
<222> LOCATION: (1166)..(1167)
<223> OTHER INFORMATION: Any amino acid
<220> FEATURE:
<221> NAME/KEY: MOD_RES
<222> LOCATION: (1169)..(1170)
<223> OTHER INFORMATION: Any amino acid
<220> FEATURE:
<221> NAME/KEY: MOD_RES
<222> LOCATION: (1172)..(1173)
<223> OTHER INFORMATION: Any amino acid
<220> FEATURE:
<221> NAME/KEY: MOD_RES
<222> LOCATION: (1175)..(1176)
<223> OTHER INFORMATION: Any amino acid
<220> FEATURE:
<221> NAME/KEY: MOD_RES
<222> LOCATION: (1178)..(1179)
<223> OTHER INFORMATION: Any amino acid
<220> FEATURE:
<221> NAME/KEY: MOD_RES
<222> LOCATION: (1181)..(1182)
<223> OTHER INFORMATION: Any amino acid
<220> FEATURE:
<221> NAME/KEY: MOD_RES
<222> LOCATION: (1184)..(1185)
<223> OTHER INFORMATION: Any amino acid
<220> FEATURE:
<221> NAME/KEY: MOD_RES
<222> LOCATION: (1187)..(1188)
<223> OTHER INFORMATION: Any amino acid
<220> FEATURE:
<221> NAME/KEY: MOD_RES
<222> LOCATION: (1190)..(1191)
<223> OTHER INFORMATION: Any amino acid
<220> FEATURE:
<221> NAME/KEY: MOD_RES
<222> LOCATION: (1193)..(1194)
<223> OTHER INFORMATION: Any amino acid
<220> FEATURE:
<221> NAME/KEY: MOD_RES
<222> LOCATION: (1196)..(1197)
<223> OTHER INFORMATION: Any amino acid
<220> FEATURE:
<221> NAME/KEY: MOD_RES
<222> LOCATION: (1199)..(1200)
<223> OTHER INFORMATION: Any amino acid
<220> FEATURE:
<221> NAME/KEY: MOD_RES
<222> LOCATION: (1202)..(1203)
<223> OTHER INFORMATION: Any amino acid
<220> FEATURE:
<221> NAME/KEY: MOD_RES
<222> LOCATION: (1205)..(1206)
<223> OTHER INFORMATION: Any amino acid
<220> FEATURE:
```

-continued

```
<221> NAME/KEY: MOD_RES
<222> LOCATION: (1208)..(1209)
<223> OTHER INFORMATION: Any amino acid
<220> FEATURE:
<221> NAME/KEY: MOD_RES
<222> LOCATION: (1211)..(1212)
<223> OTHER INFORMATION: Any amino acid
<220> FEATURE:
<221> NAME/KEY: MOD_RES
<222> LOCATION: (1214)..(1215)
<223> OTHER INFORMATION: Any amino acid
<220> FEATURE:
<221> NAME/KEY: MOD_RES
<222> LOCATION: (1217)..(1218)
<223> OTHER INFORMATION: Any amino acid
<220> FEATURE:
<221> NAME/KEY: MOD_RES
<222> LOCATION: (1220)..(1221)
<223> OTHER INFORMATION: Any amino acid
<220> FEATURE:
<221> NAME/KEY: MOD_RES
<222> LOCATION: (1223)..(1224)
<223> OTHER INFORMATION: Any amino acid
<220> FEATURE:
<221> NAME/KEY: MOD_RES
<222> LOCATION: (1226)..(1227)
<223> OTHER INFORMATION: Any amino acid
<220> FEATURE:
<221> NAME/KEY: MOD_RES
<222> LOCATION: (1229)..(1230)
<223> OTHER INFORMATION: Any amino acid
<220> FEATURE:
<221> NAME/KEY: MOD_RES
<222> LOCATION: (1232)..(1233)
<223> OTHER INFORMATION: Any amino acid
<220> FEATURE:
<221> NAME/KEY: MOD_RES
<222> LOCATION: (1235)..(1236)
<223> OTHER INFORMATION: Any amino acid
<220> FEATURE:
<221> NAME/KEY: MOD_RES
<222> LOCATION: (1238)..(1239)
<223> OTHER INFORMATION: Any amino acid
<220> FEATURE:
<221> NAME/KEY: MOD_RES
<222> LOCATION: (1241)..(1242)
<223> OTHER INFORMATION: Any amino acid
<220> FEATURE:
<221> NAME/KEY: MOD_RES
<222> LOCATION: (1244)..(1245)
<223> OTHER INFORMATION: Any amino acid
<220> FEATURE:
<221> NAME/KEY: MOD_RES
<222> LOCATION: (1247)..(1248)
<223> OTHER INFORMATION: Any amino acid
<220> FEATURE:
<221> NAME/KEY: MOD_RES
<222> LOCATION: (1250)..(1251)
<223> OTHER INFORMATION: Any amino acid
<220> FEATURE:
<221> NAME/KEY: MOD_RES
<222> LOCATION: (1253)..(1254)
<223> OTHER INFORMATION: Any amino acid
<220> FEATURE:
<221> NAME/KEY: MOD_RES
<222> LOCATION: (1256)..(1257)
<223> OTHER INFORMATION: Any amino acid
<220> FEATURE:
<221> NAME/KEY: MOD_RES
<222> LOCATION: (1259)..(1260)
<223> OTHER INFORMATION: Any amino acid
<220> FEATURE:
<221> NAME/KEY: MOD_RES
<222> LOCATION: (1262)..(1263)
<223> OTHER INFORMATION: Any amino acid
<220> FEATURE:
<221> NAME/KEY: MOD_RES
<222> LOCATION: (1265)..(1266)
<223> OTHER INFORMATION: Any amino acid
```

-continued

```
<220> FEATURE:
<221> NAME/KEY: MOD_RES
<222> LOCATION: (1268)..(1269)
<223> OTHER INFORMATION: Any amino acid
<220> FEATURE:
<221> NAME/KEY: MOD_RES
<222> LOCATION: (1271)..(1272)
<223> OTHER INFORMATION: Any amino acid
<220> FEATURE:
<221> NAME/KEY: MOD_RES
<222> LOCATION: (1274)..(1275)
<223> OTHER INFORMATION: Any amino acid
<220> FEATURE:
<221> NAME/KEY: MOD_RES
<222> LOCATION: (1277)..(1278)
<223> OTHER INFORMATION: Any amino acid
<220> FEATURE:
<221> NAME/KEY: MOD_RES
<222> LOCATION: (1280)..(1281)
<223> OTHER INFORMATION: Any amino acid
<220> FEATURE:
<221> NAME/KEY: MOD_RES
<222> LOCATION: (1283)..(1284)
<223> OTHER INFORMATION: Any amino acid
<220> FEATURE:
<221> NAME/KEY: MOD_RES
<222> LOCATION: (1286)..(1287)
<223> OTHER INFORMATION: Any amino acid
<220> FEATURE:
<221> NAME/KEY: MOD_RES
<222> LOCATION: (1289)..(1290)
<223> OTHER INFORMATION: Any amino acid
<220> FEATURE:
<221> NAME/KEY: MOD_RES
<222> LOCATION: (1292)..(1293)
<223> OTHER INFORMATION: Any amino acid
<220> FEATURE:
<221> NAME/KEY: MOD_RES
<222> LOCATION: (1295)..(1296)
<223> OTHER INFORMATION: Any amino acid
<220> FEATURE:
<221> NAME/KEY: MOD_RES
<222> LOCATION: (1298)..(1299)
<223> OTHER INFORMATION: Any amino acid
<220> FEATURE:
<221> NAME/KEY: MOD_RES
<222> LOCATION: (1301)..(1302)
<223> OTHER INFORMATION: Any amino acid
<220> FEATURE:
<221> NAME/KEY: MOD_RES
<222> LOCATION: (1304)..(1305)
<223> OTHER INFORMATION: Any amino acid
<220> FEATURE:
<221> NAME/KEY: MOD_RES
<222> LOCATION: (1307)..(1308)
<223> OTHER INFORMATION: Any amino acid
<220> FEATURE:
<221> NAME/KEY: MOD_RES
<222> LOCATION: (1310)..(1311)
<223> OTHER INFORMATION: Any amino acid
<220> FEATURE:
<221> NAME/KEY: MOD_RES
<222> LOCATION: (1313)..(1314)
<223> OTHER INFORMATION: Any amino acid
<220> FEATURE:
<221> NAME/KEY: MOD_RES
<222> LOCATION: (1316)..(1317)
<223> OTHER INFORMATION: Any amino acid
<220> FEATURE:
<221> NAME/KEY: MOD_RES
<222> LOCATION: (1319)..(1320)
<223> OTHER INFORMATION: Any amino acid
<220> FEATURE:
<221> NAME/KEY: MOD_RES
<222> LOCATION: (1322)..(1323)
<223> OTHER INFORMATION: Any amino acid
<220> FEATURE:
<221> NAME/KEY: MOD_RES
<222> LOCATION: (1325)..(1326)
```

```
<223> OTHER INFORMATION: Any amino acid
<220> FEATURE:
<221> NAME/KEY: MOD_RES
<222> LOCATION: (1328)..(1329)
<223> OTHER INFORMATION: Any amino acid
<220> FEATURE:
<221> NAME/KEY: MOD_RES
<222> LOCATION: (1331)..(1332)
<223> OTHER INFORMATION: Any amino acid
<220> FEATURE:
<221> NAME/KEY: MOD_RES
<222> LOCATION: (1334)..(1335)
<223> OTHER INFORMATION: Any amino acid
<220> FEATURE:
<221> NAME/KEY: MOD_RES
<222> LOCATION: (1337)..(1338)
<223> OTHER INFORMATION: Any amino acid
<220> FEATURE:
<221> NAME/KEY: MOD_RES
<222> LOCATION: (1340)..(1341)
<223> OTHER INFORMATION: Any amino acid
<220> FEATURE:
<221> NAME/KEY: MOD_RES
<222> LOCATION: (1343)..(1344)
<223> OTHER INFORMATION: Any amino acid
<220> FEATURE:
<221> NAME/KEY: MOD_RES
<222> LOCATION: (1346)..(1347)
<223> OTHER INFORMATION: Any amino acid
<220> FEATURE:
<221> NAME/KEY: MOD_RES
<222> LOCATION: (1349)..(1350)
<223> OTHER INFORMATION: Any amino acid
<220> FEATURE:
<221> NAME/KEY: MOD_RES
<222> LOCATION: (1352)..(1353)
<223> OTHER INFORMATION: Any amino acid
<220> FEATURE:
<221> NAME/KEY: MOD_RES
<222> LOCATION: (1355)..(1356)
<223> OTHER INFORMATION: Any amino acid
<220> FEATURE:
<221> NAME/KEY: MOD_RES
<222> LOCATION: (1358)..(1359)
<223> OTHER INFORMATION: Any amino acid
<220> FEATURE:
<221> NAME/KEY: MOD_RES
<222> LOCATION: (1361)..(1362)
<223> OTHER INFORMATION: Any amino acid
<220> FEATURE:
<221> NAME/KEY: MOD_RES
<222> LOCATION: (1364)..(1365)
<223> OTHER INFORMATION: Any amino acid
<220> FEATURE:
<221> NAME/KEY: MOD_RES
<222> LOCATION: (1367)..(1368)
<223> OTHER INFORMATION: Any amino acid
<220> FEATURE:
<221> NAME/KEY: MOD_RES
<222> LOCATION: (1370)..(1371)
<223> OTHER INFORMATION: Any amino acid
<220> FEATURE:
<221> NAME/KEY: MOD_RES
<222> LOCATION: (1373)..(1374)
<223> OTHER INFORMATION: Any amino acid
<220> FEATURE:
<221> NAME/KEY: MOD_RES
<222> LOCATION: (1376)..(1377)
<223> OTHER INFORMATION: Any amino acid
<220> FEATURE:
<221> NAME/KEY: MOD_RES
<222> LOCATION: (1379)..(1380)
<223> OTHER INFORMATION: Any amino acid
<220> FEATURE:
<221> NAME/KEY: MOD_RES
<222> LOCATION: (1382)..(1383)
<223> OTHER INFORMATION: Any amino acid
<220> FEATURE:
<221> NAME/KEY: MOD_RES
```

```
<222> LOCATION: (1385)..(1386)
<223> OTHER INFORMATION: Any amino acid
<220> FEATURE:
<221> NAME/KEY: MOD_RES
<222> LOCATION: (1388)..(1389)
<223> OTHER INFORMATION: Any amino acid
<220> FEATURE:
<221> NAME/KEY: MOD_RES
<222> LOCATION: (1391)..(1392)
<223> OTHER INFORMATION: Any amino acid
<220> FEATURE:
<221> NAME/KEY: MOD_RES
<222> LOCATION: (1394)..(1395)
<223> OTHER INFORMATION: Any amino acid
<220> FEATURE:
<221> NAME/KEY: MOD_RES
<222> LOCATION: (1397)..(1398)
<223> OTHER INFORMATION: Any amino acid
<220> FEATURE:
<221> NAME/KEY: MOD_RES
<222> LOCATION: (1400)..(1401)
<223> OTHER INFORMATION: Any amino acid
<220> FEATURE:
<221> NAME/KEY: MOD_RES
<222> LOCATION: (1403)..(1404)
<223> OTHER INFORMATION: Any amino acid
<220> FEATURE:
<221> NAME/KEY: MOD_RES
<222> LOCATION: (1406)..(1407)
<223> OTHER INFORMATION: Any amino acid
<220> FEATURE:
<221> NAME/KEY: MOD_RES
<222> LOCATION: (1409)..(1410)
<223> OTHER INFORMATION: Any amino acid
<220> FEATURE:
<221> NAME/KEY: MOD_RES
<222> LOCATION: (1412)..(1413)
<223> OTHER INFORMATION: Any amino acid
<220> FEATURE:
<221> NAME/KEY: MOD_RES
<222> LOCATION: (1415)..(1416)
<223> OTHER INFORMATION: Any amino acid
<220> FEATURE:
<221> NAME/KEY: MOD_RES
<222> LOCATION: (1418)..(1419)
<223> OTHER INFORMATION: Any amino acid
<220> FEATURE:
<221> NAME/KEY: MOD_RES
<222> LOCATION: (1421)..(1422)
<223> OTHER INFORMATION: Any amino acid
<220> FEATURE:
<221> NAME/KEY: MOD_RES
<222> LOCATION: (1424)..(1425)
<223> OTHER INFORMATION: Any amino acid
<220> FEATURE:
<221> NAME/KEY: MOD_RES
<222> LOCATION: (1427)..(1428)
<223> OTHER INFORMATION: Any amino acid
<220> FEATURE:
<221> NAME/KEY: MOD_RES
<222> LOCATION: (1430)..(1431)
<223> OTHER INFORMATION: Any amino acid
<220> FEATURE:
<221> NAME/KEY: MOD_RES
<222> LOCATION: (1433)..(1434)
<223> OTHER INFORMATION: Any amino acid
<220> FEATURE:
<221> NAME/KEY: MOD_RES
<222> LOCATION: (1436)..(1437)
<223> OTHER INFORMATION: Any amino acid
<220> FEATURE:
<221> NAME/KEY: MOD_RES
<222> LOCATION: (1439)..(1440)
<223> OTHER INFORMATION: Any amino acid
<220> FEATURE:
<221> NAME/KEY: MOD_RES
<222> LOCATION: (1442)..(1443)
<223> OTHER INFORMATION: Any amino acid
<220> FEATURE:
```

```
<221> NAME/KEY: MOD_RES
<222> LOCATION: (1445)..(1446)
<223> OTHER INFORMATION: Any amino acid
<220> FEATURE:
<221> NAME/KEY: MOD_RES
<222> LOCATION: (1448)..(1449)
<223> OTHER INFORMATION: Any amino acid
<220> FEATURE:
<221> NAME/KEY: MOD_RES
<222> LOCATION: (1451)..(1452)
<223> OTHER INFORMATION: Any amino acid
<220> FEATURE:
<221> NAME/KEY: MOD_RES
<222> LOCATION: (1454)..(1455)
<223> OTHER INFORMATION: Any amino acid
<220> FEATURE:
<221> NAME/KEY: MOD_RES
<222> LOCATION: (1457)..(1458)
<223> OTHER INFORMATION: Any amino acid
<220> FEATURE:
<221> NAME/KEY: MOD_RES
<222> LOCATION: (1460)..(1461)
<223> OTHER INFORMATION: Any amino acid
<220> FEATURE:
<221> NAME/KEY: MOD_RES
<222> LOCATION: (1463)..(1464)
<223> OTHER INFORMATION: Any amino acid
<220> FEATURE:
<221> NAME/KEY: MOD_RES
<222> LOCATION: (1466)..(1467)
<223> OTHER INFORMATION: Any amino acid
<220> FEATURE:
<221> NAME/KEY: MOD_RES
<222> LOCATION: (1469)..(1470)
<223> OTHER INFORMATION: Any amino acid
<220> FEATURE:
<221> NAME/KEY: MOD_RES
<222> LOCATION: (1472)..(1473)
<223> OTHER INFORMATION: Any amino acid
<220> FEATURE:
<221> NAME/KEY: MOD_RES
<222> LOCATION: (1475)..(1476)
<223> OTHER INFORMATION: Any amino acid
<220> FEATURE:
<221> NAME/KEY: MOD_RES
<222> LOCATION: (1478)..(1479)
<223> OTHER INFORMATION: Any amino acid
<220> FEATURE:
<221> NAME/KEY: MOD_RES
<222> LOCATION: (1481)..(1482)
<223> OTHER INFORMATION: Any amino acid
<220> FEATURE:
<221> NAME/KEY: MOD_RES
<222> LOCATION: (1484)..(1485)
<223> OTHER INFORMATION: Any amino acid
<220> FEATURE:
<221> NAME/KEY: MOD_RES
<222> LOCATION: (1487)..(1488)
<223> OTHER INFORMATION: Any amino acid
<220> FEATURE:
<221> NAME/KEY: MOD_RES
<222> LOCATION: (1490)..(1491)
<223> OTHER INFORMATION: Any amino acid
<220> FEATURE:
<221> NAME/KEY: MOD_RES
<222> LOCATION: (1493)..(1494)
<223> OTHER INFORMATION: Any amino acid
<220> FEATURE:
<221> NAME/KEY: MOD_RES
<222> LOCATION: (1496)..(1497)
<223> OTHER INFORMATION: Any amino acid
<220> FEATURE:
<221> NAME/KEY: MOD_RES
<222> LOCATION: (1499)..(1500)
<223> OTHER INFORMATION: Any amino acid
<220> FEATURE:
<221> NAME/KEY: MOD_RES
<222> LOCATION: (1502)..(1503)
<223> OTHER INFORMATION: Any amino acid
```

```
<220> FEATURE:
<221> NAME/KEY: MOD_RES
<222> LOCATION: (1505)..(1506)
<223> OTHER INFORMATION: Any amino acid
<220> FEATURE:
<221> NAME/KEY: MOD_RES
<222> LOCATION: (1508)..(1509)
<223> OTHER INFORMATION: Any amino acid
<220> FEATURE:
<221> NAME/KEY: MOD_RES
<222> LOCATION: (1511)..(1512)
<223> OTHER INFORMATION: Any amino acid
<220> FEATURE:
<221> NAME/KEY: MOD_RES
<222> LOCATION: (1514)..(1515)
<223> OTHER INFORMATION: Any amino acid
<220> FEATURE:
<221> NAME/KEY: MOD_RES
<222> LOCATION: (1517)..(1518)
<223> OTHER INFORMATION: Any amino acid
<220> FEATURE:
<221> NAME/KEY: MOD_RES
<222> LOCATION: (1520)..(1521)
<223> OTHER INFORMATION: Any amino acid
<220> FEATURE:
<221> NAME/KEY: MOD_RES
<222> LOCATION: (1523)..(1524)
<223> OTHER INFORMATION: Any amino acid
<220> FEATURE:
<221> NAME/KEY: MOD_RES
<222> LOCATION: (1526)..(1527)
<223> OTHER INFORMATION: Any amino acid
<220> FEATURE:
<221> NAME/KEY: MOD_RES
<222> LOCATION: (1529)..(1530)
<223> OTHER INFORMATION: Any amino acid
<220> FEATURE:
<221> NAME/KEY: MOD_RES
<222> LOCATION: (1532)..(1533)
<223> OTHER INFORMATION: Any amino acid
<220> FEATURE:
<221> NAME/KEY: MOD_RES
<222> LOCATION: (1535)..(1536)
<223> OTHER INFORMATION: Any amino acid
<220> FEATURE:
<221> NAME/KEY: MOD_RES
<222> LOCATION: (1538)..(1539)
<223> OTHER INFORMATION: Any amino acid
<220> FEATURE:
<221> NAME/KEY: MOD_RES
<222> LOCATION: (1541)..(1542)
<223> OTHER INFORMATION: Any amino acid
<220> FEATURE:
<221> NAME/KEY: MOD_RES
<222> LOCATION: (1544)..(1545)
<223> OTHER INFORMATION: Any amino acid
<220> FEATURE:
<221> NAME/KEY: MOD_RES
<222> LOCATION: (1547)..(1548)
<223> OTHER INFORMATION: Any amino acid
<220> FEATURE:
<221> NAME/KEY: MOD_RES
<222> LOCATION: (1550)..(1551)
<223> OTHER INFORMATION: Any amino acid
<220> FEATURE:
<221> NAME/KEY: MOD_RES
<222> LOCATION: (1553)..(1554)
<223> OTHER INFORMATION: Any amino acid
<220> FEATURE:
<221> NAME/KEY: MOD_RES
<222> LOCATION: (1556)..(1557)
<223> OTHER INFORMATION: Any amino acid
<220> FEATURE:
<221> NAME/KEY: MOD_RES
<222> LOCATION: (1559)..(1560)
<223> OTHER INFORMATION: Any amino acid
<220> FEATURE:
<221> NAME/KEY: MOD_RES
<222> LOCATION: (1562)..(1563)
```

```
<223> OTHER INFORMATION: Any amino acid
<220> FEATURE:
<221> NAME/KEY: MOD_RES
<222> LOCATION: (1565)..(1566)
<223> OTHER INFORMATION: Any amino acid
<220> FEATURE:
<221> NAME/KEY: MOD_RES
<222> LOCATION: (1568)..(1569)
<223> OTHER INFORMATION: Any amino acid
<220> FEATURE:
<221> NAME/KEY: MOD_RES
<222> LOCATION: (1571)..(1572)
<223> OTHER INFORMATION: Any amino acid
<220> FEATURE:
<221> NAME/KEY: MOD_RES
<222> LOCATION: (1574)..(1575)
<223> OTHER INFORMATION: Any amino acid
<220> FEATURE:
<221> NAME/KEY: MOD_RES
<222> LOCATION: (1577)..(1578)
<223> OTHER INFORMATION: Any amino acid
<220> FEATURE:
<221> NAME/KEY: MOD_RES
<222> LOCATION: (1580)..(1581)
<223> OTHER INFORMATION: Any amino acid
<220> FEATURE:
<221> NAME/KEY: MOD_RES
<222> LOCATION: (1583)..(1584)
<223> OTHER INFORMATION: Any amino acid
<220> FEATURE:
<221> NAME/KEY: MOD_RES
<222> LOCATION: (1586)..(1587)
<223> OTHER INFORMATION: Any amino acid
<220> FEATURE:
<221> NAME/KEY: MOD_RES
<222> LOCATION: (1589)..(1590)
<223> OTHER INFORMATION: Any amino acid
<220> FEATURE:
<221> NAME/KEY: MOD_RES
<222> LOCATION: (1592)..(1593)
<223> OTHER INFORMATION: Any amino acid
<220> FEATURE:
<221> NAME/KEY: MOD_RES
<222> LOCATION: (1595)..(1596)
<223> OTHER INFORMATION: Any amino acid
<220> FEATURE:
<221> NAME/KEY: MOD_RES
<222> LOCATION: (1598)..(1599)
<223> OTHER INFORMATION: Any amino acid
<220> FEATURE:
<221> NAME/KEY: MOD_RES
<222> LOCATION: (1601)..(1602)
<223> OTHER INFORMATION: Any amino acid
<220> FEATURE:
<221> NAME/KEY: MOD_RES
<222> LOCATION: (1604)..(1605)
<223> OTHER INFORMATION: Any amino acid
<220> FEATURE:
<221> NAME/KEY: MOD_RES
<222> LOCATION: (1607)..(1608)
<223> OTHER INFORMATION: Any amino acid
<220> FEATURE:
<221> NAME/KEY: MOD_RES
<222> LOCATION: (1610)..(1611)
<223> OTHER INFORMATION: Any amino acid
<220> FEATURE:
<221> NAME/KEY: MOD_RES
<222> LOCATION: (1613)..(1614)
<223> OTHER INFORMATION: Any amino acid
<220> FEATURE:
<221> NAME/KEY: MOD_RES
<222> LOCATION: (1616)..(1617)
<223> OTHER INFORMATION: Any amino acid
<220> FEATURE:
<221> NAME/KEY: MOD_RES
<222> LOCATION: (1619)..(1620)
<223> OTHER INFORMATION: Any amino acid
<220> FEATURE:
<221> NAME/KEY: MOD_RES
```

```
<222> LOCATION: (1622)..(1623)
<223> OTHER INFORMATION: Any amino acid
<220> FEATURE:
<221> NAME/KEY: MOD_RES
<222> LOCATION: (1625)..(1626)
<223> OTHER INFORMATION: Any amino acid
<220> FEATURE:
<221> NAME/KEY: MOD_RES
<222> LOCATION: (1628)..(1629)
<223> OTHER INFORMATION: Any amino acid
<220> FEATURE:
<221> NAME/KEY: MOD_RES
<222> LOCATION: (1631)..(1632)
<223> OTHER INFORMATION: Any amino acid
<220> FEATURE:
<221> NAME/KEY: MOD_RES
<222> LOCATION: (1634)..(1635)
<223> OTHER INFORMATION: Any amino acid
<220> FEATURE:
<221> NAME/KEY: MOD_RES
<222> LOCATION: (1637)..(1638)
<223> OTHER INFORMATION: Any amino acid
<220> FEATURE:
<221> NAME/KEY: MOD_RES
<222> LOCATION: (1640)..(1641)
<223> OTHER INFORMATION: Any amino acid
<220> FEATURE:
<221> NAME/KEY: MOD_RES
<222> LOCATION: (1643)..(1644)
<223> OTHER INFORMATION: Any amino acid
<220> FEATURE:
<221> NAME/KEY: MOD_RES
<222> LOCATION: (1646)..(1647)
<223> OTHER INFORMATION: Any amino acid
<220> FEATURE:
<221> NAME/KEY: MOD_RES
<222> LOCATION: (1649)..(1650)
<223> OTHER INFORMATION: Any amino acid
<220> FEATURE:
<221> NAME/KEY: MOD_RES
<222> LOCATION: (1652)..(1653)
<223> OTHER INFORMATION: Any amino acid
<220> FEATURE:
<221> NAME/KEY: MOD_RES
<222> LOCATION: (1655)..(1656)
<223> OTHER INFORMATION: Any amino acid
<220> FEATURE:
<221> NAME/KEY: MOD_RES
<222> LOCATION: (1658)..(1659)
<223> OTHER INFORMATION: Any amino acid
<220> FEATURE:
<221> NAME/KEY: MOD_RES
<222> LOCATION: (1661)..(1662)
<223> OTHER INFORMATION: Any amino acid
<220> FEATURE:
<221> NAME/KEY: MOD_RES
<222> LOCATION: (1664)..(1665)
<223> OTHER INFORMATION: Any amino acid
<220> FEATURE:
<221> NAME/KEY: MOD_RES
<222> LOCATION: (1667)..(1668)
<223> OTHER INFORMATION: Any amino acid
<220> FEATURE:
<221> NAME/KEY: MOD_RES
<222> LOCATION: (1670)..(1671)
<223> OTHER INFORMATION: Any amino acid
<220> FEATURE:
<221> NAME/KEY: MOD_RES
<222> LOCATION: (1673)..(1674)
<223> OTHER INFORMATION: Any amino acid
<220> FEATURE:
<221> NAME/KEY: MOD_RES
<222> LOCATION: (1676)..(1677)
<223> OTHER INFORMATION: Any amino acid
<220> FEATURE:
<221> NAME/KEY: MOD_RES
<222> LOCATION: (1679)..(1680)
<223> OTHER INFORMATION: Any amino acid
<220> FEATURE:
```

```
<221> NAME/KEY: MOD_RES
<222> LOCATION: (1682)..(1683)
<223> OTHER INFORMATION: Any amino acid
<220> FEATURE:
<221> NAME/KEY: MOD_RES
<222> LOCATION: (1685)..(1686)
<223> OTHER INFORMATION: Any amino acid
<220> FEATURE:
<221> NAME/KEY: MOD_RES
<222> LOCATION: (1688)..(1689)
<223> OTHER INFORMATION: Any amino acid
<220> FEATURE:
<221> NAME/KEY: MOD_RES
<222> LOCATION: (1691)..(1692)
<223> OTHER INFORMATION: Any amino acid
<220> FEATURE:
<221> NAME/KEY: MOD_RES
<222> LOCATION: (1694)..(1695)
<223> OTHER INFORMATION: Any amino acid
<220> FEATURE:
<221> NAME/KEY: MOD_RES
<222> LOCATION: (1697)..(1698)
<223> OTHER INFORMATION: Any amino acid
<220> FEATURE:
<221> NAME/KEY: MOD_RES
<222> LOCATION: (1700)..(1701)
<223> OTHER INFORMATION: Any amino acid
<220> FEATURE:
<221> NAME/KEY: MOD_RES
<222> LOCATION: (1703)..(1704)
<223> OTHER INFORMATION: Any amino acid
<220> FEATURE:
<221> NAME/KEY: MOD_RES
<222> LOCATION: (1706)..(1707)
<223> OTHER INFORMATION: Any amino acid
<220> FEATURE:
<221> NAME/KEY: MOD_RES
<222> LOCATION: (1709)..(1710)
<223> OTHER INFORMATION: Any amino acid
<220> FEATURE:
<221> NAME/KEY: MOD_RES
<222> LOCATION: (1712)..(1713)
<223> OTHER INFORMATION: Any amino acid
<220> FEATURE:
<221> NAME/KEY: MOD_RES
<222> LOCATION: (1715)..(1716)
<223> OTHER INFORMATION: Any amino acid
<220> FEATURE:
<221> NAME/KEY: MOD_RES
<222> LOCATION: (1718)..(1719)
<223> OTHER INFORMATION: Any amino acid
<220> FEATURE:
<221> NAME/KEY: MOD_RES
<222> LOCATION: (1721)..(1722)
<223> OTHER INFORMATION: Any amino acid
<220> FEATURE:
<221> NAME/KEY: MOD_RES
<222> LOCATION: (1724)..(1725)
<223> OTHER INFORMATION: Any amino acid
<220> FEATURE:
<221> NAME/KEY: MOD_RES
<222> LOCATION: (1727)..(1728)
<223> OTHER INFORMATION: Any amino acid
<220> FEATURE:
<221> NAME/KEY: MOD_RES
<222> LOCATION: (1730)..(1731)
<223> OTHER INFORMATION: Any amino acid
<220> FEATURE:
<221> NAME/KEY: MOD_RES
<222> LOCATION: (1733)..(1734)
<223> OTHER INFORMATION: Any amino acid
<220> FEATURE:
<221> NAME/KEY: MOD_RES
<222> LOCATION: (1736)..(1737)
<223> OTHER INFORMATION: Any amino acid
<220> FEATURE:
<221> NAME/KEY: MOD_RES
<222> LOCATION: (1739)..(1740)
<223> OTHER INFORMATION: Any amino acid
```

-continued

```
<220> FEATURE:
<221> NAME/KEY: MOD_RES
<222> LOCATION: (1742)..(1743)
<223> OTHER INFORMATION: Any amino acid
<220> FEATURE:
<221> NAME/KEY: MOD_RES
<222> LOCATION: (1745)..(1746)
<223> OTHER INFORMATION: Any amino acid
<220> FEATURE:
<221> NAME/KEY: MOD_RES
<222> LOCATION: (1748)..(1749)
<223> OTHER INFORMATION: Any amino acid
<220> FEATURE:
<221> NAME/KEY: MOD_RES
<222> LOCATION: (1751)..(1752)
<223> OTHER INFORMATION: Any amino acid
<220> FEATURE:
<221> NAME/KEY: MOD_RES
<222> LOCATION: (1754)..(1755)
<223> OTHER INFORMATION: Any amino acid
<220> FEATURE:
<221> NAME/KEY: MOD_RES
<222> LOCATION: (1757)..(1758)
<223> OTHER INFORMATION: Any amino acid
<220> FEATURE:
<221> NAME/KEY: MOD_RES
<222> LOCATION: (1760)..(1761)
<223> OTHER INFORMATION: Any amino acid
<220> FEATURE:
<221> NAME/KEY: MOD_RES
<222> LOCATION: (1763)..(1764)
<223> OTHER INFORMATION: Any amino acid
<220> FEATURE:
<221> NAME/KEY: MOD_RES
<222> LOCATION: (1766)..(1767)
<223> OTHER INFORMATION: Any amino acid
<220> FEATURE:
<221> NAME/KEY: MOD_RES
<222> LOCATION: (1769)..(1770)
<223> OTHER INFORMATION: Any amino acid
<220> FEATURE:
<221> NAME/KEY: MOD_RES
<222> LOCATION: (1772)..(1773)
<223> OTHER INFORMATION: Any amino acid
<220> FEATURE:
<221> NAME/KEY: MOD_RES
<222> LOCATION: (1775)..(1776)
<223> OTHER INFORMATION: Any amino acid
<220> FEATURE:
<221> NAME/KEY: MOD_RES
<222> LOCATION: (1778)..(1779)
<223> OTHER INFORMATION: Any amino acid
<220> FEATURE:
<221> NAME/KEY: MOD_RES
<222> LOCATION: (1781)..(1782)
<223> OTHER INFORMATION: Any amino acid
<220> FEATURE:
<221> NAME/KEY: MOD_RES
<222> LOCATION: (1784)..(1785)
<223> OTHER INFORMATION: Any amino acid
<220> FEATURE:
<221> NAME/KEY: MOD_RES
<222> LOCATION: (1787)..(1788)
<223> OTHER INFORMATION: Any amino acid
<220> FEATURE:
<221> NAME/KEY: MOD_RES
<222> LOCATION: (1790)..(1791)
<223> OTHER INFORMATION: Any amino acid
<220> FEATURE:
<221> NAME/KEY: MOD_RES
<222> LOCATION: (1793)..(1794)
<223> OTHER INFORMATION: Any amino acid
<220> FEATURE:
<221> NAME/KEY: MOD_RES
<222> LOCATION: (1796)..(1797)
<223> OTHER INFORMATION: Any amino acid
<220> FEATURE:
<221> NAME/KEY: MOD_RES
<222> LOCATION: (1799)..(1800)
```

<223> OTHER INFORMATION: Any amino acid
<220> FEATURE:
<221> NAME/KEY: MISC_FEATURE
<222> LOCATION: (1)..(1800)
<223> OTHER INFORMATION: This sequence may encompass 5 to 600 "Gly Xaa Xaa" repeating units, wherein some positions may be absent
<220> FEATURE:
<223> OTHER INFORMATION: See specification as filed for detailed description of substitutions and preferred embodiments

<400> SEQUENCE: 44

```
Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
            85                  90                  95

Gly Xaa Xaa Gly Xaa Xaa Gly Xaa Xaa Gly Xaa Xaa Gly Xaa Xaa Gly
        100                 105                 110

Xaa Xaa Gly Xaa Xaa Gly Xaa Xaa Gly Xaa Xaa Gly Xaa Xaa Gly Xaa
    115                 120                 125

Xaa Gly Xaa Xaa Gly Xaa Xaa Gly Xaa Xaa Gly Xaa Xaa Gly Xaa Xaa
130                 135                 140

Gly Xaa Xaa Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa Xaa Gly Xaa
            165                 170                 175

Xaa Gly Xaa Xaa Gly Xaa Xaa Gly Xaa Xaa Gly Xaa Xaa Gly Xaa Xaa
        180                 185                 190

Gly Xaa Xaa Gly Xaa Xaa Gly Xaa Xaa Gly Xaa Xaa Gly Xaa Xaa Gly
    195                 200                 205

Xaa Xaa Gly Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa Xaa Gly Xaa
            260                 265                 270

Xaa Gly Xaa Xaa Gly Xaa Xaa Gly Xaa Xaa Gly Xaa Xaa Gly Xaa Xaa
        275                 280                 285

Gly Xaa Xaa Gly Xaa Xaa Gly Xaa Xaa Gly Xaa Xaa Gly Xaa Xaa Gly
    290                 295                 300

Xaa Xaa Gly Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly Xaa Xaa Gly
        340                 345                 350

Xaa Xaa Gly Xaa Xaa Gly Xaa Xaa Gly Xaa Xaa Gly Xaa Xaa Gly Xaa
```

-continued

```
            355                 360                 365
Xaa Gly Xaa Xaa Gly Xaa Xaa Gly Xaa Xaa Gly Xaa Xaa
    370                 375                 380
Gly Xaa Xaa Gly Xaa Xaa Gly Xaa Xaa Gly Xaa Xaa Gly
385                 390                 395                 400
Xaa Xaa Gly Xaa Xaa Gly Xaa Xaa Gly Xaa Xaa Gly Xaa
                405                 410                 415
Xaa Gly Xaa Xaa Gly Xaa Xaa Gly Xaa Xaa Gly Xaa Xaa
        420                 425                 430
Gly Xaa Xaa Gly Xaa Xaa Gly Xaa Xaa Gly Xaa Xaa Gly
    435                 440                 445
Xaa Xaa Gly Xaa Xaa Gly Xaa Xaa Gly Xaa Xaa Gly Xaa
    450                 455                 460
Xaa Gly Xaa Xaa Gly Xaa Xaa Gly Xaa Xaa Gly Xaa Xaa
465                 470                 475                 480
Gly Xaa Xaa Gly Xaa Xaa Gly Xaa Xaa Gly Xaa Xaa Gly
                485                 490                 495
Xaa Xaa Gly Xaa Xaa Gly Xaa Xaa Gly Xaa Xaa Gly Xaa
        500                 505                 510
Xaa Gly Xaa Xaa Gly Xaa Xaa Gly Xaa Xaa Gly Xaa Xaa
    515                 520                 525
Gly Xaa Xaa Gly Xaa Xaa Gly Xaa Xaa Gly Xaa Xaa Gly
    530                 535                 540
Xaa Xaa Gly Xaa Xaa Gly Xaa Xaa Gly Xaa Xaa Gly Xaa
545                 550                 555                 560
Xaa Gly Xaa Xaa Gly Xaa Xaa Gly Xaa Xaa Gly Xaa Xaa
                565                 570                 575
Gly Xaa Xaa Gly Xaa Xaa Gly Xaa Xaa Gly Xaa Xaa Gly
        580                 585                 590
Xaa Xaa Gly Xaa Xaa Gly Xaa Xaa Gly Xaa Xaa Gly Xaa
    595                 600                 605
Xaa Gly Xaa Xaa Gly Xaa Xaa Gly Xaa Xaa Gly Xaa Xaa
    610                 615                 620
Gly Xaa Xaa Gly Xaa Xaa Gly Xaa Xaa Gly Xaa Xaa Gly
625                 630                 635                 640
Xaa Xaa Gly Xaa Xaa Gly Xaa Xaa Gly Xaa Xaa Gly Xaa
                645                 650                 655
Xaa Gly Xaa Xaa Gly Xaa Xaa Gly Xaa Xaa Gly Xaa Xaa
        660                 665                 670
Gly Xaa Xaa Gly Xaa Xaa Gly Xaa Xaa Gly Xaa Xaa Gly
    675                 680                 685
Xaa Xaa Gly Xaa Xaa Gly Xaa Xaa Gly Xaa Xaa Gly Xaa
    690                 695                 700
Xaa Gly Xaa Xaa Gly Xaa Xaa Gly Xaa Xaa Gly Xaa Xaa
705                 710                 715                 720
Gly Xaa Xaa Gly Xaa Xaa Gly Xaa Xaa Gly Xaa Xaa Gly
                725                 730                 735
Xaa Xaa Gly Xaa Xaa Gly Xaa Xaa Gly Xaa Xaa Gly Xaa
        740                 745                 750
Xaa Gly Xaa Xaa Gly Xaa Xaa Gly Xaa Xaa Gly Xaa Xaa
    755                 760                 765
Gly Xaa Xaa Gly Xaa Xaa Gly Xaa Xaa Gly Xaa Xaa Gly
    770                 775                 780
```

```
Xaa Xaa Gly Xaa Xaa Gly Xaa Gly Xaa Xaa Gly Xaa Xaa Gly Xaa
785                 790             795             800

Xaa Gly Xaa Xaa Gly Xaa Xaa Gly Xaa Xaa Gly Xaa Xaa Gly Xaa
        805             810             815

Gly Xaa Xaa Gly Xaa Xaa Gly Xaa Xaa Gly Xaa Xaa Gly Xaa Xaa Gly
            820             825             830

Xaa Xaa Gly Xaa Xaa Gly Xaa Xaa Gly Xaa Xaa Gly Xaa Xaa Gly Xaa
    835             840             845

Xaa Gly Xaa Xaa Gly Xaa Xaa Gly Xaa Xaa Gly Xaa Xaa Gly Xaa Xaa
    850             855             860

Gly Xaa Xaa Gly Xaa Xaa Gly Xaa Xaa Gly Xaa Xaa Gly Xaa Xaa Gly
865             870             875             880

Xaa Xaa Gly Xaa Xaa Gly Xaa Xaa Gly Xaa Xaa Gly Xaa Xaa Gly Xaa
            885             890             895

Xaa Gly Xaa Xaa Gly Xaa Xaa Gly Xaa Xaa Gly Xaa Xaa Gly Xaa Xaa
            900             905             910

Gly Xaa Xaa Gly Xaa Xaa Gly Xaa Xaa Gly Xaa Xaa Gly Xaa Xaa Gly
        915             920             925

Xaa Xaa Gly Xaa Xaa Gly Xaa Xaa Gly Xaa Xaa Gly Xaa Xaa Gly Xaa
    930             935             940

Xaa Gly Xaa Xaa Gly Xaa Xaa Gly Xaa Xaa Gly Xaa Xaa Gly Xaa Xaa
945             950             955             960

Gly Xaa Xaa Gly Xaa Xaa Gly Xaa Xaa Gly Xaa Xaa Gly Xaa Xaa Gly
            965             970             975

Xaa Xaa Gly Xaa Xaa Gly Xaa Xaa Gly Xaa Xaa Gly Xaa Xaa Gly Xaa
            980             985             990

Xaa Gly Xaa Xaa Gly Xaa Xaa Gly  Xaa Xaa Gly Xaa Xaa  Gly Xaa Xaa
        995             1000             1005

Gly Xaa  Xaa Gly Xaa Xaa Gly  Xaa Xaa Gly Xaa Xaa  Gly Xaa Xaa
        1010             1015             1020

Gly Xaa  Xaa Gly Xaa Xaa Gly  Xaa Xaa Gly Xaa Xaa  Gly Xaa Xaa
        1025             1030             1035

Gly Xaa  Xaa Gly Xaa Xaa Gly  Xaa Xaa Gly Xaa Xaa  Gly Xaa Xaa
        1040             1045             1050

Gly Xaa  Xaa Gly Xaa Xaa Gly  Xaa Xaa Gly Xaa Xaa  Gly Xaa Xaa
        1055             1060             1065

Gly Xaa  Xaa Gly Xaa Xaa Gly  Xaa Xaa Gly Xaa Xaa  Gly Xaa Xaa
        1070             1075             1080

Gly Xaa  Xaa Gly Xaa Xaa Gly  Xaa Xaa Gly Xaa Xaa  Gly Xaa Xaa
        1085             1090             1095

Gly Xaa  Xaa Gly Xaa Xaa Gly  Xaa Xaa Gly Xaa Xaa  Gly Xaa Xaa
        1100             1105             1110

Gly Xaa  Xaa Gly Xaa Xaa Gly  Xaa Xaa Gly Xaa Xaa  Gly Xaa Xaa
        1115             1120             1125

Gly Xaa  Xaa Gly Xaa Xaa Gly  Xaa Xaa Gly Xaa Xaa  Gly Xaa Xaa
        1130             1135             1140

Gly Xaa  Xaa Gly Xaa Xaa Gly  Xaa Xaa Gly Xaa Xaa  Gly Xaa Xaa
        1145             1150             1155

Gly Xaa  Xaa Gly Xaa Xaa Gly  Xaa Xaa Gly Xaa Xaa  Gly Xaa Xaa
        1160             1165             1170

Gly Xaa  Xaa Gly Xaa Xaa Gly  Xaa Xaa Gly Xaa Xaa  Gly Xaa Xaa
        1175             1180             1185
```

US 10,053,501 B2

179                                                                 180

-continued

Gly Xaa Xaa Gly Xaa Xaa Gly Xaa Xaa Gly Xaa Xaa Gly Xaa Xaa
    1190                1195                1200

Gly Xaa Xaa Gly Xaa Xaa Gly Xaa Xaa Gly Xaa Xaa Gly Xaa Xaa
    1205                1210                1215

Gly Xaa Xaa Gly Xaa Xaa Gly Xaa Xaa Gly Xaa Xaa Gly Xaa Xaa
    1220                1225                1230

Gly Xaa Xaa Gly Xaa Xaa Gly Xaa Xaa Gly Xaa Xaa Gly Xaa Xaa
    1235                1240                1245

Gly Xaa Xaa Gly Xaa Xaa Gly Xaa Xaa Gly Xaa Xaa Gly Xaa Xaa
    1250                1255                1260

Gly Xaa Xaa Gly Xaa Xaa Gly Xaa Xaa Gly Xaa Xaa Gly Xaa Xaa
    1265                1270                1275

Gly Xaa Xaa Gly Xaa Xaa Gly Xaa Xaa Gly Xaa Xaa Gly Xaa Xaa
    1280                1285                1290

Gly Xaa Xaa Gly Xaa Xaa Gly Xaa Xaa Gly Xaa Xaa Gly Xaa Xaa
    1295                1300                1305

Gly Xaa Xaa Gly Xaa Xaa Gly Xaa Xaa Gly Xaa Xaa Gly Xaa Xaa
    1310                1315                1320

Gly Xaa Xaa Gly Xaa Xaa Gly Xaa Xaa Gly Xaa Xaa Gly Xaa Xaa
    1325                1330                1335

Gly Xaa Xaa Gly Xaa Xaa Gly Xaa Xaa Gly Xaa Xaa Gly Xaa Xaa
    1340                1345                1350

Gly Xaa Xaa Gly Xaa Xaa Gly Xaa Xaa Gly Xaa Xaa Gly Xaa Xaa
    1355                1360                1365

Gly Xaa Xaa Gly Xaa Xaa Gly Xaa Xaa Gly Xaa Xaa Gly Xaa Xaa
    1370                1375                1380

Gly Xaa Xaa Gly Xaa Xaa Gly Xaa Xaa Gly Xaa Xaa Gly Xaa Xaa
    1385                1390                1395

Gly Xaa Xaa Gly Xaa Xaa Gly Xaa Xaa Gly Xaa Xaa Gly Xaa Xaa
    1400                1405                1410

Gly Xaa Xaa Gly Xaa Xaa Gly Xaa Xaa Gly Xaa Xaa Gly Xaa Xaa
    1415                1420                1425

Gly Xaa Xaa Gly Xaa Xaa Gly Xaa Xaa Gly Xaa Xaa Gly Xaa Xaa
    1430                1435                1440

Gly Xaa Xaa Gly Xaa Xaa Gly Xaa Xaa Gly Xaa Xaa Gly Xaa Xaa
    1445                1450                1455

Gly Xaa Xaa Gly Xaa Xaa Gly Xaa Xaa Gly Xaa Xaa Gly Xaa Xaa
    1460                1465                1470

Gly Xaa Xaa Gly Xaa Xaa Gly Xaa Xaa Gly Xaa Xaa Gly Xaa Xaa
    1475                1480                1485

Gly Xaa Xaa Gly Xaa Xaa Gly Xaa Xaa Gly Xaa Xaa Gly Xaa Xaa
    1490                1495                1500

Gly Xaa Xaa Gly Xaa Xaa Gly Xaa Xaa Gly Xaa Xaa Gly Xaa Xaa
    1505                1510                1515

Gly Xaa Xaa Gly Xaa Xaa Gly Xaa Xaa Gly Xaa Xaa Gly Xaa Xaa
    1520                1525                1530

Gly Xaa Xaa Gly Xaa Xaa Gly Xaa Xaa Gly Xaa Xaa Gly Xaa Xaa
    1535                1540                1545

Gly Xaa Xaa Gly Xaa Xaa Gly Xaa Xaa Gly Xaa Xaa Gly Xaa Xaa
    1550                1555                1560

Gly Xaa Xaa Gly Xaa Xaa Gly Xaa Xaa Gly Xaa Xaa Gly Xaa Xaa
    1565                1570                1575

Gly Xaa Xaa Gly Xaa Xaa Gly Xaa Xaa Gly Xaa Xaa Gly Xaa Xaa

```
              1580                1585                1590

Gly Xaa Xaa Gly Xaa Xaa Gly  Xaa Xaa Gly Xaa Xaa  Gly Xaa Xaa
         1595                1600                1605

Gly Xaa Xaa Gly Xaa Xaa Gly  Xaa Xaa Gly Xaa Xaa  Gly Xaa Xaa
         1610                1615                1620

Gly Xaa Xaa Gly Xaa Xaa Gly  Xaa Xaa Gly Xaa Xaa  Gly Xaa Xaa
         1625                1630                1635

Gly Xaa Xaa Gly Xaa Xaa Gly  Xaa Xaa Gly Xaa Xaa  Gly Xaa Xaa
         1640                1645                1650

Gly Xaa Xaa Gly Xaa Xaa Gly  Xaa Xaa Gly Xaa Xaa  Gly Xaa Xaa
         1655                1660                1665

Gly Xaa Xaa Gly Xaa Xaa Gly  Xaa Xaa Gly Xaa Xaa  Gly Xaa Xaa
         1670                1675                1680

Gly Xaa Xaa Gly Xaa Xaa Gly  Xaa Xaa Gly Xaa Xaa  Gly Xaa Xaa
         1685                1690                1695

Gly Xaa Xaa Gly Xaa Xaa Gly  Xaa Xaa Gly Xaa Xaa  Gly Xaa Xaa
         1700                1705                1710

Gly Xaa Xaa Gly Xaa Xaa Gly  Xaa Xaa Gly Xaa Xaa  Gly Xaa Xaa
         1715                1720                1725

Gly Xaa Xaa Gly Xaa Xaa Gly  Xaa Xaa Gly Xaa Xaa  Gly Xaa Xaa
         1730                1735                1740

Gly Xaa Xaa Gly Xaa Xaa Gly  Xaa Xaa Gly Xaa Xaa  Gly Xaa Xaa
         1745                1750                1755

Gly Xaa Xaa Gly Xaa Xaa Gly  Xaa Xaa Gly Xaa Xaa  Gly Xaa Xaa
         1760                1765                1770

Gly Xaa Xaa Gly Xaa Xaa Gly  Xaa Xaa Gly Xaa Xaa  Gly Xaa Xaa
         1775                1780                1785

Gly Xaa  Xaa Gly Xaa Xaa Gly  Xaa Xaa Gly Xaa Xaa
         1790                1795                1800

<210> SEQ ID NO 45
<211> LENGTH: 1050
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(21)
```

```
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
<222> LOCATION: (38)..(39)
<223> OTHER INFORMATION: Any amino acid
<220> FEATURE:
<221> NAME/KEY: MOD_RES
<222> LOCATION: (41)..(42)
<223> OTHER INFORMATION: Any amino acid
<220> FEATURE:
<221> NAME/KEY: MOD_RES
<222> LOCATION: (44)..(45)
<223> OTHER INFORMATION: Any amino acid
<220> FEATURE:
<221> NAME/KEY: MOD_RES
<222> LOCATION: (47)..(48)
<223> OTHER INFORMATION: Any amino acid
<220> FEATURE:
<221> NAME/KEY: MOD_RES
<222> LOCATION: (50)..(51)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(57)
<223> OTHER INFORMATION: Any amino acid
<220> FEATURE:
<221> NAME/KEY: MOD_RES
<222> LOCATION: (59)..(60)
<223> OTHER INFORMATION: Any amino acid
<220> FEATURE:
<221> NAME/KEY: MOD_RES
<222> LOCATION: (62)..(63)
<223> OTHER INFORMATION: Any amino acid
<220> FEATURE:
<221> NAME/KEY: MOD_RES
<222> LOCATION: (65)..(66)
<223> OTHER INFORMATION: Any amino acid
<220> FEATURE:
<221> NAME/KEY: MOD_RES
<222> LOCATION: (68)..(69)
<223> OTHER INFORMATION: Any amino acid
<220> FEATURE:
<221> NAME/KEY: MOD_RES
<222> LOCATION: (71)..(72)
<223> OTHER INFORMATION: Any amino acid
<220> FEATURE:
<221> NAME/KEY: MOD_RES
<222> LOCATION: (74)..(75)
<223> OTHER INFORMATION: Any amino acid
<220> FEATURE:
<221> NAME/KEY: MOD_RES
<222> LOCATION: (77)..(78)
<223> OTHER INFORMATION: Any amino acid
<220> FEATURE:
<221> NAME/KEY: MOD_RES
```

-continued

```
<222> LOCATION: (80)..(81)
<223> OTHER INFORMATION: Any amino acid
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (89)..(90)
<223> OTHER INFORMATION: Any amino acid
<220> FEATURE:
<221> NAME/KEY: MOD_RES
<222> LOCATION: (92)..(93)
<223> OTHER INFORMATION: Any amino acid
<220> FEATURE:
<221> NAME/KEY: MOD_RES
<222> LOCATION: (95)..(96)
<223> OTHER INFORMATION: Any amino acid
<220> FEATURE:
<221> NAME/KEY: MOD_RES
<222> LOCATION: (98)..(99)
<223> OTHER INFORMATION: Any amino acid
<220> FEATURE:
<221> NAME/KEY: MOD_RES
<222> LOCATION: (101)..(102)
<223> OTHER INFORMATION: Any amino acid
<220> FEATURE:
<221> NAME/KEY: MOD_RES
<222> LOCATION: (104)..(105)
<223> OTHER INFORMATION: Any amino acid
<220> FEATURE:
<221> NAME/KEY: MOD_RES
<222> LOCATION: (107)..(108)
<223> OTHER INFORMATION: Any amino acid
<220> FEATURE:
<221> NAME/KEY: MOD_RES
<222> LOCATION: (110)..(111)
<223> OTHER INFORMATION: Any amino acid
<220> FEATURE:
<221> NAME/KEY: MOD_RES
<222> LOCATION: (113)..(114)
<223> OTHER INFORMATION: Any amino acid
<220> FEATURE:
<221> NAME/KEY: MOD_RES
<222> LOCATION: (116)..(117)
<223> OTHER INFORMATION: Any amino acid
<220> FEATURE:
<221> NAME/KEY: MOD_RES
<222> LOCATION: (119)..(120)
<223> OTHER INFORMATION: Any amino acid
<220> FEATURE:
<221> NAME/KEY: MOD_RES
<222> LOCATION: (122)..(123)
<223> OTHER INFORMATION: Any amino acid
<220> FEATURE:
<221> NAME/KEY: MOD_RES
<222> LOCATION: (125)..(126)
<223> OTHER INFORMATION: Any amino acid
<220> FEATURE:
<221> NAME/KEY: MOD_RES
<222> LOCATION: (128)..(129)
<223> OTHER INFORMATION: Any amino acid
<220> FEATURE:
<221> NAME/KEY: MOD_RES
<222> LOCATION: (131)..(132)
<223> OTHER INFORMATION: Any amino acid
<220> FEATURE:
<221> NAME/KEY: MOD_RES
<222> LOCATION: (134)..(135)
<223> OTHER INFORMATION: Any amino acid
<220> FEATURE:
<221> NAME/KEY: MOD_RES
<222> LOCATION: (137)..(138)
<223> OTHER INFORMATION: Any amino acid
<220> FEATURE:
```

```
<221> NAME/KEY: MOD_RES
<222> LOCATION: (140)..(141)
<223> OTHER INFORMATION: Any amino acid
<220> FEATURE:
<221> NAME/KEY: MOD_RES
<222> LOCATION: (143)..(144)
<223> OTHER INFORMATION: Any amino acid
<220> FEATURE:
<221> NAME/KEY: MOD_RES
<222> LOCATION: (146)..(147)
<223> OTHER INFORMATION: Any amino acid
<220> FEATURE:
<221> NAME/KEY: MOD_RES
<222> LOCATION: (149)..(150)
<223> OTHER INFORMATION: Any amino acid
<220> FEATURE:
<221> NAME/KEY: MOD_RES
<222> LOCATION: (152)..(153)
<223> OTHER INFORMATION: Any amino acid
<220> FEATURE:
<221> NAME/KEY: MOD_RES
<222> LOCATION: (155)..(156)
<223> OTHER INFORMATION: Any amino acid
<220> FEATURE:
<221> NAME/KEY: MOD_RES
<222> LOCATION: (158)..(159)
<223> OTHER INFORMATION: Any amino acid
<220> FEATURE:
<221> NAME/KEY: MOD_RES
<222> LOCATION: (161)..(162)
<223> OTHER INFORMATION: Any amino acid
<220> FEATURE:
<221> NAME/KEY: MOD_RES
<222> LOCATION: (164)..(165)
<223> OTHER INFORMATION: Any amino acid
<220> FEATURE:
<221> NAME/KEY: MOD_RES
<222> LOCATION: (167)..(168)
<223> OTHER INFORMATION: Any amino acid
<220> FEATURE:
<221> NAME/KEY: MOD_RES
<222> LOCATION: (170)..(171)
<223> OTHER INFORMATION: Any amino acid
<220> FEATURE:
<221> NAME/KEY: MOD_RES
<222> LOCATION: (173)..(174)
<223> OTHER INFORMATION: Any amino acid
<220> FEATURE:
<221> NAME/KEY: MOD_RES
<222> LOCATION: (176)..(177)
<223> OTHER INFORMATION: Any amino acid
<220> FEATURE:
<221> NAME/KEY: MOD_RES
<222> LOCATION: (179)..(180)
<223> OTHER INFORMATION: Any amino acid
<220> FEATURE:
<221> NAME/KEY: MOD_RES
<222> LOCATION: (182)..(183)
<223> OTHER INFORMATION: Any amino acid
<220> FEATURE:
<221> NAME/KEY: MOD_RES
<222> LOCATION: (185)..(186)
<223> OTHER INFORMATION: Any amino acid
<220> FEATURE:
<221> NAME/KEY: MOD_RES
<222> LOCATION: (188)..(189)
<223> OTHER INFORMATION: Any amino acid
<220> FEATURE:
<221> NAME/KEY: MOD_RES
<222> LOCATION: (191)..(192)
<223> OTHER INFORMATION: Any amino acid
<220> FEATURE:
<221> NAME/KEY: MOD_RES
<222> LOCATION: (194)..(195)
<223> OTHER INFORMATION: Any amino acid
<220> FEATURE:
<221> NAME/KEY: MOD_RES
<222> LOCATION: (197)..(198)
<223> OTHER INFORMATION: Any amino acid
```

-continued

```
<220> FEATURE:
<221> NAME/KEY: MOD_RES
<222> LOCATION: (200)..(201)
<223> OTHER INFORMATION: Any amino acid
<220> FEATURE:
<221> NAME/KEY: MOD_RES
<222> LOCATION: (203)..(204)
<223> OTHER INFORMATION: Any amino acid
<220> FEATURE:
<221> NAME/KEY: MOD_RES
<222> LOCATION: (206)..(207)
<223> OTHER INFORMATION: Any amino acid
<220> FEATURE:
<221> NAME/KEY: MOD_RES
<222> LOCATION: (209)..(210)
<223> OTHER INFORMATION: Any amino acid
<220> FEATURE:
<221> NAME/KEY: MOD_RES
<222> LOCATION: (212)..(213)
<223> OTHER INFORMATION: Any amino acid
<220> FEATURE:
<221> NAME/KEY: MOD_RES
<222> LOCATION: (215)..(216)
<223> OTHER INFORMATION: Any amino acid
<220> FEATURE:
<221> NAME/KEY: MOD_RES
<222> LOCATION: (218)..(219)
<223> OTHER INFORMATION: Any amino acid
<220> FEATURE:
<221> NAME/KEY: MOD_RES
<222> LOCATION: (221)..(222)
<223> OTHER INFORMATION: Any amino acid
<220> FEATURE:
<221> NAME/KEY: MOD_RES
<222> LOCATION: (224)..(225)
<223> OTHER INFORMATION: Any amino acid
<220> FEATURE:
<221> NAME/KEY: MOD_RES
<222> LOCATION: (227)..(228)
<223> OTHER INFORMATION: Any amino acid
<220> FEATURE:
<221> NAME/KEY: MOD_RES
<222> LOCATION: (230)..(231)
<223> OTHER INFORMATION: Any amino acid
<220> FEATURE:
<221> NAME/KEY: MOD_RES
<222> LOCATION: (233)..(234)
<223> OTHER INFORMATION: Any amino acid
<220> FEATURE:
<221> NAME/KEY: MOD_RES
<222> LOCATION: (236)..(237)
<223> OTHER INFORMATION: Any amino acid
<220> FEATURE:
<221> NAME/KEY: MOD_RES
<222> LOCATION: (239)..(240)
<223> OTHER INFORMATION: Any amino acid
<220> FEATURE:
<221> NAME/KEY: MOD_RES
<222> LOCATION: (242)..(243)
<223> OTHER INFORMATION: Any amino acid
<220> FEATURE:
<221> NAME/KEY: MOD_RES
<222> LOCATION: (245)..(246)
<223> OTHER INFORMATION: Any amino acid
<220> FEATURE:
<221> NAME/KEY: MOD_RES
<222> LOCATION: (248)..(249)
<223> OTHER INFORMATION: Any amino acid
<220> FEATURE:
<221> NAME/KEY: MOD_RES
<222> LOCATION: (251)..(252)
<223> OTHER INFORMATION: Any amino acid
<220> FEATURE:
<221> NAME/KEY: MOD_RES
<222> LOCATION: (254)..(255)
<223> OTHER INFORMATION: Any amino acid
<220> FEATURE:
<221> NAME/KEY: MOD_RES
<222> LOCATION: (257)..(258)
```

-continued

```
<223> OTHER INFORMATION: Any amino acid
<220> FEATURE:
<221> NAME/KEY: MOD_RES
<222> LOCATION: (260)..(261)
<223> OTHER INFORMATION: Any amino acid
<220> FEATURE:
<221> NAME/KEY: MOD_RES
<222> LOCATION: (263)..(264)
<223> OTHER INFORMATION: Any amino acid
<220> FEATURE:
<221> NAME/KEY: MOD_RES
<222> LOCATION: (266)..(267)
<223> OTHER INFORMATION: Any amino acid
<220> FEATURE:
<221> NAME/KEY: MOD_RES
<222> LOCATION: (269)..(270)
<223> OTHER INFORMATION: Any amino acid
<220> FEATURE:
<221> NAME/KEY: MOD_RES
<222> LOCATION: (272)..(273)
<223> OTHER INFORMATION: Any amino acid
<220> FEATURE:
<221> NAME/KEY: MOD_RES
<222> LOCATION: (275)..(276)
<223> OTHER INFORMATION: Any amino acid
<220> FEATURE:
<221> NAME/KEY: MOD_RES
<222> LOCATION: (278)..(279)
<223> OTHER INFORMATION: Any amino acid
<220> FEATURE:
<221> NAME/KEY: MOD_RES
<222> LOCATION: (281)..(282)
<223> OTHER INFORMATION: Any amino acid
<220> FEATURE:
<221> NAME/KEY: MOD_RES
<222> LOCATION: (284)..(285)
<223> OTHER INFORMATION: Any amino acid
<220> FEATURE:
<221> NAME/KEY: MOD_RES
<222> LOCATION: (287)..(288)
<223> OTHER INFORMATION: Any amino acid
<220> FEATURE:
<221> NAME/KEY: MOD_RES
<222> LOCATION: (290)..(291)
<223> OTHER INFORMATION: Any amino acid
<220> FEATURE:
<221> NAME/KEY: MOD_RES
<222> LOCATION: (293)..(294)
<223> OTHER INFORMATION: Any amino acid
<220> FEATURE:
<221> NAME/KEY: MOD_RES
<222> LOCATION: (296)..(297)
<223> OTHER INFORMATION: Any amino acid
<220> FEATURE:
<221> NAME/KEY: MOD_RES
<222> LOCATION: (299)..(300)
<223> OTHER INFORMATION: Any amino acid
<220> FEATURE:
<221> NAME/KEY: MOD_RES
<222> LOCATION: (302)..(303)
<223> OTHER INFORMATION: Any amino acid
<220> FEATURE:
<221> NAME/KEY: MOD_RES
<222> LOCATION: (305)..(306)
<223> OTHER INFORMATION: Any amino acid
<220> FEATURE:
<221> NAME/KEY: MOD_RES
<222> LOCATION: (308)..(309)
<223> OTHER INFORMATION: Any amino acid
<220> FEATURE:
<221> NAME/KEY: MOD_RES
<222> LOCATION: (311)..(312)
<223> OTHER INFORMATION: Any amino acid
<220> FEATURE:
<221> NAME/KEY: MOD_RES
<222> LOCATION: (314)..(315)
<223> OTHER INFORMATION: Any amino acid
<220> FEATURE:
<221> NAME/KEY: MOD_RES
```

```
<222> LOCATION: (317)..(318)
<223> OTHER INFORMATION: Any amino acid
<220> FEATURE:
<221> NAME/KEY: MOD_RES
<222> LOCATION: (320)..(321)
<223> OTHER INFORMATION: Any amino acid
<220> FEATURE:
<221> NAME/KEY: MOD_RES
<222> LOCATION: (323)..(324)
<223> OTHER INFORMATION: Any amino acid
<220> FEATURE:
<221> NAME/KEY: MOD_RES
<222> LOCATION: (326)..(327)
<223> OTHER INFORMATION: Any amino acid
<220> FEATURE:
<221> NAME/KEY: MOD_RES
<222> LOCATION: (329)..(330)
<223> OTHER INFORMATION: Any amino acid
<220> FEATURE:
<221> NAME/KEY: MOD_RES
<222> LOCATION: (332)..(333)
<223> OTHER INFORMATION: Any amino acid
<220> FEATURE:
<221> NAME/KEY: MOD_RES
<222> LOCATION: (335)..(336)
<223> OTHER INFORMATION: Any amino acid
<220> FEATURE:
<221> NAME/KEY: MOD_RES
<222> LOCATION: (338)..(339)
<223> OTHER INFORMATION: Any amino acid
<220> FEATURE:
<221> NAME/KEY: MOD_RES
<222> LOCATION: (341)..(342)
<223> OTHER INFORMATION: Any amino acid
<220> FEATURE:
<221> NAME/KEY: MOD_RES
<222> LOCATION: (344)..(345)
<223> OTHER INFORMATION: Any amino acid
<220> FEATURE:
<221> NAME/KEY: MOD_RES
<222> LOCATION: (347)..(348)
<223> OTHER INFORMATION: Any amino acid
<220> FEATURE:
<221> NAME/KEY: MOD_RES
<222> LOCATION: (350)..(351)
<223> OTHER INFORMATION: Any amino acid
<220> FEATURE:
<221> NAME/KEY: MOD_RES
<222> LOCATION: (353)..354)
<223> OTHER INFORMATION: Any amino acid
<220> FEATURE:
<221> NAME/KEY: MOD_RES
<222> LOCATION: (356)..(357)
<223> OTHER INFORMATION: Any amino acid
<220> FEATURE:
<221> NAME/KEY: MOD_RES
<222> LOCATION: (359)..(360)
<223> OTHER INFORMATION: Any amino acid
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (365)..(366)
<223> OTHER INFORMATION: Any amino acid
<220> FEATURE:
<221> NAME/KEY: MOD_RES
<222> LOCATION: (368)..(369)
<223> OTHER INFORMATION: Any amino acid
<220> FEATURE:
<221> NAME/KEY: MOD_RES
<222> LOCATION: (371)..(372)
<223> OTHER INFORMATION: Any amino acid
<220> FEATURE:
<221> NAME/KEY: MOD_RES
<222> LOCATION: (374)..(375)
<223> OTHER INFORMATION: Any amino acid
<220> FEATURE:
```

-continued

```
<221> NAME/KEY: MOD_RES
<222> LOCATION: (377)..(378)
<223> OTHER INFORMATION: Any amino acid
<220> FEATURE:
<221> NAME/KEY: MOD_RES
<222> LOCATION: (380)..(381)
<223> OTHER INFORMATION: Any amino acid
<220> FEATURE:
<221> NAME/KEY: MOD_RES
<222> LOCATION: (383)..(384)
<223> OTHER INFORMATION: Any amino acid
<220> FEATURE:
<221> NAME/KEY: MOD_RES
<222> LOCATION: (386)..(387)
<223> OTHER INFORMATION: Any amino acid
<220> FEATURE:
<221> NAME/KEY: MOD_RES
<222> LOCATION: (389)..(390)
<223> OTHER INFORMATION: Any amino acid
<220> FEATURE:
<221> NAME/KEY: MOD_RES
<222> LOCATION: (392)..(393)
<223> OTHER INFORMATION: Any amino acid
<220> FEATURE:
<221> NAME/KEY: MOD_RES
<222> LOCATION: (395)..(396)
<223> OTHER INFORMATION: Any amino acid
<220> FEATURE:
<221> NAME/KEY: MOD_RES
<222> LOCATION: (398)..(399)
<223> OTHER INFORMATION: Any amino acid
<220> FEATURE:
<221> NAME/KEY: MOD_RES
<222> LOCATION: (401)..(402)
<223> OTHER INFORMATION: Any amino acid
<220> FEATURE:
<221> NAME/KEY: MOD_RES
<222> LOCATION: (404)..(405)
<223> OTHER INFORMATION: Any amino acid
<220> FEATURE:
<221> NAME/KEY: MOD_RES
<222> LOCATION: (407)..(408)
<223> OTHER INFORMATION: Any amino acid
<220> FEATURE:
<221> NAME/KEY: MOD_RES
<222> LOCATION: (410)..(411)
<223> OTHER INFORMATION: Any amino acid
<220> FEATURE:
<221> NAME/KEY: MOD_RES
<222> LOCATION: (413)..(414)
<223> OTHER INFORMATION: Any amino acid
<220> FEATURE:
<221> NAME/KEY: MOD_RES
<222> LOCATION: (416)..(417)
<223> OTHER INFORMATION: Any amino acid
<220> FEATURE:
<221> NAME/KEY: MOD_RES
<222> LOCATION: (419)..(420)
<223> OTHER INFORMATION: Any amino acid
<220> FEATURE:
<221> NAME/KEY: MOD_RES
<222> LOCATION: (422)..(423)
<223> OTHER INFORMATION: Any amino acid
<220> FEATURE:
<221> NAME/KEY: MOD_RES
<222> LOCATION: (425)..(426)
<223> OTHER INFORMATION: Any amino acid
<220> FEATURE:
<221> NAME/KEY: MOD_RES
<222> LOCATION: (428)..(429)
<223> OTHER INFORMATION: Any amino acid
<220> FEATURE:
<221> NAME/KEY: MOD_RES
<222> LOCATION: (431)..(432)
<223> OTHER INFORMATION: Any amino acid
<220> FEATURE:
<221> NAME/KEY: MOD_RES
<222> LOCATION: (434)..(435)
<223> OTHER INFORMATION: Any amino acid
```

-continued

```
<220> FEATURE:
<221> NAME/KEY: MOD_RES
<222> LOCATION: (437)..(438)
<223> OTHER INFORMATION: Any amino acid
<220> FEATURE:
<221> NAME/KEY: MOD_RES
<222> LOCATION: (440)..(441)
<223> OTHER INFORMATION: Any amino acid
<220> FEATURE:
<221> NAME/KEY: MOD_RES
<222> LOCATION: (443)..(444)
<223> OTHER INFORMATION: Any amino acid
<220> FEATURE:
<221> NAME/KEY: MOD_RES
<222> LOCATION: (446)..(447)
<223> OTHER INFORMATION: Any amino acid
<220> FEATURE:
<221> NAME/KEY: MOD_RES
<222> LOCATION: (449)..(450)
<223> OTHER INFORMATION: Any amino acid
<220> FEATURE:
<221> NAME/KEY: MOD_RES
<222> LOCATION: (452)..(453)
<223> OTHER INFORMATION: Any amino acid
<220> FEATURE:
<221> NAME/KEY: MOD_RES
<222> LOCATION: (455)..(456)
<223> OTHER INFORMATION: Any amino acid
<220> FEATURE:
<221> NAME/KEY: MOD_RES
<222> LOCATION: (458)..(459)
<223> OTHER INFORMATION: Any amino acid
<220> FEATURE:
<221> NAME/KEY: MOD_RES
<222> LOCATION: (461)..(462)
<223> OTHER INFORMATION: Any amino acid
<220> FEATURE:
<221> NAME/KEY: MOD_RES
<222> LOCATION: (464)..(465)
<223> OTHER INFORMATION: Any amino acid
<220> FEATURE:
<221> NAME/KEY: MOD_RES
<222> LOCATION: (467)..(468)
<223> OTHER INFORMATION: Any amino acid
<220> FEATURE:
<221> NAME/KEY: MOD_RES
<222> LOCATION: (470)..(471)
<223> OTHER INFORMATION: Any amino acid
<220> FEATURE:
<221> NAME/KEY: MOD_RES
<222> LOCATION: (473)..(474)
<223> OTHER INFORMATION: Any amino acid
<220> FEATURE:
<221> NAME/KEY: MOD_RES
<222> LOCATION: (476)..(477)
<223> OTHER INFORMATION: Any amino acid
<220> FEATURE:
<221> NAME/KEY: MOD_RES
<222> LOCATION: (479)..(480)
<223> OTHER INFORMATION: Any amino acid
<220> FEATURE:
<221> NAME/KEY: MOD_RES
<222> LOCATION: (482)..(483)
<223> OTHER INFORMATION: Any amino acid
<220> FEATURE:
<221> NAME/KEY: MOD_RES
<222> LOCATION: (485)..(486)
<223> OTHER INFORMATION: Any amino acid
<220> FEATURE:
<221> NAME/KEY: MOD_RES
<222> LOCATION: (488)..(489)
<223> OTHER INFORMATION: Any amino acid
<220> FEATURE:
<221> NAME/KEY: MOD_RES
<222> LOCATION: (491)..(492)
<223> OTHER INFORMATION: Any amino acid
<220> FEATURE:
<221> NAME/KEY: MOD_RES
<222> LOCATION: (494)..(495)
```

```
<223> OTHER INFORMATION: Any amino acid
<220> FEATURE:
<221> NAME/KEY: MOD_RES
<222> LOCATION: (497)..(498)
<223> OTHER INFORMATION: Any amino acid
<220> FEATURE:
<221> NAME/KEY: MOD_RES
<222> LOCATION: (500)..(501)
<223> OTHER INFORMATION: Any amino acid
<220> FEATURE:
<221> NAME/KEY: MOD_RES
<222> LOCATION: (503)..(504)
<223> OTHER INFORMATION: Any amino acid
<220> FEATURE:
<221> NAME/KEY: MOD_RES
<222> LOCATION: (506)..(507)
<223> OTHER INFORMATION: Any amino acid
<220> FEATURE:
<221> NAME/KEY: MOD_RES
<222> LOCATION: (509)..(510)
<223> OTHER INFORMATION: Any amino acid
<220> FEATURE:
<221> NAME/KEY: MOD_RES
<222> LOCATION: (512)..(513)
<223> OTHER INFORMATION: Any amino acid
<220> FEATURE:
<221> NAME/KEY: MOD_RES
<222> LOCATION: (515)..(516)
<223> OTHER INFORMATION: Any amino acid
<220> FEATURE:
<221> NAME/KEY: MOD_RES
<222> LOCATION: (518)..(519)
<223> OTHER INFORMATION: Any amino acid
<220> FEATURE:
<221> NAME/KEY: MOD_RES
<222> LOCATION: (521)..(522)
<223> OTHER INFORMATION: Any amino acid
<220> FEATURE:
<221> NAME/KEY: MOD_RES
<222> LOCATION: (524)..(525)
<223> OTHER INFORMATION: Any amino acid
<220> FEATURE:
<221> NAME/KEY: MOD_RES
<222> LOCATION: (527)..(528)
<223> OTHER INFORMATION: Any amino acid
<220> FEATURE:
<221> NAME/KEY: MOD_RES
<222> LOCATION: (530)..(531)
<223> OTHER INFORMATION: Any amino acid
<220> FEATURE:
<221> NAME/KEY: MOD_RES
<222> LOCATION: (533)..(534)
<223> OTHER INFORMATION: Any amino acid
<220> FEATURE:
<221> NAME/KEY: MOD_RES
<222> LOCATION: (536)..(537)
<223> OTHER INFORMATION: Any amino acid
<220> FEATURE:
<221> NAME/KEY: MOD_RES
<222> LOCATION: (539)..(540)
<223> OTHER INFORMATION: Any amino acid
<220> FEATURE:
<221> NAME/KEY: MOD_RES
<222> LOCATION: (542)..(543)
<223> OTHER INFORMATION: Any amino acid
<220> FEATURE:
<221> NAME/KEY: MOD_RES
<222> LOCATION: (545)..(546)
<223> OTHER INFORMATION: Any amino acid
<220> FEATURE:
<221> NAME/KEY: MOD_RES
<222> LOCATION: (548)..(549)
<223> OTHER INFORMATION: Any amino acid
<220> FEATURE:
<221> NAME/KEY: MOD_RES
<222> LOCATION: (551)..(552)
<223> OTHER INFORMATION: Any amino acid
<220> FEATURE:
<221> NAME/KEY: MOD_RES
```

```
<222> LOCATION: (554)..(555)
<223> OTHER INFORMATION: Any amino acid
<220> FEATURE:
<221> NAME/KEY: MOD_RES
<222> LOCATION: (557)..(558)
<223> OTHER INFORMATION: Any amino acid
<220> FEATURE:
<221> NAME/KEY: MOD_RES
<222> LOCATION: (560)..(561)
<223> OTHER INFORMATION: Any amino acid
<220> FEATURE:
<221> NAME/KEY: MOD_RES
<222> LOCATION: (563)..(564)
<223> OTHER INFORMATION: Any amino acid
<220> FEATURE:
<221> NAME/KEY: MOD_RES
<222> LOCATION: (566)..(567)
<223> OTHER INFORMATION: Any amino acid
<220> FEATURE:
<221> NAME/KEY: MOD_RES
<222> LOCATION: (569)..(570)
<223> OTHER INFORMATION: Any amino acid
<220> FEATURE:
<221> NAME/KEY: MOD_RES
<222> LOCATION: (572)..(573)
<223> OTHER INFORMATION: Any amino acid
<220> FEATURE:
<221> NAME/KEY: MOD_RES
<222> LOCATION: (575)..(576)
<223> OTHER INFORMATION: Any amino acid
<220> FEATURE:
<221> NAME/KEY: MOD_RES
<222> LOCATION: (578)..(579)
<223> OTHER INFORMATION: Any amino acid
<220> FEATURE:
<221> NAME/KEY: MOD_RES
<222> LOCATION: (581)..(582)
<223> OTHER INFORMATION: Any amino acid
<220> FEATURE:
<221> NAME/KEY: MOD_RES
<222> LOCATION: (584)..(585)
<223> OTHER INFORMATION: Any amino acid
<220> FEATURE:
<221> NAME/KEY: MOD_RES
<222> LOCATION: (587)..(588)
<223> OTHER INFORMATION: Any amino acid
<220> FEATURE:
<221> NAME/KEY: MOD_RES
<222> LOCATION: (590)..(591)
<223> OTHER INFORMATION: Any amino acid
<220> FEATURE:
<221> NAME/KEY: MOD_RES
<222> LOCATION: (593)..(594)
<223> OTHER INFORMATION: Any amino acid
<220> FEATURE:
<221> NAME/KEY: MOD_RES
<222> LOCATION: (596)..(597)
<223> OTHER INFORMATION: Any amino acid
<220> FEATURE:
<221> NAME/KEY: MOD_RES
<222> LOCATION: (599)..(600)
<223> OTHER INFORMATION: Any amino acid
<220> FEATURE:
<221> NAME/KEY: MOD_RES
<222> LOCATION: (602)..(603)
<223> OTHER INFORMATION: Any amino acid
<220> FEATURE:
<221> NAME/KEY: MOD_RES
<222> LOCATION: (605)..(606)
<223> OTHER INFORMATION: Any amino acid
<220> FEATURE:
<221> NAME/KEY: MOD_RES
<222> LOCATION: (608)..(609)
<223> OTHER INFORMATION: Any amino acid
<220> FEATURE:
<221> NAME/KEY: MOD_RES
<222> LOCATION: (611)..(612)
<223> OTHER INFORMATION: Any amino acid
<220> FEATURE:
```

```
<221> NAME/KEY: MOD_RES
<222> LOCATION: (614)..(615)
<223> OTHER INFORMATION: Any amino acid
<220> FEATURE:
<221> NAME/KEY: MOD_RES
<222> LOCATION: (617)..(618)
<223> OTHER INFORMATION: Any amino acid
<220> FEATURE:
<221> NAME/KEY: MOD_RES
<222> LOCATION: (620)..(621)
<223> OTHER INFORMATION: Any amino acid
<220> FEATURE:
<221> NAME/KEY: MOD_RES
<222> LOCATION: (623)..(624)
<223> OTHER INFORMATION: Any amino acid
<220> FEATURE:
<221> NAME/KEY: MOD_RES
<222> LOCATION: (626)..(627)
<223> OTHER INFORMATION: Any amino acid
<220> FEATURE:
<221> NAME/KEY: MOD_RES
<222> LOCATION: (629)..(630)
<223> OTHER INFORMATION: Any amino acid
<220> FEATURE:
<221> NAME/KEY: MOD_RES
<222> LOCATION: (632)..(633)
<223> OTHER INFORMATION: Any amino acid
<220> FEATURE:
<221> NAME/KEY: MOD_RES
<222> LOCATION: (635)..(636)
<223> OTHER INFORMATION: Any amino acid
<220> FEATURE:
<221> NAME/KEY: MOD_RES
<222> LOCATION: (638)..(639)
<223> OTHER INFORMATION: Any amino acid
<220> FEATURE:
<221> NAME/KEY: MOD_RES
<222> LOCATION: (641)..(642)
<223> OTHER INFORMATION: Any amino acid
<220> FEATURE:
<221> NAME/KEY: MOD_RES
<222> LOCATION: (644)..(645)
<223> OTHER INFORMATION: Any amino acid
<220> FEATURE:
<221> NAME/KEY: MOD_RES
<222> LOCATION: (647)..(648)
<223> OTHER INFORMATION: Any amino acid
<220> FEATURE:
<221> NAME/KEY: MOD_RES
<222> LOCATION: (650)..(651)
<223> OTHER INFORMATION: Any amino acid
<220> FEATURE:
<221> NAME/KEY: MOD_RES
<222> LOCATION: (653)..(654)
<223> OTHER INFORMATION: Any amino acid
<220> FEATURE:
<221> NAME/KEY: MOD_RES
<222> LOCATION: (656)..(657)
<223> OTHER INFORMATION: Any amino acid
<220> FEATURE:
<221> NAME/KEY: MOD_RES
<222> LOCATION: (659)..(660)
<223> OTHER INFORMATION: Any amino acid
<220> FEATURE:
<221> NAME/KEY: MOD_RES
<222> LOCATION: (662)..(663)
<223> OTHER INFORMATION: Any amino acid
<220> FEATURE:
<221> NAME/KEY: MOD_RES
<222> LOCATION: (665)..(666)
<223> OTHER INFORMATION: Any amino acid
<220> FEATURE:
<221> NAME/KEY: MOD_RES
<222> LOCATION: (668)..(669)
<223> OTHER INFORMATION: Any amino acid
<220> FEATURE:
<221> NAME/KEY: MOD_RES
<222> LOCATION: (671)..(672)
<223> OTHER INFORMATION: Any amino acid
```

-continued

```
<220> FEATURE:
<221> NAME/KEY: MOD_RES
<222> LOCATION: (674)..(675)
<223> OTHER INFORMATION: Any amino acid
<220> FEATURE:
<221> NAME/KEY: MOD_RES
<222> LOCATION: (677)..(678)
<223> OTHER INFORMATION: Any amino acid
<220> FEATURE:
<221> NAME/KEY: MOD_RES
<222> LOCATION: (680)..(681)
<223> OTHER INFORMATION: Any amino acid
<220> FEATURE:
<221> NAME/KEY: MOD_RES
<222> LOCATION: (683)..(684)
<223> OTHER INFORMATION: Any amino acid
<220> FEATURE:
<221> NAME/KEY: MOD_RES
<222> LOCATION: (686)..(687)
<223> OTHER INFORMATION: Any amino acid
<220> FEATURE:
<221> NAME/KEY: MOD_RES
<222> LOCATION: (689)..(690)
<223> OTHER INFORMATION: Any amino acid
<220> FEATURE:
<221> NAME/KEY: MOD_RES
<222> LOCATION: (692)..(693)
<223> OTHER INFORMATION: Any amino acid
<220> FEATURE:
<221> NAME/KEY: MOD_RES
<222> LOCATION: (695)..(696)
<223> OTHER INFORMATION: Any amino acid
<220> FEATURE:
<221> NAME/KEY: MOD_RES
<222> LOCATION: (698)..(699)
<223> OTHER INFORMATION: Any amino acid
<220> FEATURE:
<221> NAME/KEY: MOD_RES
<222> LOCATION: (701)..(702)
<223> OTHER INFORMATION: Any amino acid
<220> FEATURE:
<221> NAME/KEY: MOD_RES
<222> LOCATION: (704)..(705)
<223> OTHER INFORMATION: Any amino acid
<220> FEATURE:
<221> NAME/KEY: MOD_RES
<222> LOCATION: (707)..(708)
<223> OTHER INFORMATION: Any amino acid
<220> FEATURE:
<221> NAME/KEY: MOD_RES
<222> LOCATION: (710)..(711)
<223> OTHER INFORMATION: Any amino acid
<220> FEATURE:
<221> NAME/KEY: MOD_RES
<222> LOCATION: (713)..(714)
<223> OTHER INFORMATION: Any amino acid
<220> FEATURE:
<221> NAME/KEY: MOD_RES
<222> LOCATION: (716)..(717)
<223> OTHER INFORMATION: Any amino acid
<220> FEATURE:
<221> NAME/KEY: MOD_RES
<222> LOCATION: (719)..(720)
<223> OTHER INFORMATION: Any amino acid
<220> FEATURE:
<221> NAME/KEY: MOD_RES
<222> LOCATION: (722)..(723)
<223> OTHER INFORMATION: Any amino acid
<220> FEATURE:
<221> NAME/KEY: MOD_RES
<222> LOCATION: (725)..(726)
<223> OTHER INFORMATION: Any amino acid
<220> FEATURE:
<221> NAME/KEY: MOD_RES
<222> LOCATION: (728)..(729)
<223> OTHER INFORMATION: Any amino acid
<220> FEATURE:
<221> NAME/KEY: MOD_RES
<222> LOCATION: (731)..(732)
```

```
<223> OTHER INFORMATION: Any amino acid
<220> FEATURE:
<221> NAME/KEY: MOD_RES
<222> LOCATION: (734)..(735)
<223> OTHER INFORMATION: Any amino acid
<220> FEATURE:
<221> NAME/KEY: MOD_RES
<222> LOCATION: (737)..(738)
<223> OTHER INFORMATION: Any amino acid
<220> FEATURE:
<221> NAME/KEY: MOD_RES
<222> LOCATION: (740)..(741)
<223> OTHER INFORMATION: Any amino acid
<220> FEATURE:
<221> NAME/KEY: MOD_RES
<222> LOCATION: (743)..(744)
<223> OTHER INFORMATION: Any amino acid
<220> FEATURE:
<221> NAME/KEY: MOD_RES
<222> LOCATION: (746)..(747)
<223> OTHER INFORMATION: Any amino acid
<220> FEATURE:
<221> NAME/KEY: MOD_RES
<222> LOCATION: (749)..(750)
<223> OTHER INFORMATION: Any amino acid
<220> FEATURE:
<221> NAME/KEY: MOD_RES
<222> LOCATION: (752)..(753)
<223> OTHER INFORMATION: Any amino acid
<220> FEATURE:
<221> NAME/KEY: MOD_RES
<222> LOCATION: (755)..(756)
<223> OTHER INFORMATION: Any amino acid
<220> FEATURE:
<221> NAME/KEY: MOD_RES
<222> LOCATION: (758)..(759)
<223> OTHER INFORMATION: Any amino acid
<220> FEATURE:
<221> NAME/KEY: MOD_RES
<222> LOCATION: (761)..(762)
<223> OTHER INFORMATION: Any amino acid
<220> FEATURE:
<221> NAME/KEY: MOD_RES
<222> LOCATION: (764)..(765)
<223> OTHER INFORMATION: Any amino acid
<220> FEATURE:
<221> NAME/KEY: MOD_RES
<222> LOCATION: (767)..(768)
<223> OTHER INFORMATION: Any amino acid
<220> FEATURE:
<221> NAME/KEY: MOD_RES
<222> LOCATION: (770)..(771)
<223> OTHER INFORMATION: Any amino acid
<220> FEATURE:
<221> NAME/KEY: MOD_RES
<222> LOCATION: (773)..(774)
<223> OTHER INFORMATION: Any amino acid
<220> FEATURE:
<221> NAME/KEY: MOD_RES
<222> LOCATION: (776)..(777)
<223> OTHER INFORMATION: Any amino acid
<220> FEATURE:
<221> NAME/KEY: MOD_RES
<222> LOCATION: (779)..(780)
<223> OTHER INFORMATION: Any amino acid
<220> FEATURE:
<221> NAME/KEY: MOD_RES
<222> LOCATION: (782)..(783)
<223> OTHER INFORMATION: Any amino acid
<220> FEATURE:
<221> NAME/KEY: MOD_RES
<222> LOCATION: (785)..(786)
<223> OTHER INFORMATION: Any amino acid
<220> FEATURE:
<221> NAME/KEY: MOD_RES
<222> LOCATION: (788)..(789)
<223> OTHER INFORMATION: Any amino acid
<220> FEATURE:
<221> NAME/KEY: MOD_RES
```

```
<222> LOCATION: (791)..(792)
<223> OTHER INFORMATION: Any amino acid
<220> FEATURE:
<221> NAME/KEY: MOD_RES
<222> LOCATION: (794)..(795)
<223> OTHER INFORMATION: Any amino acid
<220> FEATURE:
<221> NAME/KEY: MOD_RES
<222> LOCATION: (797)..(798)
<223> OTHER INFORMATION: Any amino acid
<220> FEATURE:
<221> NAME/KEY: MOD_RES
<222> LOCATION: (800)..(801)
<223> OTHER INFORMATION: Any amino acid
<220> FEATURE:
<221> NAME/KEY: MOD_RES
<222> LOCATION: (803)..(804)
<223> OTHER INFORMATION: Any amino acid
<220> FEATURE:
<221> NAME/KEY: MOD_RES
<222> LOCATION: (806)..(807)
<223> OTHER INFORMATION: Any amino acid
<220> FEATURE:
<221> NAME/KEY: MOD_RES
<222> LOCATION: (809)..(810)
<223> OTHER INFORMATION: Any amino acid
<220> FEATURE:
<221> NAME/KEY: MOD_RES
<222> LOCATION: (812)..(813)
<223> OTHER INFORMATION: Any amino acid
<220> FEATURE:
<221> NAME/KEY: MOD_RES
<222> LOCATION: (815)..(816)
<223> OTHER INFORMATION: Any amino acid
<220> FEATURE:
<221> NAME/KEY: MOD_RES
<222> LOCATION: (818)..(819)
<223> OTHER INFORMATION: Any amino acid
<220> FEATURE:
<221> NAME/KEY: MOD_RES
<222> LOCATION: (821)..(822)
<223> OTHER INFORMATION: Any amino acid
<220> FEATURE:
<221> NAME/KEY: MOD_RES
<222> LOCATION: (824)..(825)
<223> OTHER INFORMATION: Any amino acid
<220> FEATURE:
<221> NAME/KEY: MOD_RES
<222> LOCATION: (827)..(828)
<223> OTHER INFORMATION: Any amino acid
<220> FEATURE:
<221> NAME/KEY: MOD_RES
<222> LOCATION: (830)..(831)
<223> OTHER INFORMATION: Any amino acid
<220> FEATURE:
<221> NAME/KEY: MOD_RES
<222> LOCATION: (833)..(834)
<223> OTHER INFORMATION: Any amino acid
<220> FEATURE:
<221> NAME/KEY: MOD_RES
<222> LOCATION: (836)..(837)
<223> OTHER INFORMATION: Any amino acid
<220> FEATURE:
<221> NAME/KEY: MOD_RES
<222> LOCATION: (839)..(840)
<223> OTHER INFORMATION: Any amino acid
<220> FEATURE:
<221> NAME/KEY: MOD_RES
<222> LOCATION: (842)..(843)
<223> OTHER INFORMATION: Any amino acid
<220> FEATURE:
<221> NAME/KEY: MOD_RES
<222> LOCATION: (845)..(846)
<223> OTHER INFORMATION: Any amino acid
<220> FEATURE:
<221> NAME/KEY: MOD_RES
<222> LOCATION: (848)..(849)
<223> OTHER INFORMATION: Any amino acid
<220> FEATURE:
```

```
<221> NAME/KEY: MOD_RES
<222> LOCATION: (851)..(852)
<223> OTHER INFORMATION: Any amino acid
<220> FEATURE:
<221> NAME/KEY: MOD_RES
<222> LOCATION: (854)..(855)
<223> OTHER INFORMATION: Any amino acid
<220> FEATURE:
<221> NAME/KEY: MOD_RES
<222> LOCATION: (857)..(858)
<223> OTHER INFORMATION: Any amino acid
<220> FEATURE:
<221> NAME/KEY: MOD_RES
<222> LOCATION: (860)..(861)
<223> OTHER INFORMATION: Any amino acid
<220> FEATURE:
<221> NAME/KEY: MOD_RES
<222> LOCATION: (863)..(864)
<223> OTHER INFORMATION: Any amino acid
<220> FEATURE:
<221> NAME/KEY: MOD_RES
<222> LOCATION: (866)..(867)
<223> OTHER INFORMATION: Any amino acid
<220> FEATURE:
<221> NAME/KEY: MOD_RES
<222> LOCATION: (869)..(870)
<223> OTHER INFORMATION: Any amino acid
<220> FEATURE:
<221> NAME/KEY: MOD_RES
<222> LOCATION: (872)..(873)
<223> OTHER INFORMATION: Any amino acid
<220> FEATURE:
<221> NAME/KEY: MOD_RES
<222> LOCATION: (875)..(876)
<223> OTHER INFORMATION: Any amino acid
<220> FEATURE:
<221> NAME/KEY: MOD_RES
<222> LOCATION: (878)..(879)
<223> OTHER INFORMATION: Any amino acid
<220> FEATURE:
<221> NAME/KEY: MOD_RES
<222> LOCATION: (881)..(882)
<223> OTHER INFORMATION: Any amino acid
<220> FEATURE:
<221> NAME/KEY: MOD_RES
<222> LOCATION: (884)..(885)
<223> OTHER INFORMATION: Any amino acid
<220> FEATURE:
<221> NAME/KEY: MOD_RES
<222> LOCATION: (887)..(888)
<223> OTHER INFORMATION: Any amino acid
<220> FEATURE:
<221> NAME/KEY: MOD_RES
<222> LOCATION: (890)..(891)
<223> OTHER INFORMATION: Any amino acid
<220> FEATURE:
<221> NAME/KEY: MOD_RES
<222> LOCATION: (893)..(894)
<223> OTHER INFORMATION: Any amino acid
<220> FEATURE:
<221> NAME/KEY: MOD_RES
<222> LOCATION: (896)..(897)
<223> OTHER INFORMATION: Any amino acid
<220> FEATURE:
<221> NAME/KEY: MOD_RES
<222> LOCATION: (899)..(900)
<223> OTHER INFORMATION: Any amino acid
<220> FEATURE:
<221> NAME/KEY: MOD_RES
<222> LOCATION: (902)..(903)
<223> OTHER INFORMATION: Any amino acid
<220> FEATURE:
<221> NAME/KEY: MOD_RES
<222> LOCATION: (905)..(906)
<223> OTHER INFORMATION: Any amino acid
<220> FEATURE:
<221> NAME/KEY: MOD_RES
<222> LOCATION: (908)..(909)
<223> OTHER INFORMATION: Any amino acid
```

```
<220> FEATURE:
<221> NAME/KEY: MOD_RES
<222> LOCATION: (911)..(912)
<223> OTHER INFORMATION: Any amino acid
<220> FEATURE:
<221> NAME/KEY: MOD_RES
<222> LOCATION: (914)..(915)
<223> OTHER INFORMATION: Any amino acid
<220> FEATURE:
<221> NAME/KEY: MOD_RES
<222> LOCATION: (917)..(918)
<223> OTHER INFORMATION: Any amino acid
<220> FEATURE:
<221> NAME/KEY: MOD_RES
<222> LOCATION: (920)..(921)
<223> OTHER INFORMATION: Any amino acid
<220> FEATURE:
<221> NAME/KEY: MOD_RES
<222> LOCATION: (923)..(924)
<223> OTHER INFORMATION: Any amino acid
<220> FEATURE:
<221> NAME/KEY: MOD_RES
<222> LOCATION: (926)..(927)
<223> OTHER INFORMATION: Any amino acid
<220> FEATURE:
<221> NAME/KEY: MOD_RES
<222> LOCATION: (929)..(930)
<223> OTHER INFORMATION: Any amino acid
<220> FEATURE:
<221> NAME/KEY: MOD_RES
<222> LOCATION: (932)..(933)
<223> OTHER INFORMATION: Any amino acid
<220> FEATURE:
<221> NAME/KEY: MOD_RES
<222> LOCATION: (935)..(936)
<223> OTHER INFORMATION: Any amino acid
<220> FEATURE:
<221> NAME/KEY: MOD_RES
<222> LOCATION: (938)..(939)
<223> OTHER INFORMATION: Any amino acid
<220> FEATURE:
<221> NAME/KEY: MOD_RES
<222> LOCATION: (941)..(942)
<223> OTHER INFORMATION: Any amino acid
<220> FEATURE:
<221> NAME/KEY: MOD_RES
<222> LOCATION: (944)..(945)
<223> OTHER INFORMATION: Any amino acid
<220> FEATURE:
<221> NAME/KEY: MOD_RES
<222> LOCATION: (947)..(948)
<223> OTHER INFORMATION: Any amino acid
<220> FEATURE:
<221> NAME/KEY: MOD_RES
<222> LOCATION: (950)..(951)
<223> OTHER INFORMATION: Any amino acid
<220> FEATURE:
<221> NAME/KEY: MOD_RES
<222> LOCATION: (953)..(954)
<223> OTHER INFORMATION: Any amino acid
<220> FEATURE:
<221> NAME/KEY: MOD_RES
<222> LOCATION: (956)..(957)
<223> OTHER INFORMATION: Any amino acid
<220> FEATURE:
<221> NAME/KEY: MOD_RES
<222> LOCATION: (959)..(960)
<223> OTHER INFORMATION: Any amino acid
<220> FEATURE:
<221> NAME/KEY: MOD_RES
<222> LOCATION: (962)..(963)
<223> OTHER INFORMATION: Any amino acid
<220> FEATURE:
<221> NAME/KEY: MOD_RES
<222> LOCATION: (965)..(966)
<223> OTHER INFORMATION: Any amino acid
<220> FEATURE:
<221> NAME/KEY: MOD_RES
<222> LOCATION: (968)..(969)
```

```
<223> OTHER INFORMATION: Any amino acid
<220> FEATURE:
<221> NAME/KEY: MOD_RES
<222> LOCATION: (971)..(972)
<223> OTHER INFORMATION: Any amino acid
<220> FEATURE:
<221> NAME/KEY: MOD_RES
<222> LOCATION: (974)..(975)
<223> OTHER INFORMATION: Any amino acid
<220> FEATURE:
<221> NAME/KEY: MOD_RES
<222> LOCATION: (977)..(978)
<223> OTHER INFORMATION: Any amino acid
<220> FEATURE:
<221> NAME/KEY: MOD_RES
<222> LOCATION: (980)..(981)
<223> OTHER INFORMATION: Any amino acid
<220> FEATURE:
<221> NAME/KEY: MOD_RES
<222> LOCATION: (983)..(984)
<223> OTHER INFORMATION: Any amino acid
<220> FEATURE:
<221> NAME/KEY: MOD_RES
<222> LOCATION: (986)..(987)
<223> OTHER INFORMATION: Any amino acid
<220> FEATURE:
<221> NAME/KEY: MOD_RES
<222> LOCATION: (989)..(990)
<223> OTHER INFORMATION: Any amino acid
<220> FEATURE:
<221> NAME/KEY: MOD_RES
<222> LOCATION: (992)..(993)
<223> OTHER INFORMATION: Any amino acid
<220> FEATURE:
<221> NAME/KEY: MOD_RES
<222> LOCATION: (995)..(996)
<223> OTHER INFORMATION: Any amino acid
<220> FEATURE:
<221> NAME/KEY: MOD_RES
<222> LOCATION: (998)..(999)
<223> OTHER INFORMATION: Any amino acid
<220> FEATURE:
<221> NAME/KEY: MOD_RES
<222> LOCATION: (1001)..(1002)
<223> OTHER INFORMATION: Any amino acid
<220> FEATURE:
<221> NAME/KEY: MOD_RES
<222> LOCATION: (1004)..(1005)
<223> OTHER INFORMATION: Any amino acid
<220> FEATURE:
<221> NAME/KEY: MOD_RES
<222> LOCATION: (1007)..(1008)
<223> OTHER INFORMATION: Any amino acid
<220> FEATURE:
<221> NAME/KEY: MOD_RES
<222> LOCATION: (1010)..(1011)
<223> OTHER INFORMATION: Any amino acid
<220> FEATURE:
<221> NAME/KEY: MOD_RES
<222> LOCATION: (1013)..(1014)
<223> OTHER INFORMATION: Any amino acid
<220> FEATURE:
<221> NAME/KEY: MOD_RES
<222> LOCATION: (1016)..(1017)
<223> OTHER INFORMATION: Any amino acid
<220> FEATURE:
<221> NAME/KEY: MOD_RES
<222> LOCATION: (1019)..(1020)
<223> OTHER INFORMATION: Any amino acid
<220> FEATURE:
<221> NAME/KEY: MOD_RES
<222> LOCATION: (1022)..(1023)
<223> OTHER INFORMATION: Any amino acid
<220> FEATURE:
<221> NAME/KEY: MOD_RES
<222> LOCATION: (1025)..(1026)
<223> OTHER INFORMATION: Any amino acid
<220> FEATURE:
<221> NAME/KEY: MOD_RES
```

```
<222> LOCATION: (1028)..(1029)
<223> OTHER INFORMATION: Any amino acid
<220> FEATURE:
<221> NAME/KEY: MOD_RES
<222> LOCATION: (1031)..(1032)
<223> OTHER INFORMATION: Any amino acid
<220> FEATURE:
<221> NAME/KEY: MOD_RES
<222> LOCATION: (1034)..(1035)
<223> OTHER INFORMATION: Any amino acid
<220> FEATURE:
<221> NAME/KEY: MOD_RES
<222> LOCATION: (1037)..(1038)
<223> OTHER INFORMATION: Any amino acid
<220> FEATURE:
<221> NAME/KEY: MOD_RES
<222> LOCATION: (1040)..(1041)
<223> OTHER INFORMATION: Any amino acid
<220> FEATURE:
<221> NAME/KEY: MOD_RES
<222> LOCATION: (1043)..(1044)
<223> OTHER INFORMATION: Any amino acid
<220> FEATURE:
<221> NAME/KEY: MOD_RES
<222> LOCATION: (1046)..(1047)
<223> OTHER INFORMATION: Any amino acid
<220> FEATURE:
<221> NAME/KEY: MOD_RES
<222> LOCATION: (1049)..(1050)
<223> OTHER INFORMATION: Any amino acid
<220> FEATURE:
<221> NAME/KEY: MISC_FEATURE
<222> LOCATION: (1)..(1050)
<223> OTHER INFORMATION: This sequence may encompass 1 to 350 "Gly Xaa
      Xaa" repeating units, wherein some positions may be absent
<220> FEATURE:
<223> OTHER INFORMATION: See specification as filed for detailed
      description of substitutions and preferred embodiments

<400> SEQUENCE: 45

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
            85                  90                  95

Gly Xaa Xaa Gly Xaa Xaa Gly Xaa Xaa Gly Xaa Xaa Gly Xaa Xaa Gly
        100                 105                 110

Xaa Xaa Gly Xaa Xaa Gly Xaa Xaa Gly Xaa Xaa Gly Xaa Xaa Gly Xaa
    115                 120                 125

Xaa Gly Xaa Xaa Gly Xaa Xaa Gly Xaa Xaa Gly Xaa Xaa Gly Xaa Xaa
130                 135                 140

Gly Xaa Xaa Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa Xaa Gly Xaa
            165                 170                 175

Xaa Gly Xaa Xaa Gly Xaa Xaa Gly Xaa Xaa Gly Xaa Xaa Gly Xaa Xaa
        180                 185                 190

Gly Xaa Xaa Gly Xaa Xaa Gly Xaa Xaa Gly Xaa Xaa Gly Xaa Xaa Gly
    195                 200                 205
```

```
Xaa Xaa Gly Xaa Xaa Gly Xaa Gly Xaa Xaa Gly Xaa Xaa Gly Xaa
        210                 215                 220

Xaa Gly Xaa Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa Xaa Gly Xaa
        260                 265                 270

Xaa Gly Xaa Xaa Gly Xaa Xaa Gly Xaa Xaa Gly Xaa Xaa Gly Xaa Xaa
        275                 280                 285

Gly Xaa Xaa Gly Xaa Xaa Gly Xaa Xaa Gly Xaa Xaa Gly Xaa Xaa Gly
290                 295                 300

Xaa Xaa Gly Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly Xaa Xaa Gly
        340                 345                 350

Xaa Xaa Gly Xaa Xaa Gly Xaa Xaa Gly Xaa Xaa Gly Xaa Xaa Gly Xaa
        355                 360                 365

Xaa Gly Xaa Xaa Gly Xaa Xaa Gly Xaa Xaa Gly Xaa Xaa Gly Xaa Xaa
370                 375                 380

Gly Xaa Xaa Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa Gly Xaa Xaa
        420                 425                 430

Gly Xaa Xaa Gly Xaa Xaa Gly Xaa Xaa Gly Xaa Xaa Gly Xaa Xaa Gly
        435                 440                 445

Xaa Xaa Gly Xaa Xaa Gly Xaa Xaa Gly Xaa Xaa Gly Xaa Xaa Gly Xaa
450                 455                 460

Xaa Gly Xaa Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa Xaa Gly Xaa
        500                 505                 510

Xaa Gly Xaa Xaa Gly Xaa Xaa Gly Xaa Xaa Gly Xaa Xaa Gly Xaa Xaa
        515                 520                 525

Gly Xaa Xaa Gly Xaa Xaa Gly Xaa Xaa Gly Xaa Xaa Gly Xaa Xaa Gly
530                 535                 540

Xaa Xaa Gly Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly Xaa Xaa Gly Xaa Xaa
            565                 570                 575

Gly Xaa Xaa Gly Xaa Xaa Gly Xaa Xaa Gly Xaa Xaa Gly Xaa Xaa Gly
        580                 585                 590

Xaa Xaa Gly Xaa Xaa Gly Xaa Xaa Gly Xaa Xaa Gly Xaa Xaa Gly Xaa
        595                 600                 605

Xaa Gly Xaa Xaa Gly Xaa Xaa Gly Xaa Xaa Gly Xaa Xaa Gly Xaa Xaa
        610                 615                 620
```

-continued

```
Gly Xaa Xaa Gly Xaa Xaa Gly Xaa Xaa Gly Xaa Xaa Gly
625                 630                 635                 640

Xaa Xaa Gly Xaa Xaa Gly Xaa Xaa Gly Xaa Xaa Gly Xaa
            645                 650                 655

Xaa Gly Xaa Xaa Gly Xaa Xaa Gly Xaa Xaa Gly Xaa Xaa
        660                 665                 670

Gly Xaa Xaa Gly Xaa Xaa Gly Xaa Xaa Gly Xaa Xaa Gly
            675                 680                 685

Xaa Xaa Gly Xaa Xaa Gly Xaa Xaa Gly Xaa Xaa Gly Xaa
690                 695                 700

Xaa Gly Xaa Xaa Gly Xaa Xaa Gly Xaa Xaa Gly Xaa Xaa
705                 710                 715                 720

Gly Xaa Xaa Gly Xaa Xaa Gly Xaa Xaa Gly Xaa Xaa Gly
            725                 730                 735

Xaa Xaa Gly Xaa Xaa Gly Xaa Xaa Gly Xaa Xaa Gly Xaa
            740                 745                 750

Xaa Gly Xaa Xaa Gly Xaa Xaa Gly Xaa Xaa Gly Xaa Xaa
        755                 760                 765

Gly Xaa Xaa Gly Xaa Xaa Gly Xaa Xaa Gly Xaa Xaa Gly
770                 775                 780

Xaa Xaa Gly Xaa Xaa Gly Xaa Xaa Gly Xaa Xaa Gly Xaa
785                 790                 795                 800

Xaa Gly Xaa Xaa Gly Xaa Xaa Gly Xaa Xaa Gly Xaa Xaa
            805                 810                 815

Gly Xaa Xaa Gly Xaa Xaa Gly Xaa Xaa Gly Xaa Xaa Gly
            820                 825                 830

Xaa Xaa Gly Xaa Xaa Gly Xaa Xaa Gly Xaa Xaa Gly Xaa
        835                 840                 845

Xaa Gly Xaa Xaa Gly Xaa Xaa Gly Xaa Xaa Gly Xaa Xaa
850                 855                 860

Gly Xaa Xaa Gly Xaa Xaa Gly Xaa Xaa Gly Xaa Xaa Gly
865                 870                 875                 880

Xaa Xaa Gly Xaa Xaa Gly Xaa Xaa Gly Xaa Xaa Gly Xaa
            885                 890                 895

Xaa Gly Xaa Xaa Gly Xaa Xaa Gly Xaa Xaa Gly Xaa Xaa
            900                 905                 910

Gly Xaa Xaa Gly Xaa Xaa Gly Xaa Xaa Gly Xaa Xaa Gly
        915                 920                 925

Xaa Xaa Gly Xaa Xaa Gly Xaa Xaa Gly Xaa Xaa Gly Xaa
930                 935                 940

Xaa Gly Xaa Xaa Gly Xaa Xaa Gly Xaa Xaa Gly Xaa Xaa
945                 950                 955                 960

Gly Xaa Xaa Gly Xaa Xaa Gly Xaa Xaa Gly Xaa Xaa Gly
            965                 970                 975

Xaa Xaa Gly Xaa Xaa Gly Xaa Xaa Gly Xaa Xaa Gly Xaa
            980                 985                 990

Xaa Gly Xaa Xaa Gly Xaa Xaa Gly Xaa Xaa Gly Xaa Xaa
        995                 1000                1005

Gly Xaa Xaa Gly Xaa Xaa Gly Xaa Xaa Gly Xaa Xaa Gly Xaa
    1010                1015                1020

Gly Xaa Xaa Gly Xaa Xaa Gly Xaa Xaa Gly Xaa Xaa Gly Xaa Xaa
    1025                1030                1035

Gly Xaa Xaa Gly Xaa Xaa Gly Xaa Xaa Gly Xaa Xaa
```

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Gly Ala Pro Gly Ala Pro Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Pro Gly Pro Pro Gly Ala
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Ala Gly Gly Lys Gly Asp Ala Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Pro Pro Gly Pro Pro Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 51

Gly Gly Lys Gly Asp Ala Gly Ala Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Pro Pro Gly Pro Pro
1               5
```

PURIFICATION OF TRIPLE HELICAL PROTEINS

CROSS REFERENCE TO OTHER APPLICATIONS

All publications, patents, patent applications and other references cited herein are incorporated by reference in their entirety as if each individual publication, patent, patent application or other reference were specifically and individually indicated to be incorporated by reference.

This application is a U.S. National Stage under 35 USC 371 patent application, claiming priority to Serial No. PCT/AU2014/000303, filed on 21 Mar. 2014, which, claims priority from Australian Patent Application No. 2013900990 entitled "Purification of triple helical proteins" filed on 21 Mar. 2013. The entirety of both is hereby incorporated by reference.

SEQUENCE LISTING

This application is filed together with a Sequence Listing in electronic form. The entire contents of the Sequence Listing are hereby incorporated by reference. The ASCII file, created on Sep. 21, 2015, is named C64A-024728US-PCT SL.txt and is 178,822 bytes in size.

FIELD OF THE DISCLOSURE

The present invention relates to a method for purifying triple-helical or collagen-like proteins recombinantly produced from a bacterial, yeast or plant host cell.

BACKGROUND

Collagens are the major structural proteins in the extracellular matrix of animals and are defined by a characteristic triple-helix structure that requires a $(Gly-Xaa-Yaa)_n$ repeating sequence. The amino acids found in the Xaa and Yaa positions are frequently proline, where Pro in the Yaa position is post-translationally modified to hydroxyproline (Hyp) which enhances triple-helical stability. In humans, a family of at least 28 collagen types is present, each with type-specific biological and structural functions. The triple helical motif is also present in other proteins, such as macrophage scavenger receptors, collectins and C1q.

The most abundant collagens are the interstitial, fibril-forming collagens, particularly type I collagen. These collagens form the major tissue structures in animals through forming fibre bundle networks that are stabilized by specific cross-links to give stability and strength to the tissues. In contrast to the 'major' fibril forming collagens (types I, II and III) the 'minor' collagens are generally less broadly distributed and are typically found in particular tissue locations where the minor collagen may be a significant and critical component; e.g., type X collagen in hypertrophic cartilage or the type IV collagen in basement membranes.

Collagen has been shown to be safe and effective in a variety of medical products in various clinical applications (Ramshaw et al, J Materials Science, Materials in Science, (2009), 20(1) pg 3-8). For medical applications, collagen is generally used in two distinct formats. In one, intact tissue is used after chemical stabilisation, such as glutaraldehyde fixed porcine heart valves, for use in aortic valve replacement. The other is through preparation of purified soluble collagen which has been reconstituted into various products, such as dry, stabilised sheets or extruded fibres useful for wound dressings, adhesion barriers or devices for meniscal repair, with the processing giving the desired shape or form for the product. If necessary, the collagen device can be stabilised, either by chemical fixation, e.g., glutaraldehyde, or by a physical method e.g., dehydrothermal cross-linking. Purified soluble collagen has also been used extensively as a collagen paste for soft tissue augmentation and also for treatment of urinary incontinence. Reconstituted products are characterised by a high biochemical purity associated with low immunogenicity, controlled turnover, often over short time periods, controlled porosity and retention of cell-matrix interactions that are important in biological functions in tissues.

In order to purify collagen from animal collagenous tissues, typical methodologies include an initial digestion and solubilisation of the tissue through the use of an enzyme digestion step that removes the cross-linked regions while leaving the triple-helix intact. The solubilised collagen can then be purified to remove potential immunogenic contaminants. U.S. Pat. No. 6,548,077 for example describes a preparation of collagen from tissues involving contacting collagen with a first proteolytic enzyme followed by a reducing agent and a second proteolytic enzyme.

Addad et al (Mar. Drugs (2011), 9(6), 967-983) describe purifying collagen from jelly fish using acid-pepsin solubilisation of the tissue extract. However, in order to obtain a stable and useful final product a crosslinking step was required. Treatment with acid, and acetic acid in particular, leads to the swelling of tissues, and after pepsin digestion, gives a soluble collagen. The resultant soluble collagen product would be a weak non fibrous material that may need reconstituting into an insoluble format for many medical applications.

Alternative published methods include grinding the natural animal tissue that is rich in collagen to very fine particles that can be washed clean of impurities, either before or after processing into a useful medical material.

The majority of commercial quantities of collagen have been derived from animals such as bovine sources but with the concern of transmissible diseases, especially bovine spongiform encephalopathy ('mad cow disease') research effort has been spent on producing recombinant forms of collagen. Moreover, animal-derived collagen is limited in that extracted collagens cannot be designed and modified to enhance or change specific biological properties. Collagens are subject to extensive post-translational modifications both prior to and after deposition in the extracellular matrix. In particular, the fibrillar collagens are subjected to intra- and inter-molecular cross-linking that continues over the life of the molecule in the extracellular space. Thus, the amount of cross-linking present in collagens is influenced by, among other things, the age and physiology of the tissue from which the collagen is harvested. These differences influence both the extractability of collagens from tissue and the biophysical characteristics of these collagens. As a result, collagens isolated from tissues exhibit significant lot-to-lot variability and, as bulk materials, are often analytically intractable.

Accordingly, attention has shifted away from isolation of animal collagen and towards production of recombinant collagens.

Further, the use of recombinant DNA technology is desirable in that it allows for the potential production of synthetic collagens and collagen fragments which may include, for example, exogenous biologically active domains (i.e. to provide additional protein function) and other useful characteristics (e.g. improved biocompatability and stability).

Host systems such as yeast have been explored to recombinantly produce human coded collagen. However, yeast systems are complicated by the need to introduce genes for proline-4 hydroxylase to form the Hyp residues needed for stability of mammalian collagens. Typically, recombinant mammalian coded collagens are expressed in *Pichia*, which requires oxygen addition to get maximum hydroxylation, as well as methanol addition for induction, creating a need for enhanced, potentially flameproof engineering.

Other collagen-like material which does not require post translational modification has been sought as replacement to hydroxylated human collagen. Recently, research on bacterial genomes has indicated there are many putative bacterial proteins that contain Gly as every third residue and a high proline content, suggesting that collagen-like, triple-helical structures may be present in certain bacterial derived proteins (Peng Y et al (2010) *Biomaterials* 31(10):2755-2761; Yoshizumi A et al (2009) *Protein Sci* 18:1241-1251). Furthermore, several of these proteins have been shown to form triple-helices that are stable around 37° C., despite the absence of Hyp. The triple helical composition has been confirmed in a number of cases. Examples include cell surface proteins on certain bacterial cells and filaments on *Bacillus anthracis* spores. It has been postulated that expression of such collagen-like constructs in prophages present in pathogenic *E coli* strains appear to be responsible for dissemination of virulence-related genes through infection (Bella J et al (2012) 7(6) PLoS 1 e37872).

Use of recombinant technology, however, still has its shortcomings and hurdles. The use of host cells to produce the foreign proteins has added challenges such as the removal of contaminating host cell proteins whose presence in the final formulation of the desired proteins can result in adverse toxic or immunological reactions. If the recombinant protein is made intracellularly, the first step of a purification process involves lysis or disruption of the cell, which releases the contents of the cell into the homogenate and in addition produces subcellular fragments. If the recombinant protein is secreted out of the cell, the natural death of cells and release of intracellular host cell proteins into the supernatant can also give rise to toxic and immunogenic contamination. To remove these contaminants, many different purification steps are typically required. Affinity chromatography is commonly adopted to achieve high purity levels. This downstream processing is generally labour and resource intensive and cost prohibitive for large scale commercial production.

The large scale production of recombinant collagen-like proteins is still in its infancy. There are certain challenges that must be addressed with large scale production, including scalability of the process, production costs, complexity of the extraction method, compliance with GMP requirements, compliance with regulatory requirements, removal of contaminating host cell proteins, complexity of the purification method, suitability of the host cell. For example, human cell lines only result in moderate yields which are not suited to cost-effective, larger scale production.

Accordingly, there is a need for methods for the purification of recombinantly produced collagens, wherein such methods are cost-effective and which result in production of collagen in high yields and sufficient purity for various applications.

SUMMARY OF THE DISCLOSURE

The present inventors have developed a method for purifying recombinant triple-helical proteins expressed by a non animal host cell, such as a bacterial, yeast or plant cell. The method provides for the purification of soluble triple-helical protein(s) which remains soluble throughout the purification method. Furthermore, the method does not result in denaturation, degradation or hydrolysis of the triple-helical protein(s).

The method of the present disclosure provides for the purification of recombinant triple-helical proteins (from any source) resulting in the production of solubilised triple-helical protein (e.g. collagen) which is stable, and is free of contaminating proteins (which can compromise the stability of triple helical proteins) and which can be produced in high yield since the process steps are minimised. Advantageously, the method provides a cost effective approach for purification of triple-helical proteins (e.g. collagen) which is stable under acidic conditions and which is produced in sufficient purity for a variety of different applications.

The present disclosure therefore provides a method for the purification of a recombinantly expressed triple-helical protein contained within a non-mammalian host cell culture extract or homogenate, the method comprising:

(i) precipitating the host cell materials from the triple-helical protein under acidic conditions and at a temperature at which the triple-helical protein remains thermally stable; followed by;

(ii) digesting host cell materials present in the precipitated host cell culture extract or homogenate by addition of a protease, wherein the triple-helical protein is resistant to the protease; and (iii) collecting the purified triple-helical protein; and optionally further comprising an additional separation step between the precipitating step and the digesting step of physically separating the triple-helical protein from insoluble host cell materials; and wherein the triple-helical protein remains soluble throughout at least steps (i) and (ii).

In one example, the triple-helical protein remains soluble throughout steps (i) to (iii).

In one example, the digestion step of host cell material is carried out using an acid protease.

In one example, the method further comprises harvesting the host cell. Preferably, the host cell is a bacterial, yeast or plant host cell. Methods for culturing the host cell of the present disclosure will be familiar to persons skilled in the art and are described elsewhere herein.

In one example, the acid conditions refer to a pH of the culture extract or homogenate being at a pH less than 7, preferably a pH less than about 6.

According to the method of the disclosure, the triple-helical protein advantageously remains thermally stable. Persons skilled in the art will be aware of certain agents or additives that may be added to the culture extract or homogenate which assist in maintaining the thermal stability of the triple-helical protein. For example, an anti-freeze agent such as NaCl may be added or other additives that provide stability such as for example, polyvinyl alcohol, polyethylene oxide, polyvinylpyrrolidone, polyacrylamide, polyethylene glycol (PEG) or derivatives thereof, methylcellulose, agarose, dextrins, hydroxyethyl starches, trimethylamine N-oxide (TMAO) etc. In one example, the thermal stability of the triple-helical protein is maintained if the precipitation step is conducted at a temperature that is less than the melting temperature of the triple-helical protein. In a further example, thermal stability of the triple-helical protein is maintained under the acidic precipitating conditions at a temperature at least 10° C. below the $T_m$ of the triple-helical protein. Methods of determining thermal stability of triple-helical proteins are described in for example U.S. Pat. No. 8,280,710.

The method of the present disclosure includes the optional intermediary separation step for separating the triple-helical protein from precipitated host cell materials such as host cell proteins and/or host cell DNA. Any separation process(es) may be employed in this optional step to remove one or both of these materials. Such processes are preferably crude separation or concentration techniques such as centrifugation, filtration, cross flow filtration, or sedimentation.

In another embodiment, a further pH adjustment may be necessary either prior to, or concurrently with the digestion step according to the present method. Depending upon the protease used in the digestion step, the pH may need to be adjusted up or down with the proviso that the triple-helical protein remains in solution. For example, if pepsin is being used as the protease, then it may be necessary to lower the pH of the culture extract or homogenate prior to the pepsin addition. Such adjustments are well within the skill of the person skilled in the art.

It will be appreciated by persons skilled in the art that the host cell which is transformed or transfected with a recombinant construct comprising a sequence encoding the triple-helical protein is cultured under conditions suitable to cause expression of the triple-helical protein. In some examples, the triple-helical protein will be produced intracellularly in which case it will be necessary to extract the triple-helical protein from the cell. Extraction methods will require rupturing the host cell. Extraction may be achieved by mechanical or chemical (e.g. enzymatic) means known to persons skilled in the art. Examples, of mechanical extraction processes may include one or more of the following, sonication, microfluidisation, lysis in a French Press or similar apparatus, osmotic shock, and disruption by vigorous agitation/milling with glass, ceramic or steel beads. Alternatively, or in conjunction with a mechanical extraction, an enzymatic extraction can also be employed. Examples, of agents suitable for enzymatic extraction include lysozyme, lysostaphin, zymolase, cellulose, mutanolysin, glycanases, proteases, mannose etc.

In some examples, the triple-helical protein is secreted from the host cell (i.e. produced extracellularly as is the case in some yeast systems). Under those circumstances, extraction is not necessary, however, the cell culture extract may be concentrated thus creating an homogenate or filtrate by methods known in the art to obtain a solution comprising the recovered soluble triple-helical protein. In another example, the cell culture medium is concentrated with the triple-helical protein by cross-flow filtration.

According, the method of the present disclosure may include an additional step of producing a host cell culture extract or homogenate which contains the triple-helical protein.

Cellular contaminants and debris from the recombinant triple-helical protein containing cell culture extract or homogenate are removed by acidic precipitation step according to the method of the present disclosure. The inventors have found that by adjusting the pH of the solution to acidic conditions at a temperature at which the triple-helical protein remains thermally stable, the recombinant triple-helical protein does not denature and remains in solution whilst many of the contaminating (i.e. non-soluble) material precipitates. Thus the invention is taking advantage of the pH stability of the triple helical proteins in this first purification step.

Preferably, the temperature is constant throughout the method. In one example, the temperature is maintained at room temperature (i.e. between about 18° C. and 24° C.).

In one example, the temperature is at least 10° C. or more below the melting temperature ($T_m$) of the recombinant triple-helical protein during the acidic precipitation step.

Acidification of the solution containing the recombinant triple-helical protein may be achieved by any suitable acid, including strong or weak acids. A single acid may be used or alternatively combinations of different acids may be used. Examples of suitable acids according to the method include hydrochloric, sulphuric, acetic, formic or lactic acid, although other acids familiar to person skilled in the art would also be suitable. Accordingly, depending upon the $T_m$ of the recombinant protein at the pH of the acidification solution the temperature at which the acidification occurs can vary between 4° C. and 30° C.

Examples of the melting temperatures of the triple helical, collagen-like (CL) domain for various bacterial species is provided in the table below.

TABLE 1

Melting temperature of collagen-like (CL) domains

| Species | Domain | Tm (neutral pH) ° C. | Tm (acidic pH) ° C. |
|---|---|---|---|
| Clostridium perfringens | CL | 38.8 | 37.2 |
| Solibacter usitatus | CL | 38.5 | 27.0 |
| Methylobacterium sp. 4-46 | CL | 35.0 | 28.3 |
| Rhodopseudomonas palustris | CL | 37.0 | 32.0 |
| Streptococcus pyogenes (Scl2) | CL | 35.9 | 25.7 |
| Streptococcus pyogenes (Scl2) | CL-CL | 36.5 | |

During the acidic precipitation step, the adjusted pH of the cell culture extract or homogenate containing the recombinant triple-helical protein will depend upon the host cell and the triple-helical protein sequence. In one example, the cell culture extract or homogenate comprising the triple-helical protein is adjusted to a pH less than 7. In another example, for bacterial host cells, a pH between 2 and 4 is preferred and for yeast host cells a pH between 4 and 6 is preferred. In a further example for plant host cells, a pH between 2 and 4.5 is preferred.

In certain examples, for plant cell expression of recombinant triple-helical proteins, the acid precipitation step may be performed at two different pH values. For example, where the most abundant plant protein in the extract is ribulose bisphosphate carboxylase oxygenase (Rubisco), this is best precipitated at a pH around 4.5. However, this pH is typically not sufficient to remove all contaminating plant proteins, in which case it may be necessary to follow with a further precipitation at pH 2.5.

Accordingly, the acidic precipitation step may require adjustment of the pH value causing successive contaminating proteins present in the extract to be precipitated. Preferably, the precipitated proteins will be removed according to methods described above between subsequent pH adjustments.

According to the method of the present disclosure, the digestion step follows the acid precipitation step. The present inventors have found that the digestion step removes host cell contaminants generated in the extraction process (in which the culture extract or homogenate is produced) or which were not removed during the recovery of the triple-helical protein in the precipitation step. Typically, the digestion step will result in the removal of contaminating host cell proteins which are prone to enzymatic digestion e.g. membrane proteins. In a further example, the digestion step is carried out using a protease, preferably an acid protease. Suitable examples of acid proteases for use according to the method of the present disclosure include pepsin, papain, papain-like enzymes such as bromelain, ficin or actinidin, or *Aspergillus saitoi* acid protease.

Non-acidic proteases may also be used in the digestion step of the present disclosure, such as trypsin and chymotrypsin. Depending upon the protease employed, it may be necessary to adjust the pH to less acidic conditions (e.g. for proteases such as papain). The person skilled in the art will be familiar with such strategies.

In some examples, protease digestion may be terminated by adjusting the pH of the culture extract or homogenate to neutral pH.

It will be appreciated that the method results in the purification of proteolytically stable triple-helical protein. The triple helical protein may also include additional non-helical protein sequences which are proteolytically stable and/or non-triple helical sequence inserts that either naturally or by design are proteolytically stable to the enzyme selected for removal of the host proteins. Thus, the method of the present disclosure also has the advantage of selectively purifying proteolytically stable proteins over proteolytically unstable proteins and thus selectively purifies triple-helical proteins over other non triple-helical proteins.

The protease digests many contaminating proteins into peptides that either can be removed by diafiltration or precipitation as they have much smaller molecular weight than the intact soluble recombinant triple-helical protein. The resulting purified recombinant triple-helical protein can then be collected. Both these processes have the added advantage of concentrating the recombinant triple-helical protein. Precipitation of the recombinant triple-helical protein can be achieved by addition of ammonium sulphate, by adjustment of pH and/or adjustment of temperature, or by use of a polymer (e.g. polyethylene glycol).

In another example, contaminating host cell nucleic acids can also be removed from the collected triple-helical protein by methods known in the art.

Depending on the end use of the triple helical protein, a polishing step of the collected triple-helical protein may be employed to further concentrate and/or purify the recombinant triple-helical protein once the host contaminants have been removed. Chromatography is one such technique that is commonly used to polish protein solutions. Examples of chromatographic processes that may be adopted include ion exchange chromatography, high performance liquid chromatography, electrophoresis, gel filtration chromatography, affinity chromatography and hydrophobic interaction chromatography. If the recombinant triple-helical protein has been precipitated by a neutral polymer, the precipitate will be low in salt and hence can be used directly for ion exchange chromatography if further polishing purification is necessary.

It will be appreciated that the method results in the generation of purified triple-helical protein. In one example, the purified triple-helical protein is stabilised. In another example, the triple-helical protein is stabilised by glutaraldehyde; however, other stabilising agents known in the art can be used.

Suitable host cells for expressing the recombinant triple-helical protein include bacterial, yeast or plant cells. Methods of recombinant production of triple-helical proteins in these cells will be familiar to persons skilled in the art.

The bacterial host cell may be selected from, but not limited to *Escherichia, Bacillus, Enterobacter, Azotobacter, Erwinia, Pseudomonas, Klebsiella, Proteus, Salmonella, Serratia, Shigella, Rhizobia, Vitreoscilla* and *Paracoccus*. In one example, the bacterial host is *Escherichia coli*. Suitable *E. coli* hosts include *E. coli* BL21 strain (Life Sciences), *E. coli* W3110 (ATCC 27,325), *E. coli* 294 (ATCC 31,446), and *E. coli* X1776 (ATCC 31,537).

The yeast host cell may be selected from *Pichia pastoris, Hansenula polymorpha, Saccharomyces cerevisiae, Kluyveromyces lactis, Schwanniomyces occidentis, Schizosaccharomyces pombe, Trichoderma reesei* and *Yarrowia lipolytica*.

The plant host cell may be selected from tobacco, maize, wheat, barley, as well as lower plants such as microalgae such as *Chlorella vulgaris*.

The expression construct comprising a nucleic acid sequence encoding the recombinant triple-helical protein purified according to the method of the present disclosure is one which comprises a sequence encoding a repeating motif (Gly-X-Y)n as defined herein. The triple-helical protein encoded by the expression construct is preferably heat stable at mammalian body temperature (i.e. between 35 and 40° C.) or can be made stable post purification by modification. The value of n may be between 5 to 600 (SEQ ID NO: 44) or between 1 to 350 (SEQ ID NO: 45) and (Gly-X-Y) represents a bacterial or animal (mammalian) or insect derived triple-helical forming domain with X and Y being independently any natural or unnatural imino or amino acid for each repeat unit. In one example, neither X or Y is hydroxyproline. However in some examples the triple-helical domain could include hydroxyproline. An insert or linker sequence may be located between each triple-helical forming domain (also referred to herein as a "collagen-like (CL) forming domain") in constructs comprising more than one CL domain, or within an individual CL domain. The insert is comprised of about 1 to 50 of any imino or amino acids. Preferably, the insert is not enzyme/protease labile.

In one example, the triple-helical protein is collagen.

The recombinant triple-helical sequence may be derived from any triple-helical or triple-helical containing protein, whether from bacteria, yeast, plant, insect or silkworm and may be hydroxylated or non-hydroxylated.

If the triple-helical protein is in a hydroxylated form, then an additional step requiring modification of proline residues can be employed prior to undertaking the present method. Such methodologies will be familiar to persons skilled in the art.

Examples sequences that encode recombinant triple-helical like proteins and that can used to design appropriate constructs of the invention include:

(i) Sequences from pathogenic or non-pathogenic bacterial organisms, where, for example the triple-helical sequence can include CL domains derived from one or more of *S. pyogenes, Methylobacterium* sp. 4-46, *Solibacter usitatus, Streptococcus equi* SclC, *Bacillus anthracis, Bacillus cereus, Clostridium perfringens, Rhodopseudomonas palustris, Streptococcus pneumoniae* A which exhibit the desired heat stability in its native state or after stabilisation by chemical cross-linking. Sequences may also include triple-helical collagen-like sequences identified in U.S. Pat. No. 6,953,839;

(ii) one or more DNA sequences isolated from organisms selected from, but not limited to *Corynebacterium diphtheria*, Actinobacteria (e.g., *Mycobacterium gilvum, Mycobacterium tuberculosis, Mycobacterium vanbaalenii, Nocardioides* species, *Rubrobacter xylanophilus, Salinispora*

*arenicola, Salinispora tropica*, and *Streptomyces* species), Alphaproteobacteria (e.g., *Anaplasma* species, *Methylobacterium radiotolerans, Nitrobacter winogradskyi, Paracoccus denitrificans, Rhizobium leguminosarum, Rhodobacter sphaeroides, Rhodopseudomonas palustris, Sphingomonas wittichii*, and *Wolbachia* species), Bacteroidetes (e.g., *Bacteroides thetaiotaomicron*), Betaproteobacteria (e.g., *Azoarcus* species, *Burkholderia ambifaria, Burkholderia cenocepacia, Burkholderia phymatum, Burkholderia vietnamiensis, Dechloromonas aromatica, Polaromonas naphthalenivorans, Ralstonia eutropha, Ralstonia metallidurans, Ralstonia pickettii,* and *Rhodoferax ferrireducens*), Cyanobacteria (e.g., *Cyanothece* species, *Synechocystis* species, *Trichodesmium erythraeum*), Deinococcus (e.g., *Deinococcus radiodurans*), Deltaproteobacteria (e.g., *Anaeromyxobacter dehalogenans*), Epsilonproteobacteria (e.g., *Campylobacter curvus*), Firmicutes (e.g., *Bacillus clausii, Bacillus halodurans, Bacillus pumilus, Bacillus subtilis, Clostridium botulinum, Clostridium phytofermentans, Enterococcus faecalis, Geobacillus kaustophilus, Lactobacillus casei, Lactobacillus plantarum, Lactococcus lactis, Lysinibacillus sphaericus, Staphylococcus haemolyticus, Streptococcus agalactiae,* and *Streptococcus pneumoniae*), and Gammaproteobacteria (e.g., *Citrobacter koseri, Enterobacter* species, *Escherichia coli, Klebsiella pneumoniae, Legionella pneumophila, Photorhabdus luminescens, Pseudomonas aeruginosa, Pseudomonas entomophila, Pseudomonas putida, Psychrobacter cryohalolentis, Saccharophagus degradans, Salmonella enterica, Salmonella typhimurium, Serratia proteamaculans, Shewanella amazonensis, Shewanella baltica, Shewanella frigidimarina, Shewanella halifaxensis, Shewanella loihica, Shewanella oneidensis, Shewanella pealeana, Shewanella putrefaciens, Shewanella sediminis, Shewanella woodyi, Shigella boydii, Shigella dysenteriae, Shigella flexneri, Shigella sonnei*, and *Vibrio harveyi*);

(iii) DNA sequences encoding for C1q, acetylcholine esterase, macrophage scavenger receptor, a lung surfactant protein, mannose binding protein, hibernation protein, *Mytilus byssus*, ectodysplasin A or gliomedin;

(iv) sequences encoding sawfly silk protein derived from a Hymenopteran, Nematini: in *Hemichroa, Pristiphora, Pachynemalus, Pikonema* and *Nematus* species (subfamily Nematinae), *Tomostethus* and *Tethida* species (subfamily Blennocampinae); and (v) sequences encoding mammalian collagen, including one or more of collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XIV, type XXV, type XXVI, type XXVII, type XXVIII.

Insert sequences may be engineered in the recombinant construct to improve the elasticity of the triple-helical protein or to otherwise serve as a natural binding domain or biological cleavage sequence. Examples of constructs, suitable for use are disclosed in WO 2010/091251.

In one example, the expressed triple-helical protein and/or triple-helical domain thereof is a homotrimer wherein identical chains are assembled to form a triple-helix.

In a further example, the expressed triple-helical protein and/or triple-helical domain thereof is a heterotrimer consisting of two or three distinct chains assembled to form a triple-helix, for example as is found in mammalian type I collagen.

In a further example, the expressed triple-helical protein is a chimeric protein comprising at least two triple-helical domains which are linked via a linker sequence. For example, the chimeric construct encoding the protein may comprise two or more triple helical forming domains of mammalian and/or bacterial triple-helical sequences which may be separated by a linker or triple-helical forming domains of different bacterial collagens, which may be separated by a linker sequence. Such chimeras, when expressed result in the production of a protein chain, which is able to form a triple-helix, and which may, for example, consist of two bacteria derived chain segments or one bacteria derived chain segment and one mammalian derived chain segment joined together in a single sequence that is able to form the triple helix.

Each triple-helical domain sequence repeat may include repeats, fragments, variants or combinations of the before mentioned sequences.

While not limited thereto, the bacterial expression vector may be a cold shock vector and the recombinant triple-helical protein may be expressed in the microorganism (e.g *E. coli*) at temperatures below 37° C. and in certain examples, at temperatures of about 15 to 23° C. In a further example, the expression vector is a pET vector (Novagen).

In another example, a yeast expression vector is selected. Examples of yeast expression vectors are known in the art and may be selected, for example, from pHIL-D2, pPIC3.5, pHIL-SI, pPIC9, pPICZ, pA0815, pBLADE, pBLARG, YepFlagl, pAMH110 or pBLURA.

In another example, the expression vector is a plant expression vector. Examples of plant expression vectors are known in the art and may include, for example pB1121, pCAmbia2301, pEAQ-HT-DEST, or PVX expression vector.

The present disclosure also provides a triple-helical protein purified by the method as described herein.

The present disclosure also provides a purified triple-helical protein obtained by the method as described herein.

In one example, the triple-helical protein is about 80%, about 85%, about 90%, about 95%, about 97% or about 98% pure.

The triple-helical protein which has been purified according to the method of the present disclosure can, where required, be converted to gelatin which can be useful for various applications. Methods of converting the triple-helical protein to gelatin will be known to persons skilled in the art and typically involves denaturing the protein, for example by a thermal or chemical denaturation process. Accordingly, the present disclosure also encompasses a triple-helical protein purified according to the present disclosure which is converted to gelatin by thermal or chemical denaturation.

KEY TO SEQUENCE LISTING

Figure 1:
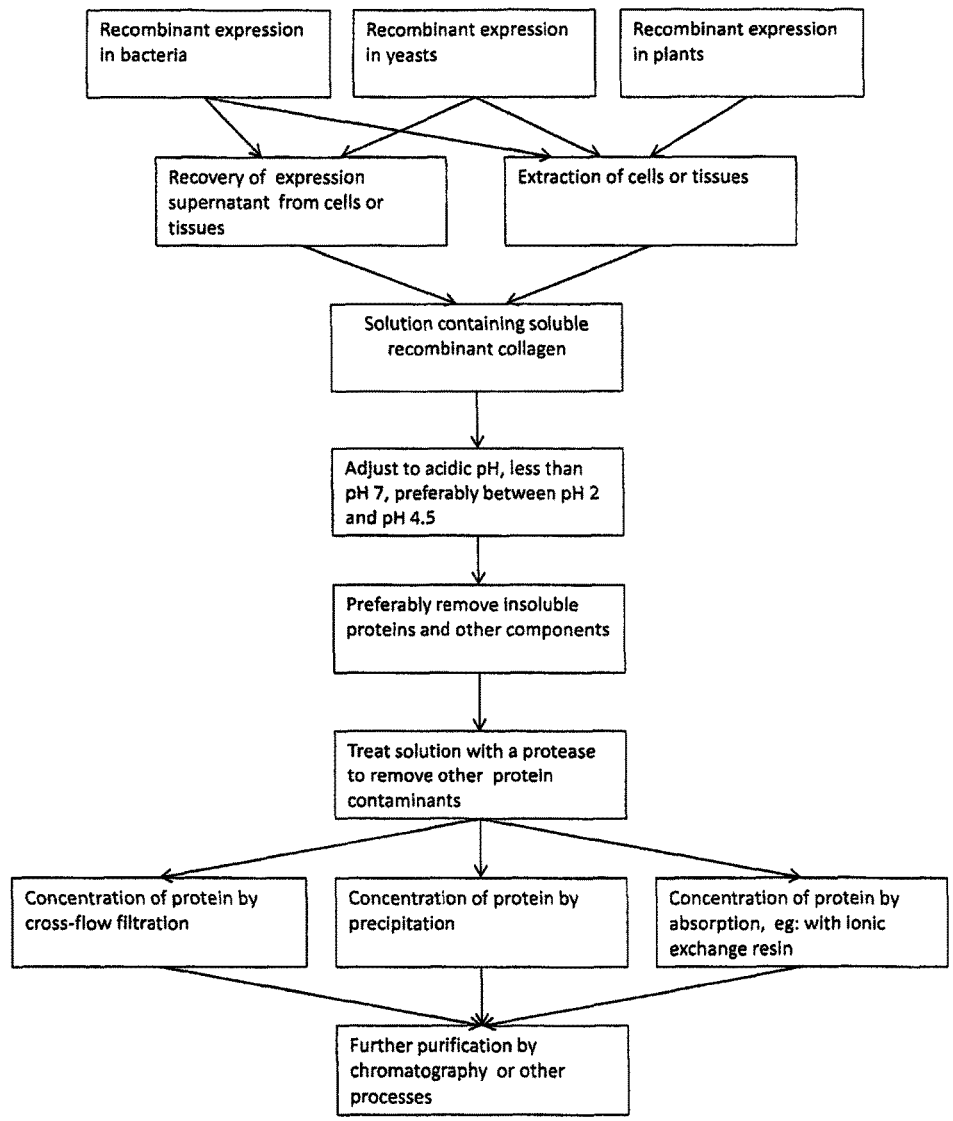
FIG. 1 shows a flowchart of the purification scheme according to one embodiment of the present disclosure.
Figure 2:
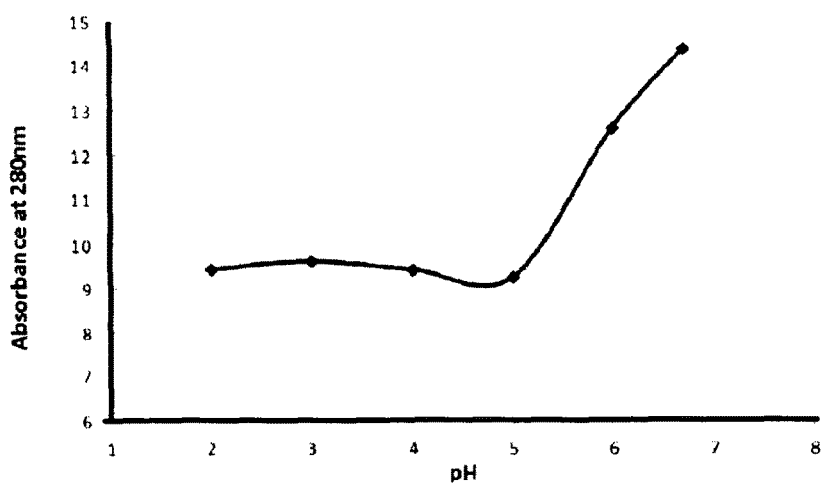
FIG. 2 shows the solubility of host proteins after acid extraction and adjusting of the pH and equilibrating for 16 h. (A) Bacterial, *E. coli*, (B) Yeast, *Saccharomyces cerevisiae* (C) Plant, *Spinacia oleracea*.
Figure 2:
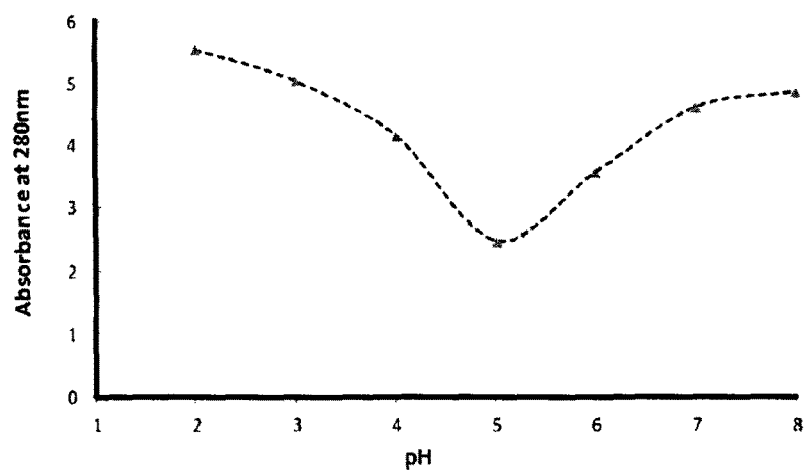
Figure 2:
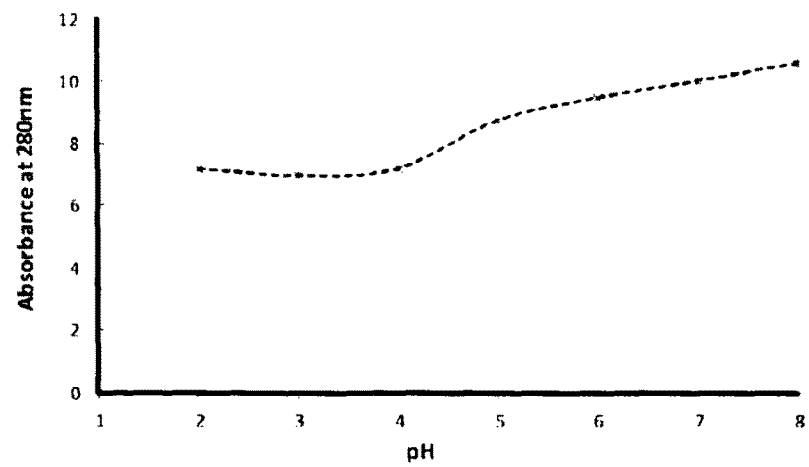

SEQ ID NO 1: thrombin/trypsin cleavage site
SEQ ID NO:2: DNA sequence of a bacterial collagen Scl2 fragment from *S. pyogenes*
SEQ ID NO:3: protein sequence of a bacterial collagen Scl2 fragment from *S. pyogenes*
SEQ ID NO 4: insert sequence
SEQ ID NO 5: forward primer
SEQ ID NO 6: reverse primer
SEQ ID NO 7: DNA sequence encoding bacterial collagen dimer of CL domains from collagen Scl2 from *S. pyogenes*
SEQ ID NO:8: protein sequence encoding bacterial collagen dimer of CL domains from collagen Scl2 from *S. pyogenes*
SEQ ID NO 9: heparin binding sequence
SEQ ID NO 10: forward primer
SEQ ID NO 11: reverse primer
SEQ ID NO 12: forward primer
SEQ ID NO 13: reverse primer
SEQ ID NO 14: forward primer
SEQ ID NO 15: reverse primer
SEQ ID NO 16: DNA sequence encoding bacterial collagen Scl2 from *Streptococcus. pyogenes* including a substituted functional sequence for heparin binding
SEQ ID NO 17: protein sequence encoding bacterial collagen Scl2 from *Streptococcus. pyogenes* including a substituted functional sequence for heparin binding
SEQ ID NO 18: integrin binding sequence
SEQ ID NO 19: forward primer
SEQ ID NO 20: reverse primer
SEQ ID NO 21: forward primer
SEQ ID NO 22: reverse primer
SEQ ID NO 23: DNA sequence encoding bacterial collagen Scl2 from *Streptococcus pyogenes* including a substituted functional sequence for integrin binding
SEQ ID NO 24: protein sequence encoding bacterial collagen Scl2 from *Streptococcus pyogenes* including a substituted functional sequence for integrin binding
SEQ ID NO 25: DNA sequence encoding bacterial collagen Scl2 from *Streptococcus pyogenes* including substituted functional sequences for both heparin and integrin binding
SEQ ID NO 26: protein sequence encoding bacterial collagen Scl2 from *Streptococcus pyogenes* including substituted functional sequences for both heparin and integrin binding
SEQ ID NO 27: DNA sequence encoding bacterial collagen from Solibacter *usitatus* using a V-domain from *Rhodopseudomonas palustris*
SEQ ID NO 28: protein sequence encoding bacterial collagen from Solibacter *usitatus* using a V-domain from *Rhodopseudomonas palustris*
SEQ ID NO 29: DNA sequence encoding an insect collagen from sawfly *Nematus oligospilus*, gene A
SEQ ID NO 30: DNA sequence encoding an insect collagen from sawfly *Nematus oligospilus*, gene A
SEQ ID NO 31: primer
SEQ ID NO 32: primer
SEQ ID NO 33: primer
SEQ ID NO 34: primer
SEQ ID NO 35: primer
SEQ ID NO 36: primer
SEQ ID NO 37: DNA sequence encoding 3 repeats of a fragment of human type III collagen
SEQ ID NO 38: protein sequence encoding 3 repeats of a fragment of human type III collagen
SEQ ID NO 39: DNA sequence encoding human type I alpha I chain CB3 fragment
SEQ ID NO 40: protein sequence encoding human type I alpha I chain CB3 fragment
SEQ ID NO 41: DNA sequence encoding chimera made from segments from human collagen type I and type III chains
SEQ ID NO 42: DNA sequence encoding a chimera of different bacterial collagen chains where two different collagen-like components are present from *Methylobacterium* sp. and *S. usitatus*
SEQ ID NO 44: DNA sequence encoding a chimera of different bacterial collagen chains where two different collagen-like components are present from *Methylobacterium* sp. and *S. usitatus*

General Techniques and Definitions

Unless specifically defined otherwise, all technical and scientific terms used herein shall be taken to have the same meaning as commonly understood by one of ordinary skill in the art (e.g., in cell culture, molecular genetics, recombinant biology, silk technology, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The term "and/or", e.g., "X and/or Y" shall be understood to mean either "X and Y" or "X or Y" and shall be taken to provide explicit support for both meanings or for either meaning. Furthermore, a list or features including the phrase "and/or" between the second last and last feature means that any one or more the listed features may be present in any combination.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "contained within a non-mammalian host cell culture extract or homogenate" is understood as referring to a cell culture extract or homogenate which prepared from a host cell according to the present disclosure which has been transfected or transformed with a construct that encodes the triple-helical protein sequence.

The term "plant" includes whole plants, vegetative structures (for example, leaves, stems, roots), floral organs/structures, seed (including embryo, endosperm, and seed coat), plant tissue (for example, vascular tissue, ground tissue, and the like), cells and progeny of the same.

By "thermally stable" it is meant the extent to which the triple-helical protein (or triple-helical part of a protein) maintains its three dimensional structure at a given temperature. A degree of tolerance in the extent to which the triple-helical structure is destabilised is permitted according to the present method, however, it is preferable that at least 70% of the triple-helical protein is maintained in the three-dimensional triple helical form.

The term "triple helical protein" as used herein is understood as referring to a homotrimeric, chimeric or heterotrimeric protein as described herein which comprises at least one region (referred to herein as a "triple-helical domain" or "collagen-like domain" depending on the context). The term "triple helical protein" also includes "collagen-like (CL) proteins" as referred to herein. The term encompasses variants and fragment(s) of the triple-helical protein and functional equivalents and derivatives thereof which preferably retain at least one structural or functional characteristic or a triple-helical or collagen-like protein, (i.e. Gly X Y)n sequence. The triple-helical protein of the present disclosure is understood to be proteolytically stable. The triple-helical protein may also include additional non-triple helical protein sequence which is proteolytically stable and/or non-triple-helical inserts that are either naturally or by design proteolytically stable to the protease enzyme selected for removal of host proteins.

As used herein, the term "collagen-like (CL)" refers to refers to a polypeptide comprising Gly-X-Y triplets, where X and Y can be any amino acid. A silk protein of the disclosure is also included within the term "collagen-like" as well as naturally occurring bacterial collagens. A collagen-like silk protein of the present disclosure does not have any hydroxyproline. In one example, a collagen-like silk protein comprises at least about 40, more preferably at least about 50, Gly-X-Y triplets. Furthermore, in another example the Gly-X-Y triplets constitute at least about 40%, more preferably at least about 50%, of the primary amino acid sequence of the proteins. In another example, a collagen-like silk polypeptide has, or is capable of forming under suitable conditions, a triple helical structure. Furthermore, it will be understood that any inserts or linkers which are included in the recombinant triple-helical protein are resistant to protease.

The term "triple-helical domain" or "collagen-like domain" refers to protein comprising the general peptide formula (Gly X Y)n, in which Gly is glycine, X and Y represent the same or different amino acids (the identities of which may vary from Gly X Y triplet to Gly X Y triplet), wherein n may be between 5 and 600 (SEQ ID NO: 44). The triple-helical domain consists of three chains characterised by the repeating (Gly X Y)n motif which are folded into a triple helical protein conformation.

As used herein, the term "triple helical forming domain" or "collagen-like forming domain" refers to a nucleotide sequence encoding an amino acid sequence, comprising a (Gly-X-Y)n motif, wherein X and Y are any other amino acid residues, that is capable of folding or associating with two other chains to form a triple helix.

The term "homotrimeric" refers to a triple-helical protein and/or triple-helical domain thereof containing all three chains of the triple helix being the same.

The term "heterotrimeric" refers to a triple helical protein and/or triple-helical domain thereof containing at least two different chains forming the triple helix.

The term "culture" as used herein refers to the propagation of a host cell in a medium that leads to their growth and all the consequent subcultures.

The term "host cell culture extract" as used herein is intended to refer to host cell cultures in which the triple-helical protein is secreted into the culture medium. The host cell culture extract can include, for example a concentrated cell culture medium in which the host cells transformed/transfected/transduced with the triple-helical protein are grown. Intact host cells can be removed or separated from the secreted triple-helical protein as described herein.

The term "host cell culture homogenate" as used herein in intended to refer to host cell cultures in which the triple-helical protein is retained within the host cell and released by rupture or extraction process. Thus, in the present context by homogenate it is meant that the cells have been disrupted so that the host cell culture homogenate comprises ruptured host cells and triple-helical protein which has been released from the ruptured cells.

The term "construct" as used herein refers to an expression cassette containing a DNA sequence which codes for a triple-helical forming domain. The construct may further include a V-domain and a histidine tag. The term also extends to vectors that can express the DNA present in the expression cassette. The DNA is functionally associated with other sequences capable of affecting their expression, for example, promoter sequences. In general, expression vectors normally used in recombinant DNA technologies are in the form of "plasmids".

The term "fragment" as used herein refers to a portion of the native amino acid or nucleotide genetic sequence, and in particular the functional derivatives of the triple helical protein.

The term "variant" as used herein refers to a sequence with deletions, insertions or substitutions of different nucleotides resulting in a polynucleotide that encodes the same or a functionally equivalent polypeptide.

The term "purified" is intended to mean a triple-helical protein which is rendered substantially free of other proteins (e.g. particular host cell proteins) or contaminating agents, by the protein purification process described herein. The protein may be rendered substantially free of other protein or contaminating agents e.g. at least about 70% or 75% or 80% or 85% or 90% or 95% or 96% or 97% or 98% or 99% free of other proteins or contaminating agents.

DETAILED DESCRIPTION OF THE INVENTION

The method of the present disclosure can be used to purify any recombinantly produced triple-helical protein from any source in non-mammalian host cells.
Triple-Helical Sequences The recombinant triple-helical protein sequences useful in the method of the present disclosure are useful as a biomaterial, a material for manufacturing, cosmetic or food additive.

The sequence encoding the triple-helical protein is comprised of one or more triple-helical forming or collagen-like (CL) forming domains wherein each CL domain is optionally separated by a non-collagen-like, protease resistant insert region. The insert region may be adapted to mimic natural breaks in the triple helical structure that are found within many human collagens or may provide a desired biological functionality (e.g. cell/tissue binding (e.g. heparin or integrin), protease cleavage site, etc). The insert region may occur between individual CL domains or within a CL domain of the recombinant triple-helical sequence. To ensure proper folding of the triple helical region of the recombinant protein, post translationally, a globular folding domain is preferably inserted at the N- or C-terminus of the recombinant construct. This globular folding domain may be removed during the subsequent protease digestion step.

In one example, the triple helical sequences which are suitable for use in the method of the present disclosure may be recombinantly derived from natural triple-helical proteins found in pathogenic or non-pathogenic bacterial organisms. For example, a bacterial collagen-like protein from *Streptococcus pyogenes* (Scl1 or Scl2), has been shown to form a stable triple-helix structure without the need for post-translational modification to form hydroxyproline. In a further example, the genome sequences of Enterohaemorrhagic *E coli* O157:H7 strains show multiple open-reading frames with collagen-like sequences that are absent from the common laboratory strain K-12 (Ghosh N et al. (2012) PLoS one e37872).

Alternative sources of naturally occurring bacterial collagen-like proteins which can be produced recombinantly can be found in *Methylobacterium* sp4-46, Solibacter *usitatus*, Streptococcus *equi* SclC, Bacillus anthracis, Bacillus cereus, Clostridium perfringens, Rhodopseudomonas palustris, Legionella pneumophila and Streptococcus pneumoniae A. Accordingly, the present disclosure extends to the sequences or fragments thereof obtained from such sources.

In another example, the triple helical protein is a recombinant protein comprising an insert sequence separating each triple-helical domain wherein the insert sequence is a non-collagen peptide sequence, which is proteolytically stable, of about 1 to 50 imino acids or amino acids. These sequences provide some biological functionality that is useful for the resulting biomaterial, cosmetic, food additive or other product (e.g. for manufacture).

The desired biological functionality of the triple helical protein may be derived from sequences that facilitate binding of the triple-helical protein to the targeted cell type or otherwise provide a natural cleavage site for degradation in the body. Binding sequences may include the integrin binding sequence from type I collagen (GERGFPGERGVE) (SEQ ID: 18) and/or one of the heparin binding sequences from the collagen tail of acetylcholine esterase (GRPGKRG-KQGQK) (SEQ ID: 9). Cleavage sequences may include, but are not limited to, one or more sequences within the family of matrix metalloproteinase (MMP)s domains e.g. MMP-I, MMP-2, MMP-8, MMP-13 and MMP-18 which cleave type I, II and III collagens, and MMP-2 and MMP-9 which cleave denatured collagens. Insert sequences may also include partial sequences of the abovementioned binding or cleavage sequences.

Additional sequences known to achieve such functionality are also contemplated by the present disclosure. Such sequences may be provided in tripeptide repeat units of 4, 5, 6 or 8 with optimal cleavage being possible but not limited to 5 or 6 tripeptide sequences.

The use of recombinant techniques allows the introduction of specific stable triple-helical motif sequences that impart greater stability, such as changes in charge pairs, or sequences that influence the proteins denaturation temperature or pl which in turn influences how it can be used in medicine.

The functional domains can be inserted within a triple-helical forming domain or between successive triple-helical forming domains. Also, more than one functional domain can be added, which could include multiple repeats within a triple-helical domain, or across several repeats of triple-helical domains where either the same or different functions could be included. Similarly, multiple functional repeats could be included between triple-helical domain repeats, or more complex combinations could be achieved using inserts within and between sequences. Together, all these approaches allow for design and manipulation of the expressed triple-helical proteins to provide specific biological functions that could provide enhanced biomedical products.

In a further example, chimeric triple-helical proteins are also encompassed in the present disclosure. For example a chimera between two or more different bacterial sequences, between two or more animal or between animal and non-animal (eg bacterial) sequences could be readily engineered by selection of specific sequences derived from various domains cognate together in a vector to result in expression of chimeric triple-helical protein.

Other triple helical proteins that are contemplated by the present disclosure and that may be recombinantly expressed include C1q, acetylcholine esterase, macrophage scavenger receptor, lung surfactant proteins, mannose binding protein, hibernation proteins, *mytilus byssus*, ectodysplasin A and gliomedin or fragments thereof.
Host Cells The host cells according to the present disclosure are any convenient non-animal cells, including cells of bacterial, yeast and plant origin. The host cells of the present invention may be naturally occurring organisms or mutated organisms capable of expressing triple-helical or collagen-like proteins. In one example, the host organism is an organism or progeny thereof which has been transformed using recombinant DNA techniques with a heterologous DNA sequence that codes for the production of a triple-helical protein.
Expression of the Triple-Helical Sequence The expression construct for the recombinant triple-helical protein may be introduced into the host cell by any convenient method known to the art.

Methods of expressing the recombinant triple-helical protein include standard expression methods that are generally known in the art, such as those described in Molecular Cloning (Sambrook and Russell (2001)).

Expression systems for production of triple-helical proteins are described in, for example US 20120116053.

Transformation, positive transformant selection and culturing methods in *Pichia pastoris* are disclosed in, for example U.S. Pat. Nos. 4,837,148; 4,855,231; 4,882,279; 4,929,555; 5,122,465; 5,324,639; 5,593,859 and 6,472,171.

Methods of producing triple-helical proteins are known in the art and are described in, for example US 20120282817, EP1809751 and WO 2012/117406.

Expression systems for production of triple-helical proteins are described in, for example, US 20120116053.

Recovery of the expressed triple-helical protein

Post-expression, cultured cells may be harvested/collected by techniques known in the art. In one example, the cells are harvested by centrifugation and resuspended in suitable media to yield a fermentation broth/solution (i.e. cell culture extract) or homogenate.

The exact method of recovery of the expressed recombinant triple-helical protein will depend on the host cell and expression construct. In microbial host cells, the triple-helical protein will be trapped within the cell wall of the host cells, even though it has been transported out of the cytoplasm. In this instance, the host cells are disrupted to recover the triple-helical protein. Alternatively, cell walls may be removed or weakened to release the protein located in the periplasm. Disruption can be accomplished by any means known in the art, including sonication, microfluidisation, lysis in a French Press or similar apparatus, disruption by vigorous agitation/milling with glass beads, lysis of osmotically fragile mutant yeast strains, or enzymatic treatment(s). Where the triple-helical protein is recovered by lysis or disruption of the recombinant host cell, the lysis or disruption is typically carried out in a buffer of sufficient ionic strength to allow the triple-helical protein to remain in soluble form. Such mechanical and enzymatic disruption methods will produce subcellular fragments that can be removed by centrifugation or by filtration to obtain a homogenate.

If the triple-helical protein is produced extracellularly, that is, as soluble secreted protein, the cells still need to be removed from the cell supernatant. Clarification is generally accomplished by centrifugation, but can also be accomplished by sedimentation and/or filtration.

Purification of Triple-Helical Proteins

The broth/solution (e.g. cell culture extract) or homogenate containing the soluble recombinant triple-helical protein is then subjected, according to the method of the present disclosure to an acid precipitation step. This is achieved by addition of an acid solution which adjusts the pH of the both/solution or homogenate. The acid solution can be any weak or strong acid, or a mixture of both. Hydrochloric, sulphuric, acetic, formic and lactic acids are all suitable. Unlike previous acidic treatments of natural collagen-containing mammalian tissue material, which are used to swell and solubilise the collagen, the acidification step employed in the method of the present disclosure has been found to precipitate out contaminating host cell proteins whilst still keeping the triple-helical protein in solution. The acidification step furthermore, does not denature the triple-helical protein. Accordingly, the method represents a convenient process for effectively separating host cell contaminants from the soluble triple-helical protein.

The acid solution may be added as a concentrated solution. The acidification may be carried out at a temperature of 4° C. but temperatures as high as 30° C. are also possible depending upon the construct. The most appropriate temperature will depend on the melting point temperature of the triple-helical protein that has been formed from the chosen nucleotide sequence. Use of temperatures below the melting point temperature ($T_m$) of the triple-helical protein, preferably at least 10° C. or more below Tm, will ensure that the triple helix will not denature. For example, at pH 2.2 *Streptococcus pyogenes* has a 234 long construct with the Gly-Xaa-Yaa motif which has a $T_m$ of 25.7° C., *Methylobacterium*, sp 4-46 with a 147 amino acid long construct has a Tm of 28.3° C., *Clostridium perfringens* has a 189 amino acid long construct and a $T_m$ of 37.2° C.

The pH of the acidic conditions will vary depending on what host system is chosen and what the sequences are used to generate the collagen-like protein. If a bacterial host cell such as *E coli* is used, a pH of between 2 and 3 is preferred. If a yeast host cell is used a pH of 4 to 6 is preferable. If a plant host cell is used a pH of 2 to 5 is preferable.

The acid precipitation step is then followed by a digestion step to remove host cell proteins that are amenable to protease digestion. The triple-helical protein remains resistant to the protease. In one example, the digestion step is carried out using an acid protease. Suitable examples of acid proteases for use according to the method of the present disclosure include pepsin, papain, papain-like enzymes such as bromelain, ficin or actinidin, or *Aspergillus* saitoi acid protease. Depending upon the protease employed, it may be necessary to adjust the pH conditions (e.g. for proteases such as papain). The person skilled in the art will be familiar with such strategies. If proteases such as trypsin or chymotrypsin are used then it may be necessary to adjust the pH to neutral or even basic conditions.

The protease digests many contaminating proteins into peptides that can be removed by diafiltration as they have much smaller molecular weight than the intact soluble recombinant triple-helical protein. The resulting recombinant triple-helical protein can then be collected. Collection via diafiltration has the added advantage of concentrating the recombinant triple-helical protein. Additionally, under certain circumstances, collection can be facilitated by precipitating the triple-helical protein, thus causing it to move out of solution. Collection by precipitation of the recombinant triple-helical protein can be achieved by addition of adjustment of ionic strength (with for example ammonium sulphate or sodium chloride) by adjustment of pH, by adjustment of temperature, or by addition of a polymer (e.g. polyethylene glycol).

Depending upon the extraction method employed in step (i) of the present invention, it may be beneficial to include an intermediate separation/purification step between the acid precipitation step and protease digestion step, such a purification step providing for the physical separation of the triple-helical protein from the precipitated host cell materials. The host cell materials may include proteins and/or DNA. Accordingly, any crude separation process may be employed to remove one or both of these materials. Such processes will be familiar to persons skilled in the art. In one example, the process includes centrifugation, (ultra) filtration, cross flow filtration and sedimentation.

Polishing

If the triple-helical protein is required for medical use, it is preferable that the acidified and protease treated product is further purified by polishing purification steps to achieve purity levels greater than 90%. Any polishing purification is suitable according to the present disclosure including, for example gel filtration, hydrophobic, affinity or ion exchange chromatography. Whilst additional precipitation steps may also be used they generally will not achieve the high purity levels required.

Stabilisation

If the purified triple-helical proteins are to be used as biomedical materials, they must be able to be fabricated into appropriate formats. Triple-helical constructs can be formed into sponges and sheets. To help achieve these formats the purified triple-helical protein can be stabilised, as is the case for animal collagens, prior to use in medical application to improve its long term stability and mechanical strength if so desired. A wide variety of suitable stabilisation strategies are possible. Glutaraldehyde is a suitable reagent for cross linking and widely used to improve in vivo stability of collagen materials. Irradiation is another physical stabilisation technique.

The triple-helical proteins purified according to the method of the present disclosure can be used in various applications and procedures including restorative, regenerative and cosmetic procedures, vascular procedures, osteogenic and chondrogenic procedures, cartilage reconstruction, bone graft substitutes, haemostasis, wound treatment and management, reinforcement and support of tissues, incontinence etc.

Non-limiting examples of biomedical products that can be produced from aggregation of the instant recombinant proteins and their possible applications include, but are not limited to, the following: soluble recombinant collagens, such as for use in dermal implants, drug carriers, coatings for medical devices, implant coatings (orthopaedic and vascular), shape-formation materials, viscosurgery, vascular sealants, cosmetics, sponge-like materials, such as for use in three-dimensional cell cultures, tissue and organ engineering, haemostatic agents, and wound therapy (artificial skin and wound dressings); fibers, such as for use in surgical sutures and haemostatic agents; gel-like materials, such as for use in tissue implants, corneal shields, contact lens, and matrices for cell culture; and membrane-like materials, such as for use in anti-adhesion membranes, drug delivery systems, artificial skin, and the like.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Examples 1-11 below describe different triple-helical constructs that may be purified according to the methods described herein.

Examples

Example 1—DNA of a Bacterial Collagen Scl2 Fragment from *S. pyogenes*

The DNA sequence for the fragment of the scl2.28 allele (Q8RLX7) encoding the combined globular and collagen-like portions of the Scl2.28 protein, but lacking the C-terminal attachment domain, was obtained from the data provided in the National Center for Biotechnology Information database (National institutes of Health, Bethesda, Md. 20894, USA) as record GenBank: AY069936.1.). To this sequence a $His_6$ tag was introduced at the N-terminal of the sequence and a thrombin/trypsin cleavage sequence LVPRGSP (SEQ ID No:1) was inserted between the N-terminal globular domain (V) and the following (Gly-Xaa-Yaa)$_n$ collagen-like domain (CL) sequence. A triplet sequence GKY was included at the C terminal of the CL domain, followed by a stop codon, with NdeI and BamHI cloning sites. The DNA for this design was synthesised commercially without any codon optimisation. SEQ ID No: 2 is the final construct.

```
                                                         DNA and Protein Sequence: (SEQ ID No: 2 & 3)
    ATGCATCACCATCACCATCACGCTGATGAACAAGAAGAGAAAGCTAAAGTTAGAACTGAATTAATTCAAGAGTTAGCTCAGGGACTAGG
1   ---------+---------+---------+---------+---------+---------+---------+---------+---------
    TACGTAGTGGTAGTGGTAGTGCGACTACTTGTTCTTCTCTTTCGATTTCAATCTTGACTTAATTAAGTTCTCAATCGAGTCCCTGATCC
  > M  H  H  H  H  H  A  D  E  Q  E  E  K  A  K  V  R  T  E  L  I  Q  E  L  A  Q  G  L  G
                                                                                 GGGTATTGAGA
                                                                                 +---------+   100
                                                                                 CCCATAACTCT
                                                                                  G  I  E  K AAAAAATTTTCCAACTCTAGGTGATGAAGATTTAGATCATACTTATATGACAAAGCTATTAACATACCTACAGGAACGAGAACAAGCT
101 ---------+---------+---------+---------+---------+---------+---------+---------+---------
    TTTTTTTAAAAGGTTGAGATCCACTACTTCTAAATCTAGTATGAATATACTGTTTCGATAATTGTATGGATGTCCTTGCTCTTGTTCGA
  > K  N  F  P  T  L  G  D  E  D  L  D  H  T  Y  M  T  K  L  L  T  Y  L  Q  E  R  E  Q  A
                                                                                 GAGAATAGTTG
                                                                                 +---------+   200
                                                                                 CTCTTATCAAC
                                                                                  E  N  S  W GCGAAAAGACTACTAAAGGGTATACAAGATCATGCCCTTGATCTGGTGCCACGCGGTAGTCCCGGGCTGCCAGGGCCCAGAGGGGAAC
201 ---------+---------+---------+---------+---------+---------+---------+---------+---------
    CGCTTTTCTGATGATTTCCCATATGTTCTAGTACGGGAACTAGACCACGGTGCGCCATCAGGGCCCGACGGTCCCGGGTCTCCCCTTG
  __> R  K  R  L  L  K  G  I  Q  D  H  A  L  D  L  V  P  R  G  S  P  G  L  P  G  P  R  G  E  Q
                                                                                 AAGGACCAACA
                                                                                 +---------+   300
                                                                                 TTCCTGGTTGT
                                                                                  G  P  T
```

-continued

```
        GGTCCAACCGGACCTGCTGGTCCACGAGGTCTACAAGGTCTACAAGGTCTACAAGGTGAAAGAGGGGAACAAGGACCAACAGGTCCCGC
301 ---------+---------+---------+---------+---------+---------+---------+---------+---------
        CCAGGTTGGCCTGGACGACCAGGTGCTCCAGATGTTCCAGATGTTCCAGATGTTCCACTTTCTCCCCTTGTTCCTGGTTGTCCAGGGCG
   __>G  P  T  G  P  A  G  P  R  G  L  Q  G  L  Q  G  L  Q  G  E  R  G  E  Q  G  P  T  G  P  A
                                                                                    TGGTCCACGAG
                                                                                    +---------+       400
                                                                                    ACCAGGTGCTC
                                                                                     G  P  R  G

GTCTACAAGGTGAAAGAGGGGAACAAGGACCAACAGGTCTCGCTGGTAAAGCCGGTGAAGCTGGAGCCAAAGGCGAAACCGGCCCCGCT
401 ---------+---------+---------+---------+---------+---------+---------+---------+---------
        CAGATGTTCCACTTTCTCCCCTTGTTCCTGGTTGTCCAGAGCGACCATTTCGGCCACTTCGACCTCGGTTTCCGCTTTGGCCGGGGCGA
     >  L  Q  G  E  R  G  E  Q  G  P  T  G  L  A  G  K  A  G  E  A  G  A  K  G  E  T  G  P  A
                                                                                    GGTCCACAGGG
                                                                                    +---------+       500
                                                                                    CCAGGTGTCCC
                                                                                     G  P  Q  G

TCCACGTGGTGAACAAGGCCCGCAAGGTCTTCCAGGTAAAGATGGTGAAGCTGGTGCTCAAGGCCCAGCAGGTCCAATGGGTCCTGCTG
501 ---------+---------+---------+---------+---------+---------+---------+---------+---------
        AGGTGCACCACTTGTTCCGGGCGTTCCAGAAGGTCCATTTCTACCACTTCGACCACGAGTTCCGGGTCGTCCAGGTTACCCAGGACGAC
   __> P  R  G  E  Q  G  P  Q  G  L  P  G  K  D  G  E  A  G  A  Q  G  P  A  G  P  M  G  P  A  G
                                                                                    GTGAGCGAGGT
                                                                                    +---------+       600
                                                                                    CACTCGCTCCA
                                                                                     E  R  G

GAAAAAGGAGAACCTGGTACCCAAGGCGCTAAAGGTGATCGCGGTGAAACCGGTCCAGTAGGTCCACGTGGTGAGCGAGGCGAAGCCGG
601 ---------+---------+---------+---------+---------+---------+---------+---------+---------
        CTTTTTCCTCTTGGACCATGGGTTCCGCGATTTCCACTAGCGCCACTTTGGCCAGGTCATCCAGGTGCACCACTCGCTCCGCTTCGGCC
   __>E  K  G  E  P  G  T  Q  G  A  K  G  D  R  G  E  T  G  P  V  G  P  R  G  E  R  G  E  A  G
                                                                                    TCCCGCTGGAA
                                                                                    +---------+       700
                                                                                    AGGGCGACCTT
                                                                                     P  A  G  K

AAGATGGTGAACGTGGTCCAGTAGGTCCAGCTGGTAAGGACGGCCAAAACGGCCAAGATGGTCTTCCAGGTAAAGACGGTAAGGACGGC
701 ---------+---------+---------+---------+---------+---------+---------+---------+---------
        TTCTACCACTTGCACCAGGTCATCCAGGTCGACCATTCCTGCCGGTTTTGCCGGTTCTACCAGAAGGTCCATTTCTGCCATTCCTGCCG
     >  D  G  E  R  G  P  V  G  P  A  G  K  D  G  Q  N  G  Q  D  G  L  P  G  K  D  G  K  D  G
                                                                                    CAAAACGGTAA
                                                                                    +---------+       800
                                                                                    GTTTTGCCATT
                                                                                     Q  N  G  K

AGATGGTCTTCCAGGTAAAGACGGTAAGGACGGCCAAAACGGTAAAGATGGTCTTCCAGGTAAAGACGGTAAGGACGGTCAAGATGGTA
801 ---------+---------+---------+---------+---------+---------+---------+---------+---------
        TCTACCAGAAGGTCCATTTCTGCCATTCCTGCCGGTTTTGCCATTTCTACCAGAAGGTCCATTTCTGCCATTCCTGCCAGTTCTACCAT
   __> D  G  L  P  G  K  D  G  K  D  G  Q  N  G  K  D  G  L  P  G  K  D  G  K  D  G  Q  D  G  K
                                                                                    AAGACGGCCTC
                                                                                    +---------+       900
                                                                                    TTCTGCCGGAG
                                                                                     D  G  L

CCAGGTAAAGACGGTAAAGATGGCCTCCCAGGTAAGGACGGTAAGGACGGTCAACCAGGTAAACCGGGTAAATATTAA
901 ---------+---------+---------+---------+---------+---------+---------+---------
        GGTCCATTTCTGCCATTTCTACCGGAGGGTCCATTCCTGCCATTCCTGCCAGTTGGTCCATTTGGCCCATTTATAATT
   __>P  G  K  D  G  K  D  G  L  P  G  K  D  G  K  D  G  Q  P  G  K  P  G  K  Y  *
```

Example 2: DNA for Bacterial Collagen Dimer of CL Domains from Collagen Scl2 from *S. pyogenes*

The DNA sequence for the fragment of the scl2.28 allele from *S. pyogenes* comprising the globular and collagen-like portions, but lacking the C-terminal attachment domain, was as described in Example 1. It also included an additional N-terminal His$_6$ tag sequence (SEQ ID NO: 46), a thrombin/trypsin cleavage sequence LVPRGSP (SEQ ID No:1) between the N-terminal globular domain (V) and the following (Gly-Xaa-Yaa)$_n$ collagen-like domain (CL) sequence, a triplet sequence GKY was included at the C terminal of the CL domain, followed by a stop codon. A second construct containing an insert, GAAGVM (SEQ ID No:4), was added into the Scl2 gene using Site Directed Mutagenesis prior to the start of the CL domain, using the following oligonucleotides:

(SEQ ID No: 5)
5' ACGCGGTAGTCCCGGGGCAGCGGGTGTTATGGGGCCCAGAGG 3'
Forward and (SEQ ID No: 6)
3' CCTGTGGGCCGCATAACACCCGCTGCCCCGGGACTACCGCGT 5'
Reverse This second construct, containing the GAAGVM insert (SEQ ID NO: 4), was then digested with 5' SmaI (Blunt) and 3' SspI (Blunt). This digested insert was then subcloned back into the original Scl2 gene at the SmaI site at the end of the original (Example 1) construct. The final sequence construct is shown in SEQ ID No: 7. Since the insert was cloned in as a blunt fragment, colonies were chosen, grown up in 1×YT and midi preps were carried out to select clones that include the additional sequence and with this second sequence in the correct orientation.

DNA and Protein Sequence: (SEQ ID No: 7 & 8).

```
      ATGCATCACCATCACCATCACGATGAACAAGAAGAGAAAGCTAAAGTTAGAACTGAATTAATTCAAGAGTTAGCTCAGGGACTAGGGGG
  1   ---------+---------+---------+---------+---------+---------+---------+---------+---------+---------
      TACGTAGTGGTAGTGGTAGTGCTACTTGTTCTTCTCTTTCGATTTCAATCTTGACTTAATTAAGTTCTCAATCGAGTCCCTGATCCCCC
  ...>  M  H  H  H  H  H  H  D  E  Q  E  E  K  A  K  V  R  T  E  L  I  Q  E  L  A  Q  G  L  G  G
                                                                                           TTTTGAGAAAA
                                                                                           +---------+      100
                                                                                           AAAACTCTTTT
                                                                                             F  E  K  K

AAAATTTTCCAACTCTAGGTGATGAAGATTTAGATCATACTTATATGACAAAGCTATTAACATACCTACAGGAACGAGAACAAGCTGAG
 101  ---------+---------+---------+---------+---------+---------+---------+---------+---------+---------
      TTTTAAAAGGTTGAGATCCACTACTTCTAAATCTAGTATGAATATACTGTTTCGATAATTGTATGGATGTCCTTGCTCTTGTTCGACTC
  ...>   N  F  P  T  L  G  D  E  D  L  D  H  T  Y  M  T  K  L  L  T  Y  L  Q  E  R  E  Q  A  E
                                                                                           AATAGTTGGCG
                                                                                           +---------+      200
                                                                                           TTATCAACCGC
                                                                                             N  S  W  R

AAAAAGACTACTAAAGGGTATACAAGATCATGCCCTTGATCTGGTGCCACGCGGTAGTCCCgggctgccaGGTCCCAGAGGGGAACAAG
 201  ---------+---------+---------+---------+---------+---------+---------+---------+---------+---------
      TTTTTCTGATGATTTCCCATATGTTCTAGTACGGGAACTAGACCACGGTGCGCCATCAGGGcccgacggtCCAGGGTCTCCCCTTGTTC
     >  K  R  L  L  K  G  I  Q  D  H  A  L  D  L  V  P  R  G  S  P  G  L  P  G  P  R  G  E  Q  G
                                                                                           GACCAACAGGT
                                                                                           +---------+      300
                                                                                           CTGGTTGTCCA
                                                                                             P  T  G CCAACCGGACCTGCTGGTCCACGAGGTCTACAAGGTCTACAAGGTCTACAAGGTGAAAGAGGGGAACAAGGACCAACAGGTCCCGCTGG
 301  ---------+---------+---------+---------+---------+---------+---------+---------+---------+---------
      GGTTGGCCTGGACGACCAGGTGCTCCAGATGTTCCAGATGTTCCAGATGTTCCACTTTCTCCCCTTGTTCCTGGTTGTCCAGGGCGACC
  ...>  P  T  G  P  A  G  P  R  G  L  Q  G  L  Q  G  L  Q  G  E  R  G  E  Q  G  P  T  G  P  A  G
                                                                                           TCCACGAGGTC
                                                                                           +---------+      400
                                                                                           AGGTGCTCCAG
                                                                                             P  R  G  L TACAAGGTGAAAGAGGGGAACAAGGACCAACAGGTCTCGCTGGTAAAGCCGGTGAAGCTGGAGCCAAAGGCGAAACCGGCCCCGCTGGT
 401  ---------+---------+---------+---------+---------+---------+---------+---------+---------+---------
      ATGTTCCACTTTCTCCCCTTGTTCCTGGTTGTCCAGAGCGACCATTTCGGCCACTTCGACCTCGGTTTCCGCTTTGGCCGGGGCGACCA
  ...>   Q  G  E  R  G  E  Q  G  P  T  G  L  A  G  K  A  G  E  A  G  A  K  G  E  T  G  P  A  G
                                                                                           CCACAGGGTCC
                                                                                           +---------+      500
                                                                                           GGTGTCCCAGG
                                                                                             P  Q  G  P ACGTGGTGAACAAGGCCCGCAAGGTCTTCCAGGTAAAGATGGTGAAGCTGGTGCTCAAGGCCCAGCAGGTCCAATGGGTCCTGCTGGTG
 501  ---------+---------+---------+---------+---------+---------+---------+---------+---------+---------
      TGCACCACTTGTTCCGGGCGTTCCAGAAGGTCCATTTCTACCACTTCGACCACGAGTTCCGGGTCGTCCAGGTTACCCAGGACGACCAC
     >  R  G  E  Q  G  P  Q  G  L  P  G  K  D  G  E  A  G  A  Q  G  P  A  G  P  M  G  P  A  G  E
                                                                                           AGCGAGGTGAA
                                                                                           +---------+      600
                                                                                           TCGCTCCACTT
                                                                                             R  G  E AAAGGAGAACCTGGTACCCAAGGCGCTAAAGGTGATCGCGGTGAAACCGGTCCAGTAGGTCCACGTGGTGAGCGAGGCGAAGCCGGTCC
 601  ---------+---------+---------+---------+---------+---------+---------+---------+---------+---------
      TTTCCTCTTGGACCATGGGTTCCGCGATTTCCACTAGCGCCACTTTGGCCAGGTCATCCAGGTGCACCACTCGCTCCGCTTCGGCCAGG
     >  K  G  E  P  G  T  Q  G  A  K  G  D  R  G  E  T  G  P  V  G  P  R  G  E  R  G  E  A  G  P
                                                                                           CGCTGGAAAAG
                                                                                           +---------+      700
                                                                                           GCGACCTTTTC
                                                                                             A  G  K  D ATGGTGAACGTGGTCCAGTAGGTCCAGCTGGTAAGGACGGCCAAAACGGCCAAGATGGTCTTCCAGGTAAAGACGGTAAGGACGGCCAA
 701  ---------+---------+---------+---------+---------+---------+---------+---------+---------+---------
      TACCACTTGCACCAGGTCATCCAGGTCGACCATTCCTGCCGGTTTTGCCGGTTCTACCAGAAGGTCCATTTCTGCCATTCCTGCCGGTT
  ...>   G  E  R  G  P  V  G  P  A  G  K  D  G  Q  N  G  Q  D  G  L  P  G  K  D  G  K  D  G  Q
                                                                                           AACGGTAAAGA
                                                                                           +---------+      800
                                                                                           TTGCCATTTCT
                                                                                             N  G  K  D TGGTCTTCCAGGTAAAGACGGTAAGGACGGCCAAAACGGTAAAGATGGTCTTCCAGGTAAAGACGGTAAGGACGGTCAAGATGGTAAAG
 801  ---------+---------+---------+---------+---------+---------+---------+---------+---------+---------
      ACCAGAAGGTCCATTTCTGCCATTCCTGCCGGTTTTGCCATTTCTACCAGAAGGTCCATTTCTGCCATTCCTGCCAGTTCTACCATTTC
  ...>   G  L  P  G  K  D  G  K  D  G  Q  N  G  K  D  G  L  P  G  K  D  G  K  D  G  Q  D  G  K  D
                                                                                           ACGGCCTCCCA
                                                                                           +---------+      900
                                                                                           TGCCGGAGGGT
                                                                                             G  L  P
```

-continued

```
         GGTAAAGACGGTAAAGATGGCCTCCCAGGTAAGGACGGTAAGGACGGTCAACCAGGTAAACCCGGGGCAGCGGGTGTTATGGGGCCCAG
  901    ---------+---------+---------+---------+---------+---------+---------+---------+---------+
         CCATTTCTGCCATTTCTACCGGAGGGTCCATTCCTGCCATTCCTGCCAGTTGGTCCATTTGGGCCCCGTCGCCCACAATACCCCGGGTC
      >  G  K  D  G  K  D  G  L  P  G  K  D  G  K  D  G  Q  P  G  K  P  G  A  A  G  V  M  G  P  R
                                                                                                    AGGGGAACAAG
                                                                                                    +---------+  1000
                                                                                                    TCCCCTTGTTC
                                                                                                     G  E  Q  G

GACCAACAGGTCCAACCGGACCTGCTGGTCCACGAGGTCTACAAGGTCTACAAGGTCTACAAGGTGAAAGAGGGGAACAAGGACCAACA
  1001   ---------+---------+---------+---------+---------+---------+---------+---------+---------+
         CTGGTTGTCCAGGTTGGCCTGGACGACCAGGTGCTCCAGATGTTCCAGATGTTCCAGATGTTCCACTTTCTCCCCTTGTTCCTGGTTGT
      ...>  P  T  G  P  T  G  P  A  G  P  R  G  L  Q  G  L  Q  G  L  Q  G  E  R  G  E  Q  G  P  T
                                                                                                    GGTCCCGCTGG
                                                                                                    +---------+  1100
                                                                                                    CCAGGGCGACC
                                                                                                     G  P  A  G

TCCACGAGGTCTACAAGGTGAAAGAGGGGAACAAGGACCAACAGGTCTCGCTGGTAAAGCCGGTGAAGCTGGAGCCAAAGGCGAAACCG
  1101   ---------+---------+---------+---------+---------+---------+---------+---------+---------+
         AGGTGCTCCAGATGTTCCACTTTCTCCCCTTGTTCCTGGTTGTCCAGAGCGACCATTTCGGCCACTTCGACCTCGGTTTCCGCTTTGGC
      ...>  P  R  G  L  Q  G  E  R  G  E  Q  G  P  T  G  L  A  G  K  A  G  E  A  G  A  K  G  E  T  G
                                                                                                    GCCCCGCTGGT
                                                                                                    +---------+  1200
                                                                                                    CGGGGCGACCA
                                                                                                     P  A  G

CCACAGGGTCCACGTGGTGAACAAGGCCCGCAAGGTCTTCCAGGTAAAGATGGTGAAGCTGGTGCTCAAGGCCCAGCAGGTCCAATGGG
  1201   ---------+---------+---------+---------+---------+---------+---------+---------+---------+
         GGTGTCCCAGGTGCACCACTTGTTCCGGGCGTTCCAGAAGGTCCATTTCTACCACTTCGACCACGAGTTCCGGGTCGTCCAGGTTACCC
      ...>  P  Q  G  P  R  G  E  Q  G  P  Q  G  L  P  G  K  D  G  E  A  G  A  Q  G  P  A  G  P  M  G
                                                                                                    TCCTGCTGGTG
                                                                                                    +---------+  1300
                                                                                                    AGGACGACCAC
                                                                                                     P  A  G  E

AGCGAGGTGAAAAGGAGAACCTGGTACCCAAGGCGCTAAAGGTGATCGCGGTGAAACCGGTCCAGTAGGTCCACGTGGTGAGCGAGGC
  1301   ---------+---------+---------+---------+---------+---------+---------+---------+---------+
         TCGCTCCACTTTTTCCTCTTGGACCATGGGTTCCGCGATTTCCACTAGCGCCACTTTGGCCAGGTCATCCAGGTGCACCACTCGCTCCG
      ...>  R  G  E  K  G  E  P  G  T  Q  G  A  K  G  D  R  G  E  T  G  P  V  G  P  R  G  E  R  G
                                                                                                    GAAGCCGGTCC
                                                                                                    +---------+  1400
                                                                                                    CTTCGGCCAGG
                                                                                                     E  A  G  P

CGCTGGAAAAGATGGTGAACGTGGTCCAGTAGGTCCAGCTGGTAAGGACGGCCAAAACGGCCAAGATGGTCTTCCAGGTAAAGACGGTA
  1401   ---------+---------+---------+---------+---------+---------+---------+---------+---------+
         GCGACCTTTTCTACCACTTGCACCAGGTCATCCAGGTCGACCATTCCTGCCGGTTTTGCCGGTTCTACCAGAAGGTCCATTTCTGCCAT
      ...>  A  G  K  D  G  E  R  G  P  V  G  P  A  G  K  D  G  Q  N  G  Q  D  G  L  P  G  K  D  G  K
                                                                                                    AGGACGGCCAA
                                                                                                    +---------+  1500
                                                                                                    TCCTGCCGGTT
                                                                                                     D  G  Q

AACGGTAAAGATGGTCTTCCAGGTAAAGACGGTAAGGACGGCCAAAACGGTAAAGATGGTCTTCCAGGTAAAGACGGTAAGGACGGTCA
  1501   ---------+---------+---------+---------+---------+---------+---------+---------+---------+
         TTGCCATTTCTACCAGAAGGTCCATTTCTGCCATTCCTGCCGGTTTTGCCATTTCTACCAGAAGGTCCATTTCTGCCATTCCTGCCAGT
      ...>  N  G  K  D  G  L  P  G  K  D  G  K  D  G  Q  N  G  K  D  G  L  P  G  K  D  G  K  D  G  Q
                                                                                                    AGATGGTAAAG
                                                                                                    +---------+  1600
                                                                                                    TCTACCATTTC
                                                                                                     D  G  K

ACGGCCTCCCAGGTAAAGACGGTAAGGATGGCCTCCCAGGTAAGGACGGTAAGGACGGTCAACCAGGTAAACCGGGTAAATATTAA
  1601   ---------+---------+---------+---------+---------+---------+---------+---------+------
         TGCCGGAGGGTCCATTTCTGCCATTTCTACCGGAGGGTCCATTCCTGCCATTCCTGCCAGTTGGTCCATTTGGGCCCATTTATAATT
      ...>  G  L  P  G  K  D  G  K  D  G  L  P  K  D  G  K  D  G  Q  P  G  K  P  G  K  Y  *
```

Example 3: DNA from Bacterial Collagen Scl2 from *S. pyogenes* Including a Substituted Functional Sequence for Heparin Binding The Scl2 gene, as given in Example 1, was cloned into the shuttle vector pSL1180 using the restriction sites 5' NdeI and 3' BamHI. This clone was then used to carry out Site Directed Mutagenesis to introduce a new binding motif within the sequence. A heparin binding sequence (GRPG-KRGKQGQK; SEQ ID No:9) was added to the Scl2 gene at base pair 561 using 3 sequential site directed mutagenesis PCR reactions, since the heparin insert was 12 amino acids and the sequence around the insertion site was very repetitive. For the first reaction, the following olignucleotides were used:

(SEQ ID No: 10)
5' TGAAGCTGGTGCTCAAGGCAGGCCGGGTCCAATGGGTCCTGCTG 3' Forward and (SEQ ID No: 11)
3' CAGCAGGACCCATTGGACCGGCCTGCCTTGAGCACCAGCTTCA 5' Reverse For the second reaction, the following oligonucleotides were used:

(SEQ ID No: 12)
5' CAAGGCAGGCCGGGTAAGCGGGGTCCTGCTGGTGAGCG 3' Forward and (SEQ ID NO: 13)
3' CGCTCACCAGCAGGACCCCGCTTACCCGGCCTGCCTTG 5' Reverse For the third reaction, the following oligonucleotides were used:

(SEQ ID NO: 14)
5' CCGGGTAAGCGGGGTAAACAGGGCCAGAAGGGTGAAAAAGGAGAACCTGG 3' and (SEQ ID NO: 15)
3' CCAGGTTCTCCTTTTTCACCCTTCTGGCCCTGTTTACCCCGCTTACCCGG 5'

PCR product was treated with the enzyme DpnI, to ensure that all parental DNA was digested, and subsequently transformed into the *E. coli* host strain XLI-BLUE. The final sequence construct is described in SEQ ID No 16. Colonies were chosen, grown in antibiotic selective media and Qiagen mini preps carried out. Clones that contained the introduced heparin site were identified and stored at −20° C.

```
DNA and Protein Sequence: (SEQ No: 16 & 17)
       ATGCATCACCATCACCATCACGCTGATGAACAAGAAGAGAAAGCTAAAGTTAGAACTGAATTAATTCAAGAGTTAGCTCAGGGACTAGG
  1    ---------+---------+---------+---------+---------+---------+---------+---------+---------
       TACGTAGTGGTAGTGGTAGTGCGACTACTTGTTCTTCTCTTTCGATTTCAATCTTGACTTAATTAAGTTCTCAATCGAGTCCCTGATCC
   ...> M  H  H  H  H  H  H  A  D  E  Q  E  E  K  A  K  V  R  T  E  L  I  Q  E  L  A  Q  G  L  G
                                                                                      GGGTATTGAGA
                                                                                      +---------+   100
                                                                                      CCCATAACTCT
                                                                                      G  I  E  K AAAAAAATTTTCCAACTCTAGGTGATGAAGATTTAGATCATACTTATATGACAAAGCTATTAACATACCTACAGGAACGAGAACAAGCT
  101  ---------+---------+---------+---------+---------+---------+---------+---------+---------
       TTTTTTTAAAAGGTTGAGATCCACTACTTCTAAATCTAGTATGAATATACTGTTTCGATAATTGTATGGATGTCCTTGCTCTTGTTCGA
   ...>   K  N  F  P  T  L  G  D  E  D  L  D  H  T  Y  M  T  K  L  L  T  Y  L  Q  E  R  E  Q  A
                                                                                      GAGAATAGTTG
                                                                                      +---------+   200
                                                                                      CTCTTATCAAC
                                                                                      E  N  S  W GCGAAAAAGACTACTAAAGGGTATACAAGATCATGCCCTTGATCTGGTGCCACGCGGTAGTCCCGGGCTGCCAGGGCCCAGAGGGGAAC
  201  ---------+---------+---------+---------+---------+---------+---------+---------+---------
       CGCTTTTTCTGATGATTTCCCATATGTTCTAGTACGGGAACTAGACCACGGTGCGCCATCAGGGCCCGACGGTCCCGGGTCTCCCCTTG
     > R  K  R  L  L  K  G  I  Q  D  H  A  L  D  L  V  P  R  G  S  P  G  L  P  G  P  R  G  E  Q
                                                                                      AAGGACCAACA
                                                                                      +---------+   300
                                                                                      TTCCTGGTTGT
                                                                                      G  P  T GGTCCAACCGGACCTGCTGGTCCACGAGGTCTACAAGGTCTACAAGGTCTACAAGGTGAAAGAGGGGAACAAGGACCAACAGGTCCCGC
  301  ---------+---------+---------+---------+---------+---------+---------+---------+---------
       CCAGGTTGGCCTGGACGACCAGGTGCTCCAGATGTTCCAGATGTTCCAGATGTTCCACTTTCTCCCCTTGTTCCTGGTTGTCCAGGGCG
   ...> G  P  T  G  P  A  G  P  R  G  L  Q  G  L  Q  G  L  Q  G  E  R  G  E  Q  G  P  T  G  P  A
                                                                                      TGGTCCACGAG
                                                                                      +---------+   400
                                                                                      ACCAGGTGCTC
                                                                                      G  P  R  G GTCTACAAGGTGAAAGAGGGGAACAAGGACCAACAGGTCTCGCTGGTAAAGCCGGTGAAGCTGGAGCCAAAGGCGAAACCGGCCCCGCT
  401  ---------+---------+---------+---------+---------+---------+---------+---------+---------
       CAGATGTTCCACTTTCTCCCCTTGTTCCTGGTTGTCCAGAGCGACCATTTCGGCCACTTCGACCTCGGTTTCCGCTTTGGCCGGGGCGA
   ...>   L  Q  G  E  R  G  E  Q  G  P  T  G  L  A  G  K  A  G  E  A  G  A  K  G  E  T  G  P  A
                                                                                      GGTCCACAGGG
                                                                                      +---------+   500
                                                                                      CCAGGTGTCCC
                                                                                      G  P  Q  G
```

-continued

```
    TCCACGTGGTGAACAAGGCCCGCAAGGTCTTCCAGGTAAAGATGGTGAAGCTGGTGCTCAAGGCAGGCCGGGTAAGCGGGGTAAACAGG
501 ---------+---------+---------+---------+---------+---------+---------+---------+---------
    AGGTGCACCACTTGTTCCGGGCGTTCCAGAAGGTCCATTTCTACCACTTCGACCACGAGTTCCGTCCGGCCCATTCGCCCCATTTGTCC
      P  R  G  E  Q  G  P  Q  G  L  P  G  K  D  G  E  A  G  A  Q  G  R  P  G  K  R  G  K  Q  G
                                                                                   GCCAGAAGGGT
                                                                                   +---------+   600
                                                                                   CGGTCTTCCCA
                                                                                      Q  K  G

GAAAAAGGAGAACCTGGTACCCAAGGCGCTAAAGGTGATCGCGGTGAAACCGGTCCAGTAGGTCCACGTGGTGAGCGAGGCGAAGCCGG
601 ---------+---------+---------+---------+---------+---------+---------+---------+---------
    CTTTTTCCTCTTGGACCATGGGTTCCGCGATTTCCACTAGCGCCACTTTGGCCAGGTCATCCAGGTGCACCACTGCTCCGCTTCGGCC
...> E  K  G  E  P  G  T  Q  G  A  K  G  D  R  G  E  T  G  P  V  G  P  R  G  E  R  G  E  A  G
                                                                                   TCCCGCTGGAA
                                                                                   +---------+   700
                                                                                   AGGGCGACCTT
                                                                                      P  A  G  K

AAGATGGTGAACGTGGTCCAGTAGGTCCAGCTGGTAAGGACGGCCAAAACGGCCAAGATGGTCTTCCAGGTAAAGACGGTAAGGACGGC
701 ---------+---------+---------+---------+---------+---------+---------+---------+---------
    TTCTACCACTTGCACCAGGTCATCCAGGTCGACCATTCCTGCCGGTTTTGCCGGTTCTACCAGAAGGTCCATTTCTGCCATTCCTGCCG
  >    D  G  E  R  G  P  V  G  P  A  G  K  D  G  Q  N  G  Q  D  G  L  P  G  K  D  G  K  D  G
                                                                                   CAAAACGGTAA
                                                                                   +---------+   800
                                                                                   GTTTTGCCATT
                                                                                      Q  N  G  K

AGATGGTCTTCCAGGTAAAGACGGTAAGGACGGCCAAAACGGTAAAGATGGTCTTCCAGGTAAAGACGGTAAGGACGGTCAAGATGGTA
801 ---------+---------+---------+---------+---------+---------+---------+---------+---------
    TCTACCAGAAGGTCCATTTCTGCCATTCCTGCCGGTTTTGCCATTTCTACCAGAAGGTCCATTTCTGCCATTCCTGCCAGTTCTACCAT
...> D  G  L  P  G  K  D  G  K  D  G  Q  N  G  K  D  G  L  P  G  K  D  G  K  D  G  Q  D  G  K
                                                                                   AAGACGGCCTC
                                                                                   +---------+   900
                                                                                   TTCTGCCGGAG
                                                                                      D  G  L

CCAGGTAAAGACGGTAAAGATGGCCTCCCAGGTAAGGACGGTAAGGACGGTCAACCAGGTAAACCGGGTAAATATTAAGGA
901 ---------+---------+---------+---------+---------+---------+---------+---------+-           981
    GGTCCATTTCTGCCATTTCTACCGGAGGGTCATTCCTGCCATTCCTGCCAGTTGGTCCATTTGGCCCATTTATAATTCCT
...> P  G  K  D  G  K  D  G  L  P  G  K  D  G  K  D  G  Q  P  G  K  P  G  K  Y  *
```

Example 4: DNA from Bacterial Collagen Scl2 from *S. pyogenes* Including a Substituted Functional Sequence for Integrin Binding The Scl2 gene, as given in Example 1, was cloned into the shuttle vector pSL1180 using the restriction sites 5' NdeI and 3' BamHI. This clone was then used to carry out Site Directed Mutagenesis to introduce a new binding motif within the sequence. An integrin binding sequence (GERGFPGERGVE; SEQ ID No:18) was added to the Scl2 gene at base pair 705 via PCR directed integration, using two sequential steps. The oligonucleotides used for step 1 were:

(SEQ ID No: 19)
5' GGAAAAGATGGTGAACGTGGTTTCCCGGGTCCAGCTGGTAAGG
ACG 3' Forward and -continued (SEQ ID No: 20)
3' CGTCCTTACCAGCTGGACCCGGGAAACCACGTTCACCATCTTT
TCC 5' Reverse The oligonucleotides used for step 2 were:

(SEQ ID No: 21)
5' GAACGTGGTTTCCCGGGTGAGAGGGGCGTCGAGGGCCAAAACG
GCCAAGAT 3' Forward and (SEQ ID No: 22)
3' ATCTTGGCCGTTTTGGCCCTCGACGCCCCTCTCACCCGGGAAA
CCACGTTC 5' Reverse PCR product was treated with the enzyme DpnI, to ensure that all parental DNA was digested, and subsequently transformed into the *E. coli* host strain XLI-BLUE. The final sequence construct is described in SEQ ID No 23. Colonies were chosen, grown in antibiotic selective media and Qiagen mini preps carried out. Clones that contained the introduced integrin site were identified and stored at −20° C.

DNA and Protein Sequence: (SEQ ID No: 23 & 24)

```
     ATGCATCACCATCACCATCACGCTGATGAACAAGAAGAGAAAGCTAAAGTTAGAACTGAATTAATTCAAGAGTTAGCTCAGGGACTAGG
  1  ---------+---------+---------+---------+---------+---------+---------+---------+---------
     TACGTAGTGGTAGTGGTAGTGCGACTACTTGTTCTTCTCTTTCGATTTCAATCTTGACTTAATTAAGTTCTCAATCGAGTCCCTGATCC
...> M  H  H  H  H  H  H  A  D  E  Q  E  E  K  A  K  V  R  T  E  L  I  Q  E  L  A  Q  G  L  G
                                                                                    GGGTATTGAGA
                                                                                    +---------+      100
                                                                                    CCCATAACTCT
                                                                                     G  I  E  K
```

```
                AAAAAAATTTTCCAACTCTAGGTGATGAAGATTTAGATCATACTTATATGACAAAGCTATTAACATACCTACAGGAACGAGAACAAGCT
     101        ---------+---------+---------+---------+---------+---------+---------+---------+---------+---------
                TTTTTTTAAAAGGTTGAGATCCACTACTTCTAAATCTAGTATGAATATACTGTTTCGATAATTGTATGGATGTCCTTGCTCTTGTTCGA
        ...>     K  N  F  P  T  L  G  D  E  D  L  D  H  T  Y  M  T  K  L  L  T  Y  L  Q  E  R  E  Q  A
                                                                                                      GAGAATAGTTG
                                                                                                      +---------+      200
                                                                                                      CTCTTATCAAC
                                                                                                       E  N  S  W

GCGAAAAAGACTACTAAAGGGTATACAAGATCATGCCCTTGATCTGGTGCCACGCGGTAGTCCCGGGCTGCCAGGGCCCAGAGGGGAAC
     201        ---------+---------+---------+---------+---------+---------+---------+---------+---------+---------
                CGCTTTTTCTGATGATTTCCCATATGTTCTAGTACGGGAACTAGACCACGGTGCGCCATCAGGGCCCGACGGTCCCGGGTCTCCCCTTG
        ...>     R  K  R  L  L  K  G  I  Q  D  H  A  L  D  L  V  P  R  G  S  P  G  L  P  G  P  R  G  E  Q
                                                                                                      AAGGACCAACA
                                                                                                      +---------+      300
                                                                                                      TTCCTGGTTGT
                                                                                                       G  P  T

GGTCCAACCGGACCTGCTGGTCCACGAGGTCTACAAGGTCTACAAGGTCTACAAGGTGAAAGAGGGGAACAAGGACCAACAGGTCCCGC
     301        ---------+---------+---------+---------+---------+---------+---------+---------+---------+---------
                CCAGGTTGGCCTGGACGACCAGGTGCTCCAGATGTTCCAGATGTTCCAGATGTTCCACTTTCTCCCCTTGTTCCTGGTTGTCCAGGGCG
        ...>     G  P  T  G  P  A  G  P  R  G  L  Q  G  L  Q  G  L  Q  G  E  R  G  E  Q  G  P  T  G  P  A
                                                                                                      TGGTCCACGAG
                                                                                                      +---------+      400
                                                                                                      ACCAGGTGCTC
                                                                                                       G  P  R  G

GTCTACAAGGTGAAAGAGGGGAACAAGGACCAACAGGTCTCGCTGGTAAAGCCGGTGAAGCTGGAGCCAAAGGCGAAACCGGCCCCGCT
     401        ---------+---------+---------+---------+---------+---------+---------+---------+---------+---------
                CAGATGTTCCACTTTCTCCCCTTGTTCCTGGTTGTCCAGAGCGACCATTTCGGCCACTTCGACCTCGGTTTCCGCTTTGGCCGGGGCGA
        ...>     L  Q  G  E  R  G  E  Q  G  P  T  G  L  A  G  K  A  G  E  A  G  A  K  G  E  T  G  P  A
                                                                                                      GGTCCACAGGG
                                                                                                      +---------+      500
                                                                                                      CCAGGTGTCCC
                                                                                                       G  P  Q  G

TCCACGTGGTGAACAAGGCCCGCAAGGTCTTCCAGGTAAAGATGGTGAAGCTGGTGCTCAAGGCCCAGCAGGTCCAATGGGTCCTGCTG
     501        ---------+---------+---------+---------+---------+---------+---------+---------+---------+---------
                AGGTGCACCACTTGTTCCGGGCGTTCCAGAAGGTCCATTTCTACCACTTCGACCACGAGTTCCGGGTCGTCCAGGTTACCCAGGACGAC
        ...>     P  R  G  E  Q  G  P  Q  G  L  P  G  K  D  G  E  A  G  A  Q  G  P  A  G  P  M  G  P  A  G
                                                                                                      GTGAGCGAGGT
                                                                                                      +---------+      600
                                                                                                      CACTCGCTCCA
                                                                                                       E  R  G

GAAAAGGAGAACCTGGTACCCAAGGCGCTAAAGGTGATCGCGGTGAAACCGGTCCAGTAGGTCCACGTGGTGAGCGAGGCGAAGCCGG
     601        ---------+---------+---------+---------+---------+---------+---------+---------+---------+---------
                CTTTTCCTCTTGGACCATGGGTTCCGCGATTTCCACTAGCGCCACTTTGGCCAGGTCATCCAGGTGCACCACTCGCTCCGCTTCGGCC
        ...>     E  K  G  E  P  G  T  Q  G  A  K  G  D  R  G  E  T  G  P  V  G  P  R  G  E  R  G  E  A  G
                                                                                                      TCCCGCTGGAA
                                                                                                      +---------+      700
                                                                                                      AGGGCGACCTT
                                                                                                       P  A  G  K

AAGATGGTgaacgtggtttcccgggtgagagggggcgtcgagGGCCAAAACGGCCAAGATGGTCTTCCAGGTAAAGACGGTAAGGACGGC
     701        ---------+---------+---------+---------+---------+---------+---------+---------+---------+---------
                TTCTACCActtgcaccaaagggcccactctccccgcagctcCCGGTTTTGCCGGTTCTACCAGAAGGTCCATTTCTGCCATTCCTGCCG
          >      D  G  E  R  G  F  P  G  E  R  G  V  E  G  Q  N  G  Q  D  G  L  P  G  K  D  G  K  D  G
                                                                                                      CAAAACGGTAA
                                                                                                      +---------+      800
                                                                                                      GTTTTGCCATT
                                                                                                       Q  N  G  K AGATGGTCTTCCAGGTAAAGACGGTAAGGACGGCCAAAACGGTAAAGATGGTCTTCCAGGTAAAGACGGTAAGGACGGTCAAGATGGTA
     801        ---------+---------+---------+---------+---------+---------+---------+---------+---------+---------
                TCTACCAGAAGGTCCATTTCTGCCATTCCTGCCGGTTTTGCCATTTCTACCAGAAGGTCCATTTCTGCCATTCCTGCCAGTTCTACCAT
          >      D  G  L  P  G  K  D  G  K  D  G  Q  N  G  K  D  G  L  P  G  K  D  G  K  D  G  Q  D  G
                                                                                                      AAGACGGCCTC
                                                                                                      +---------+      900
                                                                                                      TTCTGCCGGAG
                                                                                                       K  D  G  L CCAGGTAAAGACGGTAAAGATGGCCTCCCAGGTAAGGACGGTAAGGACGGTCAACCAGGTAAACCGGGTAAATATTAA
     901        ---------+---------+---------+---------+---------+---------+---------+--------
                GGTCCATTTCTGCCATTTCTACCGGAGGGTCCATTCCTGCCATTCCTGCCAGTTGGTCCATTTGGCCCATTTATAATT
          >      P  G  K  D  G  K  D  G  L  P  G  K  D  G  K  D  G  Q  P  G  K  P  G  K  Y  *
```

Example 5: DNA from Bacterial Collagen Scl2 from *S. pyogenes* Including Substituted Functional Sequences for Both Heparin and Integrin Binding An Scl2 gene containing an introduced heparin binding site, as described in Example 3, was used. A selected clone that contained the confirmed introduced heparin site was put through a second round of Site Directed Mutagenesis to introduce an integrin binding domain (GERGFPGERGVE; SEQ ID No:18) at base pair 705 of the Scl2 gene, using oligonucleotides as described in Example 4. PCR product was treated with the enzyme DpnI, to ensure that all parental DNA was digested, and subsequently transformed into the *E. coli* host strain XLI-BLUE. The final sequence construct is described in SEQ ID No 25. Colonies were chosen, grown in antibiotic selective media and Qiagen mini preps carried out. Clones that contained the introduced integrin site as well as the heparin binding site were identified and stored at −20° C.

```
DNA and Protein sequence: (SEQ ID No: 25 & 26)
        ATGCATCACCATCACCATCACGCTGATGAACAAGAAGAGAAAGCTAAAGTTAGAACTGAATTAATTCAAGAGTTAGCTCAGGGACTAGG
    1   ---------+---------+---------+---------+---------+---------+---------+---------+---------
        TACGTAGTGGTAGTGGTAGTGCGACTACTTGTTCTTCTCTTTCGATTTCAATCTTGACTTAATTAAGTTCTCAATCGAGTCCCTGATCC
  ...>  M  H  H  H  H  H  H  A  D  E  Q  E  E  K  A  K  V  R  T  E  L  I  Q  E  L  A  Q  G  L  G
                                                                                        GGGTATTGAGA
                                                                                        +---------+    100
                                                                                        CCCATAACTCT
                                                                                         G  I  E  K AAAAAAATTTTCCAACTCTAGGTGATGAAGATTTAGATCATACTTATATGACAAAGCTATTAACATACCTACAGGAACGAGAACAAGCT
   101  ---------+---------+---------+---------+---------+---------+---------+---------+---------
        TTTTTTTAAAAGGTTGAGATCCACTACTTCTAAATCTAGTATGAATATACTGTTTCGATAATTGTATGGATGTCCTTGCTCTTGTTCGA
  ...>    K  N  F  P  T  L  G  D  E  D  L  D  H  T  Y  M  T  K  L  L  T  Y  L  Q  E  R  E  Q  A
                                                                                        GAGAATAGTTG
                                                                                        +---------+    200
                                                                                        CTCTTATCAAC
                                                                                         E  N  S  W GCGAAAAAGACTACTAAAGGGTATACAAGATCATGCCCTTGATCTGGTGCCACGCGGTAGTCCCGGGCTGCCAGGGCCCAGAGGGGAAC
   201  ---------+---------+---------+---------+---------+---------+---------+---------+---------
        CGCTTTTTCTGATGATTTCCCATATGTTCTAGTACGGGAACTAGACCACGGTGCGCCATCAGGGCCCGACGGTCCCGGGTCTCCCCTTG
  ...>  R  K  R  L  L  K  G  I  Q  D  H  A  L  D  L  V  P  R  G  S  P  G  L  P  G  P  R  G  E  Q
                                                                                        AAGGACCAACA
                                                                                        +---------+    300
                                                                                        TTCCTGGTTGT
                                                                                         G  P  T GGTCCAACCGGACCTGCTGGTCCACGAGGTCTACAAGGTCTACAAGGTGAAAGAGGGGAACAAGGACCAACAGGTCCCGC
   301  ---------+---------+---------+---------+---------+---------+---------+---------+---------
        CCAGGTTGGCCTGGACGACCAGGTGCTCCAGATGTTCCAGATGTTCCACTTTCTCCCCTTGTTCCTGGTTGTCCAGGGCG
  ...>  G  P  T  G  P  A  G  P  R  G  L  Q  G  L  Q  G  E  R  G  E  Q  G  P  T  G  P  A
                                                                                        TGGTCCACGAG
                                                                                        +---------+    400
                                                                                        ACCAGGTGCTC
                                                                                         G  P  R  G GTCTACAAGGTGAAAGAGGGGAACAAGGACCAACAGGTCTCGCTGGTAAAGCCGGTGAAGCTGGAGCCAAAGGCGAAACCGGCCCCGCT
   401  ---------+---------+---------+---------+---------+---------+---------+---------+---------
        CAGATGTTCCACTTTCTCCCCTTGTTCCTGGTTGTCCAGAGCGACCATTTCGGCCACTTCGACCTCGGTTTCCGCTTTGGCCGGGGCGA
  ...>    L  Q  G  E  R  G  E  Q  G  P  T  G  L  A  G  K  A  G  E  A  G  A  K  G  E  T  G  P  A
                                                                                        GGTCCACAGGG
                                                                                        +---------+    500
                                                                                        CCAGGTGTCCC
                                                                                         G  P  Q  G TCCACGTGGTGAACAAGGCCCGCAAGGTCTTCCAGGTAAAGATGGTGAAGCTGGTGCTCAAGGCAGGCCGGGTAAGCGGGGTAAACAGG
   501  ---------+---------+---------+---------+---------+---------+---------+---------+---------
        AGGTGCACCACTTGTTCCGGGCGTTCCAGAAGGTCCATTTCTACCACTTCGACCACGAGTTCCGTCCGGCCCATTCGCCCCATTTGTCC
  ...>  P  R  G  E  Q  G  P  Q  G  L  P  G  K  D  G  E  A  G  A  Q  G  R  P  G  K  R  G  K  Q  G
                                                                                        GCCAGAAGGGT
                                                                                        +---------+    600
                                                                                        CGGTCTTCCCA
                                                                                         Q  K  G GAAAAAGGAGAACCTGGTACCCAAGGCGCTAAAGGTGATCGCGGTGAAACCGGTCCAGTAGGTCCACGTGGTGAGCGAGGCGAAGCCGG
   601  ---------+---------+---------+---------+---------+---------+---------+---------+---------
        CTTTTTCCTCTTGGACCATGGGTTCCGCGATTTCCACTAGCGCCACTTTGGCCAGGTCATCCAGGTGCACCACTCGCTCCGCTTCGGCC
  ...>  E  K  G  E  P  G  T  Q  G  A  K  G  D  R  G  E  T  G  P  V  G  P  R  G  E  R  G  E  A  G
                                                                                        TCCCGCTGGAA
                                                                                        +---------+    700
                                                                                        AGGGCGACCTT
                                                                                         P  A  G  K
```

-continued

```
      AAGATGGTgaacgtggtttcccgggtgagaggggcgtcgagGGCCAAAACGGCCAAGATGGTCTTCCAGGTAAAGACGGTAAGGACGGC
701   ---------+---------+---------+---------+---------+---------+---------+---------+---------
      TTCTACCActtgcaccaaagggcccactctccccgcagctcCCGGTTTTGCCGGTTCTACCAGAAGGTCATTTCTGCCATTCCTGCCG
...>   D  G  E  R  G  F  P  G  E  R  G  V  E  G  Q  N  G  Q  D  G  L  P  G  K  D  G  K  D  G
                                                                                      CAAAACGGTAA
                                                                                      +---------+   800
                                                                                      GTTTTGCCATT
                                                                                       Q  N  G  K AGATGGTCTTCCAGGTAAAGACGGTAAGGACGGCCAAAACGGTAAAGATGGTCTTCCAGGTAAAGACGGTAAGGACGGTCAAGATGGTA
801   ---------+---------+---------+---------+---------+---------+---------+---------+---------
      TCTACCAGAAGGTCCATTTCTGCCATTCCTGCCGGTTTTGCCATTTCTACCAGAAGGTCCATTTCTGCCATTCCTGCCAGTTCTACCAT
...>   D  G  L  P  G  K  D  G  K  D  G  Q  N  G  K  D  G  L  P  G  K  D  G  K  D  G  Q  D  G  K
                                                                                      AAGACGGCCTC
                                                                                      +---------+   900
                                                                                      TTCTGCCGGAG
                                                                                       D  G  L CCAGGTAAAGACGGTAAAGATGGCCTCCCAGGTAAGGACGGTAAGGACGGTCAACCAGGTAAACCGGGTAAATATTAA
901   ---------+---------+---------+---------+---------+---------+---------+---------+---------
      GGTCCATTTCTGCCATTTCTACCGGAGGGTCCATTCCTGCCATTCCTGCCAGTTGGTCCATTTGGCCCATTTATAATT
    >  P  G  K  D  G  K  D  G  L  P  G  K  D  G  K  D  G  Q  P  G  K  P  G  K  Y  *
```

Example 6: DNA from Bacterial Collagen from *Solibacter usitatus* Using a V-Domain from *Rhodopseudomonas palustris*

The DNA sequence for the triple helix repeat-containing collagen from *Candidatus Solibacter usitatus* Ellin6076 was obtained from the data provided in the National Center for Biotechnology Information database (National institutes of Health, Bethesda, Md. 20894, USA) as record ABJ82342. The DNA sequence for the V-domain from *R. palustris* was obtained from the data provided in the National Center for Biotechnology Information database (National institutes of Health, Bethesda, Md. 20894, USA) as YP_001993084. The protein sequences were translated into nominal DNA sequences and a composite gene was designed that maintained the correct coding framework, with a Met initiation signal followed by the CL domain from *S. usitatus*, then the V-domain from *R. palustris*, followed finally by a C-terminal $His_6$-tag (SEQ ID NO: 46) and a termination codon. Terminal restriction sites outside the coding sequence were added as NdeI and EcoRI for 5' and were SaiI and HindIII for 3'. This construct was synthesised (GeneArt® Gene Synthesis, Regensburg, Germany) with a DNA sequence that retained the original amino acid sequence while optimising for expression in a desired host system, *E coli*. The final sequence construct is described in SEQ ID No: 27.

```
DNA and Protein Sequence: (SEQ ID No: 27 & 28)
      atgggccggcgggcccggcgggcccgcagggcccggcgggcccggcgggcgcgcagggcccggcgggcccggcgggcccgcagggccc
  1   ---------+---------+---------+---------+---------+---------+---------+---------+---------
      tacccggccgccgggccgcccgggcgtcccgggccgccgccgccgcccgggccgcccgccggccgccgccgccgccgggcgtcccggg
...>   M  G  P  A  G  P  A  G  P  Q  G  P  A  G  P  A  G  A  Q  G  P  A  G  P  A  G  P  Q  G  P
                                                                                       ggcgggcccgc
                                                                                       +---------+   100
                                                                                       ccgcccgggcg
                                                                                        A  G  P  Q agggcagcgcgggcgcgcagggcccgaaaggcgataccggcgcggcgggcccggcgggcgaagcgggcccgaaaggcgaaaccggcgcg
 101  ---------+---------+---------+---------+---------+---------+---------+---------+---------
      tcccgtcgcgcccgcgcgtcccgggctttccgctatggccgcgccgcccgggccgcccgcttcgcccgggctttccgcttggccgcgc
    >  G  S  A  G  A  Q  G  P  K  G  D  T  G  A  A  G  P  A  G  E  A  G  P  K  G  E  T  G  A
                                                                                       gcgggcccgaa
                                                                                       +---------+   200
                                                                                       cgcccgggctt
                                                                                        A  G  P  K aggcgataccggcgcggcgggcccggcgggcccgaaaggcgataccggcgcggcgggcccggcgggcccgaaaggcgataccggcgcgg
 201  ---------+---------+---------+---------+---------+---------+---------+---------+---------
      tccgctatggccgcgccgcccgggccgcccgggctttccgctatggccgcgccgcccgggccgcccgggctttccgctatggccgcgcc
...>   G  D  T  G  A  A  G  P  A  G  P  K  G  D  T  G  A  A  G  P  A  G  P  K  G  D  T  G  A  A
                                                                                       cgggcgcgacc
                                                                                       +---------+   300
                                                                                       gcccgcgctgg
                                                                                        G  A  T ggcccgaaaggcgaaaaaggcgaaaccggcgcggcgggcccgaaaggcgataaaggcgaaaccggcgcggcgggcccgaaaggcgataa
 301  ---------+---------+---------+---------+---------+---------+---------+---------+---------
      ccgggctttccgcttttccgctttggccgcgccgcccgggctttccgctatttccgctttggccgcgccgcccgggctttccgctatt
...>   G  P  K  G  E  K  G  E  T  G  A  A  G  P  K  G  D  K  G  E  T  G  A  A  G  P  K  G  D  K
                                                                                       aggcgaaaccg
                                                                                       +---------+   400
                                                                                       tccgctttggc
                                                                                        G  E  T  G
```

```
     gcgcggcggcgggcccgaaaggcgaaaaaggcgaaaccggcgcggtgggcccgaaaggcgataaaggcgaaaccggcgcggcgggcccgaaa
 401 ---------+---------+---------+---------+---------+---------+---------+---------+---------
     cgcgccgccgggctttccgcttttccgctttggccgcgccacccgggctttccgctatttccgctttggccgcgccgcccgggcttt
   >  A  A  G  P  K  G  E  K  G  E  T  G  A  V  G  P  K  G  D  K  G  E  T  G  A  A  G  P  K ggcgatcgcgg
                                                                               +---------+   500
                                                                               ccgctagcgcc
                                                                                G  D  R  G cgaaaccggcgcggtgggcccgaaaggcgataaaggcgaaaccggcgcggtgggcccgaaaggcgataaaggcgaaaccggcgcgattg
 501 ---------+---------+---------+---------+---------+---------+---------+---------+---------
     gctttggccgcgccacccgggctttccgctatttccgctttggccgcgccacccgggctttccgctatttccgctttggccgcgctaac
...>  E  T  G  A  V  G  P  K  G  D  K  G  E  T  G  A  V  G  P  K  G  D  K  G  E  T  G  A  I  G gcccgaaaggc
                                                                               +---------+   600
                                                                               cgggctttccg
                                                                                P  K  G gataaaggcgataaaggcgataaaggcgatgcgggcgtggcgggcccgcagggcattcagggcgtgaaaggcgataccggcctgcaggg
 601 ---------+---------+---------+---------+---------+---------+---------+---------+---------
     ctatttccgctatttccgctatttccgctacgcccgcaccgccgggcgtcccgtaagtcccgcactttccgctatggccggacgtccc
...>  D  K  G  D  K  G  D  K  G  D  A  G  V  A  G  P  Q  G  I  Q  G  V  K  G  D  T  G  L  Q  G cccgaaaggcg
                                                                               +---------+   700
                                                                               gggctttccgc
                                                                                P  K  G  D atgcgggcccgcagggcgcgccgggcacccccgggcggcccgagcattgaacaggtgatgccgtggctgcatctgattttgatgcgtat
 701 ---------+---------+---------+---------+---------+---------+---------+---------+---------
     tacgcccgggcgtcccgcgcggcccgtggggcccgccgggctcgtaacttgtccactacggcaccgacgtagactaaaaactacgcata
   >  A  G  P  Q  G  A  P  G  T  P  G  G  P  S  I  E  Q  V  M  P  W  L  H  L  I  F  D  A  Y gaagattataa
                                                                               +---------+   800
                                                                               cttctaatatt
                                                                                E  D  Y  K agcgcagcgcgcgcgcgaagcgcgcgaactggaagaacgcctggcggcggaagcgctggaacaggcggcgcgcgaagcggcggaacgcg
 801 ---------+---------+---------+---------+---------+---------+---------+---------+---------
     tcgcgtcgcgcgcgcgcttcgcgcgcttgaccttcttgcggaccgccgccttcgcgaccttgtccgccgcgcgcttcgccgccttgcgc
...>  A  Q  R  A  R  E  A  R  E  L  E  E  R  L  A  A  E  A  L  E  Q  A  A  R  E  A  A  E  R  E aagtggcggcg
                                                                               +---------+   900
                                                                               ttcaccgccgc
                                                                                V  A  A gcgattgaagcggcgaacgcggaagcggaaattatgctggatgatgaaacccatgcggaaggcggcaaaaaaaaaaaaaaacgcaaaca
 901 ---------+---------+---------+---------+---------+---------+---------+---------+---------
     cgctaacttcgccgcttgcgccttcgccttttaatacgacctactactttgggtacgccttccgccgttttttttttttttgcgtttgt
...>  A  I  E  A  A  N  A  E  A  E  I  M  L  D  D  E  T  H  A  E  G  G  K  K  K  K  K  R  K  H taaagatcacc
                                                                               +---------+  1000
                                                                               atttctagtgg
                                                                                K  D  H  H accatcaccatcattaa
1001 -------+-------                                                                          1017
     tggtagtggtagtaatt
   >   H  H  H  H  *
```

Example 7: DNA for an Insect Collagen from Sawfly, *Nematus oligospilus*, Gene A The DNA for a triple helical collagen-like entity from *N. oligospilus* silk gland was obtained from a reported sequence for a Type A chain (A279), as described previously (U.S. 61/615,745). A gene construct was synthesised (GeneArt® Gene Synthesis, Regensburg, Germany), which included NdeI and EcoRI restriction sites, and with conservative base substitutions introduced that retained the original amino acid sequence while optimising for expression in a desired host system, *E coli*.

The final sequence construct is described in SEQ No: 29.

```
DNA and Protein Sequence: (SEQ ID No: 29 & 30)
SF21 (A279) - sawfly collagen type A gene
GGTACCATAT GCGTCAGGTT AGCTATTTTA TCCTGGCAGC AGTTGCACTG TTTGCAATTT TTGCAGAAGC AGTTCCGGTT GCAACCCCGA
            M  R  Q  V   S  Y  F    I  L  A   A  V  A  L   F  A  I   F  A  E   A  V  P  V   A  T  P
                                                                                                GCAAAGGTAG
                                                                                                 S  K  G CAAAAGCGGT CATGGTGGTG AAAGCGGTAA TTATGGTCAT GGTGGCCGTG GTGGTGATGG TTCTGATGGT GGTGCCGGTG GTGTTGGTGG
 S  K  S  G  H  G  G   E  S  G   N  Y  G  H   G  G  R    G  G  D   G  S  D  G  G  A  G    G  V  G
                                                                                                TGGTCGTAGC
                                                                                                 G  G  R  S GGTGGTAGCG GTTGGGCAGG TCCGCAAGGT CCGCGTGGTG CAGATGGTAA AATTGGTCCG GCTGGTCCGC AGGGTCCTTC TGGTCCGGCA
  G  G  S   G  W  A   G  P  Q  G   P  R  G   A  D  G    K  I  G  P   A  G  P   Q  G  P    S  G  P  A
                                                                                                GGTCCAACAG
                                                                                                 G  P  T GTCCGGTGGG TCCTCGTGGT GATGCAGGTC GTCCGGGTGC AACCGGTGCT ACAGGTCCGG ATGGTCCGAA AGGTGAATTT GGTCCTCAGG
 G  P  V   G  P  R  G   D  A  G   R  P  G   A  T  G  A   T  G  P   D  G  P    K  G  E  F   G  P  Q
                                                                                                GTCCGAGCGG
                                                                                                 G  P  S TCCACGTGGT GCACCAGGTC CACAGGGTCC TGCAGGTCCT ACCGGTCGTG ATGGTCCTAA AGGCGCAGCA GGTCCGGCAG GCGCAGCTGG
 G  P  R  G   A  P  G   P  Q  G   P  A  G  P   T  G  R   D  G  P   K  G  A  A   G  P  A   G  A  A
                                                                                                TCCTGCTGGT
                                                                                                 G  P  A  G TCTCCGGGTG CACAGGGTGA AACCGGTGAT CGTGGTGATC GCGGTCTGAA AGGTGATGTT GGTGCGCAGG GTGGTAAAGG TATTCCGGGT
   S  P  G   A  Q  G   E  T  G  D   R  G  D   R  G  L    K  G  D  V   G  A  Q   G  G  K    G  I  P  G
                                                                                                CCGGCAGGAC
                                                                                                 P  A  G CTCGTGGTCA GACCGGTCCG AATGGTCTGC CTGGTGCAAA AGGCGAAACC GGTCCGAAAG GCGCTCAAGG TCCGGCTGGC CCTGCCGGTC
 P  R  G   Q  T  G  P    N  G  L   P  G  A    K  G  E  T   G  P  K   G  A  Q    G  P  A  G    P  A  G
                                                                                                CTAAAGGTGA
                                                                                                 P  K  G AGATGGTGCC ACCGGTGAAA CAGGTCCTCG TGGCCCTGCA GGTCCAGCCG GTGCAGCAGG TAAAGATATT ATCATTTGGA AAGGTCAGAA
 E  D  G  A   T  G  E   T  G  P   R  G  P  A   G  P  A   G  A  A    G  K  D  I   I  I  W   K  G  Q
                                                                                                AGGTTGGCGT
                                                                                                 K  G  W  R AGCCCGAGCG AACGTAAAAG CTATCATCAT CATCACCATC ATTAATAAGA ATTCGAGCTC
  S  P  S    E  R  K   S  Y  H  H   H  H  H  H  -  -
```

Example 8: DNA for 3 Repeats of a Fragment of Human Type III Collagen

The template for the PCR reactions was based on cDNA Clone MGC:39848 (Image 5405119) (ATCC, Manassas, Va.), which contains the human COL3A1 gene, with limited base changes introduced that do not change the amino acid sequence but decrease the possibility of secondary structure formation.

PCR products were separated by electrophoresis and excised bands were extracted using a QIAquick Gel Extraction Kit (Qiagen).

The oligonucleotides used for PCR generation of three separate fragments for cloning were:

```
                  M   A   P   G   A   P   G                         (SEQ ID NO: 47)
EcoRI up      5'-CCG G/AATTC GGT GCC ATG GGT GCT CCA GGT GCT CCA GGT -3' (SEQ ID No: 31)
                    EcoRI a   g   p   p   g   p   p                        (SEQ ID NO: 48)
XmaI down     5'-TCCCC/CCCGG AGC ACC TGG TGG ACC TGG TGG AC-3'        (SEQ ID No: 32)
                    XmaI D   A   G   G   K   G   D   A   G                  (SEQ ID NO: 49)
XmaI up       5'-TCCC C/CCGGG GAT GCC GGT GGT AAG GTT GAC GCT GGT-3'  (SEQ ID No: 33)
                    XmaI G   p   p   g   p   p   g                          (SEQ ID NO: 50)
BamHI down    5'-CGCG/GATCC ACC TGG TGG ACC TGG TGG ACC A-3'          (SEQ ID No: 34)
                    BamHI G   G   K   G   D   A   G   A   P                  (SEQ ID NO: 50)
BamHI up      5'-CCG G/GATCC GGT GGT AAG GGT GAC GCT GGT GCT CCA-3'   (SEQ ID No: 35)
```

The PCR fragments were subjected to paired restriction enzyme digestion (EcoRI & XmaI, XmaI & BamHI, BamHI & SacII), and fragments purified by extraction from agarose gels. Production of the three-repeat DNA segment was achieved in conjunction with sequential ligation into vector YepFlagl (Eastman Kodak/IBI, New Haven, Conn.). Vector DNA was prepared using appropriate enzymes. Purified PCR fragments were ligated into sequential vector constructs, each at a ratio of 3 mol insert to 1 mol vector. Ligation mixtures were used to transform *E. coli* using standard procedures. The *Escherichia coli* strain XL1 Blue (Stratagene, La Jolla, Calif.) was routinely used for maintenance, propagation and transformation of plasmids. Separate DNA could be isolated from this vector if desired. The final sequence construct is shown in SEQ ID No:37.

```
DNA and protein sequence: (SEQ No: 37 & 38)
            FLAG Peptide      EcoRI
GAC TAC AAG GAT GAC GAT GAC AAG GAA TTC GGT GCC ATG GGT GCT CCA GGT GCT CCA GGT
 D   Y   K   D   D   D   D   K   E   S   G   A   M   G   A   P   G   A   P   G GGT AAG GGT GAC GCT GGT GCT CCA GGT GAA AGA GGT CCA CCA GGT TTG GCT GGT GCT CCA
 G   K   G   D   A   G   A   P   G   E   R   G   P   P   G   L   A   G   A   P GGT TTG AGA GGT GGT GCT GGT CCA CCA GGT CCA GAA GGT GGT AAG GGT GCT GCT GGT CCA
 G   L   R   G   G   A   G   P   P   G   P   E   G   G   K   G   A   A   G   P CCA GGT CCA CCA GGT GCT CCC GGT GGT AAG GGT GAC GCT GGT GCT CCA GGT GAA AGA GGT
 P   G   P   P   G   A   P   G   G   K   G   D   A   G   A   P   G   E   R   G CCA CCA GGT TTG GCT GGT GCT CCA GGT TTG AGA GGT GGT GCT GGT CCA CCA GGT CCA GAA
 P   P   G   L   A   G   A   P   G   L   R   G   G   A   G   P   P   G   P   E GGT GGT AAG GGT GCT GCT GGT CCA CCA GGT CCA CCA GGT GGA TCC GGT GGT AAG GGT GAC
 G   G   K   G   A   A   G   P   P   G   P   P   G   G   S   G   G   K   G   D GCT GGT GCT CCA GGT GAA AGA GGT CCA CCA GGT TTG GCT GGT GCT CCA GGT TTG AGA GGT
 A   G   A   P   G   E   R   G   P   P   G   L   A   G   A   P   G   L   R   G GGT GCT GGT CCA CCA GGT CCA GAA GGT GGT AAG GGT GCT GCT GGT CCA CCA GGT CCA CCA
 G   A   G   P   P   G   P   E   G   G   K   G   A   A   G   P   P   G   P   P GGG CCA CCT TAA CCG CGG TAA
 G   P   P   stop
```

Example 9: DNA for Human Type I Alpha 1 Chain CB3 Fragment

The DNA sequence for the CB3 fragment of the human type I collagen alpha 1 chain was obtained from the data provided in the National Center for Biotechnology Information database (National institutes of Health, Bethesda, Md. 20894, USA) as record # GenBank: Z74615.1. The sequence was modified by adding a C-terminal His$_6$-tag (SEQ ID NO: 46) and a termination codon and had 5' NdeI and 3' EcoRI and HindIII restriction sites added, making the construct suitable for inserting into the pCold IV vector. The stability of the triple helical protein produced from this DNA means that all manipulations must be performed at 4° C. The construct was synthesised (GeneArt® Gene Synthesis, Regensburg. Germany) with conservative substitutions that retained the original amino acid sequence while optimising for expression in a desired host system, E. coli.

The final sequence construct is described in SEQ ID No: 39 insert preparations were ligated using the T4 DNA ligase kit (Invitrogen). The ligation mixture was then transformed into Top10 cells and plated onto ampicillin selective media. Colony PCR was used to detect clones that contained the engineered chimeras. PCR products containing potentially engineered clones were analysed on 1% agarose electrophoresis. The 4.5 kb collagen 1 gene insert was sub-cloned from its parental vector pUC19 using the restriction sites XbaI (5') and SspI (3') and was cloned into the bacterial shuttle vector pBluescript II KS+(Stratagene) using sites XbaI (5') and SmaI (3'). This cloning allowed the internal BamHI site in collagen 1, at base pairs 2929-2934, to act as a unique site in this vector. Two truncations of collagen 1 (N and C) terminal were constructed. The N terminal truncation contained a 2.7 kb fragment of collagen cloned into pBluescript II KS+ at sites XbaI (5') and BamHI (3'), whilst the C terminal truncation, 1.8 kb in size was sub-cloned into the shuttle vector pUC19 using restriction sites BamHI (5') and HindIII (3'). To the C terminal truncation, an NaeI restriction site (silent mutation) was introduced using the QuickChange

```
DNA and Protein Sequence: (SEQ ID No: 39 & 40)
    1   H   M   G   F   P   G   P   K   G   A   A   G   E   P   G   K   A   G   E   R   G   V   P   G
        CAT ATG GGT TTT CCG GGT CCG AAA GGT GCA GCC GGT GAA CCG GGT AAA GCC GGT GAA CGT GGT GTT CCG GGT 25   P   P   G   A   V   G   P   A   G   K   D   G   E   A   G   A   Q   G   P   P   G   P   A   G
  101   CCG CCT GGT GCA GTT GGT CCG GCA GGC AAA GAT GGT GAA GCC GGT GCA CAG GGT CCT CCA GGT CCG GCT GGT 49   P   A   G   E   R   G   E   Q   G   P   A   G   S   P   G   F   Q   G   L   P   G   P   A   G
  201   CCT GCA GGC GAA CGT GGT GAA CAG GGT CCG GCT GGC TCT CCG GGT TTT CAG GGT CTG CCT GGT CCT GCT GGT 73   P   P   G   E   A   G   K   P   G   E   Q   G   V   P   G   D   L   G   A   P   G   P   S   G
  301   CCG CCA GGT GAA GCA GGC AAA CCG GGT GAA CAA GGC GTT CCG GGT GAT CTG GGT GCA CCG GGT CCG TCA GGT 97   A   R   G   E   R   G   F   P   G   E   R   G   V   Q   G   P   P   G   P   A   G   P   R   G
  401   GCA CGT GGT GAA CGT GGC TTT CCT GGT GAA CGC GGT GTG CAG GGT CCA CCA GGA CCA GCA GGC CCT CGT GGT 121     A   N   G   A   P   G   N   D   G   A   K   G   D   A   G   A   P   G   A   P   G   S   Q   G
        GCA AAT GGT GCT CCG GGT AAT GAT GGT GCA AAA GGT GAT GCA GGC GCA CCG GGT GCA CCT GGT AGC CAG GGT 145   A   P   G   L   Q   G   M   H   H   H   H   H   -   I   Q   A
        GCA CCA GGT CTG CAG GGT ATG CAC CAC CAT CAC CAT CAT TGA ATT CAA GCT T
```

Example 10: DNA for a Chimera Made from Segments from Human Collagen Type I and Type III Chains Human collagen type I, alpha I c-DNA with ATCC accession number 95498 and human collagen type III, alpha I c-DNA with ATCC accession number 95502 were used in the production of chimeric DNA.

Initially, 10 ng of c-DNA encoding the collagen I and III genes was transformed into 50 μl of the E. coli host strain, using the heat shock method at 42° C. Colonies resistant to ampicillin were recovered and grown overnight in 150 mls of YT media.

Restriction digests of parental clones were carried out and were then analysed on 1% agarose gel electrophoresis, and collagen bands isolated and purified. Vector and purified II Site—Directed Mutagenesis Kit (Invitrogen) at base pairs 3706-3711 of the C telopeptide. A HincII site (GTCAAC) was added directly after the collagen I stop codon for ease of cloning of the full length chimeras into a vector system. To the N terminal truncation, PCR was used to introduce a kozak sequence upstream of the initiating methionine residue. Splice overlap PCR was used to interchange regions of the collagen I α helix with that of the collagen III α helix. An overlap that spanned base pairs 3288-3711 of the CoII I α helix and was interchanged with that of residues 3283-3708 of the CoII III α helix. The 5' overlap oligo contained an introduced BamHI site and the 3' oligo contained an introduced NaeI site. The PCR product was cloned into the pTOPO vector using the Zero Blunt TOPO PCR Cloning Kit (Invitrogen). The overlap was digested from pTOPO with BamHI (5') and NaeI (3') and was interchanged with the wild type (WT) C terminal clone of collagen 1 containing the introduced NaeI site in pUC19. Removal of the N-propeptide from collagen 1, residues 193-609, was performed using deletion mutagenesis on the N terminal truncated construct. The gene was then cloned into the C terminal sub-fragment of collagen to create the full length gene lacking the N-propeptide. The final sequence is represented by SEQ No: 41.

```
DNA Sequence: SEQ ID No: 41
   1 GCGGCCGACC ATGTTCAGCT TTGTGGACCT CCGGCTCCTG CTCCTCTTAG CGGCCACCGC CCTCCTGACG CACGGCCAGC TGTCTTATGG
                                                                                             CTATGATGAG
 101 AAATCAACCG GTGGAATTTC CGTGCCTGGC CCCATGGGTC CCTCTGGTCC TCGTGGTCTC CCTGGCCCCC TGGTGCACC  TGGTCCCCAA
                                                                                             GGCTTCCAAG
 201 GTCCCCCTGG TGAGCCTGGC GAGCCTGGAG CTTCAGGTCC CATGGGTCCC CGAGGTCCCC CAGGTCCCCC TGGAAAGAAT GGAGATGATG
                                                                                             GGGAAGCTGG
 301 AAAACCTGGT CGTCCTGGTG AGCGTGGGCC TCCTGGGCCT CAGGGTGCTC GAGGATTGCC CGGAACAGCT GGCCTCCCTG GAATGAAGGG
                                                                                             ACACAGAGGT
 401 TTCAGTGGTT TGGATGGTGC CAAGGGAGAT GCTGGTCCTG CTGGTCCTAA GGGTGAGCCT GGCAGCCCTG GTGAAAATGG AGCTCCTGGT
                                                                                             CAGATGGGCC
 501 CTAGGGGCCT GCCTGGTGAG AGAGGTCGCC CTGGAGCCCC TGGCCCTGCT GGTGCTCGTG GAAATGATGG TGCTACTGGT GCTGCCGGGC
                                                                                             CCCCTGGTCC
 601 CACCGGCCCC GCTGGTCCTC CTGGCTTCCC TGGTGCTGTT GGTGCTAAGG GTGAAGCTGG TCCCCAAGGG CCCCGAGGCT CTGAAGGTCC
                                                                                             CCAGGGTGTG
 701 CGTGGTGAGC CTGGCCCCCC TGGCCCTGCT GGTGCTGCTG GCCCTGCTGG AAACCCTGGT GCTGATGGAC AGCCTGGTGC TAAAGGTGCC
                                                                                             AATGGTGCTC
 801 CTGGTATTGC TGGTGCTCCT GGCTTCCCTG GTGCCCGAGG CCCCTCTGGA CCCCAGGGCC CCGGCGGCCC TCCTGGTCCC AAGGGTAACA
                                                                                             GCGGTGAACC
 901 TGGTGCTCCT GGCAGCAAAG GAGACACTGG TGCTAAGGGA GAGCCTGGCC CTGTTGGTGT TCAAGGACCC CCTGGCCCTG CTGGAGAGGA
                                                                                             AGGAAAGCGA
1001 GGAGCTCGAG GTGAACCCGG ACCCACTGGC CTGCCCGGAC CCCCTGGCGA GCGTGGTGGA CCTGGTAGCC GTGGTTTCCC TGGCGCAGAT
                                                                                             GGTGTTGCTG
1101 GTCCCAAGGG TCCCGCTGGT GAACGTGGTT CTCCTGGCCC TGCTGGCCCC AAAGGATCTC CTGGTGAAGC TGGTCGTCCC GGTGAAGCTG
                                                                                             GTCTGCCTGG
1201 TGCCAAGGGT CTGACTGGAA GCCCTGGCAG CCCTGGTCCT GATGGCAAAA CTGGCCCCCC TGGTCCCGCC GGTCAAGATG GTCGCCCCGG
                                                                                             ACCCCCAGGC
1301 CCACCTGGTG CCCGTGGTCA GGCTGGTGTG ATGGGATTCC CTGGACCTAA AGGTGCTGCT GGAGAGCCCG GCAAGGCTGG AGAGCGAGGT
                                                                                             GTTCCCGGAC
1401 CCCCTGGCGC TGTCGGTCCT GCTGGCAAAG ATGGAGAGGC TGGAGCTCAG GGACCCCCTG GCCCTGCTGG TCCCGCTGGC GAGAGAGGTG
                                                                                             AACAAGGCCC
1501 TGCTGGCTCC CCCGGATTCC AGGGTCTCCC TGGTCCTGCT GGTCCTCCAG GTGAAGCAGG CAAACCTGGT GAACAGGGTG TTCCTGGAGA
                                                                                             CCTTGGCGCC
1601 CCTGGCCCCT CTGGAGCAAG AGGCGAGAGA GGTTTCCCTG GCGAGCGTGG TGTGCAAGGT CCCCCTGGTC CTGCTGGTCC CCGAGGGGCC
                                                                                             AACGGTGCTC
1701 CCGGCAACGA TGGTGCTAAG GGTGATGCTG GTGCCCCTGG AGCTCCCGGT AGCCAGGGCG CCCCTGGCCT TCAGGGAATG CCTGGTGAAC
                                                                                             GTGGTGCAGC
1801 TGGTCTTCCA GGGCCTAAGG GTGACAGAGG TGATGCTGGT CCCAAAGGTG CTGATGGCTC TCCTGGCAAA GATGGCGTCC GTGGTCTGAC
                                                                                             TGGCCCCATT
1901 GGTCCTCCTG GCCCTGCTGG TGCCCCTGGT GACAAGGGTG AAAGTGGTCC CAGCGGCCCT GCTGGTCCCA CTGGAGCTCG TGGTGCCCCC
                                                                                             GGAGACCGTG
2001 GTGAGCCTGG TCCCCCCGGC CCTGCTGGCT TTGCTGGCCC CCTGGTGCT GACGGCCAAC CTGGTGCTAA GGCGAACCT  GGTGATGCTG
                                                                                             GTGCTAAAGG
2101 CGATGCTGGT CCCCCTGGCC CTGCCGGACC CGCTGGACCC CTGGCCCCA TTGGTAATGT TGGTGCTCCT GGAGCCAAAG GTGCTCGCGG
                                                                                             CAGCGCTGGT
2201 CCCCCTGGTG CTACTGGTTT CCCTGGTGCT GCTGGCCGAG TCGGTCCTCC TGGCCCCTCT GGAAATGCTG GACCCCCTGG CCCTCCTGGT
                                                                                             CCTGCTGGCA
2301 AAGAAGGCGG CAAAGGTCCC CGTGGTGAGA CTGGCCCTGC TGGACGTCCT GGTGAAGTTG GTCCCCCTGG TCCCCCTGGC CCTGCTGGCG
                                                                                             AGAAAGGATC
2401 CCCTGGTGCT GATGGTCCTG CTGGTGCTCC TGGTACTCCC GGGCCTCAAG GTATTGCTGG ACAGCGTGGT GTGGTCGGCC TGCCTGGTCA
                                                                                             GAGAGGAGAG
```

-continued

```
2501 AGAGGCTTCC CTGGTCTTCC TGGCCCCTCT GGTGAACCTG GCAAACAAGG TCCCTCTGGA GCAAGTGGTG AACGTGGTCC CCCTGGTCCC
                                                                                               ATGGGCCCCC

2601 CTGGATTGGC TGGACCCCCT GGTGAATCTG GACGTGAGGG GGCTCCTGGT GCCGAAGGTT CCCCTGGACG AGACGGTTCT CCTGGCGCCA
                                                                                               AGGGTGACCG

2701 TGGTGAGACC GGCCCCGCTG GACCCCCTGG TGCTCCTGGT GCTCCTGGTG CCCCTGGTCC TGTCGGTCCA GCTGGAAAGA GTGGTGACAG
                                                                                               AGGAGAAAGT

2801 GGCCCTGCTG GCCCTGCTGG TGCTCCCGGT CCTGCTGGTT CCCGAGGTGC TCTGGTCCTC AAGGCCCACG TGGTGACAAA GGTGAAACAG
                                                                                               GTGAACGTGG

2901 AGCTGCTGGC ATCAAAGGAC ATCGAGGATT CCCTGGTAAT CCAGGTGCCC CAGGTTCTCC AGGCCCTGCT GGTCAGCAGG GTGCAATCGG
                                                                                               CAGTCCAGGA

3001 CCTGCAGGCC CCAGAGGACC TGTTGGACCC AGTGGACCTC CTGGCAAAGA TGGAACCAGT GGACATCCAG GTCCCATTGG ACCACCAGGG
                                                                                               CCTCGAGGTA

3101 ACAGAGGTGA AAGAGGATCT GAGGGCTCCC CAGGCCACCC AGGGCAACCA GGCCCTCCTG GCTTGCTGTA CCTCCTGGTG CCCCTGGTCC
                                                                                               TTGCTGTGCC

3201 GGCTTCGACT TCAGCTTCCT GCCCCAGCCA CCTCAAGAGA AGGCTCACGA TGGTGGCCGC TACTACCGGG CTGATGATGC CAATGTGGTT
                                                                                               CGTGACCGTG

3301 ACCTCGAGGT GGACACCACC CTCAAGAGCC TGAGCCAGCA GATCGAGAAC ATCCGGAGCC AGAGGGCAG CCGCAAGAAC CCCGCCCGCA
                                                                                               CCTGCCGTGA

3401 CCTCAAGATG TGCCACTCTG ACTGGAAGAG TGGAGAGTAC TGGATTGACC CCAACCAAGG CTGCAACCTG GATGCCATCA AAGTCTTCTG
                                                                                               CAACATGGAG

3501 ACTGGTGAGA CCTGCGTGTA CCCCACTCAG CCCAGTGTGG CCCAGAAGAA CTGGTACATC AGCAAGAACC CCAAGGACAA GAGGCATGTC
                                                                                               TGGTTCGGCG

3601 AGAGCATGAC CGATGGATTC CAGTTCGAGT ATGGCGGCCA GGGCTCCGAC CCTGCCGATG TGGCCATCCA GCTGACCTTC CTGCGCCTGA
                                                                                               TGCCACCGAG

3701 GCCTCCCAGA ACATCACCTA CCACTGCAAG AACAGCGTGG CCTACATGGA CCAGCAGACT GGCAACCTCA AGAAGGCCCT GCTCCTCCAG
                                                                                               GGCTCCAACG

3801 AGATCGAGAT CCGCGCCGAG GGCAACAGCC GCTTCACCTA CAGCGTCACT GTCGATGGCT GCACGAGTCA CACCGGAGCC TGGGGCAAGA
                                                                                               CAGTGATTGA

3901 ATACAAAACC ACCAAGACCT CCCGCCTGCC CATCATCGAT GTGGCCCCCT TGGACGTTGG TGCCCCAGAC CAGGAATTCG GCTTCGACGT
                                                                                               TGGCCCTGTC

4001 TGCTTCCTGT AAGTCGAC
                HincII
```

Example 11: DNA for a Chimera of Different Bacterial Collagen Chains where Two Different Collagen-Like Components are Present from *Methylobacterium* sp. and *S. usitatus*

The DNA sequence for the triple helix repeat-containing collagens from *Candidatus Solibacter usitatus* Ellin6076 and *Methylobacterium* sp. were obtained from the data provided in the National Center for Biotechnology Information database (National institutes of Health, Bethesda, Md. 20894, USA) as record ABJ82342 for *S. usitatus* and record ACA18713.1 for *Methylobacterium*.

The protein sequences were translated into nominal DNA sequence and a composite gene was designed that maintained the correct coding framework, with a Met initiation signal followed by the V and CL domains from *Methylobacterium*, followed by the CL domain from *S. usitatus*, followed finally by a termination codon. Terminal restriction sites outside the coding sequence were added as NdeI and EcoRI for 5' and were SalI and HindIII for 3'. This construct was then optimised for expression in the host system and synthesised (GeneArt® Gene Synthesis, Regensburg, Germany) with a DNA sequence that retained the original amino acid sequence while optimising for expression in a desired host system, *E coli*.

The final sequence is described in SEQ ID No: 42.

```
DNA Sequence: SEQ ID NO 42 & 43
     CATATGGGTGAAGCAGCACCGGCACCGGCAGCACCGAAACCTGAAGCACCGCGTGGTGCAGCACGTAAACCGGCAAGCAGCGCAATTCA
   1 ---------+---------+---------+---------+---------+---------+---------+---------+---------
     GTATACCCACTTCGTCGTGGCCGTGGCCGTCGTGGCTTTGGACTTCGTGGCGCACCACGTCGTGCATTTGGCCGTTCGTCGCGTTAAGT
 ...  H   M   G   E   A   A   P   A   P   A   A   P   K   P   E   A   P   R   G   A   A   R   K   P   A   S   S   A   I   Q GATTTGGGATG
                                                                                         +---------+ 100
                                                                                         CTAAACCCTAC
                                                                                          I   W   D   A
```

-continued

```
    CACGTATTGAAGGTGGTGATCTGCGTATTAGCGGTAATGTTGGTAAAGCCGGTGTTACCGTTAGCCTGGATGATGAAGTTGCAGTTCAG
101 ---------+---------+---------+---------+---------+---------+---------+---------+---------
    GTGCATAACTTCCACCACTAGACGCATAATCGCCATTACAACCATTTCGGCCACAATGGCAATCGGACCTACTACTTCAACGTCAAGTC
     R  I  E  G  G  D  L  R  I  S  G  N  V  G  K  A  G  V  T  V  S  L  D  D  E  V  A  V  Q
                                                                             AGCGATCGTCG
                                                                             +---------+  200
                                                                             TCGCTAGCAGC
                                                                              S  D  R  R

TGGTCGTTTTGCAATTAAAGTTCCGTATGTTCCGCAGACCTGTGTTGCAACCCTGACCGCAGGCGAAGAAAGCCGTGAAGTTGCCGTTG
201 ---------+---------+---------+---------+---------+---------+---------+---------+---------
    ACCAGCAAAACGTTAATTTCAAGGCATACAAGGCGTCTGGACACAACGTTGGGACTGGCGTCCGCTTCTTTCGGCACTTCAACGGCAAC
 ... G  R  F  A  I  K  V  P  Y  V  P  Q  T  C  V  A  T  L  T  A  G  E  E  S  R  E  V  A  V  A
                                                                             CAAATTGTGCA
                                                                             +---------+  300
                                                                             GTTTAACACGT
                                                                              N  C  A

CCGCAGCGTGCAGGTCAGCCTGGTCCGGCAGGTCAACCGGGTCCTACAGGTCCGCAGGGTGTTGCCGGTCTGCCAGGTCCGAAAGGTGA
301 ---------+---------+---------+---------+---------+---------+---------+---------+---------
    GGCGTCGCACGTCCAGTCGGACCAGGCCGTCCAGTTGGCCCAGGATGTCCAGGCGTCCCACAACGGCCAGACGGTCCAGGCTTTCCACT
 ... P  Q  R  A  G  Q  P  G  P  A  G  Q  P  G  P  T  G  P  Q  G  V  A  G  L  P  G  P  K  G  D
                                                                             TCCGGGTCCGC
                                                                             +---------+  400
                                                                             AGGCCCAGGCG
                                                                              P  G  P  Q

AAGGTCCTGCGGGTCCTAAAGGCGAACCGGGACCAAAAGGTGAACCTGGTCCGAAAGGCGAGCCTGGCCCTAAAGGTGAGCCAGGGCCA
401 ---------+---------+---------+---------+---------+---------+---------+---------+---------
    TTCCAGGACGCCCAGGATTTCCGCTTGGCCCTGGTTTTCCACTTGGACCAGGCTTTCCGCTCGGACCGGGATTTCCACTCGGTCCCGGT
 ...  G  P  A  G  P  K  G  E  P  G  P  K  G  E  P  G  P  K  G  E  P  G  P  K  G  E  P  G  P
                                                                             AAAGGCGAACC
                                                                             +---------+  500
                                                                             TTTCCGCTTGG
                                                                              K  G  E  P

AGGTCCTAAAGGTGAACCAGGCCCTAAAGGTGAGCCTGGACCGAAAGGTGAACCGGGACCTCGTGGTGAAGCCGGTCCTCAGGGTGCAC
501 ---------+---------+---------+---------+---------+---------+---------+---------+---------
    TCCAGGATTTCCACTTGGTCCGGGATTTCCACTCGGACCTGGCTTTCCACTTGGCCCTGGAGCACCACTTCGGCCAGGAGTCCCACGTG
     G  P  K  G  E  P  G  P  K  G  E  P  G  P  K  G  E  P  G  P  R  G  E  A  G  P  Q  G  A  L
                                                                             TGGGACCGAAA
                                                                             +---------+  600
                                                                             ACCCTGGCTTT
                                                                              G  P  K

GGCGAAGCAGGTAGCCGTGGTGAACCAGGTCCGCGTGGCGAACCAGGCCCAAAAGGCGAGGCAGGTCTGGCAGGCGCACCTGGACCTAA
601 ---------+---------+---------+---------+---------+---------+---------+---------+---------
    CCGCTTCGTCCATCGGCACCACTTGGTCCAGGCGCACCGCTTGGTCCGGGTTTTCCGCTCCGTCCAGACCGTCCGCGTGGACCTGGATT
     G  E  A  G  S  R  G  E  P  G  P  R  G  E  P  G  P  K  G  E  A  G  L  A  G  A  P  G  P  K
                                                                             AGGCGAAGCCG
                                                                             +---------+  700
                                                                             TCCGCTTCGGC
                                                                              G  E  A  G

GTCCGCGTGGTCCGCAGGGCGAACGTGGTCCTCCTGGTGCTCCGGGTGCAGCAGGTCCGGCTGGTCCTGCAGGTCCGCAGGGTCCAGCC
701 ---------+---------+---------+---------+---------+---------+---------+---------+---------
    CAGGCGCACCAGGCGTCCCGCTTGCACCAGGAGGACCACGAGGCCCACGTCGTCCAGGCCGACCAGGACGTCCAGGCGTCCCAGGTCGG
      P  R  G  P  Q  G  E  R  G  P  P  G  A  P  G  A  A  G  P  A  G  P  A  G  P  Q  G  P  A
                                                                             GGTCCAGCTGG
                                                                             +---------+  800
                                                                             CCAGGTCGACC
                                                                              G  P  A  G

TGCACAAGGTCCAGCAGGCCCTGCCGGTCCTCAAGGTCCTGCTGGCCCACAGGGTAGTGCCGGTGCCCAGGGTCCGAAAGGTGATACCG
801 ---------+---------+---------+---------+---------+---------+---------+---------+---------
    ACGTGTTCCAGGTCGTCCGGGACGGCCAGGAGTTCCAGGACGACCGGGTGTCCCATCACGGCCACGGGTCCCAGGCTTTCCACTATGGC
     A  Q  G  P  A  G  P  A  G  P  Q  G  P  A  G  P  Q  G  S  A  G  A  Q  G  P  K  G  D  T  G
                                                                             GTGCAGCAGGT
                                                                             +---------+  900
                                                                             CACGTCGTCCA
                                                                              A  A  G

CCTGCGGGTGAAGCGGGTCCTAAAGGCGAAACAGGCGCAGCGGGACCAAAAGGTGACACTGGCGCTGCGGGTCCGGCAGGACCGAAAGG
901 ---------+---------+---------+---------+---------+---------+---------+---------+---------
    GGACGCCCACTTCGCCCAGGATTTCCGCTTTGTCCGCGTCGCCCTGGTTTTCCACTGTGACCGCGACGCCCAGGCCGTCCTGGCTTTCC
     P  A  G  E  A  G  P  K  G  E  T  G  A  A  G  P  K  G  D  T  G  A  A  G  P  A  G  P  K  G
                                                                             CGACACAGGTG
                                                                             +---------+ 1000
                                                                             GCTGTGTCCAC
                                                                              D  T  G  A
```

-continued

```
       CTGCAGGCCCAGCAGGTCCAAAAGGCGATACGGGTGCCGCTGGTGCAACAGGCCCTAAAGGTGAGAAAGGTGAAACAGGTGCGGCTGGT
1001   ---------+---------+---------+---------+---------+---------+---------+---------+---------
       GACGTCCGGGTCGTCCAGGTTTTCCGCTATGCCCACGGCGACCACGTTGTCCGGGATTTCCACTCTTTCCACTTTGTCCACGCCGACCA
        A  G  P  A  G  P  K  G  D  T  G  A  A  G  D  T  G  P  K  G  E  K  G  E  T  G  A  A  G
                                                                                  CCGAAAGGCGA
                                                                                  +---------+   1100
                                                                                  GGCTTTCCGCT
                                                                                   P  K  G  D

TAAAGGCGAAACCGGTGCTGCCGGTCCTAAAGGTGACAAAGGCGAGACTGGCGCAGCTGGCCCTAAAGGTGAAAAAGGGGAGACAGGGG
1101   ---------+---------+---------+---------+---------+---------+---------+---------+---------
       ATTTCCGCTTTGGCCACGACGGCCAGGATTTCCACTGTTTCCGCTCTGACCGCGTCGACCGGGATTTCCACTTTTTCCCCTCTGTCCCC
    ... K  G  E  T  G  A  A  G  P  K  G  D  K  G  E  T  G  A  A  G  P  K  G  E  K  G  E  T  G  A
                                                                                  CAGTAGGACCT
                                                                                  +---------+   1200
                                                                                  GTCATCCTGGA
                                                                                   V  G  P

AAAGGCGATAAAGGTGAGACTGGTGCCGCAGGGCCTAAAGGCGACCGTGGTGAAACCGGTGCCGTGGGACCGAAAGGTGATAAAGGGGA
1201   ---------+---------+---------+---------+---------+---------+---------+---------+---------
       TTTCCGCTATTTCCACTCTGACCACGGCGTCCCGGATTTCCGCTGGCACCACTTTGGCCACGGCACCCTGGCTTTCCACTATTTCCCT
    ... K  G  D  K  G  E  T  G  A  A  G  P  K  G  D  R  G  E  T  G  A  V  G  P  K  G  D  K  G  E
                                                                                  AACTGGCGCTG
                                                                                  +---------+   1300
                                                                                  TTGACCGCGAC
                                                                                   T  G  A  V

TTGGGCCAAAAGGCGACAAAGGTGAAACGGGTGCAATTGGCCCAAAAGGTGATAAAGGCGACAAAGGCGATAAAGGGGATGCAGGCGTT
1301   ---------+---------+---------+---------+---------+---------+---------+---------+---------
       AACCCGGTTTTCCGCTGTTTCCACTTTGCCCACGTTAACCGGGTTTTCCACTATTTCCGCTGTTTCCGCTATTTCCCCTACGTCCGCAA
    ...  G  P  K  G  D  K  G  E  T  G  A  I  G  P  K  G  D  K  G  D  K  G  D  K  G  D  A  G  V
                                                                                  GCCGGTCCGCA
                                                                                  +---------+   1400
                                                                                  CGGCCAGGCGT
                                                                                   A  G  P  Q

GGGCATTCAGGGTGTTAAAGGTGATACAGGTCTGCAAGGTCCAAAAGGTGATGCAGGTCCTCAGGGTGCACCGGGTACACCGGGTGGTG
1401   ---------+---------+---------+---------+---------+---------+---------+---------+---------
       CCCGTAAGTCCCACAATTTCCACTATGTCCAGACGTTCCAGGTTTTCCACTACGTCCAGGAGTCCCACGTGGCCCATGTGGCCCACCAC
        G  I  Q  G  V  K  G  D  T  G  L  Q  G  P  K  G  D  A  G  P  Q  G  A  P  G  T  P  G  G  G
                                                                                  GTTAAgtcgac
                                                                                  +---------+   1500
                                                                                  CAATTcagctg
                                                                                   *  V  D
```

Examples 12-17 describe different expression host cell systems for several different constructs.

Example 12: Expression of a DNA Construct for a Triple Helical Protein

Any one of the aforementioned DNA constructions of for example SEQ ID Nos: 2, 6, 14, 20, 21 can be cloned into *E. coli* and be made to express triple-helical proteins according to the following method.

The DNA sequence was sub-cloned into the *E. coli* expression vector system pColdIII using the unique sites 5' NdeI and 3' BamHI. The PCR colony screening technique was then used to detect positive clones. These clones were grown up in 100 ml culture volumes and Qiagen midi preps carried out to expand the vector quantity. For expression, a selected positive clone was transformed into the *E. coli* host BL21-DE3. Cells were grown in 2×YT Media (or Defined media could also be used in some circumstances such as with SEQ ID No 2) containing 16 g tryptone, 10 g yeast extract and 5 g NaCl per liter. The Defined medium (DM) used contained per liter: KH2PO4, 10.6 g; (NH4)2HPO4, 4 g; citric acid, 1.7 g; glucose, 25 g; MgSO4.7H2O, 1.23 g; ampicillin (50 μg/ml), 200 mg; thiamine hydrochloride, 4.4 mg; and trace salts solution 5 mL. The trace salts solution contained per liter: CuSO4.5H2O, 2.0 g; NaI, 0.08 g; MnSO4.H2O, 3.0 g; Na2MoO4.2H2O, 0.2 g; boric acid, 0.02 g; CoCl2.6H2O, 0.5 g; ZnCl2, 7 g; FeSO4.7H2O, 22 g; CaSO4.2H2O, 05 g and H2SO4, 1 mL. As required glucose, magnesium, trace salts, thiamine and ampicillin were aseptically added as concentrated stock solutions to the media after sterilisation.

Cells were growth at 37° C. for 24 h and cell culture optical density at A600 reached around 3-6. The culture was then incubated at 25° C. and 1 mM isopropyl beta-D-thiogalactopyranoside (IPTG) added to induce protein expression. After 10 h incubation at 25° C., the temperature was decreased to 15° C. for another 14 h incubation. After 24 h incubation, cells were harvested by centrifugation.

For the construct of SEQ ID No: 31 of the CB3 fragment, after expression, the cells were held for 14 h at 4° C., with all subsequent processing also at 4° C., instead of 15° C.

Example 13: Expression of a DNA Construct for a Triple Helical Protein, a Bacterial Collagen Fragment from *S. usitatus*, with a V-Domain from *R. palustris*, Using a pET Vector in *E. coli*

DNA was taken as described in Example 6. The composite gene was cloned into the pET21a vector using 5' EcoRI and 3' HindIII sites. Sequencing of the clone was carried out prior to transforming into the competent *E. coli* host cell line BL21 DE3. Transformed cells were plated onto YT plus Ampicillin plates and grown overnight at 37° C. A single colony was picked from this plate and grown overnight in YT plus Ampicillin media at 37° C.

Recombinant bacterial collagens were produced in 2 L stirred tank bioreactors connected to a Biostat B (Sartorius Stedim Germany) control system. The initial volume of medium in the fermenter was 1.6 L and glucose as used as the carbon source. A volume of the secondary seed culture was added to the bioreactor to attain an initial optical density (measured at 600 nm) of 0.25. Foaming was controlled via the automatic addition of 10% (v/v) polypropylene glycol 2025; 3 mL of the antifoam solution was added prior to inoculation. The pH setpoint was 7.0, controlled by automatic addition of either 10% (v/v) $H_3PO_4$ or 10% (v/v) $NH_3$ solutions. The dissolved oxygen setpoint was 20% of saturation and a two-step cascade control was used to maintain the dissolved oxygen above the specified setpoint. The agitator speed ranged from 500 rpm to 1200 rpm and airflow (supplemented with 5% pure $O_2$) ranged from 0.3 L/min to 1.5 L/min. For high cell density fed-batch processes, the feed solution was comprised of 400 mL of 660 g/L glucose solution to which 40 mL of 1 M $MgSO_47H_2O$ was added. The feed flow rate was 15 mL/hr and the feed was initiated 8.5 hr after inoculation. Incubation times and temperatures for individual experiments varied depending on the construct, host cell system, amongst other things. The culture was cooled (over a 20 minute period) to the required temperature 24 hr after inoculation to activate the cold shock component of the vector and protein expression induced by addition of 1 mM (final concentration in the culture) IPTG. Cells were then harvested by centrifugation.

Example 14: Expression of a DNA Construct for a Triple Helical Protein, a Sawfly Silk Collagen, Using a pCold Vector in *E. coli*

The introduction of restriction enzyme digestion sites into the sawfly DNA isolate of SEQ ID No: 23 allowed isolation of the DNA for a sawfly silk gene and its insertion into an expression vector. Sawfly collagen-like silk type A gene was inserted into pColdI vector via NdeI and EcoRI sites. The PCR colony screening technique was used to detect positive clones. These clones were grown up in 100 ml culture volumes and Qiagen midi preps carried out to expand the vector quantity. For expression, a selected positive clone was transformed into competent *E. coli* BL21 cells. For expression of the sawfly silk protein gene, one colony of cells was added to 100 ml starter culture medium, 2× YT-Amp and incubated at 37° C. with 200 rpm shaking overnight. This culture then had 100 ml fresh 2×YT-2% Glucose-Amp added, and was induced with 1 mM IPTG at 25° C. for 10 hour, then 20° C. for another 16 hour. The cell paste was harvested by centrifugation (3000×g for 30 min). The protein was associated with the cell pellet.

Example 15: Expression of a DNA Construct for a Triple Helical Protein, a Repeat of a Fragment from Type III Collagen, in *Saccharomyces cerevisiae*

Yeast transformations were performed, using the DNA/vector (YepFlag1) such as in Example 8 where a DNA construct comprising an in frame fusion of α-factor signal α-pro sequence/FLAG tag/three repeats of a collagen III fragment, by electroporation into *S. cerevisiae* yeast strain BJ5462 (α ura3-52 trp1 leu2_1 his3_200 pep4::HIS3 prb_1.6R) (Yeast Genetic Stock Center, Berkeley, Calif.). Transformants were grown with aeration at 28° C. for 48 h on SDahI plus Ura medium. After selection, portions were diluted into non-selective YPHSM medium (1% dextrose, 1% yeast extract, 8% peptone, 3% glycerol, 20 mM $CaCl_2$) and growth continued for 96 h at 28° C. with vigorous shaking. Cell pellets were removed by centrifugation at 12,000×g for 20 min. The presence of FLAG provides an option for protein identification.

Expression of DNA constructs for human collagen type I and type III chains can follow the same methodology.

Example 16: Expression of a DNA Construct for a Triple Helical Protein, a Bacterial Collagen Fragment from *S. usitatus*, with a V-Domain from *R. palustris*, Using *Pichia pastoris*

The bacterial collagen gene was prepared as described in Example 6. Optionally, the gene could be further optimised for *Pichia* expression. The gene construct was assembled in *E. coli*.

The collagen gene construct was incorporated into an appropriate vector system, pA0815 HIS4, to allow chromosomal integration of the gene construct into the yeast host cell, *P.pastoris*. Optionally other vector systems such as pA0815-SX HIS4, pPIC9 HIS4, pPICZ ZeoR, pPICZa ZeoR, pBLADE-IX ADEI, pBLARG-IX ARG4, pBLARG-SX ARG4 or pBLURA URA3 could be used. The system is characterized by methylotrophic expression in which a strong constitutive promoter (GAP) and a strong inducible promoter (preferably AOXI-alcohol oxidase) are present. Addition of methanol, which can be used as the sole carbon source, allows simple, complete induction. This system uses chromosomal integration of the inserted gene, eliminating the need for continual selection (eg antibiotic) during fermentation. The vector pA0815 including the collagen gene was linearised with BamHI. Linearised plasmid was transformed into *P. pastoris* by electroporation. Various *Pichia* strains are suitable, including GSI15 his4. Transformants were selected as His+ cells for expression of the collagen construct. Selected cells were grown in shake flasks in a basal salt medium with glycerol, pH 5.0. When an appropriate wet cell density was attained, methanol was added and fermentation continued for a further 72 h.

Example 17: Expression of a DNA Construct for a Triple Helical Protein, a Bacterial Collagen Fragment from *S. usitatus*, with a V-Domain from *R. palustris*, Using Transient Expression in *Nicotinia* sp.

A synthetic gene encoding the bacterial collagen CL domain from *S. usitatus* and the V-domain from *R. palustris*, as described in Example 4 are used, except that the sequence is optimised for expression in *Nicotinia* sp. and restriction site for 5' AgeI and 3' XhoI introduced. The gene is PCR amplified and cloned into pENTR DTOPO. The integrity of the sequence is then confirmed. The pENTR DTOPO constructs are BspHI digested and purified to remove the kanamycin resistance gene, thus allowing appropriate selection with kanamycin after LR clonase recombination of the gene into the binary pEAQ-HT-DEST GATEWAY destination vector (Sainsbury et al. (2009) Plant Biotechnol J 7(7):682-93). Binary plasmids were transformed into and maintained in *A. tumefaciens* strain LBA4404. Constructs are grown in LB medium containing appropriate antibiotics, until the stationary phase is reached. Cultures are centrifuged and the pellets are resuspended into infiltration medium comprising 10 mM MES, 10 mM MgCl2, 20 mM acetosyringone, to an OD 600 of 0.5. Cultures are incubated in darkness at room temperature for 4 h before syringe infiltration (Sainsbury et al. (2009) Plant Biotechnol J 7(7): 682-93) into *Nicotiana benthamiana* grown to the five leaf stage. Leaves are harvested 5 days after infiltration.

Examples 18-32 describe the purification steps of this invention as illustrated in the Flowsheet of FIG. 1.

Example 18: Extraction of Triple Helical Protein from a Bacterial Cell, *E. coli*, Using Sonication For extraction, each 1 gram of cell paste, derived for example from the above examples, 12-17, was resuspended in 20 ml of 50 mM acetic acid/HCl buffer pH2, and the cells burst by sonication, using a Misonix S4000 instrument, with a Enhance Booster #1 probe, at 30 A (instrument scale) for 5 minutes. Optionally, the cell lysate mixture was clarified by centrifugation (12,000×g for 60 min) and the clear supernatant containing the triple helical protein was retained.

Example 19: Extraction of Triple Helical Protein from a Bacterial Cell, *E. coli*, Using a French Press Frozen cell paste, derived for example from Examples 12-17, was thawed and mixed 1:10 w/w with 50 mM acetic acid pH2. This mixture was passed through an Apv2000 French press homogeniser 3 times at 700 bar pressure with an additional 1 h cooling period between runs. After processing, the paste was optionally clarified by centrifugation at 12,000×g for 60 min and the clear supernatant, containing extracted triple-helical protein, was retained.

Example 20: Extraction of Triple Helical Protein from a Yeast Cell, *S. cerevisiae*

The cell paste, obtained from any one of the yeast expression systems, was resuspended in breaking buffer (50 mM sodium phosphate buffer pH7.4, 0.5 mM EDTA, 2 mM PMSF, 5% Glycerol, 0.1% Triton X-100) at the ratio of 1 g of cell paste per 20 ml of buffer and an equal volume of Glass beads (Sigma Glass beads #G8772) was added. The mixture was then vortexed (1400 rpm) the mixture for 30 seconds, rest for another 30 seconds. Repeat the vortex for 10× more times. The whole extraction process was kept at 5° C. throughout. The mixture was then centrifuged for 1 min at 10,000×g to collect the soluble extract.

Example 21: Extraction of Triple Helical Protein from Plant Leaves, *Nicotinia* sp.

Leaf material, such as from Example 17, preferably having been frozen at −20° C., is put into 20 mM sodium acetate buffer, pH 4.5 at 1:10 w/w leaf to buffer, and extracted in a Waring Blender at full speed.

Example 22: Validation of a Soluble Triple-Helical Protein Following Expression and Secretion or Extraction The presence of soluble triple helical protein, after expression such as in Examples 12-17, and extraction such as in Examples 18-21 or a triple helical protein expressed as a soluble product, as in Example 16, was established by centrifugation of the cellular material followed by SDS-PAGE. If any tags are present on the construct used for expression, such as a His$_6$-tag (SEQ ID NO: 46), or a Flag tag, then Western Blotting can be used with an appropriate antibody, such as monoclonal anti-poly-histidine conjugated to horse radish peroxidase for detection of soluble protein.

Example 23: Selection of pH for Precipitation for Cell Extracts

Expression host cells were mechanically extracted, as in Examples 18-19, and the extract incubated at a selected pH, between pH 2 and pH 8. Optionally the cell debris material was then removed. Samples of the extracted cell lysate was then adjusted to a precipitation pH, with various pH's selected, at 1 pH unit intervals, or preferably 0.5 pH unit intervals, and the samples held at 4° C. for 16 hours. Precipitate was then removed by centrifugation and the protein content of the supernatant estimated by absorption at 280 nm. The retention of solubility of the triple helical construct was again confirmed as in Example 22.

Example 24: Precipitation of Expression Cell Host Proteins from *E. coli*, while Retaining Soluble Triple Helical Protein Extracted protein from *E. coli*, containing soluble collagen-like protein from *S. pyogenes*, as in Example 1, and clarified after extraction by centrifugation, was adjusted to pH 2.2, was left a 4° C. for 16 h to allow precipitation. The sample was then centrifuged for 30 min and 15,000× g and the supernatant, containing the triple-helical protein, was retained.

Example 25: Precipitation of Expression Cell Host Proteins from *S. cerevisiae* while Retaining Soluble Triple Helical Protein from a Repeating Fragment of Human Type III Collagen The clarified supernatant, containing soluble triple-helical proteins, is adjusted to pH 5.0 using acetic acid or NaOH solution and is left at 4° C. for 16 h. The resultant precipitate is removed by centrifugation, 10,000×g for 30 min, and the supernatant retained.

Example 26: Precipitation of Expression Cell Host Proteins from *Nicotinia* sp. while Retaining Soluble Triple Helical Protein from *S. usitatus*

The clarified supernatant, containing soluble triple-helical proteins, is adjusted to pH 4.5 using acetic acid or NaOH solution and is left at 4° C. for 16 h. The resultant precipitate is removed by centrifugation, 10,000×g for 30 min. The supernatant is then adjusted to pH 2.5, with acetic acid and HCl and left a further 20 h. The solution is clarified by centrifugation, 10,000×g for 30 min, and the supernatant retained.

Example 27: Digestion of Post-Precipitation Residual Soluble Host Cell Contaminants The supernatant obtained after removal of acid precipitated proteins, such as in the above experiments was adjusted according to any one of the following conditions.
  pH 2.5 and pepsin (0.01 mg/ml) for 0.16 h at 4° C. and was then optionally terminated by adjusting the pH of the digest to pH 7.
  pH 6.5 and Na EDTA (50 mM) and cysteine (50 mM), papain (0.01 mg/ml) for 16 h at 4° C. pH 3.0 and fungal acid protease type XIII (0.01 mg/ml), 16 h at 4° C. and was then optionally terminated by adjusting the pH of the digest to pH 7. pH 8.0 and trypsin and chymotrypsin were both added to 0.01 mg/ml, 16 h at 4° C. and was then optionally terminated by adjusting the pH of the digest to pH 4.

The following examples follow the purification steps of this invention and relate to the collection, concentration and possibly final polishing and purification of the protein.

Example 28: Isolation of Triple Helical Protein Product by Ammonium Sulfate Precipitation Fractions containing recombinant triple-helical protein after removal of impurities by acid precipitation followed by protease treatment, as discussed in the previous example, were pooled and the pH of the solution adjusted to pH 4.0 to 7.0 and the triple-helical protein precipitated though addition of solid ammonium sulfate. All steps were performed at temperatures less that the melting temperature of the triple-helix, preferably at 4° C. The amount of solid ammonium sulphate required for precipitation was followed by centrifugation of samples, visual examination for precipitation and analysis by SDS-PAGE. For small non-animal collagens, such as from S. pyogenes, a 35% saturation of ammonium sulfate is required.

Example 29: Isolation of Triple Helical Protein Product by Polymer Precipitation Fractions containing recombinant triple-helical protein after removal of impurities by acid precipitation followed by protease treatment, as discussed in previous experiments, were pooled and the pH of the solution adjusted to pH 7.0±1.0 and the triple-helical protein precipitated though addition of polyethylene glycol-4000, from a 40% aqueous stock solution. All steps were performed at temperatures less that the melting temperature of the triple-helix, preferably at 4° C. The amount of polyethylene glycol required for precipitation was followed by centrifugation of samples, visual examination for precipitation and analysis by SDS-PAGE. For small non-animal collagens, such as from S. pyogenes, a 10% w/v of polyethylene glycol-4000 is required.

Figure 3:
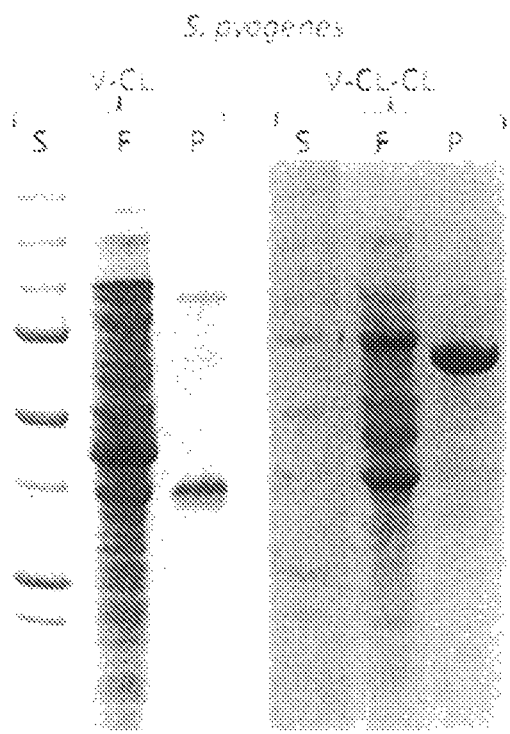
FIG. 3 shows SDS PAGE illustrating the final purification of the triple-helical protein following acid precipitation and then protease digestion; S=protein standard; F=fermentation extract and P=product after pH2.0 precipitation and pepsin digestion, for initial DNA construct of *S. pyrogenes* V-CL and V-CL-CL, giving products after precipitation and proteolysis of CL and CL-CL.

The purity of the proteins obtained is illustrated in FIG. 3.

Example 30: Isolation of Triple Helical Protein Product by Ultrafiltration

Fractions containing recombinant triple-helical protein after removal of impurities by acid precipitation followed by protease treatment, as discussed in previous examples, were pooled and then concentrated and exchanged into 20 mM sodium phosphate buffer, pH8.0, using a 10 kDa cross-flow filtration membrane apparatus (Pall Life Sciences). All steps were performed at temperatures less that the melting temperature of the triple-helix, preferably at 4° C.

Example 31: Isolation of Triple Helical Protein Product by Absorption

Fractions containing recombinant triple-helical protein after removal of impurities by acid precipitation followed by protease treatment, as discussed in previous examples, are pooled and the pH of the solution adjusted to pH 8.0±0.5 with Tris. For the triple-helical protein from S. pyogenes, the pooled sample are then absorbed onto a Mono-Q column (GE HealthCare), which has —CH2-N+(CH$_3$)$_3$ as the charged group, pre-equilibrated in 50 mM Tris/HCl buffer, pH 8.0. After loading, the column is washed with 5 column volumes of equilibrating buffer, and then eluted by a linear NaCl gradient from 0 to 1 M in the same buffer. Protein is detected by absorption at 214 nm and confirmed by SDS-PAGE.

The following examples illustrate how the purified triple helical protein can be used in clinical applications.

Example 32: Fabrication—Preparation of Bacterial Collagen-Like Samples for In Vivo Utility If the purified collagen proteins are to be used as biomedical material it is most likely they need further "polishing" using methods known to those skilled in the art. Also the protein may need to be stabilised, as is the case for animal collagens, prior to use in medical applications.

In this example a sponge is prepared by freeze drying S. pyogenes collagen stabilised by glutaraldehyde vapour at 20° C. for 18 h in a closed vessel. This approach led to a protein sponge that was stable at >37° C. The increase in the shrinkage temperature depended on the extent of the stabilisation, but up to ~25 C extra stability could be obtained. The thermal stability of the stabilised samples was examined by differential scanning calorimetry (DSC) using samples in PBS.

For assessment of cell attachment, stabilised, PBS washed CL samples were treated for 2 h with 120 µg/ml penicillin and 200 µg/ml streptomycin in MEM and then seeded with 1×10$^4$ L929 cells per sample in MEM supplemented with 1% NEAA and 10% FCS in 96 well plates. Attachment was assessed at 3 h and 16 h after samples were rinsed twice in PBS. Cell viability was tested after 16 h at 37° C. with a Live/Dead® Viability/Cytotoxicity Kit (Molecular Probes) assay.

Figure 4:
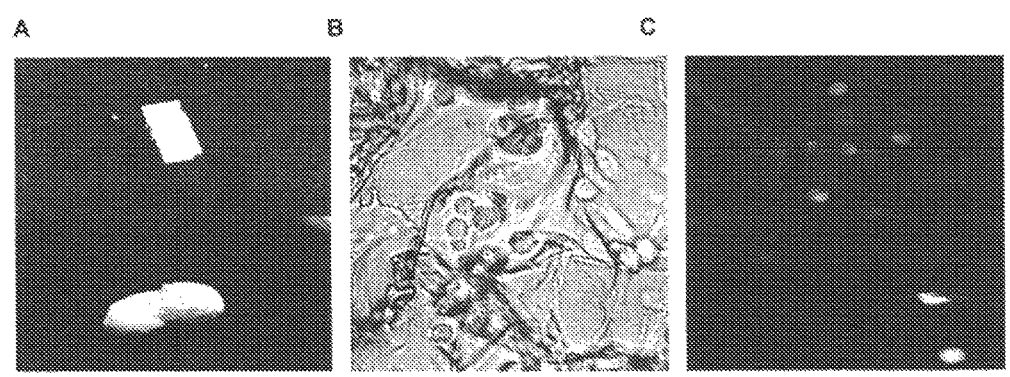
FIG. 4 shows *S. pyogenes* collagen sponge and cell evaluation, showing (A) stabilised sheet (upper) and sponge (lower) (B) cell attachment at 3 h, and (C) cell viability after 16 h.

These data showed that the collagen sponge material was a mixture of small fibres and larger aggregates. Good attachment of the L929 cells was seen at 3 h to both the smaller fibres and to the aggregates. After 16 h, the L929 cells show excellent viability in a Live/Dead™ assay. The degree of spreading is very limited at this time point, consistent with the 'blank slate' observation. The GA stabilised matrix is slightly auto-fluorescent (FIG. 4).

The invention claimed is:

1. A method for the purification of a recombinantly expressed triple-helical protein contained within a non-mammalian host cell culture extract or homogenate, the method comprising:
   (i) precipitating host cell materials in the host cell culture extract or homogenate from the triple-helical protein under acidic conditions and at a temperature in which the triple-helical protein remains thermally stable; followed by
   (ii) digesting host cell materials present in the precipitated host cell culture extract or homogenate by addition of a protease which is functional under said acidic conditions, wherein the triple-helical protein is resistant to the protease; and
   (iii) collecting the purified triple-helical protein;
wherein the triple-helical protein remains in-solution throughout at least steps (i) and (ii).

2. The method according to claim 1, wherein the triple-helical protein remains soluble throughout steps (i) to (iii).

3. The method according to claim 1, wherein the digestion is carried out using a protease selected from the group consisting of pepsin, papain, or papain-like enzymes selected from bromelain, ficin or actinidin, *Aspergillus saitoi* acid protease, trypsin or chymotrypsin.

4. The method according to claim 1, wherein the host cell is a bacterial, yeast or plant host cell.

5. The method according to claim 1, wherein acid conditions refers to a pH less than 7.

6. The method according claim 1, wherein the precipitation step is conducted at a temperature that is less than the melting temperature of the triple-helical protein.

7. The method according to claim 1, further comprising an additional separation step between the precipitating step and the digesting step of physically separating the triple-helical protein from precipitated host cell materials.

8. The method according to claim 7, wherein the intermediary separation step is selected from one or more of centrifugation, filtration, cross flow filtration, or sedimentation.

9. The method according to claim 1, wherein the expressed triple-helical protein is produced intracellularly within the host cell.

10. The method according to claim 1, wherein the expressed triple-helical protein is secreted from the host cell.

11. The method according to claim 1, comprising an additional step prior to step (i) of producing the host cell culture extract or homogenate which contains the triple-helical protein.

12. The method according to claim 1, wherein the method is carried out at a temperature which is the melting temperature (Tm) of the recombinant triple-helical protein.

13. The method according to claim 1, wherein the temperature is at least 10° C. or more below the Tm of the recombinant triple-helical protein.

14. The method according to claim 5, wherein the pH is between 2 and 4 and the host cell is a bacterial host cell.

15. The method according to claim 5, wherein the pH is between 4 and 6 and the host cell is a yeast host cell.

16. The method according to claim 5, wherein the pH is between 2 and 4.5 and the host cell is a plant host cell.

17. The method according to claim 3, wherein the triple-helical protein is proteolytically stable.

18. The method according to claim 3, wherein the method selectively purifies proteolytically stable protein over proteolytically unstable protein.

19. The method according to claim 1, wherein host cell nucleic acid is removed from the collected triple-helical protein.

20. The method according to claim 1, wherein collecting the purified triple helical protein is performed by precipitation or diafiltration.

21. The method according to claim 1, wherein the collected triple-helical protein is stabilised by a stabilising agent.

22. The method according to claim 1 wherein the triple-helical protein comprises a repeating (Gly-X-Y)n motif, where n is between 5 and 600.

23. The method according to claim 1, wherein the triple-helical protein is collagen.

24. The method according to claim 1, wherein the triple-helical protein sequence is derived from a bacteria, yeast, plant, insect, or silkworm.

25. The method according to claim 20, wherein precipitation of the collected protein is achieved by addition of ammonium sulphate, by adjustment of pH or adjustment of temperature, and/or by use of polyethylene glycol.

* * * * *

UNITED STATES PATENT AND TRADEMARK OFFICE
CERTIFICATE OF CORRECTION

PATENT NO. : 10,053,501 B2
APPLICATION NO. : 14/778845
DATED : August 21, 2018
INVENTOR(S) : John Alan Maurice Ramshaw et al.

It is certified that error appears in the above-identified patent and that said Letters Patent is hereby corrected as shown below:

On the Title Page

(71) Applicant:
Reads "Commonwealth Scientific and Industrial Research Organization, Campbell, Australian Capital Territory (AU)"
Should read --Commonwealth Scientific and Industrial Organisation, Clunies Ross Street, Acton ACT 2601, Australia--

Signed and Sealed this
Sixteenth Day of October, 2018

Andrei Iancu
*Director of the United States Patent and Trademark Office*